United States Patent
Nagata et al.

(10) Patent No.: US 6,348,334 B1
(45) Date of Patent: Feb. 19, 2002

(54) DNA ENCODING FAS LIGAND

(75) Inventors: Shigekazu Nagata; Takashi Suda, both of Osaka-fu; Tomohiro Takahashi; Norio Nakamura, both of Tokyo, all of (JP)

(73) Assignees: Mochida Pharmaceutical Co., Ltd., Tokyo (JP); Osaka Bioscience Institute, Osaka-fu (JP)

(*) Notice: Subject to any disclaimer, the term of this patent is extended or adjusted under 35 U.S.C. 154(b) by 0 days.

(21) Appl. No.: 08/339,214

(22) Filed: Nov. 10, 1994

(30) Foreign Application Priority Data

| Nov. 10, 1993 | (JP) | 5-305975 |
| Dec. 13, 1993 | (JP) | 5-342526 |
| Mar. 18, 1994 | (JP) | 6-74344 |
| Jul. 8, 1994 | (JP) | 6-180955 |
| Sep. 7, 1994 | (JP) | 6-239363 |
| Oct. 18, 1994 | (JP) | 6-278378 |

(51) Int. Cl.⁷ .......... C07H 21/04; C12N 5/00; C12N 15/00; C12P 21/00
(52) U.S. Cl. .......... 435/69.5; 435/70.1; 435/252.3; 435/320.1; 435/325; 435/254.2; 536/23.1; 536/23.5
(58) Field of Search .............. 536/23.5, 23.1; 435/69.4, 240.2, 252.3, 320.1, 69.5, 70.1, 325; 530/350

(56) References Cited

FOREIGN PATENT DOCUMENTS

| EP | 0510691 | 10/1992 |
| WO | WO91/10448 | 7/1991 |
| WO | WO95/18819 | 7/1995 |

OTHER PUBLICATIONS

Yonehara et al, J. Exp. Med., vol. 169, pp. 1747–1756 (May 1989).
Itoh et al, Cell, vol. 66, pp. 233–243 (Jul. 26, 1991).
Watanabe–Fukunaga et al, The Journal of Immunology, vol. 148, No. 4, pp. 1274–1279 (Feb. 15, 1992).
Kobayashi et al, Nikkei Science, vol. 6, pp. 34–41 (1993).
Ogasawara et al, Nature, vol. 364, pp. 806–809 (Aug. 26, 1993).
Hiramatsu et al, Hepatology, vol. 19, No. 6, pp. 1354–1359 (Jun. 1994).
Watanabe–Fukunaga et al, Nature, vol. 356, pp. 314–317 (Mar. 26, 1992).
Rouvier et al, J. Exp. Med., vol. 177, pp. 195–200 (Jan. 1993).
Morimoto et al, Cancer Research, vol. 53, pp. 2591–2596 (Jun. 1, 1993).
Kimura et al, Biochem. and Biophys. Res. Comm ., vol. 198., No. 2, pp. 666–674 (Jan. 28, 1994).
Creighton, J. Mol. Biol., vol. 87, pp. 563–577 (1974).
Itoh et al, The Journal of Immunology, vol. 151, No. 2, pp. 621–627 (Jul. 15, 1993).
Mizushima et al, Nucleic Acids Research, vol. 18, No. 17, p. 5322 (1990).
Loetscher et al, The Journal of Biological Chemistry, vol. 266, No. 27, pp. 18324–18329 (Sep. 25, 1991).
Shaw et al, Nucleic Acids Research, vol. 11, No. 3 (1983).
Morishita et al, Thrombosis Research, vol. 73, Nos. 3/4, pp. 193–204 (1994).
Suda et al, Cell, vol. 75, pp. 1169–1178 (Dec. 17, 1993).
Suda et al, J. Exp. Med., vol. 179, pp. 873–879 (Mar. 1994).
Takahashi et al, Cell, vol. 76, pp. 969–976 (Mar. 25, 1994).
Cory, Nature, vol. 367, pp. 317–318 (Jan. 27, 1994).
Takahashi et al, International Immunology, vol. 6, No. 10, pp. 1567–1574 (1994).

*Primary Examiner*—Elizabeth Kemmerer
*Assistant Examiner*—Bridget E. Bunner
(74) *Attorney, Agent, or Firm*—Birch, Stewart, Kolasch & Birch, LLP

(57) ABSTRACT

This invention provides a novel polypeptide useful in the field of medicines, a novel DNA which encodes the novel polypeptide, a recombinant DNA molecule which contains the novel DNA, a transformant transformed with the novel DNA or the recombinant DNA molecule, a process for the purification of the novel polypeptide, a process for the production of the novel polypeptide, an antibody which recognize the novel polypeptide, an oligonucleotide complementary to the novel DNA and a novel screening method. Particularly this invention provides a novel polypeptide which is Fas ligand or a fragment thereof. This novel polypeptide can be used as an effective ingredient of a medicament for regulating the apoptosis in a living body. This novel polypeptide is obtained by identifying a DNA fragment which encodes the novel polpeptide, transforming a desired host with a recombinant DNA molecule which contains the DNA fragment and purifying the novel polypeptide produced by the resulting transformant. This novel polypeptide has a cytoplasmic domain, a transmembrane domain and extracellular domain and takes part in apoptosis.

25 Claims, 42 Drawing Sheets

FIG. 2-1

```
                    TCAGAGTCCTGTCCTTGACACTTCAGTCTCCACAAGACTGAGAGAGGAAACCCTTTCCTGGGGCTGGGTGCC
                                                            50

ATG CAG CAG CCC GTG AAT TAC CCA TGT CCC CAG ATC TAC TGG GTA GAC AGC AGT GCC ACT TCT CCT TGG GCT CCT
Met Gln Gln Pro Val Asn Tyr Pro Cys Pro Gln Ile Tyr Trp Val Asp Ser Ser Ala Thr Ser Pro Trp Ala Pro
                                    10                                      20
150                                                 200
CCA GGG TCA GTT TTT TCT TGT CCA TCC TCT GGG CCT AGA GGG CCA CAA AGG AGA CCA CAA CCG CCT CCA CCA CCA
Pro Gly Ser Val Phe Ser Cys Pro Ser Ser Gly Pro Arg Gly Pro Gln Arg Arg Pro Gln Arg Arg Pro Pro Pro
                30                                              40                              50
            250
CCT CCA TCA CCA CTA CCA CCA CCC CCT CCC CAA CCA CCC CCG CTG CCT CCA CTA AGC CCT CTA AAG AAG GAC AAC
Pro Pro Ser Pro Leu Pro Pro Pro Pro Pro Gln Pro Pro Pro Leu Pro Pro Leu Ser Pro Leu Lys Lys Asp Asn
                60                                              70
300                                 350
ATA GAG CTG TGG CTA CCG GTG CTA CCG ATA TTT TTC ATG GTG CTG GTT GGA ATG CTG GTT GGA ATG TAT CAA
Ile Glu Leu Trp Leu Pro Val Ile Phe Met Val Leu Val Ala Leu Val Gly Met Gly Leu Met Tyr Gln
                80                                              90                              100
            400
CTC TTT CAT CTA CAG AAG GAA CTG GCA GAA CTC CGT GAG TTC ACC AAC CAC AGC CTT AGA GTA TCA TCT TTT GAA
Leu Phe His Leu Gln Lys Glu Leu Ala Glu Leu Arg Glu Phe Thr Asn His Ser Leu Arg Val Ser Ser Phe Glu
                110                                     *       120
450                                                 500
AAG CAA ATA GCC AAC CCC AGC TCT GAA ACC ACA GGG AGT GTG GCC CAC TTA ACA GGG AAC CCC
Lys Gln Ile Ala Asn Pro Ser Thr Pro Ser Glu Thr Thr Lys Pro Arg Ser Val Ala His Leu Thr Gly Asn Pro
            *                               140                                     150
            550
CGC TCA AGG TCC ATC CCT CTG GAA TGG GAA GAC ACA TAT GGA ACT GCT TTG ATC TCT GGA GTG AAG TAT AAG AAA
Arg Ser Arg Ser Ile Pro Leu Glu Trp Glu Asp Thr Tyr Gly Thr Ala Leu Ile Ser Gly Val Lys Tyr Lys Lys
                160                                             170
```

FIG. 2-2

```
600
GGC CTT GTG ATC AAT GAG GCT GGG TTG TAC TTC GTA TAT TCC AAA GTA TAC TTC CGG GGT CAG TCT TGC AAC
Gly Leu Val Ile Asn Glu Ala Gly Leu Tyr Phe Val Tyr Ser Lys Val Tyr Phe Arg Gly Gln Ser Cys Asn
        180                                   190                                   200
                                700                                 650
AGC CAG CCC CTA AGC CAC AAG GTC TAT ATG AGG AAC TTT AAG TAT CCT GGG GAT CTG GTG CTA ATG GAG AAG
Ser Gln Pro Leu Ser His Lys Val Tyr Met Arg Asn Phe Lys Tyr Pro Gly Asp Leu Val Leu Met Glu Lys
                                      210                                   220
750                                                 800
AAG TTG AAT TAC TGC ACT ACT GGC ATA TGG GCC CAC AGC TAC CTA GGG GCA GTA TTT AAT CTT ACC GTT
Lys Leu Asn Tyr Cys Thr Thr Gly Gln Ile Trp Ala His Ser Tyr Leu Gly Ala Val Phe Asn Leu Thr Val
        230                                   240                              *      250
```

FIG. 3

```
                                850
GCT GAC CAT TTA TAT GTC AAC ATA TCT CAA CTC TCT CTG ATC AAT TTT GAG GAA TCT AAG ACC TTT TTT GGC TTA
Ala Asp His Leu Tyr Val Asn Ile Ser Gln Leu Ser Leu Ile Asn Phe Glu Glu Ser Lys Thr Phe Phe Gly Leu
                                          260                                                   270
900                                                 950
TAT AAG CTT TAA AGGAAAAAGCATTTAGAATGATCTATTATTCTTTATCATGGATGCCAGGAATATTGTCTTCAATGAGTCTTCTTAAGACC
Tyr Lys Leu ***
1000                                    1050                                    1100
AATTGAGCCACAAAGACCACAAGGTCCAACAGGTCAGCTACCCTTCATTTTCTAGAGGTCCATGGAGTGGTCCTTAATGCCTGCATCATGAGCCAGATG
                                                1150                                    1200
GGAAGAAGACTGTTCCTGAGGAACATAAAGTTTGGGCTGCTGCTGTGGCAATGCAGAGGCAAAGAGAAGGAACTGTCTGATGTAAATGGCCAAGAGCA
                                1250                                    1300
TTTTAGCCATTGAAGAAAAAAAAAAACCTTTAAACTCACCTTCCAGGGTGGGTCCTACTTGCTACCTCACAGGAGGCCGTCTTTTAGACACATGGTTGTGG
                                        1350                                    1400
TATGACTATACAAGGGTGAGAAAGGATGCTAGGTTTCATGGATAAGCTAGAGACTGAAAAAAGCCAGTGTCCCATTGGCATCATCTTTATTTTTAACTG
                                                1450                                    1500
ATGTTTCTGAGCCCACCTTTGATGCTAACAGAGAAATAAGAGGGGTGTTTGAGGCACAAGTCATTCTCTACATAGCATGTACCTCCAGTGCAATGA
                                1550
TGTCTGTGTGTTTTTATGTATGAGAGTAGAGCGATTCTAAAGAGTCACAAGCGTACAACGCGTACATTGAGTACATATTAGAAACGTATGTGTT
1600
ACATTTGATGCTAGAATATCTGAATGTTTCTTGCTA
```

FIG. 15

```
                    Asn Pro Arg                     Ile
                    Lys Ser Asn Ser Arg Ser Met Pro Leu Glu Trp Glu Asp Thr Tyr Gly
GATTATTCAG GC       AAG TCC AAC TCA AGG TCC ATG CCT CTG GAA TGG GAA GAC ACC TAT GGA
                     G   C   CG                   C                           A

Thr Ala     Ile                                                             Ala
Ile Val Leu Leu Ser Gly Val Lys Tyr Lys Lys Gly Leu Val Ile Asn Glu Thr Gly
ATT GTC CTG CTT TCT GGA GTG AAG TAT AAG AAG GGT CTT GTG ATC AAT GAA ACT GGG
 C   CT  T   A  C                         A  C                      G  G

Ser Gln
Leu Tyr Phe Val Tyr Ser Lys Val Tyr Phe Arg Gly Gln Ser Gln Asn Leu Pro Leu
CTG TAT TTT GTA TAT TCC AAA GTA TAC TTC CGG GGT CAA TCT CAA AAC CTG CCC CTG
 T           C                                       G            G   A   A

Gly                         Glu
Ser His Lys Val Tyr Met Arg Asn Gln Asp Leu Val Met Met Glu Met Gly Gly Ala
AGC CAC AAG GTC TAC ATG AGG AAC CAG GAT CTG GTG ATG ATG GAG ATG GGG GGG GCA
             T                    GG      C A          C A              A

Val         Phe             Ile         His
Lys Met Met Ser Cys Thr Ser Lys Tyr Pro Met Trp Ala Arg Ser Ser Tyr Leu Gly Ala
AAG ATG ATG AGC TGC ACT TCT AAG TAT CCC ATG TGG GCC CGC AGC AGC TAC CTG GGG GCA
 A   T   AT      T              T           A        A                    A

Val                                     Ile         Gln
Val Phe Asn Leu Thr Ala Asp His Leu Tyr Val Asn Val Val Ser Glu Leu Ser Leu Val
GTG TTC AAT CTT AGT GCT GAT CAT TTA TAT GTC AAC GTA GTA TCT GAG CTC TCT CTG GTC
 A   T       GT  C                                   A      C.A              A

Lys
Asn Phe Glu Gln Thr Phe Phe Gly Leu Tyr Lys Leu
AAT TTT GAG TCT CAG ACG TTT TTC GGC TTA TAT AAG CTC TAA GAGAAGCACTTTGGGATTC
             A          C               T           T
```

FIG. 16

```
AATTATAATGTATAAAAAGCATGCAATTATAATTCATAAATTATAGCCCCACTGACCATTCTCCTGTAGCTGGGAGCAGTTCACACTAACAGGCTA
TACCCCATGCTGACCTGCTCTGCAGATCCCAGGAAGTGAGCATAGCCTTGAGGTAGCACAGCAGCAACTGAGGCCTTGAAGGC
TGTTATCAGAAAATTGTGGGCGGAAACTTCCAGGGGTTTGCTCTGAGCTTCTTGAGGCTTCAGCTGCAAAGTGAGTGGGTGTTTCTTTGAG
AAGCAGAATCAGAGAGAGAGATAGAAAGAGAGACAGAGGTGTTTCCCTTAGCTATGGAAACTCTATAAGAGAGATCCAGCTGCCTCCTTG
AGCAGTCAGCAACAGGGTCCCGTCCTTGACACCTCAGCCTCTACAGGACTGAGAAGAATAAACCGTTTGCTGGGCTGGCCTGACTCACCAGCTGCC
                                                                              20
Met Gln Gln Pro Phe Asn Tyr Pro Gln Ile Tyr Trp Val Asp Ser Ser Ala Ser Pro Trp Ala Pro
ATG CAG CAG CCC TTC AAT TAC CCA CAG ATC TAC TGG GTG GAC AGT AGC AGC GCC TCT CCC TGG GCC CCT

Pro Gly Thr Val Leu Pro Cys Pro Thr Ser Val Pro Arg Arg Pro Gly Gln Arg Arg Pro Pro Pro Pro
CCA GGC ACA GTT CTT CCC TGT CCA ACC TCT GTG CCC AGA AGG CCT GGT CAA AGG AGG CCA CCA CCG CCA
                                                 40

Pro Pro Leu Pro Pro Pro Pro Pro Pro Pro Pro Leu Pro Pro Leu Lys Lys Arg Gly
CCG CCA CCA CTA CCT CCA CCG CCG CCT CCA CTA CCG CCC CTG AAG AAG AGA GGG
                                                 60

Asn His Ser Thr Gly Leu Leu Cys Leu Val Met Phe Phe Met Val Leu Val Ala Leu Val Gly Leu Gly
AAC CAC AGC ACA GGC CTG TGT CTC CTT GTG ATG TTT TTC ATG GTT CTG GCC TTG GTA GGA TTG GGC CTG GGG

Met Phe Gln Leu Phe His Leu Gln Lys Glu Leu Ala Glu Leu Arg Glu
ATG TTT CAG CTC TTC CAC CTA CAG AAG GAG CTG GCA GAA CTC CGA GAG  ......... GATTCTGCCTCTCTTTTGCTTAAAGAATTTATTTTTATTATACATCTTTTCTC
                                                 80
ACCAGGCATAAGGGATGGAGGGCCCACTGCCTGGC.........
                                                     120
                   Ser Thr Ser Gln Met His Thr Ala Ser Ser Leu Glu Lys Gln Ile G
TTTCTGTTTTACTAG TCT ACC AGC CAG ATG CAC ACA GCA TCA TCT TTG GAG AAG CAA ATA G GTGAGTCTTTTTTCGCATGTA

CATTGAGTTCCCAAAGATGATCCTCAGCACAGAACTATGTTAATGGAATGCCTTAAATTCTGTCCCACACTTTGGTTTCTGTACACTATAAGAGGAATT
```

FIG. 17

```
C..........TTCCCACCAAAATAATAGTTGCTATTTCATTTAACATATATTTTCCTCTCTCTATGATACAG
                                        140
               ly His Pro Ser Pro Pro Glu Leu Arg Lys Val Ala His Leu Thr G
               GC CAC CCC AGT CCA CCC CCT GAA CTG AGG AAA GTG GCC CAT TTA ACA G GTCTGTATC

TGGAAGGTACAGAGTGAGAT..........CTGCAGGTGAGAAGATGGACCAGAGTGTCCCTAAGATCCTTCCCAACTTTAGAACTTTAGAGTTC
CTTGGGATTTGGCTTTTTCCTTCAGGAAGGACTTCAAAGCCTAGCAGATTTGGTGTGCTAGTTCTGAAGATAGTAAAATCTTTGTTCCAGAGAGCAAATAT
TTTCTCAATAATTCTTACTGCAATGGATTACGGGTATATACTATTGTTCCAATTGTGTGGATGACAAAATAGGACAAAATAGGACAACGTTGTTGAGGAAATTCTGTG
ATGGATCAAGTTCTGACCCCTCAGCCAGTTCTATACCAGCTGTCATTCTCGGGTGAAACATTGTTGAAGGAAGGCCCACAGTTTGCCTTAGAAACTT
                                                                                160
AGTTTGTTGGATGCATGACTATTCCTTGCTGAAAGCTCCTTTTGGATTTATTCAG GC AAG TCC AAC TCA AGG TCC ATG CCT CTG GAA
                                                         ly Lys Ser Asn Ser Arg Ser Met Pro Leu Glu
                                                                         180

Trp Glu Asp Thr Tyr Gly Ile Val Leu Leu Ser Gly Val Lys Tyr Lys Lys Gly Leu Val Ile Asn Glu Thr
TGG GAA GAC ACC TAT GGA ATT GTC CTG CTT TCT GGA GTG AAG TAT AAG AAG GGT GGC CTT GTG ATC AAT GAA ACT
                                                 200                                              *

Gly Leu Tyr Phe Val Tyr Phe Val Tyr Ser Lys Tyr Pro Gln Asp Leu Val Met Met Glu Gly Lys Met Ser Tyr Cys Thr Thr Gly
GGG CTG TAC TTT GTA TAC TTC CGG GGT CAA TCT TGC AAC AAC CTG CCC CTG AGC CAC AAG GTC

Tyr Met Arg Asn Ser Lys Tyr Pro Gln Asp Leu Val Met Met Glu Gly Lys Met Ser Tyr Cys Thr Thr Gly
TAC ATG AGG AAC TCT AAG TAT CCC CAG GAT CTT GTG ATG ATG GAG GGG AAG ATG AGC TAC TGC ACT GGG
             240                                                                              260

Gln Met Trp Ala Arg Ser Ser Ser Tyr Leu Gly Ala Val Phe Asn Leu Thr Ser Ala Asp His Leu Tyr Val Asn Val
CAG ATG TGG GCC CGC AGC AGC AGC TAC CTG GGG GCA GTG TTC AAT CTT ACC AGT GCT GAT CAT TTA TAT GTC AAC GTA

Ser Glu Leu Ser Leu Val Asn Phe Glu Glu Ser Gln Thr Phe Phe Gly Leu Tyr Lys Leu
TCT GAG CTC TCT CTG GTC AAT TTT GAG GAA TCT CAG ACG TTT TTC GGC TTA TAT AAG CTC TAA GAGAAGCACTTTGGG
                                                                          280
```

FIG. 18

ATTCTTTCCATTATGATTCTTTGTTACAGGCACCGAGAATGTGTATTCAGTGAGGGTCTTCTTACATGCATTTGAGG
TCAAGTAAGAAGACATGAACCAAGTGACCTTGAGACCACAGGGTTCAAAATGTCTGTAGCTCCTCAACTCACCTA
ATGTTTATGAGCCAGACAAATGGAGGAATATGACGGAAGAACATAGAACTCTGGGCTGCCATGTGAAGAGGGAGA
AGCATGAAAAAGCAGCTACCAGGTGTTCTACACTCATCTTAGTGCCTGAGAGTATTAGGCAGATTGAAAGGACA
CC

FIG. 19

```
                    CTACAGGACT GAGAAGAAGT AAAACCGTTT GCTGGGGCTG GCCTGACTCA CCAGCTGCC
                                    10                              20
Met Gln Pro Phe Asn Tyr Pro Gln Ile Tyr Trp Val Asp Ser Ser Ala Ser
ATG CAG CAG CCC TTC AAT TAC CCA CAG ATC TAC TGG GTG GAC AGC AGT GCC AGC
                    30                              40
Ser Pro Trp Ala Pro Pro Gly Thr Val Leu Pro Cys Pro Thr Ser Val Pro Arg Arg Pro
TCT CCC TGG GCC CCT CCA GGC ACA GTT CTT CCC TGT CCA ACC TCT GTG CCC AGA AGG CCT
                    50                              60
Gly Gln Arg Arg Pro Pro Pro Pro Pro Pro Leu Pro Pro Leu Lys Arg Gly Asn His Ser Thr Gly
GGT CAA AGG AGG CCA CCA CCG CCA CCT CTA CCC CTG CCA AAG AGA GGG AAC CAC AGC ACA GGC
                    70                              80                       100
Pro Pro Leu Pro Leu Pro Pro Leu Pro Pro Leu Lys Arg Gly Asn His Ser Thr Gly
CCA CCA CCT CCA CTA CCG CTG CCA CCC AAG AGA GGG AAC CAC AGC ACA GGC
                                    90                              100
Leu Cys Leu Leu Val Met Phe Phe Met Val Leu Val Ala Leu Val Gly Leu Gly
CTG TGT CTC CTT GTG ATG TTT TTC ATG GTT CTG GTT GCC TTG GTA GGA TTG GGG
                    110                             120
Met Phe Gln Leu Phe His Leu Gln Lys Glu Leu Ala Glu Leu Arg Glu Ser Thr Ser Gln
ATG TTT CAG CTC TTC CAC CTA CAG AAG GAG CTG GCA GAA CTC CGA GAG TCT ACC AGC CAG
                    130                             140
Met His Thr Ala Ser Leu Glu Lys Gln Ile Gly His Pro Ser Pro Pro Glu Lys
ATG CAC ACA GCA TCA TTG GAG CAA ATA GGC CAC CCC AGT CCA CCC CCT GAA AAA
                    150                             160
Lys Glu Leu Arg Lys Val Ala His Leu Thr Gly Lys Ser Asn Ser Arg Ser Met Pro Leu
AAG GAG CTG AGG AAA GTG GCC CAT TTA ACA GGC AAG TCC AAC TCA AGG TCC ATG CCT CTG
```

FIG. 20

```
                                                                          170                        180
Glu Trp Glu Asp Thr Tyr Gly Ile Val Leu Leu Ser Gly Val Lys Tyr Lys Lys Gly
GAA TGG GAA GAC ACC TAT GGA ATT GTC CTG CTT TCT GGA GTG AAG TAT AAG AAG GGT
                                                                                                     200
                            190
Leu Val Ile Asn Glu Thr Gly Leu Tyr Phe Val Tyr Ser Lys Val Tyr Phe Arg Gly Gln
CTT GTG ATC AAT GAA ACT GGG CTG TAC TTT GTA TAT TCC AAA GTA TAC TTC CGG GGT CAA
                                                        210                                          220
Ser Cys Asn Asn Leu Pro Leu Ser His Lys Val Tyr Met Arg Asn Ser Lys Tyr Pro Gln
TCT TGC AAC AAC CTG CCC CTG AGC CAC AAG GTC TAC ATG AGG AAC TCT AAG TAT CCC CAG
                                            230                                                      240
Asp Leu Val Met Met Glu Gly Lys Met Ser Tyr Cys Thr Thr Gly Gln Met Trp Ala
GAT CTG GTG ATG ATG GAG GGG AAG ATG AGC TAC TGC ACT ACT GGG CAG ATG TGG GCC
                250                                                                                  260
Arg Ser Ser Tyr Leu Gly Ala Val Phe Asn Leu Thr Ser Ala Asp His Leu Tyr Val Asn
CGC AGC AGC TAC CTG GGG GCA GTG TTC AAT CTT ACC AGT GCT GAT CAT TTA TAT GTC AAC
                                270                                                                  280
Val Ser Glu Leu Ser Leu Val Asn Phe Glu Ser Gln Thr Phe Phe Gly Leu Tyr Lys
GTA TCT GAG CTC TCT CTG GTC AAT TTT GAG TCT CAG ACG TTT TTC GGC TTA TAT AAG

Leu
CTC TAA GAGAAGCACTTTGGGATTC
```

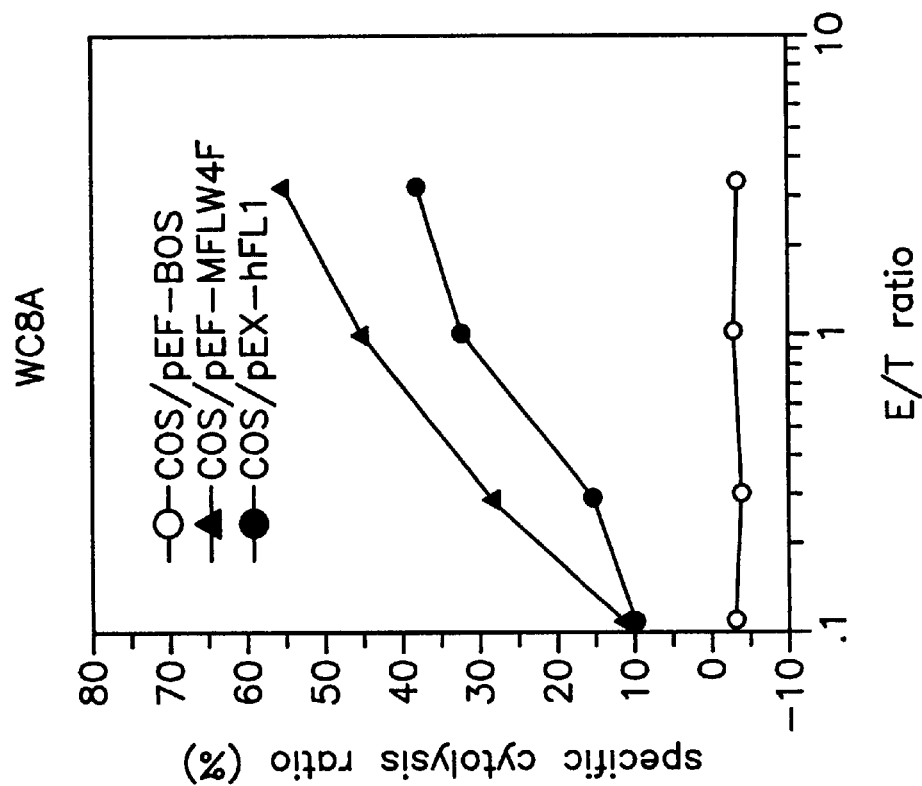
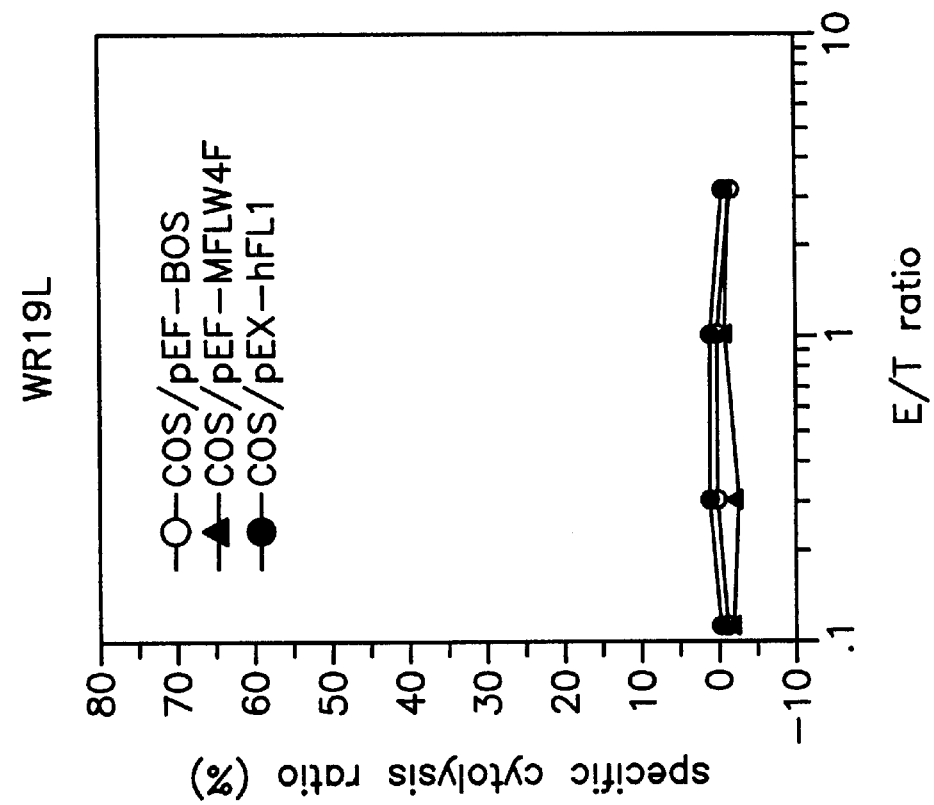

FIG. 23

```
CTGCGGAAACTTTATAAAGAAAACT
TAGCTTCTCTGGAGCAGTCAGCGTCAGAGTTCTGTCCTTGACACCTGAGTCTCCTCCACAAGGCTGTGAGAAGGAAACCCTTTCCTGGGGCTGGGTGCC

ATG CAG CCC ATG AAT TAC CCA CAG TGT CCC CAG ATC TTC TGG GTA GAC AGC AGT GCC ACT TCA TCT TGG GCT CCT
Met Gln Pro Met Asn Tyr Pro Gln Cys Pro Gln Ile Phe Trp Val Asp Ser Ser Ala Thr Ser Ser Trp Ala Pro

CCA GGG TCA GTT TTT CCC TGT CCA TCT TGT GGG CCT AGA GGG CCG GAC CAA AGG AGA CCG CCA CCT CCA CCA CCA
Pro Gly Ser Val Phe Pro Cys Pro Ser Cys Gly Pro Arg Gly Pro Asp Gln Arg Arg Pro Pro Pro Pro Pro Pro

CCT GTG TCA CCA CTA CCA CCG CCA TCA CAA CCG CTC CCG ACC CTA AAG AAG CCT CTA AAG GAC CAC
Pro Val Ser Pro Leu Pro Pro Pro Ser Gln Pro Leu Pro Thr Leu Lys Lys Pro Leu Lys Asp His

AAC ACA AAT CTG TGG CTA CCG GTG GTA TTT TTC ATG GTT CTG GCT CTG GTT GGA ATG TTA GGA ATG TAT
Asn Thr Asn Leu Trp Leu Pro Val Val Phe Phe Met Val Leu Ala Leu Val Gly Met Gly Leu Met Tyr

CAG CTC TTC CAC CTG CAG CTG AAG GAA CTG GCA CTC CGT GAG TTC CGT GAA AAA CAA AGC CTT AAA GTA TCA TCT TTT
Gln Leu Phe His Leu Gln Leu Lys Glu Leu Ala Leu Arg Glu Phe Arg Glu Lys Gln Ser Leu Lys Val Ser Ser Phe
                                                                                    *

GAA AAG CAA ATA GCC AAC CCC AGT ACA CCC TCT GAA AAA GAG CCG AGT GTG GCC CAT TTA ACA GGG AAC
Glu Lys Gln Ile Ala Asn Pro Ser Thr Pro Ser Glu Lys Glu Pro Ser Val Ala His Leu Thr Gly Asn
                *

CCC CAC TCA AGG TCC ATC CCT CTG GAA TGG GAA GAC ACA TAT GGA ACC CTG ATC TCT GGA GTG AAG TAT AAG
Pro His Ser Arg Ser Ile Pro Leu Glu Trp Glu Asp Thr Tyr Gly Thr Leu Ile Ser Gly Val Lys Tyr Lys

AAA GGT GGC CTT GTG ATC AAC GAA ACT GGG TTG TAC TTC GTG TAT TCC AAA GTA TAC TTC CGG CAG TCT TGC
Lys Gly Gly Leu Val Ile Asn Glu Thr Gly Leu Tyr Phe Val Tyr Ser Lys Val Tyr Phe Arg Gly Gln Ser Cys
                   *
```

FIG. 24

```
AAC AAC CAG CCC CTA AAC CAC AAG GTC TAT ATG AGG AAC TCT AAG TAT CCT GAG GAT CTG GTG CTA ATG GAG GAG
Asn Asn Gln Pro Leu Asn His Lys Val Tyr Met Arg Asn Ser Lys Tyr Pro Glu Asp Leu Val Leu Met Glu Glu

AAG AGG TTG AAC TAC TGC ACT ACT GGA CAG ATA TGG GCC CAC AGC TAC CTG GGG GCA GTA TTC AAT CTT ACC
Lys Arg Leu Asn Tyr Cys Thr Thr Gly Gln Ile Trp Ala His Ser Ser Tyr Leu Gly Ala Val Phe Asn Leu Thr
                                                                                                  *

AGT GCT GAC CAT TTA TAT GTC AAC ATA TCT CAA CTC TCT CTG ATC AAT TTT GAG GAA TCT AAG ACC TTT TTC GGC
Ser Ala Asp His Leu Tyr Val Asn Ile Ser Gln Leu Ser Leu Ile Asn Phe Glu Glu Ser Lys Thr Phe Phe Gly
                                    *

TTG TAT AAG CTT TAA AAGAAAAAGCATTTTAAAAATGATCTACTATTCTTTATCATGGCACCAGGAATATTGTCTTGAATGAGAGTCTTCTTAA
Leu Tyr Lys Leu

GACCTATTGAGATTAATTAAGACTACATGAGCCACAAAGACCTCATGACCGCAAGGTCCAACAGGTCAGCTATCCTTCATTTTCTCGAGTCCATGGAG
TGGTCCTTAATGCCTGCATCATGATGTTAAATGCCAAGAGATGGAAGGAGTCTGTGACTGAGGGACATAAAGCTTTGGGCTGCTGTGTGACAATGCAGAGGCACAGAGA
AAGAACTGTCTGATGTTAAATGGCCAAGAGAATTTTAACCATTGAAG----AAGACACCCTTTACACTCA-CTTCCAGGTGGTCTACTTACTACCTCA
CAG-AGGCCGTTTTTGAGACATA--GTTGTGGTATGAATATACAAGGGTGAGAAAGGAGGCT-CATTTGACTGATAAGCTAGAGACTGAAAAAAGACA
GTGTCTCATTGGCACCATCTTTACTGTTACCTAATGTTTTCTGAGCCGACCTTTGATCCTAACGGAGAAGTAAGAGGGATGTTTGAGGCACAAATCATT
CTCTACATAGCATGCATACCTCCAGTGCAATGATGTCTGTGT--TTGTATGTATGAGAGCAAACAGATTCTAAGGAGTCATATAAATAAAATATGTA
CATTATGGAGTACATATTAGAAACC-----TGTTACATTTGATGCTAGA-TATCTGAATGTTTCTGGCAATAAACTCTAATAGTCT
```

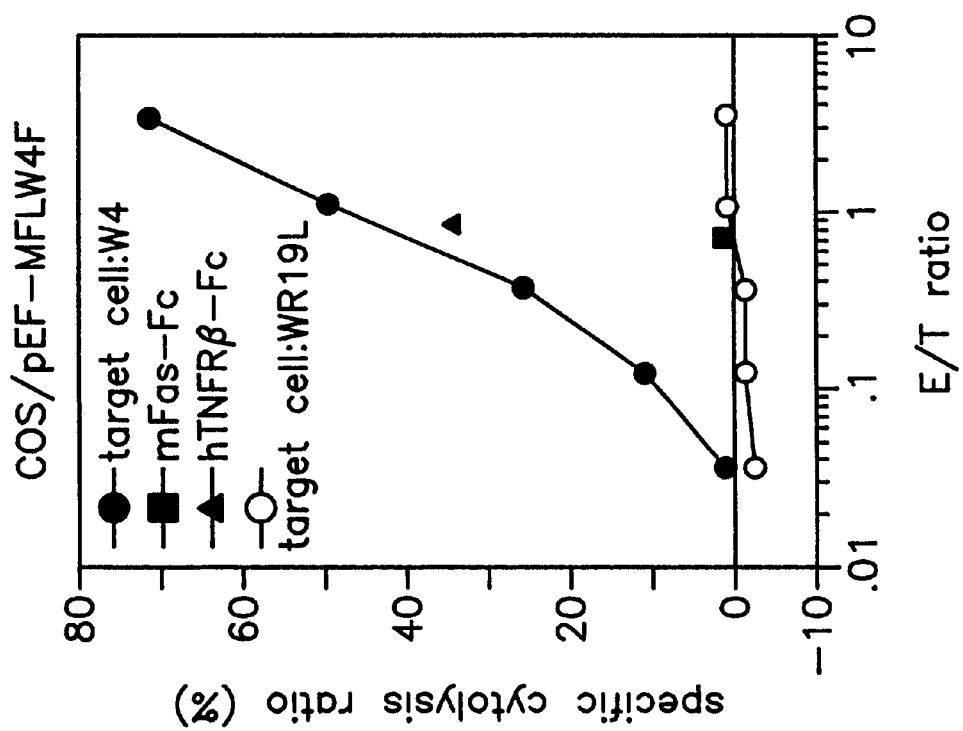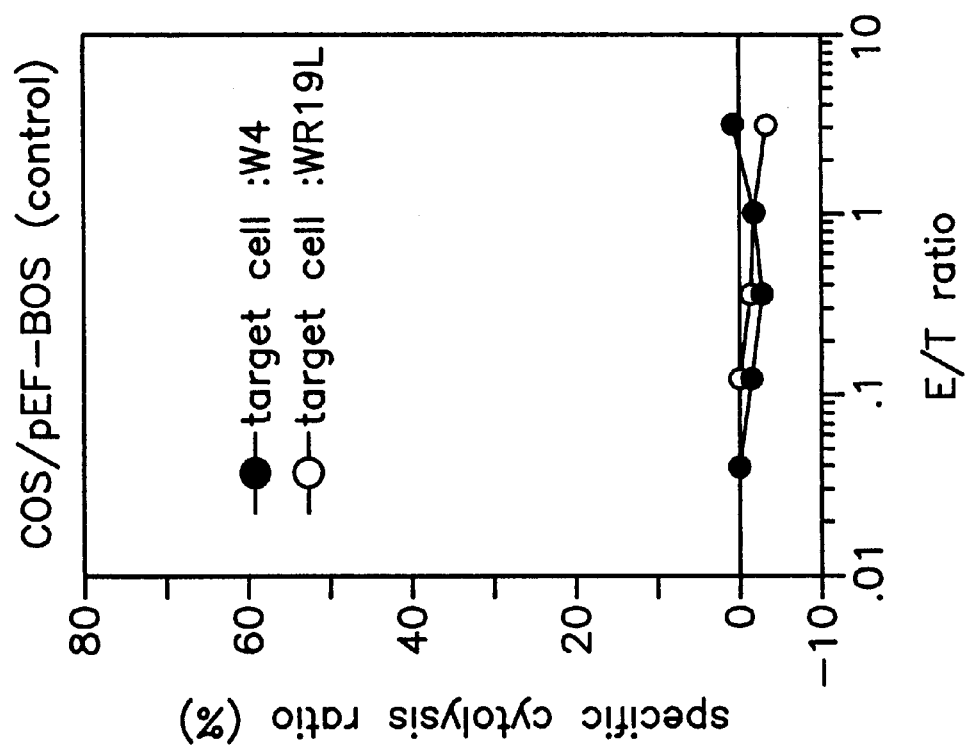

SEQUENCE LISTING (1) GENERAL INFORMATION:

(iii) NUMBER OF SEQUENCES: 103

(2) INFORMATION FOR SEQ ID NO:1:

(i) SEQUENCE CHARACTERISTICS:
      (A) LENGTH: 411 base pairs
      (B) TYPE: nucleic acid
      (C) STRANDEDNESS: Not Relevant
      (D) TOPOLOGY: Not Relevant (ii) MOLECULE TYPE: cDNA (iii) HYPOTHETICAL: NO (iv) ANTI-SENSE: NO (vi) ORIGINAL SOURCE:
      (A) ORGANISM: Human (ix) FEATURE:
      (A) NAME/KEY: CDS
      (B) LOCATION: 1..411

(xi) SEQUENCE DESCRIPTION: SEQ ID NO:1:

```
AAA GTG GCC CAT TTA ACA GGC AAG TCC AAC TCA AGG TCC ATG CCT CTG      48
Lys Val Ala His Leu Thr Gly Lys Ser Asn Ser Arg Ser Met Pro Leu
 1               5                  10                  15

GAA TGG GAA GAC ACC TAT GGA ATT GTC CTG CTT TCT GGA GTG AAG TAT      96
Glu Trp Glu Asp Thr Tyr Gly Ile Val Leu Leu Ser Gly Val Lys Tyr
             20                  25                  30

AAG AAG GGT GGC CTT GTG ATC AAT GAA ACT GGG CTG TAC TTT GTA TAT     144
Lys Lys Gly Gly Leu Val Ile Asn Glu Thr Gly Leu Tyr Phe Val Tyr
         35                  40                  45

TCC AAA GTA TAC TTC CGG GGT CAA TCT TGC AAC AAC CTG CCC CTG AGC     192
Ser Lys Val Tyr Phe Arg Gly Gln Ser Cys Asn Asn Leu Pro Leu Ser
     50                  55                  60

CAC AAG GTC TAC ATG AGG AAC TCT AAG TAT CCC CAG GAT CTG GTG ATG     240
His Lys Val Tyr Met Arg Asn Ser Lys Tyr Pro Gln Asp Leu Val Met
 65                  70                  75                  80

ATG GAG GGG AAG ATG ATG AGC TAC TGC ACT ACT GGG CAG ATG TGG GCC     288
Met Glu Gly Lys Met Met Ser Tyr Cys Thr Thr Gly Gln Met Trp Ala
                 85                  90                  95

CGC AGC AGC TAC CTG GGG GCA GTG TTC AAT CTT ACC AGT GCT GAT CAT     336
Arg Ser Ser Tyr Leu Gly Ala Val Phe Asn Leu Thr Ser Ala Asp His
            100                 105                 110

TTA TAT GTC AAC GTA TCT GAG CTC TCT CTG GTC AAT TTT GAG GAA TCT     384
Leu Tyr Val Asn Val Ser Glu Leu Ser Leu Val Asn Phe Glu Glu Ser
        115                 120                 125

CAG ACG TTT TTC GGC TTA TAT AAG CTC                                 411
Gln Thr Phe Phe Gly Leu Tyr Lys Leu
    130                 135
```

(2) INFORMATION FOR SEQ ID NO:2:

(i) SEQUENCE CHARACTERISTICS:
      (A) LENGTH: 137 amino acids
      (B) TYPE: amino acid
      (D) TOPOLOGY: linear (ii) MOLECULE TYPE: protein (xi) SEQUENCE DESCRIPTION: SEQ ID NO:2:

```
Lys Val Ala His Leu Thr Gly Lys Ser Asn Ser Arg Ser Met Pro Leu
 1               5                  10                  15

Glu Trp Glu Asp Thr Tyr Gly Ile Val Leu Leu Ser Gly Val Lys Tyr
             20                  25                  30

Lys Lys Gly Gly Leu Val Ile Asn Glu Thr Gly Leu Tyr Phe Val Tyr
         35                  40                  45

Ser Lys Val Tyr Phe Arg Gly Gln Ser Cys Asn Asn Leu Pro Leu Ser
     50                  55                  60

His Lys Val Tyr Met Arg Asn Ser Lys Tyr Pro Gln Asp Leu Val Met
 65                  70                  75                  80

Met Glu Gly Lys Met Met Ser Tyr Cys Thr Thr Gly Gln Met Trp Ala
                 85                  90                  95

Arg Ser Ser Tyr Leu Gly Ala Val Phe Asn Leu Thr Ser Ala Asp His
            100                 105                 110

Leu Tyr Val Asn Val Ser Glu Leu Ser Leu Val Asn Phe Glu Glu Ser
            115                 120                 125

Gln Thr Phe Phe Gly Leu Tyr Lys Leu
            130                 135

(2) INFORMATION FOR SEQ ID NO:3:

(i) SEQUENCE CHARACTERISTICS:
        (A) LENGTH: 414 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: Human (ix) FEATURE:
        (A) NAME/KEY: CDS
        (B) LOCATION: 1..414

(xi) SEQUENCE DESCRIPTION: SEQ ID NO:3:

AGG AAA GTG GCC CAT TTA ACA GGC AAG TCC AAC TCA AGG TCC ATG CCT      48
Arg Lys Val Ala His Leu Thr Gly Lys Ser Asn Ser Arg Ser Met Pro
            140                 145                 150

CTG GAA TGG GAA GAC ACC TAT GGA ATT GTC CTG CTT TCT GGA GTG AAG      96
Leu Glu Trp Glu Asp Thr Tyr Gly Ile Val Leu Leu Ser Gly Val Lys
    155                 160                 165

TAT AAG AAG GGT GGC CTT GTG ATC AAT GAA ACT GGG CTG TAC TTT GTA     144
Tyr Lys Lys Gly Gly Leu Val Ile Asn Glu Thr Gly Leu Tyr Phe Val
170                 175                 180                 185

TAT TCC AAA GTA TAC TTC CGG GGT CAA TCT TGC AAC AAC CTG CCC CTG     192
Tyr Ser Lys Val Tyr Phe Arg Gly Gln Ser Cys Asn Asn Leu Pro Leu
                190                 195                 200

AGC CAC AAG GTC TAC ATG AGG AAC TCT AAG TAT CCC CAG GAT CTG GTG     240
Ser His Lys Val Tyr Met Arg Asn Ser Lys Tyr Pro Gln Asp Leu Val
            205                 210                 215

ATG ATG GAG GGG AAG ATG ATG AGC TAC TGC ACT ACT GGG CAG ATG TGG     288
Met Met Glu Gly Lys Met Met Ser Tyr Cys Thr Thr Gly Gln Met Trp
        220                 225                 230

GCC CGC AGC AGC TAC CTG GGG GCA GTG TTC AAT CTT ACC AGT GCT GAT     336
Ala Arg Ser Ser Tyr Leu Gly Ala Val Phe Asn Leu Thr Ser Ala Asp
        235                 240                 245
```

```
CAT TTA TAT GTC AAC GTA TCT GAG CTC TCT CTG GTC AAT TTT GAG GAA        384
His Leu Tyr Val Asn Val Ser Glu Leu Ser Leu Val Asn Phe Glu Glu
250                 255                 260                 265

TCT CAG ACG TTT TTC GGC TTA TAT AAG CTC                                414
Ser Gln Thr Phe Phe Gly Leu Tyr Lys Leu
                270                 275
```

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:4:

```
Arg Lys Val Ala His Leu Thr Gly Lys Ser Asn Ser Arg Ser Met Pro
1               5                   10                  15

Leu Glu Trp Glu Asp Thr Tyr Gly Ile Val Leu Leu Ser Gly Val Lys
                20                  25                  30

Tyr Lys Lys Gly Gly Leu Val Ile Asn Glu Thr Gly Leu Tyr Phe Val
            35                  40                  45

Tyr Ser Lys Val Tyr Phe Arg Gly Gln Ser Cys Asn Asn Leu Pro Leu
        50                  55                  60

Ser His Lys Val Tyr Met Arg Asn Ser Lys Tyr Pro Gln Asp Leu Val
65                  70                  75                  80

Met Met Glu Gly Lys Met Met Ser Tyr Cys Thr Thr Gly Gln Met Trp
                85                  90                  95

Ala Arg Ser Ser Tyr Leu Gly Ala Val Phe Asn Leu Thr Ser Ala Asp
                100                 105                 110

His Leu Tyr Val Asn Val Ser Glu Leu Ser Leu Val Asn Phe Glu Glu
                115                 120                 125

Ser Gln Thr Phe Phe Gly Leu Tyr Lys Leu
                130                 135
```

(2) INFORMATION FOR SEQ ID NO:5:

(i) SEQUENCE CHARACTERISTICS:
        (A) LENGTH: 537 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: Human (ix) FEATURE:
        (A) NAME/KEY: CDS
        (B) LOCATION: 1..537

(xi) SEQUENCE DESCRIPTION: SEQ ID NO:5:

```
CAG CTC TTC CAC CTA CAG AAG GAG CTG GCA GAA CTC CGA GAG TCT ACC        48
Gln Leu Phe His Leu Gln Lys Glu Leu Ala Glu Leu Arg Glu Ser Thr
                140                 145                 150

AGC CAG ATG CAC ACA GCA TCA TCT TTG GAG AAG CAA ATA GGC CAC CCC        96
Ser Gln Met His Thr Ala Ser Ser Leu Glu Lys Gln Ile Gly His Pro
155                 160                 165                 170
```

```
AGT CCA CCC CCT GAA AAA AAG GAG CTG AGG AAA GTG GCC CAT TTA ACA    144
Ser Pro Pro Pro Glu Lys Lys Glu Leu Arg Lys Val Ala His Leu Thr
            175                 180                 185

GGC AAG TCC AAC TCA AGG TCC ATG CCT CTG GAA TGG GAA GAC ACC TAT    192
Gly Lys Ser Asn Ser Arg Ser Met Pro Leu Glu Trp Glu Asp Thr Tyr
            190                 195                 200

GGA ATT GTC CTG CTT TCT GGA GTG AAG TAT AAG AAG GGT GGC CTT GTG    240
Gly Ile Val Leu Leu Ser Gly Val Lys Tyr Lys Lys Gly Gly Leu Val
            205                 210                 215

ATC AAT GAA ACT GGG CTG TAC TTT GTA TAT TCC AAA GTA TAC TTC CGG    288
Ile Asn Glu Thr Gly Leu Tyr Phe Val Tyr Ser Lys Val Tyr Phe Arg
            220                 225                 230

GGT CAA TCT TGC AAC AAC CTG CCC CTG AGC CAC AAG GTC TAC ATG AGG    336
Gly Gln Ser Cys Asn Asn Leu Pro Leu Ser His Lys Val Tyr Met Arg
235                 240                 245                 250

AAC TCT AAG TAT CCC CAG GAT CTG GTG ATG ATG GAG GGG AAG ATG ATG    384
Asn Ser Lys Tyr Pro Gln Asp Leu Val Met Met Glu Gly Lys Met Met
                255                 260                 265

AGC TAC TGC ACT ACT GGG CAG ATG TGG GCC CGC AGC AGC TAC CTG GGG    432
Ser Tyr Cys Thr Thr Gly Gln Met Trp Ala Arg Ser Ser Tyr Leu Gly
            270                 275                 280

GCA GTG TTC AAT CTT ACC AGT GCT GAT CAT TTA TAT GTC AAC GTA TCT    480
Ala Val Phe Asn Leu Thr Ser Ala Asp His Leu Tyr Val Asn Val Ser
            285                 290                 295

GAG CTC TCT CTG GTC AAT TTT GAG GAA TCT CAG ACG TTT TTC GGC TTA    528
Glu Leu Ser Leu Val Asn Phe Glu Glu Ser Gln Thr Phe Phe Gly Leu
300                 305                 310

TAT AAG CTC                                                       537
Tyr Lys Leu
315
```

(2) INFORMATION FOR SEQ ID NO:6:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:6:

```
Gln Leu Phe His Leu Gln Lys Glu Leu Ala Glu Leu Arg Glu Ser Thr
1               5                   10                  15

Ser Gln Met His Thr Ala Ser Ser Leu Glu Lys Gln Ile Gly His Pro
                20                  25                  30

Ser Pro Pro Pro Glu Lys Lys Glu Leu Arg Lys Val Ala His Leu Thr
            35                  40                  45

Gly Lys Ser Asn Ser Arg Ser Met Pro Leu Glu Trp Glu Asp Thr Tyr
        50                  55                  60

Gly Ile Val Leu Leu Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
                85                  90                  95

Gly Gln Ser Cys Asn Asn Leu Pro Leu Ser His Lys Val Tyr Met Arg
            100                 105                 110

Asn Ser Lys Tyr Pro Gln Asp Leu Val Met Met Glu Gly Lys Met Met
        115                 120                 125

Ser Tyr Cys Thr Thr Gly Gln Met Trp Ala Arg Ser Ser Tyr Leu Gly
    130                 135                 140
```

```
Ala Val Phe Asn Leu Thr Ser Ala Asp His Leu Tyr Val Asn Val Ser
145                 150                 155                 160

Glu Leu Ser Leu Val Asn Phe Glu Glu Ser Gln Thr Phe Phe Gly Leu
                165                 170                 175

Tyr Lys Leu
```

(2) INFORMATION FOR SEQ ID NO:7:

(i) SEQUENCE CHARACTERISTICS:
        (A) LENGTH: 843 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: Human
        (F) TISSUE TYPE: T lymphocyte (ix) FEATURE:
        (A) NAME/KEY: CDS
        (B) LOCATION: 1..843

(xi) SEQUENCE DESCRIPTION: SEQ ID NO:7:

```
ATG CAG CAG CCC TTC AAT TAC CCA TAT CCC CAG ATC TAC TGG GTG GAC      48
Met Gln Gln Pro Phe Asn Tyr Pro Tyr Pro Gln Ile Tyr Trp Val Asp
180                 185                 190                 195

AGC AGT GCC AGC TCT CCC TGG GCC CCT CCA GGC ACA GTT CTT CCC TGT      96
Ser Ser Ala Ser Ser Pro Trp Ala Pro Pro Gly Thr Val Leu Pro Cys
                200                 205                 210

CCA ACC TCT GTG CCC AGA AGG CCT GGT CAA AGG AGG CCA CCA CCA CCA     144
Pro Thr Ser Val Pro Arg Arg Pro Gly Gln Arg Arg Pro Pro Pro Pro
            215                 220                 225

CCG CCA CCG CCA CCA CTA CCA CCT CCG CCG CCG CCA CCA CTG CCT         192
Pro Pro Pro Pro Pro Leu Pro Pro Pro Pro Pro Pro Pro Leu Pro
        230                 235                 240

CCA CTA CCG CTG CCA CCC CTG AAG AAG AGA GGG AAC CAC AGC ACA GGC     240
Pro Leu Pro Leu Pro Pro Leu Lys Lys Arg Gly Asn His Ser Thr Gly
    245                 250                 255

CTG TGT CTC CTT GTG ATG TTT TTC ATG GTT CTG GTT GCC TTG GTA GGA     288
Leu Cys Leu Leu Val Met Phe Phe Met Val Leu Val Ala Leu Val Gly
260                 265                 270                 275

TTG GGC CTG GGG ATG TTT CAG CTC TTC CAC CTA CAG AAG GAG CTG GCA     336
Leu Gly Leu Gly Met Phe Gln Leu Phe His Leu Gln Lys Glu Leu Ala
                280                 285                 290

GAA CTC CGA GAG TCT ACC AGC CAG ATG CAC ACA GCA TCA TCT TTG GAG     384
Glu Leu Arg Glu Ser Thr Ser Gln Met His Thr Ala Ser Ser Leu Glu
            295                 300                 305

AAG CAA ATA GGC CAC CCC AGT CCA CCC CCT GAA AAA AAG GAG CTG AGG     432
Lys Gln Ile Gly His Pro Ser Pro Pro Pro Glu Lys Lys Glu Leu Arg
        310                 315                 320

AAA GTG GCC CAT TTA ACA GGC AAG TCC AAC TCA AGG TCC ATG CCT CTG     480
Lys Val Ala His Leu Thr Gly Lys Ser Asn Ser Arg Ser Met Pro Leu
    325                 330                 335

GAA TGG GAA GAC ACC TAT GGA ATT GTC CTG CTT TCT GGA GTG AAG TAT     528
Glu Trp Glu Asp Thr Tyr Gly Ile Val Leu Leu Ser Gly Val Lys Tyr
340                 345                 350                 355

AAG AAG GGT GGC CTT GTG ATC AAT GAA ACT GGG CTG TAC TTT GTA TAT     576
Lys Lys Gly Gly Leu Val Ile Asn Glu Thr Gly Leu Tyr Phe Val Tyr
```

```
TCC AAA GTA TAC TTC CGG GGT CAA TCT TGC AAC AAC CTG CCC CTG AGC      624
Ser Lys Val Tyr Phe Arg Gly Gln Ser Cys Asn Asn Leu Pro Leu Ser
            375                 380                 385

CAC AAG GTC TAC ATG AGG AAC TCT AAG TAT CCC CAG GAT CTG GTG ATG      672
His Lys Val Tyr Met Arg Asn Ser Lys Tyr Pro Gln Asp Leu Val Met
            390                 395                 400

ATG GAG GGG AAG ATG ATG AGC TAC TGC ACT ACT GGG CAG ATG TGG GCC      720
Met Glu Gly Lys Met Met Ser Tyr Cys Thr Thr Gly Gln Met Trp Ala
            405                 410                 415

CGC AGC AGC TAC CTG GGG GCA GTG TTC AAT CTT ACC AGT GCT GAT CAT      768
Arg Ser Ser Tyr Leu Gly Ala Val Phe Asn Leu Thr Ser Ala Asp His
420                 425                 430                 435

TTA TAT GTC AAC GTA TCT GAG CTC TCT CTG GTC AAT TTT GAG GAA TCT      816
Leu Tyr Val Asn Val Ser Glu Leu Ser Leu Val Asn Phe Glu Glu Ser
                440                 445                 450

CAG ACG TTT TTC GGC TTA TAT AAG CTC                                  843
Gln Thr Phe Phe Gly Leu Tyr Lys Leu
            455                 460
```

(2) INFORMATION FOR SEQ ID NO:8:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro
            35                  40                  45

Pro Pro Pro Pro Pro Leu Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
            210                 215                 220
```

```
Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
            245                 250                 255

Leu Tyr Val Asn Val Ser Glu Leu Ser Leu Val Asn Phe Glu Glu Ser
        260                 265                 270

Gln Thr Phe Phe Gly Leu Tyr Lys Leu
    275                 280
```

(2) INFORMATION FOR SEQ ID NO:9:

(i) SEQUENCE CHARACTERISTICS:
        (A) LENGTH: 411 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: Rat (ix) FEATURE:
        (A) NAME/KEY: CDS
        (B) LOCATION: 1..411

(xi) SEQUENCE DESCRIPTION: SEQ ID NO:9:

```
AGT GTG GCC CAC TTA ACA GGG AAC CCC CGC TCA AGG TCC ATC CCT CTG      48
Ser Val Ala His Leu Thr Gly Asn Pro Arg Ser Arg Ser Ile Pro Leu
            285                 290                 295

GAA TGG GAA GAC ACA TAT GGA ACT GCT TTG ATC TCT GGA GTG AAG TAT      96
Glu Trp Glu Asp Thr Tyr Gly Thr Ala Leu Ile Ser Gly Val Lys Tyr
        300                 305                 310

AAG AAA GGC GGC CTT GTG ATC AAT GAG GCT GGG TTG TAC TTC GTA TAT     144
Lys Lys Gly Gly Leu Val Ile Asn Glu Ala Gly Leu Tyr Phe Val Tyr
    315                 320                 325

TCC AAA GTA TAC TTC CGG GGT CAG TCT TGC AAC AGC CAG CCC CTA AGC     192
Ser Lys Val Tyr Phe Arg Gly Gln Ser Cys Asn Ser Gln Pro Leu Ser
330                 335                 340                 345

CAC AAG GTC TAT ATG AGG AAC TTT AAG TAT CCT GGG GAT CTG GTG CTA     240
His Lys Val Tyr Met Arg Asn Phe Lys Tyr Pro Gly Asp Leu Val Leu
            350                 355                 360

ATG GAG GAG AAG AAG TTG AAT TAC TGC ACT ACT GGC CAG ATA TGG GCC     288
Met Glu Glu Lys Lys Leu Asn Tyr Cys Thr Thr Gly Gln Ile Trp Ala
        365                 370                 375

CAC AGC AGC TAC CTA GGG GCA GTA TTT AAT CTT ACC GTT GCT GAC CAT     336
His Ser Ser Tyr Leu Gly Ala Val Phe Asn Leu Thr Val Ala Asp His
    380                 385                 390

TTA TAT GTC AAC ATA TCT CAA CTC TCT CTG ATC AAT TTT GAG GAA TCT     384
Leu Tyr Val Asn Ile Ser Gln Leu Ser Leu Ile Asn Phe Glu Glu Ser
395                 400                 405

AAG ACC TTT TTT GGC TTA TAT AAG CTT                                 411
Lys Thr Phe Phe Gly Leu Tyr Lys Leu
410                 415
```

(2) INFORMATION FOR SEQ ID NO:10:

(i) SEQUENCE CHARACTERISTICS:
        (A) LENGTH: 137 amino acids
        (B) TYPE: amino acid (D) TOPOLOGY: linear (ii) MOLECULE TYPE: protein (xi) SEQUENCE DESCRIPTION: SEQ ID NO:10:

```
Ser Val Ala His Leu Thr Gly Asn Pro Arg Ser Arg Ser Ile Pro Leu
 1               5                  10                  15

Glu Trp Glu Asp Thr Tyr Gly Thr Ala Leu Ile Ser Gly Val Lys Tyr
            20                  25                  30

Lys Lys Gly Gly Leu Val Ile Asn Glu Ala Gly Leu Tyr Phe Val Tyr
        35                  40                  45

Ser Lys Val Tyr Phe Arg Gly Gln Ser Cys Asn Ser Gln Pro Leu Ser
    50                  55                  60

His Lys Val Tyr Met Arg Asn Phe Lys Tyr Pro Gly Asp Leu Val Leu
65                  70                  75                  80

Met Glu Glu Lys Lys Leu Asn Tyr Cys Thr Thr Gly Gln Ile Trp Ala
                85                  90                  95

His Ser Ser Tyr Leu Gly Ala Val Phe Asn Leu Thr Val Ala Asp His
            100                 105                 110

Leu Tyr Val Asn Ile Ser Gln Leu Ser Leu Ile Asn Phe Glu Glu Ser
        115                 120                 125

Lys Thr Phe Phe Gly Leu Tyr Lys Leu
    130                 135
```

(2) INFORMATION FOR SEQ ID NO:11:

(i) SEQUENCE CHARACTERISTICS:
        (A) LENGTH: 414 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: rat (ix) FEATURE:
        (A) NAME/KEY: CDS
        (B) LOCATION: 1..414

(xi) SEQUENCE DESCRIPTION: SEQ ID NO:11:

```
AGG AGT GTG GCC CAC TTA ACA GGG AAC CCC CGC TCA AGG TCC ATC CCT      48
Arg Ser Val Ala His Leu Thr Gly Asn Pro Arg Ser Arg Ser Ile Pro
        140                 145                 150

CTG GAA TGG GAA GAC ACA TAT GGA ACT GCT TTG ATC TCT GGA GTG AAG      96
Leu Glu Trp Glu Asp Thr Tyr Gly Thr Ala Leu Ile Ser Gly Val Lys
    155                 160                 165

TAT AAG AAA GGC GGC CTT GTG ATC AAT GAG GCT GGG TTG TAC TTC GTA     144
Tyr Lys Lys Gly Gly Leu Val Ile Asn Glu Ala Gly Leu Tyr Phe Val
170                 175                 180                 185

TAT TCC AAA GTA TAC TTC CGG GGT CAG TCT TGC AAC AGC CAG CCC CTA     192
Tyr Ser Lys Val Tyr Phe Arg Gly Gln Ser Cys Asn Ser Gln Pro Leu
                190                 195                 200

AGC CAC AAG GTC TAT ATG AGG AAC TTT AAG TAT CCT GGG GAT CTG GTG     240
Ser His Lys Val Tyr Met Arg Asn Phe Lys Tyr Pro Gly Asp Leu Val
            205                 210                 215

CTA ATG GAG GAG AAG AAG TTG AAT TAC TGC ACT ACT GGC CAG ATA TGG     288
Leu Met Glu Glu Lys Lys Leu Asn Tyr Cys Thr Thr Gly Gln Ile Trp
```

```
            220                 225                 230
GCC CAC AGC AGC TAC CTA GGG GCA GTA TTT AAT CTT ACC GTT GCT GAC        336
Ala His Ser Ser Tyr Leu Gly Ala Val Phe Asn Leu Thr Val Ala Asp
    235                 240                 245

CAT TTA TAT GTC AAC ATA TCT CAA CTC TCT CTG ATC AAT TTT GAG GAA        384
His Leu Tyr Val Asn Ile Ser Gln Leu Ser Leu Ile Asn Phe Glu Glu
250                 255                 260                 265

TCT AAG ACC TTT TTT GGC TTA TAT AAG CTT                                 414
Ser Lys Thr Phe Phe Gly Leu Tyr Lys Leu
                270                 275
```

(2) INFORMATION FOR SEQ ID NO:12:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:12:

```
Arg Ser Val Ala His Leu Thr Gly Asn Pro Arg Ser Arg Ser Ile Pro
1               5                   10                  15

Leu Glu Trp Glu Asp Thr Tyr Gly Thr Ala Leu Ile Ser Gly Val Lys
                20                  25                  30

Tyr Lys Lys Gly Gly Leu Val Ile Asn Glu Ala Gly Leu Tyr Phe Val
            35                  40                  45

Tyr Ser Lys Val Tyr Phe Arg Gly Gln Ser Cys Asn Ser Gln Pro Leu
        50                  55                  60

Ser His Lys Val Tyr Met Arg Asn Phe Lys Tyr Pro Gly Asp Leu Val
65                  70                  75                  80

Leu Met Glu Glu Lys Lys Leu Asn Tyr Cys Thr Thr Gly Gln Ile Trp
                85                  90                  95

Ala His Ser Ser Tyr Leu Gly Ala Val Phe Asn Leu Thr Val Ala Asp
            100                 105                 110

His Leu Tyr Val Asn Ile Ser Gln Leu Ser Leu Ile Asn Phe Glu Glu
        115                 120                 125

Ser Lys Thr Phe Phe Gly Leu Tyr Lys Leu
    130                 135
```

(2) INFORMATION FOR SEQ ID NO:13:

(i) SEQUENCE CHARACTERISTICS:
        (A) LENGTH: 537 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: rat (ix) FEATURE:
        (A) NAME/KEY: CDS
        (B) LOCATION: 1..537

(xi) SEQUENCE DESCRIPTION: SEQ ID NO:13:

```
CAA CTC TTT CAT CTA CAG AAG GAA CTG GCA GAA CTC CGT GAG TTC ACC         48
Gln Leu Phe His Leu Gln Lys Glu Leu Ala Glu Leu Arg Glu Phe Thr
```

```
                                                                              96
AAC CAC AGC CTT AGA GTA TCA TCT TTT GAA AAG CAA ATA GCC AAC CCC
Asn His Ser Leu Arg Val Ser Ser Phe Glu Lys Gln Ile Ala Asn Pro
155                 160                 165                 170

AGC ACA CCC TCT GAA ACC AAA AAG CCA AGG AGT GTG GCC CAC TTA ACA     144
Ser Thr Pro Ser Glu Thr Lys Lys Pro Arg Ser Val Ala His Leu Thr
                175                 180                 185

GGG AAC CCC CGC TCA AGG TCC ATC CCT CTG GAA TGG GAA GAC ACA TAT     192
Gly Asn Pro Arg Ser Arg Ser Ile Pro Leu Glu Trp Glu Asp Thr Tyr
                190                 195                 200

GGA ACT GCT TTG ATC TCT GGA GTG AAG TAT AAG AAA GGC GGC CTT GTG     240
Gly Thr Ala Leu Ile Ser Gly Val Lys Tyr Lys Lys Gly Gly Leu Val
                205                 210                 215

ATC AAT GAG GCT GGG TTG TAC TTC GTA TAT TCC AAA GTA TAC TTC CGG     288
Ile Asn Glu Ala Gly Leu Tyr Phe Val Tyr Ser Lys Val Tyr Phe Arg
220                 225                 230

GGT CAG TCT TGC AAC AGC CAG CCC CTA AGC CAC AAG GTC TAT ATG AGG     336
Gly Gln Ser Cys Asn Ser Gln Pro Leu Ser His Lys Val Tyr Met Arg
235                 240                 245                 250

AAC TTT AAG TAT CCT GGG GAT CTG GTG CTA ATG GAG GAG AAG AAG TTG     384
Asn Phe Lys Tyr Pro Gly Asp Leu Val Leu Met Glu Glu Lys Lys Leu
                255                 260                 265

AAT TAC TGC ACT ACT GGC CAG ATA TGG GCC CAC AGC AGC TAC CTA GGG     432
Asn Tyr Cys Thr Thr Gly Gln Ile Trp Ala His Ser Ser Tyr Leu Gly
                270                 275                 280

GCA GTA TTT AAT CTT ACC GTT GCT GAC CAT TTA TAT GTC AAC ATA TCT     480
Ala Val Phe Asn Leu Thr Val Ala Asp His Leu Tyr Val Asn Ile Ser
                285                 290                 295

CAA CTC TCT CTG ATC AAT TTT GAG GAA TCT AAG ACC TTT TTT GGC TTA     528
Gln Leu Ser Leu Ile Asn Phe Glu Glu Ser Lys Thr Phe Phe Gly Leu
300                 305                 310

TAT AAG CTT                                                          537
Tyr Lys Leu
315

(2) INFORMATION FOR SEQ ID NO:14:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:14:

Gln Leu Phe His Leu Gln Lys Glu Leu Ala Glu Leu Arg Glu Phe Thr
1               5                   10                  15

Asn His Ser Leu Arg Val Ser Ser Phe Glu Lys Gln Ile Ala Asn Pro
                20                  25                  30

Ser Thr Pro Ser Glu Thr Lys Lys Pro Arg Ser Val Ala His Leu Thr
                35                  40                  45

Gly Asn Pro Arg Ser Arg Ser Ile Pro Leu Glu Trp Glu Asp Thr Tyr
                50                  55                  60

Gly Thr Ala Leu Ile Ser Gly Val Lys Tyr Lys Lys Gly Gly Leu Val
65                  70                  75                  80

Ile Asn Glu Ala Gly Leu Tyr Phe Val Tyr Ser Lys Val Tyr Phe Arg
                85                  90                  95

Gly Gln Ser Cys Asn Ser Gln Pro Leu Ser His Lys Val Tyr Met Arg
                100                 105                 110
```

```
Asn Phe Lys Tyr Pro Gly Asp Leu Val Leu Met Glu Glu Lys Lys Leu
            115                 120                 125

Asn Tyr Cys Thr Thr Gly Gln Ile Trp Ala His Ser Ser Tyr Leu Gly
            130                 135                 140

Ala Val Phe Asn Leu Thr Val Ala Asp His Leu Tyr Val Asn Ile Ser
145                 150                 155                 160

Gln Leu Ser Leu Ile Asn Phe Glu Glu Ser Lys Thr Phe Phe Gly Leu
                165                 170                 175

Tyr Lys Leu
```

(2) INFORMATION FOR SEQ ID NO:15:

(i) SEQUENCE CHARACTERISTICS:
        (A) LENGTH: 834 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: rat (ix) FEATURE:
        (A) NAME/KEY: CDS
        (B) LOCATION: 1..834

(xi) SEQUENCE DESCRIPTION: SEQ ID NO:15:

```
ATG CAG CAG CCC GTG AAT TAC CCA TGT CCC CAG ATC TAC TGG GTA GAC        48
Met Gln Gln Pro Val Asn Tyr Pro Cys Pro Gln Ile Tyr Trp Val Asp
180                 185                 190                 195

AGC AGT GCC ACT TCT CCT TGG GCT CCT CCA GGG TCA GTT TTT TCT TGT        96
Ser Ser Ala Thr Ser Pro Trp Ala Pro Pro Gly Ser Val Phe Ser Cys
                200                 205                 210

CCA TCC TCT GGG CCT AGA GGG CCA GGA CAA AGG AGA CCA CCG CCT CCA       144
Pro Ser Ser Gly Pro Arg Gly Pro Gly Gln Arg Arg Pro Pro Pro Pro
            215                 220                 225

CCA CCA CCT CCA TCA CCA CTA CCA CCG CCT TCC CAA CCA CCC CCG CTG       192
Pro Pro Pro Pro Ser Pro Leu Pro Pro Pro Ser Gln Pro Pro Pro Leu
        230                 235                 240

CCT CCA CTA AGC CCT CTA AAG AAG AAG GAC AAC ATA GAG CTG TGG CTA       240
Pro Pro Leu Ser Pro Leu Lys Lys Lys Asp Asn Ile Glu Leu Trp Leu
    245                 250                 255

CCG GTG ATA TTT TTC ATG GTG CTG GTG GCT CTG GTT GGA ATG GGG TTA       288
Pro Val Ile Phe Phe Met Val Leu Val Ala Leu Val Gly Met Gly Leu
260                 265                 270                 275

GGA ATG TAT CAA CTC TTT CAT CTA CAG AAG GAA CTG GCA GAA CTC CGT       336
Gly Met Tyr Gln Leu Phe His Leu Gln Lys Glu Leu Ala Glu Leu Arg
                280                 285                 290

GAG TTC ACC AAC CAC AGC CTT AGA GTA TCA TCT TTT GAA AAG CAA ATA       384
Glu Phe Thr Asn His Ser Leu Arg Val Ser Ser Phe Glu Lys Gln Ile
            295                 300                 305

GCC AAC CCC AGC ACA CCC TCT GAA ACC AAA AAG CCA AGG AGT GTG GCC       432
Ala Asn Pro Ser Thr Pro Ser Glu Thr Lys Lys Pro Arg Ser Val Ala
        310                 315                 320

CAC TTA ACA GGG AAC CCC CGC TCA AGG TCC ATC CCT CTG GAA TGG GAA       480
His Leu Thr Gly Asn Pro Arg Ser Arg Ser Ile Pro Leu Glu Trp Glu
    325                 330                 335

GAC ACA TAT GGA ACT GCT TTG ATC TCT GGA GTG AAG TAT AAG AAA GGC       528
```

```
Asp Thr Tyr Gly Thr Ala Leu Ile Ser Gly Val Lys Tyr Lys Gly
340                 345                 350                 355

GGC CTT GTG ATC AAT GAG GCT GGG TTG TAC TTC GTA TAT TCC AAA GTA      576
Gly Leu Val Ile Asn Glu Ala Gly Leu Tyr Phe Val Tyr Ser Lys Val
                360                 365                 370

TAC TTC CGG GGT CAG TCT TGC AAC AGC CAG CCC CTA AGC CAC AAG GTC      624
Tyr Phe Arg Gly Gln Ser Cys Asn Ser Gln Pro Leu Ser His Lys Val
            375                 380                 385

TAT ATG AGG AAC TTT AAG TAT CCT GGG GAT CTG GTG CTA ATG GAG GAG      672
Tyr Met Arg Asn Phe Lys Tyr Pro Gly Asp Leu Val Leu Met Glu Glu
        390                 395                 400

AAG AAG TTG AAT TAC TGC ACT ACT GGC CAG ATA TGG GCC CAC AGC AGC      720
Lys Lys Leu Asn Tyr Cys Thr Thr Gly Gln Ile Trp Ala His Ser Ser
    405                 410                 415

TAC CTA GGG GCA GTA TTT AAT CTT ACC GTT GCT GAC CAT TTA TAT GTC      768
Tyr Leu Gly Ala Val Phe Asn Leu Thr Val Ala Asp His Leu Tyr Val
420                 425                 430                 435

AAC ATA TCT CAA CTC TCT CTG ATC AAT TTT GAG GAA TCT AAG ACC TTT      816
Asn Ile Ser Gln Leu Ser Leu Ile Asn Phe Glu Glu Ser Lys Thr Phe
                440                 445                 450

TTT GGC TTA TAT AAG CTT                                              834
Phe Gly Leu Tyr Lys Leu
            455
```

(2) INFORMATION FOR SEQ ID NO:16:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:16:

```
Met Gln Gln Pro Val Asn Tyr Pro Cys Pro Gln Ile Tyr Trp Val Asp
1               5                   10                  15

Ser Ser Ala Thr Ser Pro Trp Ala Pro Pro Gly Ser Val Phe Ser Cys
            20                  25                  30

Pro Ser Ser Gly Pro Arg Gly Pro Gly Gln Arg Arg Pro Pro Pro Pro
        35                  40                  45

Pro Pro Pro Ser Pro Leu Pro Pro Ser Gln Pro Pro Leu
    50                  55                  60

Pro Pro Leu Ser Pro Leu Lys Lys Asp Asn Ile Glu Leu Trp Leu
65                  70                  75                  80

Pro Val Ile Phe Phe Met Val Leu Val Ala Leu Val Gly Met Gly Leu
                85                  90                  95

Gly Met Tyr Gln Leu Phe His Leu Gln Lys Glu Leu Ala Glu Leu Arg
                100                 105                 110

Glu Phe Thr Asn His Ser Leu Arg Val Ser Ser Phe Glu Lys Gln Ile
            115                 120                 125

Ala Asn Pro Ser Thr Pro Ser Glu Thr Lys Lys Pro Arg Ser Val Ala
        130                 135                 140

His Leu Thr Gly Asn Pro Arg Ser Arg Ser Ile Pro Leu Glu Trp Glu
145                 150                 155                 160

Asp Thr Tyr Gly Thr Ala Leu Ile Ser Gly Val Lys Tyr Lys Gly
                165                 170                 175

Gly Leu Val Ile Asn Glu Ala Gly Leu Tyr Phe Val Tyr Ser Lys Val
            180                 185                 190
```

```
Tyr Phe Arg Gly Gln Ser Cys Asn Ser Gln Pro Leu Ser His Lys Val
        195                 200                 205

Tyr Met Arg Asn Phe Lys Tyr Pro Gly Asp Leu Val Leu Met Glu Glu
        210                 215                 220

Lys Lys Leu Asn Tyr Cys Thr Thr Gly Gln Ile Trp Ala His Ser Ser
225                 230                 235                 240

Tyr Leu Gly Ala Val Phe Asn Leu Thr Val Ala Asp His Leu Tyr Val
                245                 250                 255

Asn Ile Ser Gln Leu Ser Leu Ile Asn Phe Glu Glu Ser Lys Thr Phe
            260                 265                 270

Phe Gly Leu Tyr Lys Leu
        275

(2) INFORMATION FOR SEQ ID NO:17:

(i) SEQUENCE CHARACTERISTICS:
        (A) LENGTH: 411 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: mouse (ix) FEATURE:
        (A) NAME/KEY: CDS
        (B) LOCATION: 1..411

(xi) SEQUENCE DESCRIPTION: SEQ ID NO:17:

AGT GTG GCC CAT TTA ACA GGG AAC CCC CAC TCA AGG TCC ATC CCT CTG       48
Ser Val Ala His Leu Thr Gly Asn Pro His Ser Arg Ser Ile Pro Leu
280                 285                 290

GAA TGG GAA GAC ACA TAT GGA ACC GCT CTG ATC TCT GGA GTG AAG TAT       96
Glu Trp Glu Asp Thr Tyr Gly Thr Ala Leu Ile Ser Gly Val Lys Tyr
295                 300                 305                 310

AAG AAA GGT GGC CTT GTG ATC AAC GAA ACT GGG TTG TAC TTC GTG TAT      144
Lys Lys Gly Gly Leu Val Ile Asn Glu Thr Gly Leu Tyr Phe Val Tyr
                315                 320                 325

TCC AAA GTA TAC TTC CGG GGT CAG TCT TGC AAC AAC CAG CCC CTA AAC      192
Ser Lys Val Tyr Phe Arg Gly Gln Ser Cys Asn Asn Gln Pro Leu Asn
            330                 335                 340

CAC AAG GTC TAT ATG AGG AAC TCT AAG TAT CCT GAG GAT CTG GTG CTA      240
His Lys Val Tyr Met Arg Asn Ser Lys Tyr Pro Glu Asp Leu Val Leu
            345                 350                 355

ATG GAG GAG AAG AGG TTG AAC TAC TGC ACT ACT GGA CAG ATA TGG GCC      288
Met Glu Glu Lys Arg Leu Asn Tyr Cys Thr Thr Gly Gln Ile Trp Ala
        360                 365                 370

CAC AGC AGC TAC CTG GGG GCA GTA TTC AAT CTT ACC AGT GCT GAC CAT      336
His Ser Ser Tyr Leu Gly Ala Val Phe Asn Leu Thr Ser Ala Asp His
375                 380                 385                 390

TTA TAT GTC AAC ATA TCT CAA CTC TCT CTG ATC AAT TTT GAG GAA TCT      384
Leu Tyr Val Asn Ile Ser Gln Leu Ser Leu Ile Asn Phe Glu Glu Ser
                395                 400                 405

AAG ACC TTT TTC GGC TTG TAT AAG CTT                                  411
Lys Thr Phe Phe Gly Leu Tyr Lys Leu
            410                 415
```

(2) INFORMATION FOR SEQ ID NO:18:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Val Ala His Leu Thr Gly Asn Pro His Ser Arg Ser Ile Pro Leu
 1               5                  10                  15
Glu Trp Glu Asp Thr Tyr Gly Thr Ala Leu Ile Ser Gly Val Lys Tyr
                20                  25                  30
Lys Lys Gly Gly Leu Val Ile Asn Glu Thr Gly Leu Tyr Phe Val Tyr
            35                  40                  45
Ser Lys Val Tyr Phe Arg Gly Gln Ser Cys Asn Asn Gln Pro Leu Asn
        50                  55                  60
His Lys Val Tyr Met Arg Asn Ser Lys Tyr Pro Glu Asp Leu Val Leu
65                  70                  75                  80
Met Glu Glu Lys Arg Leu Asn Tyr Cys Thr Thr Gly Gln Ile Trp Ala
                85                  90                  95
His Ser Ser Tyr Leu Gly Ala Val Phe Asn Leu Thr Ser Ala Asp His
            100                 105                 110
Leu Tyr Val Asn Ile Ser Gln Leu Ser Leu Ile Asn Phe Glu Glu Ser
        115                 120                 125
Lys Thr Phe Phe Gly Leu Tyr Lys Leu
        130                 135
```

(2) INFORMATION FOR SEQ ID NO:19:

(i) SEQUENCE CHARACTERISTICS:
        (A) LENGTH: 414 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: mouse (ix) FEATURE:
        (A) NAME/KEY: CDS
        (B) LOCATION: 1..414

(xi) SEQUENCE DESCRIPTION: SEQ ID NO:19:

```
AGG AGT GTG GCC CAT TTA ACA GGG AAC CCC CAC TCA AGG TCC ATC CCT       48
Arg Ser Val Ala His Leu Thr Gly Asn Pro His Ser Arg Ser Ile Pro
        140                 145                 150

CTG GAA TGG GAA GAC ACA TAT GGA ACC GCT CTG ATC TCT GGA GTG AAG       96
Leu Glu Trp Glu Asp Thr Tyr Gly Thr Ala Leu Ile Ser Gly Val Lys
155                 160                 165

TAT AAG AAA GGT GGC CTT GTG ATC AAC GAA ACT GGG TTG TAC TTC GTG      144
Tyr Lys Lys Gly Gly Leu Val Ile Asn Glu Thr Gly Leu Tyr Phe Val
170                 175                 180                 185

TAT TCC AAA GTA TAC TTC CGG GGT CAG TCT TGC AAC AAC CAG CCC CTA      192
Tyr Ser Lys Val Tyr Phe Arg Gly Gln Ser Cys Asn Asn Gln Pro Leu
        190                 195                 200

AAC CAC AAG GTC TAT ATG AGG AAC TCT AAG TAT CCT GAG GAT CTG GTG      240
```

```
Asn His Lys Val Tyr Met Arg Asn Ser Lys Tyr Pro Glu Asp Leu Val
            205                 210                 215

CTA ATG GAG GAG AAG AGG TTG AAC TAC TGC ACT ACT GGA CAG ATA TGG      288
Leu Met Glu Glu Lys Arg Leu Asn Tyr Cys Thr Thr Gly Gln Ile Trp
        220                 225                 230

GCC CAC AGC AGC TAC CTG GGG GCA GTA TTC AAT CTT ACC AGT GCT GAC      336
Ala His Ser Ser Tyr Leu Gly Ala Val Phe Asn Leu Thr Ser Ala Asp
        235                 240                 245

CAT TTA TAT GTC AAC ATA TCT CAA CTC TCT CTG ATC AAT TTT GAG GAA      384
His Leu Tyr Val Asn Ile Ser Gln Leu Ser Leu Ile Asn Phe Glu Glu
250                 255                 260                 265

TCT AAG ACC TTT TTC GGC TTG TAT AAG CTT                              414
Ser Lys Thr Phe Phe Gly Leu Tyr Lys Leu
                270                 275
```

(2) INFORMATION FOR SEQ ID NO:20:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:20:

```
Arg Ser Val Ala His Leu Thr Gly Asn Pro His Ser Arg Ser Ile Pro
1               5                   10                  15

Leu Glu Trp Glu Asp Thr Tyr Gly Thr Ala Leu Ile Ser Gly Val Lys
            20                  25                  30

Tyr Lys Lys Gly Gly Leu Val Ile Asn Glu Thr Gly Leu Tyr Phe Val
        35                  40                  45

Tyr Ser Lys Val Tyr Phe Arg Gly Gln Ser Cys Asn Asn Gln Pro Leu
    50                  55                  60

Asn His Lys Val Tyr Met Arg Asn Ser Lys Tyr Pro Glu Asp Leu Val
65                  70                  75                  80

Leu Met Glu Glu Lys Arg Leu Asn Tyr Cys Thr Thr Gly Gln Ile Trp
                85                  90                  95

Ala His Ser Ser Tyr Leu Gly Ala Val Phe Asn Leu Thr Ser Ala Asp
            100                 105                 110

His Leu Tyr Val Asn Ile Ser Gln Leu Ser Leu Ile Asn Phe Glu Glu
        115                 120                 125

Ser Lys Thr Phe Phe Gly Leu Tyr Lys Leu
    130                 135
```

(2) INFORMATION FOR SEQ ID NO:21:

(i) SEQUENCE CHARACTERISTICS:
        (A) LENGTH: 537 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: mouse (ix) FEATURE:
        (A) NAME/KEY: CDS
        (B) LOCATION: 1..537

(xi) SEQUENCE DESCRIPTION: SEQ ID NO:21:

```
CAG CTC TTC CAC CTG CAG AAG GAA CTG GCA GAA CTC CGT GAG TTC ACC        48
Gln Leu Phe His Leu Gln Lys Glu Leu Ala Glu Leu Arg Glu Phe Thr
140                 145                 150

AAC CAA AGC CTT AAA GTA TCA TCT TTT GAA AAG CAA ATA GCC AAC CCC        96
Asn Gln Ser Leu Lys Val Ser Ser Phe Glu Lys Gln Ile Ala Asn Pro
155                 160                 165                 170

AGT ACA CCC TCT GAA AAA AAA GAG CCG AGG AGT GTG GCC CAT TTA ACA       144
Ser Thr Pro Ser Glu Lys Lys Glu Pro Arg Ser Val Ala His Leu Thr
                175                 180                 185

GGG AAC CCC CAC TCA AGG TCC ATC CCT CTG GAA TGG GAA GAC ACA TAT       192
Gly Asn Pro His Ser Arg Ser Ile Pro Leu Glu Trp Glu Asp Thr Tyr
                190                 195                 200

GGA ACC GCT CTG ATC TCT GGA GTG AAG TAT AAG AAA GGT GGC CTT GTG       240
Gly Thr Ala Leu Ile Ser Gly Val Lys Tyr Lys Lys Gly Gly Leu Val
                205                 210                 215

ATC AAC GAA ACT GGG TTG TAC TTC GTG TAT TCC AAA GTA TAC TTC CGG       288
Ile Asn Glu Thr Gly Leu Tyr Phe Val Tyr Ser Lys Val Tyr Phe Arg
220                 225                 230

GGT CAG TCT TGC AAC AAC CAG CCC CTA AAC CAC AAG GTC TAT ATG AGG       336
Gly Gln Ser Cys Asn Asn Gln Pro Leu Asn His Lys Val Tyr Met Arg
235                 240                 245                 250

AAC TCT AAG TAT CCT GAG GAT CTG GTG CTA ATG GAG GAG AAG AGG TTG       384
Asn Ser Lys Tyr Pro Glu Asp Leu Val Leu Met Glu Glu Lys Arg Leu
                255                 260                 265

AAC TAC TGC ACT ACT GGA CAG ATA TGG GCC CAC AGC AGC TAC CTG GGG       432
Asn Tyr Cys Thr Thr Gly Gln Ile Trp Ala His Ser Ser Tyr Leu Gly
                270                 275                 280

GCA GTA TTC AAT CTT ACC AGT GCT GAC CAT TTA TAT GTC AAC ATA TCT       480
Ala Val Phe Asn Leu Thr Ser Ala Asp His Leu Tyr Val Asn Ile Ser
                285                 290                 295

CAA CTC TCT CTG ATC AAT TTT GAG GAA TCT AAG ACC TTT TTC GGC TTG       528
Gln Leu Ser Leu Ile Asn Phe Glu Glu Ser Lys Thr Phe Phe Gly Leu
300                 305                 310

TAT AAG CTT                                                           537
Tyr Lys Leu
315
```

(2) INFORMATION FOR SEQ ID NO:22:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:22:

```
Gln Leu Phe His Leu Gln Lys Glu Leu Ala Glu Leu Arg Glu Phe Thr
1               5                   10                  15

Asn Gln Ser Leu Lys Val Ser Ser Phe Glu Lys Gln Ile Ala Asn Pro
                20                  25                  30

Ser Thr Pro Ser Glu Lys Lys Glu Pro Arg Ser Val Ala His Leu Thr
                35                  40                  45

Gly Asn Pro His Ser Arg Ser Ile Pro Leu Glu Trp Glu Asp Thr Tyr
            50                  55                  60

Gly Thr Ala Leu Ile Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
```

```
                       85                  90                      95
Gly Gln Ser Cys Asn Asn Gln Pro Leu Asn His Lys Val Tyr Met Arg
                100             105             110

Asn Ser Lys Tyr Pro Glu Asp Leu Val Leu Met Glu Glu Lys Arg Leu
        115             120             125

Asn Tyr Cys Thr Thr Gly Gln Ile Trp Ala His Ser Ser Tyr Leu Gly
    130             135             140

Ala Val Phe Asn Leu Thr Ser Ala Asp His Leu Tyr Val Asn Ile Ser
145             150             155             160

Gln Leu Ser Leu Ile Asn Phe Glu Glu Ser Lys Thr Phe Phe Gly Leu
            165             170             175

Tyr Lys Leu (2) INFORMATION FOR SEQ ID NO:23:

(i) SEQUENCE CHARACTERISTICS:
        (A) LENGTH: 837 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: mouse (ix) FEATURE:
        (A) NAME/KEY: CDS
        (B) LOCATION: 1..837

(xi) SEQUENCE DESCRIPTION: SEQ ID NO:23:

ATG CAG CAG CCC ATG AAT TAC CCA TGT CCC CAG ATC TTC TGG GTA GAC       48
Met Gln Gln Pro Met Asn Tyr Pro Cys Pro Gln Ile Phe Trp Val Asp
180             185             190             195

AGC AGT GCC ACT TCA TCT TGG GCT CCT CCA GGG TCA GTT TTT CCC TGT       96
Ser Ser Ala Thr Ser Ser Trp Ala Pro Pro Gly Ser Val Phe Pro Cys
                200             205             210

CCA TCT TGT GGG CCT AGA GGG CCG GAC CAA AGG AGA CCG CCA CCT CCA      144
Pro Ser Cys Gly Pro Arg Gly Pro Asp Gln Arg Arg Pro Pro Pro Pro
            215             220             225

CCA CCA CCT GTG TCA CCA CTA CCA CCG CCA TCA CAA CCA CTC CCA CTG      192
Pro Pro Pro Val Ser Pro Leu Pro Pro Pro Ser Gln Pro Leu Pro Leu
        230             235             240

CCG CCA CTG ACC CCT CTA AAG AAG AAG GAC CAC AAC ACA AAT CTG TGG      240
Pro Pro Leu Thr Pro Leu Lys Lys Lys Asp His Asn Thr Asn Leu Trp
    245             250             255

CTA CCG GTG GTA TTT TTC ATG GTT CTG GTG GCT CTG GTT GGA ATG GGA      288
Leu Pro Val Val Phe Phe Met Val Leu Val Ala Leu Val Gly Met Gly
260             265             270             275

TTA GGA ATG TAT CAG CTC TTC CAC CTG CAG AAG GAA CTG GCA GAA CTC      336
Leu Gly Met Tyr Gln Leu Phe His Leu Gln Lys Glu Leu Ala Glu Leu
                280             285             290

CGT GAG TTC ACC AAC CAA AGC CTT AAA GTA TCA TCT TTT GAA AAG CAA      384
Arg Glu Phe Thr Asn Gln Ser Leu Lys Val Ser Ser Phe Glu Lys Gln
            295             300             305

ATA GCC AAC CCC AGT ACA CCC TCT GAA AAA AAA GAG CCG AGG AGT GTG      432
Ile Ala Asn Pro Ser Thr Pro Ser Glu Lys Lys Glu Pro Arg Ser Val
        310             315             320
```

-continued

```
GCC CAT TTA ACA GGG AAC CCC CAC TCA AGG TCC ATC CCT CTG GAA TGG      480
Ala His Leu Thr Gly Asn Pro His Ser Arg Ser Ile Pro Leu Glu Trp
325                 330                 335

GAA GAC ACA TAT GGA ACC GCT CTG ATC TCT GGA GTG AAG TAT AAG AAA      528
Glu Asp Thr Tyr Gly Thr Ala Leu Ile Ser Gly Val Lys Tyr Lys Lys
340                 345                 350                 355

GGT GGC CTT GTG ATC AAC GAA ACT GGG TTG TAC TTC GTG TAT TCC AAA      576
Gly Gly Leu Val Ile Asn Glu Thr Gly Leu Tyr Phe Val Tyr Ser Lys
                360                 365                 370

GTA TAC TTC CGG GGT CAG TCT TGC AAC AAC CAG CCC CTA AAC CAC AAG      624
Val Tyr Phe Arg Gly Gln Ser Cys Asn Asn Gln Pro Leu Asn His Lys
            375                 380                 385

GTC TAT ATG AGG AAC TCT AAG TAT CCT GAG GAT CTG GTG CTA ATG GAG      672
Val Tyr Met Arg Asn Ser Lys Tyr Pro Glu Asp Leu Val Leu Met Glu
        390                 395                 400

GAG AAG AGG TTG AAC TAC TGC ACT ACT GGA CAG ATA TGG GCC CAC AGC      720
Glu Lys Arg Leu Asn Tyr Cys Thr Thr Gly Gln Ile Trp Ala His Ser
    405                 410                 415

AGC TAC CTG GGG GCA GTA TTC AAT CTT ACC AGT GCT GAC CAT TTA TAT      768
Ser Tyr Leu Gly Ala Val Phe Asn Leu Thr Ser Ala Asp His Leu Tyr
420                 425                 430                 435

GTC AAC ATA TCT CAA CTC TCT CTG ATC AAT TTT GAG GAA TCT AAG ACC      816
Val Asn Ile Ser Gln Leu Ser Leu Ile Asn Phe Glu Glu Ser Lys Thr
                440                 445                 450

TTT TTC GGC TTG TAT AAG CTT                                          837
Phe Phe Gly Leu Tyr Lys Leu
                455
```

(2) INFORMATION FOR SEQ ID NO:24:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO:24:

```
Met Gln Gln Pro Met Asn Tyr Pro Cys Pro Gln Ile Phe Trp Val Asp
1               5                   10                  15

Ser Ser Ala Thr Ser Ser Trp Ala Pro Gly Ser Val Phe Pro Cys
            20                  25                  30

Pro Ser Cys Gly Pro Arg Gly Pro Asp Gln Arg Arg Pro Pro Pro
        35                  40                  45

Pro Pro Pro Val Ser Pro Leu Pro Pro Ser Gln Pro Leu Pro Leu
    50                  55                  60

Pro Pro Leu Thr Pro Leu Lys Lys Lys Asp His Asn Thr Asn Leu Trp
65                  70                  75                  80

Leu Pro Val Val Phe Phe Met Val Leu Val Ala Leu Val Gly Met Gly
                85                  90                  95

Leu Gly Met Tyr Gln Leu Phe His Leu Gln Lys Glu Leu Ala Glu Leu
                100                 105                 110

Arg Glu Phe Thr Asn Gln Ser Leu Lys Val Ser Ser Phe Glu Lys Gln
            115                 120                 125

Ile Ala Asn Pro Ser Thr Pro Ser Glu Lys Lys Glu Pro Arg Ser Val
        130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
```

```
                    165                 170                 175
Gly Gly Leu Val Ile Asn Glu Thr Gly Leu Tyr Phe Val Tyr Ser Lys
                180                 185                 190

Val Tyr Phe Arg Gly Gln Ser Cys Asn Asn Gln Pro Leu Asn His Lys
        195                 200                 205

Val Tyr Met Arg Asn Ser Lys Tyr Pro Glu Asp Leu Val Leu Met Glu
        210                 215                 220

Glu Lys Arg Leu Asn Tyr Cys Thr Thr Gly Gln Ile Trp Ala His Ser
225                 230                 235                 240

Ser Tyr Leu Gly Ala Val Phe Asn Leu Thr Ser Ala Asp His Leu Tyr
                245                 250                 255

Val Asn Ile Ser Gln Leu Ser Leu Ile Asn Phe Glu Glu Ser Lys Thr
                260                 265                 270

Phe Phe Gly Leu Tyr Lys Leu
                275

(2) INFORMATION FOR SEQ ID NO:25:

(i) SEQUENCE CHARACTERISTICS:
        (A) LENGTH: 1623 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
         (A) ORGANISM: rat (ix) FEATURE:
         (A) NAME/KEY: CDS
         (B) LOCATION: 74..907
         (D) OTHER INFORMATION: /label= Figs_2-3

(xi) SEQUENCE DESCRIPTION: SEQ ID NO:25:

TCAGAGTCCT GTCCTTGACA CTTCAGTCTC CACAAGACTG AGAGGAGGAA ACCCTTTCCT      60

GGGGCTGGGT GCC ATG CAG CAG CCC GTG AAT TAC CCA TGT CCC CAG ATC       109
            Met Gln Gln Pro Val Asn Tyr Pro Cys Pro Gln Ile
                280                 285                 290

TAC TGG GTA GAC AGC AGT GCC ACT TCT CCT TGG GCT CCT CCA GGG TCA      157
Tyr Trp Val Asp Ser Ser Ala Thr Ser Pro Trp Ala Pro Pro Gly Ser
            295                 300                 305

GTT TTT TCT TGT CCA TCC TCT GGG CCT AGA GGG CCA GGA CAA AGG AGA      205
Val Phe Ser Cys Pro Ser Ser Gly Pro Arg Gly Pro Gly Gln Arg Arg
            310                 315                 320

CCA CCG CCT CCA CCA CCA CCT CCA TCA CCA CTA CCA CCG CCT TCC CAA      253
Pro Pro Pro Pro Pro Pro Pro Ser Pro Leu Pro Pro Pro Ser Gln
325                 330                 335

CCA CCC CCG CTG CCT CCA CTA AGC CCT CTA AAG AAG AAG GAC AAC ATA      301
Pro Pro Pro Leu Pro Pro Leu Ser Pro Leu Lys Lys Lys Asp Asn Ile
340                 345                 350                 355

GAG CTG TGG CTA CCG GTG ATA TTT TTC ATG GTG CTG GTG GCT CTG GTT      349
Glu Leu Trp Leu Pro Val Ile Phe Phe Met Val Leu Val Ala Leu Val
                360                 365                 370

GGA ATG GGG TTA GGA ATG TAT CAA CTC TTT CAT CTA CAG AAG GAA CTG      397
Gly Met Gly Leu Gly Met Tyr Gln Leu Phe His Leu Gln Lys Glu Leu
            375                 380                 385

GCA GAA CTC CGT GAG TTC ACC AAC CAC AGC CTT AGA GTA TCA TCT TTT      445
```

```
Ala Glu Leu Arg Glu Phe Thr Asn His Ser Leu Arg Val Ser Ser Phe
        390                 395                 400

GAA AAG CAA ATA GCC AAC CCC AGC ACA CCC TCT GAA ACC AAA AAG CCA      493
Glu Lys Gln Ile Ala Asn Pro Ser Thr Pro Ser Glu Thr Lys Lys Pro
        405                 410                 415

AGG AGT GTG GCC CAC TTA ACA GGG AAC CCC CGC TCA AGG TCC ATC CCT      541
Arg Ser Val Ala His Leu Thr Gly Asn Pro Arg Ser Arg Ser Ile Pro
420                 425                 430                 435

CTG GAA TGG GAA GAC ACA TAT GGA ACT GCT TTG ATC TCT GGA GTG AAG      589
Leu Glu Trp Glu Asp Thr Tyr Gly Thr Ala Leu Ile Ser Gly Val Lys
                440                 445                 450

TAT AAG AAA GGC GGC CTT GTG ATC AAT GAG GCT GGG TTG TAC TTC GTA      637
Tyr Lys Lys Gly Gly Leu Val Ile Asn Glu Ala Gly Leu Tyr Phe Val
            455                 460                 465

TAT TCC AAA GTA TAC TTC CGG GGT CAG TCT TGC AAC AGC CAG CCC CTA      685
Tyr Ser Lys Val Tyr Phe Arg Gly Gln Ser Cys Asn Ser Gln Pro Leu
            470                 475                 480

AGC CAC AAG GTC TAT ATG AGG AAC TTT AAG TAT CCT GGG GAT CTG GTG      733
Ser His Lys Val Tyr Met Arg Asn Phe Lys Tyr Pro Gly Asp Leu Val
        485                 490                 495

CTA ATG GAG GAG AAG AAG TTG AAT TAC TGC ACT ACT GGC CAG ATA TGG      781
Leu Met Glu Glu Lys Lys Leu Asn Tyr Cys Thr Thr Gly Gln Ile Trp
500                 505                 510                 515

GCC CAC AGC AGC TAC CTA GGG GCA GTA TTT AAT CTT ACC GTT GCT GAC      829
Ala His Ser Ser Tyr Leu Gly Ala Val Phe Asn Leu Thr Val Ala Asp
                520                 525                 530

CAT TTA TAT GTC AAC ATA TCT CAA CTC TCT CTG ATC AAT TTT GAG GAA      877
His Leu Tyr Val Asn Ile Ser Gln Leu Ser Leu Ile Asn Phe Glu Glu
            535                 540                 545

TCT AAG ACC TTT TTT GGC TTA TAT AAG CTT TAAAGGAAAA AGCATTTTAG        927
Ser Lys Thr Phe Phe Gly Leu Tyr Lys Leu
            550                 555

AATGATCTAT TATTCTTTAT CATGGATGCC AGGAATATTG TCTTCAATGA GAGTCTTCTT    987

AAGACCAATT GAGCCACAAA GACCACAAGG TCCAACAGGT CAGCTACCCT TCATTTTCTA   1047

GAGGTCCATG GAGTGGTCCT TAATGCCTGC ATCATGAGCC AGATGGGAAG AAGACTGTTC   1107

CTGAGGAACA TAAAGTTTTG GGCTGCTGTG TGGCAATGCA GAGGCAAAGA GAAGGAACTG   1167

TCTGATGTTA AATGGCCAAG AGCATTTTAG CCATTGAAGA AAAAAAAAAC CTTTAAACTC   1227

ACCTTCCAGG GTGGGTCTAC TTGCTACCTC ACAGGAGGCC GTCTTTTAGA CACATGGTTG   1287

TGGTATGACT ATACAAGGGT GAGAAAGGAT GCTAGGTTTC ATGGATAAGC TAGAGACTGA   1347

AAAAAGCCAG TGTCCCATTG GCATCATCTT TATTTTTAAC TGATGTTTTC TGAGCCCACC   1407

TTTGATGCTA ACAGAGAAAT AAGAGGGGTG TTTGAGGCAC AAGTCATTCT CTACATAGCA   1467

TGTGTACCTC CAGTGCAATG ATGTCTGTGT GTGTTTTTAT GTATGAGAGT AGAGCGATTC   1527

TAAAGAGTCA CATGAGTACA ACGCGTACAT TACGGAGTAC ATATTAGAAA CGTATGTGTT   1587

ACATTTGATG CTAGAATATC TGAATGTTTC TTGCTA                             1623
```

(2) INFORMATION FOR SEQ ID NO:26:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO:26:

```
Met Gln Gln Pro Val Asn Tyr Pro Cys Pro Gln Ile Tyr Trp Val Asp
  1               5                  10                  15

Ser Ser Ala Thr Ser Pro Trp Ala Pro Pro Gly Ser Val Phe Ser Cys
             20                  25                  30

Pro Ser Ser Gly Pro Arg Gly Pro Gly Gln Arg Arg Pro Pro Pro Pro
         35                  40                  45

Pro Pro Pro Pro Ser Pro Leu Pro Pro Ser Gln Pro Pro Pro Leu
 50                  55                  60

Pro Pro Leu Ser Pro Leu Lys Lys Lys Asp Asn Ile Glu Leu Trp Leu
 65                  70                  75                  80

Pro Val Ile Phe Phe Met Val Leu Val Ala Leu Val Gly Met Gly Leu
                 85                  90                  95

Gly Met Tyr Gln Leu Phe His Leu Gln Lys Glu Leu Ala Glu Leu Arg
            100                 105                 110

Glu Phe Thr Asn His Ser Leu Arg Val Ser Ser Phe Glu Lys Gln Ile
            115                 120                 125

Ala Asn Pro Ser Thr Pro Ser Glu Thr Lys Lys Pro Arg Ser Val Ala
            130                 135                 140

His Leu Thr Gly Asn Pro Arg Ser Arg Ser Ile Pro Leu Glu Trp Glu
145                 150                 155                 160

Asp Thr Tyr Gly Thr Ala Leu Ile Ser Gly Val Lys Tyr Lys Lys Gly
            165                 170                 175

Gly Leu Val Ile Asn Glu Ala Gly Leu Tyr Phe Val Tyr Ser Lys Val
            180                 185                 190

Tyr Phe Arg Gly Gln Ser Cys Asn Ser Gln Pro Leu Ser His Lys Val
            195                 200                 205

Tyr Met Arg Asn Phe Lys Tyr Pro Gly Asp Leu Val Leu Met Glu Glu
            210                 215                 220

Lys Lys Leu Asn Tyr Cys Thr Thr Gly Gln Ile Trp Ala His Ser Ser
225                 230                 235                 240

Tyr Leu Gly Ala Val Phe Asn Leu Thr Val Ala Asp His Leu Tyr Val
            245                 250                 255

Asn Ile Ser Gln Leu Ser Leu Ile Asn Phe Glu Glu Ser Lys Thr Phe
            260                 265                 270

Phe Gly Leu Tyr Lys Leu
            275
```

(2) INFORMATION FOR SEQ ID NO:27:

(i) SEQUENCE CHARACTERISTICS:
        (A) LENGTH: 426 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
        (A) ORGANISM: human (vii) IMMEDIATE SOURCE:
        (B) CLONE: pBL-hFL4H (ix) FEATURE:
        (A) NAME/KEY: CDS
        (B) LOCATION: 15..404

(xi) SEQUENCE DESCRIPTION: SEQ ID NO:27:

```
GATTTATTTC AGGC AAG TCC AAC TCA AGG TCC ATG CCT CTG GAA TGG GAA          50
               Lys Ser Asn Ser Arg Ser Met Pro Leu Glu Trp Glu
               280                 285                 290

GAC ACC TAT GGA ATT GTC CTG CTT TCT GGA GTG AAG TAT AAG AAG GGT          98
Asp Thr Tyr Gly Ile Val Leu Leu Ser Gly Val Lys Tyr Lys Lys Gly
                295                 300                 305

GGC CTT GTG ATC AAT GAA ACT GGG CTG TAC TTT GTA TAT TCC AAA GTA         146
Gly Leu Val Ile Asn Glu Thr Gly Leu Tyr Phe Val Tyr Ser Lys Val
            310                 315                 320

TAC TTC CGG GGT CAA TCT TGC AAC AAC CTG CCC CTG AGC CAC AAG GTC         194
Tyr Phe Arg Gly Gln Ser Cys Asn Asn Leu Pro Leu Ser His Lys Val
        325                 330                 335

TAC ATG AGG AAC TCT AAG TAT CCC CAG GAT CTG GTG ATG ATG GAG GGG         242
Tyr Met Arg Asn Ser Lys Tyr Pro Gln Asp Leu Val Met Met Glu Gly
    340                 345                 350

AAG ATG ATG AGC TAC TGC ACT ACT GGG CAG ATG TGG GCC CGC AGC AGC         290
Lys Met Met Ser Tyr Cys Thr Thr Gly Gln Met Trp Ala Arg Ser Ser
355                 360                 365                 370

TAC CTG GGG GCA GTG TTC AAT CTT ACC AGT GCT GAT CAT TTA TAT GTC         338
Tyr Leu Gly Ala Val Phe Asn Leu Thr Ser Ala Asp His Leu Tyr Val
                375                 380                 385

AAC GTA TCT GAG CTC TCT CTG GTC AAT TTT GAG GAA TCT CAG ACG TTT         386
Asn Val Ser Glu Leu Ser Leu Val Asn Phe Glu Glu Ser Gln Thr Phe
            390                 395                 400

TTC GGC TTA TAT AAG CTC TAAGAGAAGC ACTTTGGGAT TC                        426
Phe Gly Leu Tyr Lys Leu
            405
```

(2) INFORMATION FOR SEQ ID NO:28:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:28:

```
Lys Ser Asn Ser Arg Ser Met Pro Leu Glu Trp Glu Asp Thr Tyr Gly
 1               5                  10                  15

Ile Val Leu Leu Ser Gly Val Lys Tyr Lys Lys Gly Gly Leu Val Ile
                20                  25                  30

Asn Glu Thr Gly Leu Tyr Phe Val Tyr Ser Lys Val Tyr Phe Arg Gly
            35                  40                  45

Gln Ser Cys Asn Asn Leu Pro Leu Ser His Lys Val Tyr Met Arg Asn
        50                  55                  60

Ser Lys Tyr Pro Gln Asp Leu Val Met Met Glu Gly Lys Met Met Ser
65                  70                  75                  80

Tyr Cys Thr Thr Gly Gln Met Trp Ala Arg Ser Ser Tyr Leu Gly Ala
                85                  90                  95

Val Phe Asn Leu Thr Ser Ala Asp His Leu Tyr Val Asn Val Ser Glu
            100                 105                 110

Leu Ser Leu Val Asn Phe Glu Glu Ser Gln Thr Phe Phe Gly Leu Tyr
        115                 120                 125

Lys Leu
    130
```

(2) INFORMATION FOR SEQ ID NO:29:

(i) SEQUENCE CHARACTERISTICS:
    (A) LENGTH: 2432 base pairs
    (B) TYPE: nucleic acid
    (C) STRANDEDNESS: Not Relevant
    (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
    (A) ORGANISM: human (vii) IMMEDIATE SOURCE:
    (B) CLONE: LambdaFL5

(ix) FEATURE:
    (A) NAME/KEY: CDS
    (B) LOCATION: join(496..843, 982..1027, 1213..1269,
        1716..2107)
    (D) OTHER INFORMATION: /label= Figs_16-18

(xi) SEQUENCE DESCRIPTION: SEQ ID NO:29:

```
AATTATAATG TATAAAAAAG CATGCAATTA TAATTCATAA AATTATAGCC CCACTGACCA      60

TTCTCCTGTA GCTGGGAGCA GTTCACACTA ACAGGGCTAT ACCCCCATGC TGACCTGCTC     120

TGCAGGATCC CAGGAAGGTG AGCATAGCCT ACTAACCTGT TTGGGTAGCA CAGCGACAGC     180

AACTGAGGCC TTGAAGGCTG TTATCAGAAA ATTGTGGGCG GAAACTTCCA GGGGTTTGCT     240

CTGAGCTTCT TGAGGCTTCT CAGCTTCAGC TGCAAAGTGA GTGGGTGTTT CTTTGAGAAG     300

CAGAATCAGA GAGAGAGAGA TAGAGAAAGA GAAAGACAGA GGTGTTTCCC TTAGCTATGG     360

AAACTCTATA AGAGAGATCC AGCTTGCCTC CTCTTGAGCA GTCAGCAACA GGGTCCCGTC     420

CTTGACACCT CAGCCTCTAC AGGACTGAGA AGAAGTAAAA CCGTTTGCTG GGGCTGGCCT     480

GACTCACCAG CTGCC ATG CAG CAG CCC TTC AAT TAC CCA TAT CCC CAG ATC     531
                Met Gln Gln Pro Phe Asn Tyr Pro Tyr Pro Gln Ile
                  1               5                  10

TAC TGG GTG GAC AGC AGT GCC AGC TCT CCC TGG GCC CCT CCA GGC ACA     579
Tyr Trp Val Asp Ser Ser Ala Ser Ser Pro Trp Ala Pro Pro Gly Thr
         15                  20                  25

GTT CTT CCC TGT CCA ACC TCT GTG CCC AGA AGG CCT GGT CAA AGG AGG     627
Val Leu Pro Cys Pro Thr Ser Val Pro Arg Arg Pro Gly Gln Arg Arg
 30                  35                  40

CCA CCA CCA CCA CCG CCA CCG CCA CCA CTA CCA CCT CCG CCG CCG CCG     675
Pro Pro Pro Pro Pro Pro Pro Pro Leu Pro Pro Pro Pro Pro Pro
 45                  50                  55                  60

CCA CCA CTG CCT CCA CTA CCG CTG CCA CCC CTG AAG AAG AGA GGG AAC     723
Pro Pro Leu Pro Pro Leu Pro Leu Pro Pro Leu Lys Lys Arg Gly Asn
              65                  70                  75

CAC AGC ACA GGC CTG TGT CTC CTT GTG ATG TTT TTC ATG GTT CTG GTT     771
His Ser Thr Gly Leu Cys Leu Leu Val Met Phe Phe Met Val Leu Val
             80                  85                  90

GCC TTG GTA GGA TTG GGC CTG GGG ATG TTT CAG CTC TTC CAC CTA CAG     819
Ala Leu Val Gly Leu Gly Leu Gly Met Phe Gln Leu Phe His Leu Gln
         95                 100                 105

AAG GAG CTG GCA GAA CTC CGA GAG GTAAGCCTGC CGGCAGACTG CTGTGCCCTG     873
Lys Glu Leu Ala Glu Leu Arg Glu
110                 115

GAGGCACCAG GCATAAGGGG ATGGAGGGCC CACTGCCTGG CGATTCTGCC TCTTTTGCTT     933

AAAGAATTTT ATTTTTATTA TACATCTTTT CTCTTTCTGT TTTACTAG TCT ACC AGC     990
                                                   Ser Thr Ser
```

```
CAG ATG CAC ACA GCA TCA TCT TTG GAG AAG CAA ATA G GTGAGTCTTT         1037
Gln Met His Thr Ala Ser Ser Leu Glu Lys Gln Ile
120             125                 130

TTTCGCATGT ACATTGAGTT CCCAAAGATG ATCCTCAGCA CAGAACTATG TTAATGGAAT    1097

GCCTTAAATT CTGTCCCACA CTTTGGTTTC TGTACACTAT AAGAGGAATT CTTCCCACCA    1157

AAATAATAGT TGCTATTTCA TTTTAACATA TATTTTTCCT CTCTCTATGA TACAG  GC     1214
                                                             Gly

CAC CCC AGT CCA CCC CCT GAA AAA AAG GAG CTG AGG AAA GTG GCC CAT      1262
His Pro Ser Pro Pro Pro Glu Lys Lys Glu Leu Arg Lys Val Ala His
        135                 140                 145

TTA ACA G GTCTGTATCT GGAAGGTACA GGTGAGATCT GCAGGTGAGA                1309
Leu Thr
    150

AGATGGACCA GATGGTCCCT AAGATCCTTC CCAACTTTAG AACTTTAGAG TTCCTTGGAT    1369

TTGGCTTTTT CCTTCAGGAA AGGACTTCAA AGCCTAGCAG ATTTGGTGCT AGTTCTGAAG    1429

ATAGTAAAAT CTTTGTTCCA GAGAGCAAAT ATTTTCTCAA TAATTTCTTA CTGCAATGGA    1489

TTACGGGTAT ATACTATTGT TCCAATTGTG TGGATGACAA AATAGGACAA CGTTGTTGAG    1549

GAAATTCTGT GATGGATCAA GTTCTGACCC CTCAGCCAGT TCTATACCAG CTGTCATTCT    1609

GGGTGAAACA TTTGTTGAAG GAAGGGCCCA CAGTTTTGCC TTAGAAACTT AGTTTGTTGG    1669

ATGCATGACT ATTCCTTGCT GAAAGCTCCT TTTGGATTTA TTTCAG  GC AAG TCC       1723
                                                     Gly Lys Ser

AAC TCA AGG TCC ATG CCT CTG GAA TGG GAA GAC ACC TAT GGA ATT GTC      1771
Asn Ser Arg Ser Met Pro Leu Glu Trp Glu Asp Thr Tyr Gly Ile Val
        155                 160                 165

CTG CTT TCT GGA GTG AAG TAT AAG AAG GGT GGC CTT GTG ATC AAT GAA      1819
Leu Leu Ser Gly Val Lys Tyr Lys Lys Gly Gly Leu Val Ile Asn Glu
170             175                 180                     185

ACT GGG CTG TAC TTT GTA TAT TCC AAA GTA TAC TTC CGG GGT CAA TCT      1867
Thr Gly Leu Tyr Phe Val Tyr Ser Lys Val Tyr Phe Arg Gly Gln Ser
                190                 195                 200

TGC AAC AAC CTG CCC CTG AGC CAC AAG GTC TAC ATG AGG AAC TCT AAG      1915
Cys Asn Asn Leu Pro Leu Ser His Lys Val Tyr Met Arg Asn Ser Lys
                205                 210                 215

TAT CCC CAG GAT CTG GTG ATG ATG GAG GGG AAG ATG ATG AGC TAC TGC      1963
Tyr Pro Gln Asp Leu Val Met Met Glu Gly Lys Met Met Ser Tyr Cys
                220                 225                 230

ACT ACT GGG CAG ATG TGG GCC CGC AGC AGC TAC CTG GGG GCA GTG TTC      2011
Thr Thr Gly Gln Met Trp Ala Arg Ser Ser Tyr Leu Gly Ala Val Phe
    235                 240                 245

AAT CTT ACC AGT GCT GAT CAT TTA TAT GTC AAC GTA TCT GAG CTC TCT      2059
Asn Leu Thr Ser Ala Asp His Leu Tyr Val Asn Val Ser Glu Leu Ser
250             255                 260                 265

CTG GTC AAT TTT GAG GAA TCT CAG ACG TTT TTC GGC TTA TAT AAG CTC      2107
Leu Val Asn Phe Glu Glu Ser Gln Thr Phe Phe Gly Leu Tyr Lys Leu
                270                 275                 280

TAAGAGAAGC ACTTTGGGAT TCTTTCCATT ATGATTCTTT GTTACAGGCA CCGAGAATGT    2167

TGTATTCAGT GAGGGTCTTC TTACATGCAT TTGAGGTCAA GTAAGAAGAC ATGAACCAAG    2227

TGGACCTTGA GACCACAGGG TTCAAAATGT CTGTAGCTCC TCAACTCACC TAATGTTTAT    2287

GAGCCAGACA AATGGAGGAA TATGACGGAA GAACATAGAA CTCTGGGCTG CCATGTGAAG    2347

AGGGAGAAGC ATGAAAAAGC AGCTACCAGG TGTTCTACAC TCATCTTAGT GCCTGAGAGT    2407

ATTTAGGCAG ATTGAAAAGG ACACC                                         2432
```

(2) INFORMATION FOR SEQ ID NO:30:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:30:

```
Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280
```

(2) INFORMATION FOR SEQ ID NO:31:

(i) SEQUENCE CHARACTERISTICS:
        (A) LENGTH: 1707 base pairs
        (B) TYPE: nucleic acid
        (C) STRANDEDNESS: Not Relevant
        (D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
            (A) ORGANISM: mouse (vii) IMMEDIATE SOURCE:
            (B) CLONE: LambdaMFL5, LambdaMFL18

(ix) FEATURE:
            (A) NAME/KEY: CDS
            (B) LOCATION: 125..961
            (D) OTHER INFORMATION: /label= Figs_23-24

(xi) SEQUENCE DESCRIPTION: SEQ ID NO:31:

```
CTGCGGAAAC TTTATAAAGA AAACTTAGCT TCTCTGGAGC AGTCAGCGTC AGAGTTCTGT      60

CCTTGACACC TGAGTCTCCT CCACAAGGCT GTGAGAAGGA AACCCTTTCC TGGGGCTGGG     120
```

| | | | | | | | | | | | | | | | | |
|---|---|---|---|---|---|---|---|---|---|---|---|---|---|---|---|---|
| TGCC | ATG | CAG | CAG | CCC | ATG | AAT | TAC | CCA | TGT | CCC | CAG | ATC | TTC | TGG | GTA | 169 |
| | Met | Gln | Gln | Pro | Met | Asn | Tyr | Pro | Cys | Pro | Gln | Ile | Phe | Trp | Val | |
| | | | 285 | | | | | 290 | | | | | 295 | | | |
| GAC | AGC | AGT | GCC | ACT | TCA | TCT | TGG | GCT | CCT | CCA | GGG | TCA | GTT | TTT | CCC | 217 |
| Asp | Ser | Ser | Ala | Thr | Ser | Ser | Trp | Ala | Pro | Pro | Gly | Ser | Val | Phe | Pro | |
| | | | 300 | | | | | 305 | | | | | 310 | | | |
| TGT | CCA | TCT | TGT | GGG | CCT | AGA | GGG | CCG | GAC | CAA | AGG | AGA | CCG | CCA | CCT | 265 |
| Cys | Pro | Ser | Cys | Gly | Pro | Arg | Gly | Pro | Asp | Gln | Arg | Arg | Pro | Pro | Pro | |
| | | 315 | | | | | 320 | | | | | 325 | | | | |
| CCA | CCA | CCA | CCT | GTG | TCA | CCA | CTA | CCA | CCG | CCA | TCA | CAA | CCA | CTC | CCA | 313 |
| Pro | Pro | Pro | Pro | Val | Ser | Pro | Leu | Pro | Pro | Pro | Ser | Gln | Pro | Leu | Pro | |
| | 330 | | | | | 335 | | | | | 340 | | | | | |
| CTG | CCG | CCA | CTG | ACC | CCT | CTA | AAG | AAG | AAG | GAC | CAC | AAC | ACA | AAT | CTG | 361 |
| Leu | Pro | Pro | Leu | Thr | Pro | Leu | Lys | Lys | Lys | Asp | His | Asn | Thr | Asn | Leu | |
| 345 | | | | | 350 | | | | | 355 | | | | | 360 | |
| TGG | CTA | CCG | GTG | GTA | TTT | TTC | ATG | GTT | CTG | GTG | GCT | CTG | GTT | GGA | ATG | 409 |
| Trp | Leu | Pro | Val | Val | Phe | Phe | Met | Val | Leu | Val | Ala | Leu | Val | Gly | Met | |
| | | | | 365 | | | | | 370 | | | | | 375 | | |
| GGA | TTA | GGA | ATG | TAT | CAG | CTC | TTC | CAC | CTG | CAG | AAG | GAA | CTG | GCA | GAA | 457 |
| Gly | Leu | Gly | Met | Tyr | Gln | Leu | Phe | His | Leu | Gln | Lys | Glu | Leu | Ala | Glu | |
| | | | | 380 | | | | | 385 | | | | | 390 | | |
| CTC | CGT | GAG | TTC | ACC | AAC | CAA | AGC | CTT | AAA | GTA | TCA | TCT | TTT | GAA | AAG | 505 |
| Leu | Arg | Glu | Phe | Thr | Asn | Gln | Ser | Leu | Lys | Val | Ser | Ser | Phe | Glu | Lys | |
| | | 395 | | | | | 400 | | | | | 405 | | | | |
| CAA | ATA | GCC | AAC | CCC | AGT | ACA | CCC | TCT | GAA | AAA | AAA | GAG | CCG | AGG | AGT | 553 |
| Gln | Ile | Ala | Asn | Pro | Ser | Thr | Pro | Ser | Glu | Lys | Lys | Glu | Pro | Arg | Ser | |
| | | 410 | | | | | 415 | | | | | 420 | | | | |
| GTG | GCC | CAT | TTA | ACA | GGG | AAC | CCC | CAC | TCA | AGG | TCC | ATC | CCT | CTG | GAA | 601 |
| Val | Ala | His | Leu | Thr | Gly | Asn | Pro | His | Ser | Arg | Ser | Ile | Pro | Leu | Glu | |
| 425 | | | | | 430 | | | | | 435 | | | | | 440 | |
| TGG | GAA | GAC | ACA | TAT | GGA | ACC | GCT | CTG | ATC | TCT | GGA | GTG | AAG | TAT | AAG | 649 |
| Trp | Glu | Asp | Thr | Tyr | Gly | Thr | Ala | Leu | Ile | Ser | Gly | Val | Lys | Tyr | Lys | |
| | | | | 445 | | | | | 450 | | | | | 455 | | |
| AAA | GGT | GGC | CTT | GTG | ATC | AAC | GAA | ACT | GGG | TTG | TAC | TTC | GTG | TAT | TCC | 697 |
| Lys | Gly | Gly | Leu | Val | Ile | Asn | Glu | Thr | Gly | Leu | Tyr | Phe | Val | Tyr | Ser | |
| | | | | 460 | | | | | 465 | | | | | 470 | | |
| AAA | GTA | TAC | TTC | CGG | GGT | CAG | TCT | TGC | AAC | AAC | CAG | CCC | CTA | AAC | CAC | 745 |
| Lys | Val | Tyr | Phe | Arg | Gly | Gln | Ser | Cys | Asn | Asn | Gln | Pro | Leu | Asn | His | |
| | | | 475 | | | | | 480 | | | | | 485 | | | |
| AAG | GTC | TAT | ATG | AGG | AAC | TCT | AAG | TAT | CCT | GAG | GAT | CTG | GTG | CTA | ATG | 793 |
| Lys | Val | Tyr | Met | Arg | Asn | Ser | Lys | Tyr | Pro | Glu | Asp | Leu | Val | Leu | Met | |
| | | | 490 | | | | | 495 | | | | | 500 | | | |
| GAG | GAG | AAG | AGG | TTG | AAC | TAC | TGC | ACT | ACT | GGA | CAG | ATA | TGG | GCC | CAC | 841 |
| Glu | Glu | Lys | Arg | Leu | Asn | Tyr | Cys | Thr | Thr | Gly | Gln | Ile | Trp | Ala | His | |
| 505 | | | | | 510 | | | | | 515 | | | | | 520 | |

-continued

```
AGC AGC TAC CTG GGG GCA GTA TTC AAT CTT ACC AGT GCT GAC CAT TTA        889
Ser Ser Tyr Leu Gly Ala Val Phe Asn Leu Thr Ser Ala Asp His Leu
                525                 530                 535

TAT GTC AAC ATA TCT CAA CTC TCT CTG ATC AAT TTT GAG GAA TCT AAG        937
Tyr Val Asn Ile Ser Gln Leu Ser Leu Ile Asn Phe Glu Glu Ser Lys
                540                 545                 550

ACC TTT TTC GGC TTG TAT AAG CTT TAAAAGAAAA AGCATTTTAA AATGATCTAC       991
Thr Phe Phe Gly Leu Tyr Lys Leu
                555                 560

TATTCTTTAT CATGGGCACC AGGAATATTG TCTTGAATGA GAGTCTTCTT AAGACCTATT     1051

GAGATTAATT AAGACTACAT GAGCCACAAA GACCTCATGA CCGCAAGGTC CAACAGGTCA     1111

GCTATCCTTC ATTTTCTCGA GGTCCATGGA GTGGTCCTTA ATGCCTGCAT CATGAGCCAG     1171

ATGGAAGGAG GTCTGTGACT GAGGGACATA AAGCTTTGGG CTGCTGTGTG ACAATGCAGA     1231

GGCACAGAGA AAGAACTGTC TGATGTTAAA TGGCCAAGAG AATTTTAACC ATTGAAGAAG     1291

ACACCTTTAC ACTCACTTCC AGGGTGGGTC TACTTACTAC CTCACAGAGG CCGTTTTTGA     1351

GACATAGTTG TGGTATGAAT ATACAAGGGT GAGAAAGGAG GCTCATTTGA CTGATAAGCT     1411

AGAGACTGAA AAAAGACAG TGTCTCATTG GCACCATCTT TACTGTTACC TAATGTTTTC     1471

TGAGCCGACC TTTGATCCTA ACGGAGAAGT AAGAGGGATG TTTGAGGCAC AAATCATTCT     1531

CTACATAGCA TGCATACCTC CAGTGCAATG ATGTCTGTGT GTTTGTATGT ATGAGAGCAA     1591

ACAGATTCTA AGGAGTCATA TAAATAAAAT ATGTACATTA TGGAGTACAT ATTAGAAACC     1651

TGTTACATTT GATGCTAGAT ATCTGAATGT TTCTTGGCAA TAAACTCTAA TAGTCT         1707
```

(2) INFORMATION FOR SEQ ID NO:32:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO:32:

```
Met Gln Gln Pro Met Asn Tyr Pro Cys Pro Gln Ile Phe Trp Val Asp
 1               5                  10                  15

Ser Ser Ala Thr Ser Ser Trp Ala Pro Pro Gly Ser Val Phe Pro Cys
                20                  25                  30

Pro Ser Cys Gly Pro Arg Gly Pro Asp Gln Arg Arg Pro Pro Pro Pro
                35                  40                  45

Pro Pro Pro Val Ser Pro Leu Pro Pro Ser Gln Pro Leu Pro Leu
        50                  55                  60

Pro Pro Leu Thr Pro Leu Lys Lys Lys Asp His Asn Thr Asn Leu Trp
65                  70                  75                  80

Leu Pro Val Val Phe Phe Met Val Leu Val Ala Leu Val Gly Met Gly
                85                  90                  95

Leu Gly Met Tyr Gln Leu Phe His Leu Gln Lys Glu Leu Ala Glu Leu
                100                 105                 110

Arg Glu Phe Thr Asn Gln Ser Leu Lys Val Ser Ser Phe Glu Lys Gln
            115                 120                 125

Ile Ala Asn Pro Ser Thr Pro Ser Glu Lys Lys Glu Pro Arg Ser Val
            130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
```

```
                165                170                175
Gly Gly Leu Val Ile Asn Glu Thr Gly Leu Tyr Phe Val Tyr Ser Lys
                    180                185                190

Val Tyr Phe Arg Gly Gln Ser Cys Asn Asn Gln Pro Leu Asn His Lys
        195                200                205

Val Tyr Met Arg Asn Ser Lys Tyr Pro Glu Asp Leu Val Leu Met Glu
        210                215                220

Glu Lys Arg Leu Asn Tyr Cys Thr Thr Gly Gln Ile Trp Ala His Ser
225                230                235                240

Ser Tyr Leu Gly Ala Val Phe Asn Leu Thr Ser Ala Asp His Leu Tyr
                245                250                255

Val Asn Ile Ser Gln Leu Ser Leu Ile Asn Phe Glu Glu Ser Lys Thr
                260                265                270

Phe Phe Gly Leu Tyr Lys Leu
                275
```

(2) INFORMATION FOR SEQ ID NO:33:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(iii) HYPOTHETICAL: NO (iv) ANTI-SENSE: YES (vi) ORIGINAL SOURCE:
        (A) ORGANISM: human (xi) SEQUENCE DESCRIPTION: SEQ ID NO:33:

```
GAATCCCAAA GTGCTTCTCT TAGAGCTTAT ATAAGCCGAA AAACGTCTGA GATTCCTCAA    60
AATTGACCAG AGAGAGCTCA GATACGTTGA CATATAAATG ATCAGCACTG GTAAGATTGA   120
ACACTGCCCC CAGGTAGCTG CTGCGGGCCC ACATCTGCCC AGTAGTGCAG TAGCTCATCA   180
TCTTCCCCTC CATCATCACC AGATCCTGGG GATACTTAGA GTTCCTCATG TAGACCTTGT   240
GGCTCAGGGG CAGGTTGTTG CAAGATTGAC CCCGGAAGTA TACTTTGGAA TATACAAAGT   300
ACAGCCCAGT TTCATTGATC ACAAGGCCAC CCTTCTTATA CTTCACTCCA GAAAGCAGGA   360
CAATTCCATA GGTGTCTTCC CATTCCAGAG GCATGGACCT TGAGTTGGAC TTGCCTGTTA   420
AATGGGCCAC TTTCCTCAGC TCCTTTTTTT CAGGGGTGG ACTGGGGTGG CCTATTTGCT    480
TCTCCAAAGA TGATGCTGTG TGCATCTGGC TGGTAGACTC TCGGAGTTCT GCCAGCTCCT   540
TCTGTAGGTG GAAGAGCTGA AACATCCCCA GGCCCAATCC TACCAAGGCA ACCAGAACCA   600
TGAAAAACAT CACAAGGAGA CACAGGCCTG TGCTGTGGTT CCCTCTCTTC TTCAGGGGTG   660
GCAGCGGTAG TGGAGGCAGT GGTGGCGGCG GCGGCGGAGG TGGTAGTGGT GGCGGTGGCG   720
GTGGTGGTGG TGGCCTCCTT TGACCAGGCC TTCTGGGCAC AGAGGTTGGA CAGGGAAGAA   780
CTGTGCCTGG AGGGGCCCAG GGAGAGCTGG CACTGCTGTC CACCCAGTAG ATCTGGGGAT   840
ATGGGTAATT GAAGGGCTGC TGCATGGCAG CTGGTGAGTC AGGCCAGCCC CAGCAAACGG   900
TTTTACTTCT TCTCAGTCCT GTAG                                         924
```

(2) INFORMATION FOR SEQ ID NO:34:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "RNA"

(iii) HYPOTHETICAL: NO (iv) ANTI-SENSE: YES (vi) ORIGINAL SOURCE:
        (A) ORGANISM: human (xi) SEQUENCE DESCRIPTION: SEQ ID NO:34:

| | | | | |
|---|---|---|---|---|
| GAAUCCCAAA | GUGCUUCUCU | UAGAGCUUAU | AUAAGCCGAA | AAACGUCUGA | GAUUCCUCAA | 60 |
| AAUUGACCAG | AGAGAGCUCA | GAUACGUUGA | CAUAUAAAUG | AUCAGCACUG | GUAAGAUUGA | 120 |
| ACACUGCCCC | CAGGUAGCUG | CUGCGGGCCC | ACAUCUGCCC | AGUAGUGCAG | UAGCUCAUCA | 180 |
| UCUUCCCCUC | CAUCAUCACC | AGAUCCUGGG | GAUACUUAGA | GUUCCUCAUG | UAGACCUUGU | 240 |
| GGCUCAGGGG | CAGGUUGUUG | CAAGAUUGAC | CCCGGAAGUA | UACUUUGGAA | UAUACAAAGU | 300 |
| ACAGCCCAGU | UUCAUUGAUC | ACAAGGCCAC | CCUUCUUAUA | CUUCACUCCA | GAAAGCAGGA | 360 |
| CAAUUCCAUA | GGUGUCUUCC | CAUUCCAGAG | GCAUGGACCU | UGAGUUGGAC | UUGCCUGUUA | 420 |
| AAUGGGCCAC | UUUCCUCAGC | UCCUUUUUUU | CAGGGGUGG | ACUGGGGUGG | CCUAUUUGCU | 480 |
| UCUCCAAAGA | UGAUGCUGUG | UGCAUCUGGC | UGGUAGACUC | UCGGAGUUCU | GCCAGCUCCU | 540 |
| UCUGUAGGUG | GAAGAGCUGA | AACAUCCCCA | GGCCCAAUCC | UACCAAGGCA | ACCAGAACCA | 600 |
| UGAAAAACAU | CACAAGGAGA | CACAGGCCUG | UGCUGUGGUU | CCCUCUCUUC | UUCAGGGGUG | 660 |
| GCAGCGGUAG | UGGAGGCAGU | GGUGGCGGCG | GCGGCGGAGG | UGGUAGUGGU | GGCGGUGGCG | 720 |
| GUGGUGGUGG | UGGCCUCCUU | UGACCAGGCC | UUCGGGCAC | AGAGGUUGGA | CAGGGAAGAA | 780 |
| CUGUGCCUGG | AGGGGCCCAG | GGAGAGCUGG | CACUGCUGUC | CACCCAGUAG | AUCUGGGGAU | 840 |
| AUGGGUAAUU | GAAGGGCUGC | UGCAUGGCAG | CUGGUGAGUC | AGGCCAGCCC | CAGCAAACGG | 900 |
| UUUUACUUCU | UCUCAGUCCU | GUAG | | | | 924 |

(2) INFORMATION FOR SEQ ID NO:35:

(i) SEQUENCE CHARACTERISTICS:
        (A) LENGTH: 924 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (iv) ANTI-SENSE: NO (ix) FEATURE:
        (A) NAME/KEY: 5'UTR
        (B) LOCATION: 1..59

(ix) FEATURE:
        (A) NAME/KEY: 3'UTR
        (B) LOCATION: 906..924

(ix) FEATURE:
        (A) NAME/KEY: -
        (B) LOCATION: 1..924
        (D) OTHER INFORMATION: /note= "pBH-hFL1"

(xi) SEQUENCE DESCRIPTION: SEQ ID NO:35:

```
CTACAGGACT GAGAAGAAGT AAAACCGTTT GCTGGGCTG GCCTGACTCA CCAGCTGCCA    60

TGCAGCAGCC CTTCAATTAC CCATATCCCC AGATCTACTG GGTGGACAGC AGTGCCAGCT   120

CTCCCTGGGC CCCTCCAGGC ACAGTTCTTC CCTGTCCAAC CTCTGTGCCC AGAAGGCCTG   180

GTCAAAGGAG GCCACCACCA CCACCGCCAC CGCCACCACT ACCACCTCCG CCGCCGCCGC   240

CACCACTGCC TCCACTACCG CTGCCACCCC TGAAGAAGAG AGGGAACCAC AGCACAGGCC   300

TGTGTCTCCT TGTGATGTTT TTCATGGTTC TGGTTGCCTT GGTAGGATTG GGCCTGGGGA   360

TGTTTCAGCT CTTCCACCTA CAGAAGGAGC TGGCAGAACT CCGAGAGTCT ACCAGCCAGA   420

TGCACACAGC ATCATCTTTG GAGAAGCAAA TAGGCCACCC CAGTCCACCC CCTGAAAAAA   480

AGGAGCTGAG GAAAGTGGCC CATTTAACAG GCAAGTCCAA CTCAAGGTCC ATGCCTCTGG   540

AATGGGAAGA CACCTATGGA ATTGTCCTGC TTTCTGGAGT GAAGTATAAG AAGGGTGGCC   600

TTGTGATCAA TGAAACTGGG CTGTACTTTG TATATTCCAA AGTATACTTC CGGGGTCAAT   660

CTTGCAACAA CCTGCCCCTG AGCCACAAGG TCTACATGAG GAACTCTAAG TATCCCCAGG   720

ATCTGGTGAT GATGGAGGGG AAGATGATGA GCTACTGCAC TACTGGGCAG ATGTGGGCCC   780

GCAGCAGCTA CCTGGGGGCA GTGTTCAATC TTACCAGTGC TGATCATTTA TATGTCAACG   840

TATCTGAGCT CTCTCTGGTC AATTTTGAGG AATCTCAGAC GTTTTTCGGC TTATATAAGC   900

TCTAAGAGAA GCACTTTGGG ATTC                                          924
```

(2) INFORMATION FOR SEQ ID NO:36:

(i) SEQUENCE CHARACTERISTICS:
        (A) LENGTH: 927 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (iv) ANTI-SENSE: YES (ix) FEATURE:
        (A) NAME/KEY: 5'UTR
        (B) LOCATION: 1..32

(ix) FEATURE:
        (A) NAME/KEY: 3'UTR
        (B) LOCATION: 872..927

(xi) SEQUENCE DESCRIPTION: SEQ ID NO:36:

```
GAGAAGGAAA CCCTTTCCTG GGGCTGGGTG CCATGCAGCA GCCCATGAAT TACCCATGTC    60

CCCAGATCTT CTGGGTAGAC AGCAGTGCCA CTTCATCTTG GGCTCCTCCA GGGTCAGTTT   120

TTCCCTGTCC ATCTTGTGGG CCTAGAGGGC CGGACCAAAG GAGACCGCCA CCTCCACCAC   180

CACCTGTGTC ACCACTACCA CCGCCATCAC AACCACTCCC ACTGCCGCCA CTGACCCCTC   240

TAAAGAAGAA GGACCACAAC ACAAATCTGT GGCTACCGGT GGTATTTTTC ATGGTTCTGG   300

TGGCTCTGGT TGGAATGGGA TTAGGAATGT ATCAGCTCTT CCACCTGCAG AAGGAACTGG   360

CAGAACTCCG TGAGTTCACC AACCAAAGCC TTAAAGTATC ATCTTTTGAA AAGCAAATAG   420

CCAACCCCAG TACACCCTCT GAAAAAAAAG AGCCGAGGAG TGTGGCCCAT TAACAGGGA    480

ACCCCCACTC AAGGTCCATC CCTCTGGAAT GGGAAGACAC ATATGGAACC GCTCTGATCT   540

CTGGAGTGAA GTATAAGAAA GGTGGCCTTG TGATCAACGA AACTGGGTTG TACTTCGTGT   600

ATTCCAAAGT ATACTTCCGG GGTCAGTCTT GCAACAACCA GCCCCTAAAC CACAAGGTCT   660
```

```
ATATGAGGAA CTCTAAGTAT CCTGAGGATC TGGTGCTAAT GGAGGAGAAG AGGTTGAACT      720

ACTGCACTAC TGGACAGATA TGGGCCCACA GCAGCTACCT GGGGGCAGTA TTCAATCTTA      780

CCAGTGCTGA CCATTTATAT GTCAACATAT CTCAACTCTC TCTGATCAAT TTTGAGGAAT      840

CTAAGACCTT TTTCGGCTTG TATAAGCTTT AAAAGAAAAA GCATTTTAAA ATGATCTACT      900

ATTCTTTATC ATGGGCACCA GGAATAT                                          927
```

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "intron 4 synthetic primer"

(iii) HYPOTHETICAL: NO (iv) ANTI-SENSE: NO (xi) SEQUENCE DESCRIPTION: SEQ ID NO:37:

```
GATTTTCAAC CACTCAGTCG                                                   20
```

(2) INFORMATION FOR SEQ ID NO:38:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "intron 5 synthetic primer"

(iii) HYPOTHETICAL: NO (iv) ANTI-SENSE: YES (xi) SEQUENCE DESCRIPTION: SEQ ID NO:38:

```
ATGCGGCCGC TGGATCCTTT GTATGAAATT GAGTAAT                                37
```

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 1 synthetic
            nucleic acid"

(iii) HYPOTHETICAL: NO (iv) ANTI-SENSE: NO (xi) SEQUENCE DESCRIPTION: SEQ ID NO:39:

```
ATGCCCAAGT GACTGACATC AACT                                              24
```

(2) INFORMATION FOR SEQ ID NO:40:

(i) SEQUENCE CHARACTERISTICS:
        (A) LENGTH: 50 base pairs
        (B) TYPE: nucleic acid
        (C) STRANDEDNESS: single

```
            (D) TOPOLOGY: Not Relevant (ii) MOLECULE TYPE: other nucleic acid
            (A) DESCRIPTION: /desc = "antisense primer 1
                synthetic nucleic acid"

(iii) HYPOTHETICAL: NO (iv) ANTI-SENSE: YES (xi) SEQUENCE DESCRIPTION: SEQ ID NO:40:

GCGCGGATCC AGGAAGTGGG AAAGGATTAC CTTCCTCTTT GCACTTGGTG              50

(2) INFORMATION FOR SEQ ID NO:41:

(i) SEQUENCE CHARACTERISTICS:
            (A) LENGTH: 10 base pairs
            (B) TYPE: nucleic acid
            (C) STRANDEDNESS: Not Relevant
            (D) TOPOLOGY: Not Relevant (ii) MOLECULE TYPE: other nucleic acid
            (A) DESCRIPTION: /desc = "descriptive only"

(iii) HYPOTHETICAL: YES (ix) FEATURE:
            (A) NAME/KEY: -
            (B) LOCATION: 1..10
            (D) OTHER INFORMATION: /note= ""Kozak" sequence"

(xi) SEQUENCE DESCRIPTION: SEQ ID NO:41:

CCAGCCATGG                                                         10

(2) INFORMATION FOR SEQ ID NO:42:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "sense primer 2 synthetic
                DNA"

(iii) HYPOTHETICAL: NO (iv) ANTI-SENSE: NO (xi) SEQUENCE DESCRIPTION: SEQ ID NO:42:

AAGACCACAA GGTCCAACAG                                              20

(2) INFORMATION FOR SEQ ID NO:43:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "sense primer 3 synthetic
                DNA"

(iii) HYPOTHETICAL: NO (iv) ANTI-SENSE: NO (xi) SEQUENCE DESCRIPTION: SEQ ID NO:43:

GGTGAGAAAG GATGCTAGGT                                              20
```

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 2
            synthetic DNA"

(iii) HYPOTHETICAL: NO (iv) ANTI-SENSE: YES (xi) SEQUENCE DESCRIPTION: SEQ ID NO:44:

```
CATGGATAAG CTAGAGACTG                                         20
```

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 3
            synthetic DNA"

(iii) HYPOTHETICAL: NO (iv) ANTI-SENSE: YES (xi) SEQUENCE DESCRIPTION: SEQ ID NO:45:

```
GTACAACGCG TACATTACGG                                         20
```

(2) INFORMATION FOR SEQ ID NO:46:

(i) SEQUENCE CHARACTERISTICS:
        (A) LENGTH: 925 base pairs
        (B) TYPE: nucleic acid
        (C) STRANDEDNESS: Not Relevant
        (D) TOPOLOGY: Not Relevant (ii) MOLECULE TYPE: cDNA to rRNA (iii) HYPOTHETICAL: NO (iv) ANTI-SENSE: NO (vii) IMMEDIATE SOURCE:
        (B) CLONE: plasmid pTN24-15

(ix) FEATURE:
        (A) NAME/KEY: 5'UTR
        (B) LOCATION: 1..31

(ix) FEATURE:
        (A) NAME/KEY: 3'UTR
        (B) LOCATION: 869..925

(xi) SEQUENCE DESCRIPTION: SEQ ID NO:46:

```
AGGAGGAAAC CCTTTCCTGG GGCTGGGTGC CATGCAGCAG CCCGTGAATT ACCCATGTCC    60

CCAGATCTAC TGGGTAGACA GCAGTGCCAC TTCTCCTTGG GCTCCTCCAG GGTCAGTTTT   120

TTCTTGTCCA TCCTCTGGGC CTAGAGGGCC AGGACAAAGG AGACCACCGC CTCCACCACC   180

ACCTCCATCA CCACTACCAC CGCCTTCCCA ACCACCCCCG CTGCCTCCAC TAAGCCCTCT   240

AAAGAAGAAG GACAACATAG AGCTGTGGCT ACCGGTGATA TTTTTCATGG TGCTGGTGGC   300
```

```
TCTGGTTGGA ATGGGGTTAG GAATGTATCA ACTCTTTCAT CTACAGAAGG AACTGGCAGA    360

ACTCCGTGAG TTCACCAACC ACAGCCTTAG AGTATCATCT TTTGAAAAGC AAATAGCCAA    420

CCCCAGCACA CCCTCTGAAA CCAAAAAGCC AAGGAGTGTG GCCCACTTAA CAGGGAACCC    480

CCGCTCAAGG TCCATCCCTC TGGAATGGGA AGACACATAT GGAACTGCTT TGATCTCTGG    540

AGTGAAGTAT AAGAAAGGCG GCCTTGTGAT CAATGAGGCT GGGTTGTACT TCGTATATTC    600

CAAAGTATAC TTCCGGGGTC AGTCTTGCAA CAGCCAGCCC CTAAGCCACA AGGTCTATAT    660

GAGGAACTTT AAGTATCCTG GGGATCTGGT GCTAATGGAG GAGAAGAAGT TGAATTACTG    720

CACTACTGGC CAGATATGGG CCCACAGCAG CTACCTAGGG GCAGTATTTA ATCTTACCGT    780

TGCTGACCAT TTATATGTCA ACATATCTCA ACTCTCTCTG ATCAATTTTG AGGAATCTAA    840

GACCTTTTTT GGCTTATATA AGCTTTAAAG GAAAAAGCAT TTTAGAATGA TCTATTATTC    900

TTTATCATGG ATGCCAGGAA TATTG                                         925
```

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 4 synthetic
            DNA"

(iii) HYPOTHETICAL: NO (iv) ANTI-SENSE: NO (xi) SEQUENCE DESCRIPTION: SEQ ID NO:47:

```
AGAACTCCGT GAGTTCACCA                                                20
```

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 4
            synthetic DNA"

(iii) HYPOTHETICAL: NO (iv) ANTI-SENSE: YES (xi) SEQUENCE DESCRIPTION: SEQ ID NO:48:

```
CAATATTCCT GGCATCCATG                                                20
```

(2) INFORMATION FOR SEQ ID NO:49:

(i) SEQUENCE CHARACTERISTICS:
        (A) LENGTH: 568 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "PCR product probe 1 DNA"

(iii) HYPOTHETICAL: NO (xi) SEQUENCE DESCRIPTION: SEQ ID NO:49:

```
AGAACTCCGT GAGTTCACCA ACCACAGCCT TAGAGTATCA TCTTTTGAAA AGCAAATAGC      60

CAACCCCAGC ACACCCTCTG AAACCAAAAA GCCAAGGAGT GTGGCCCACT TAACAGGGAA     120

CCCCCGCTCA AGGTCCATCC CTCTGGAATG GGAAGACACA TATGGAACTG CTTTGATCTC     180

TGGAGTGAAG TATAAGAAAG GCGGCCTTGT GATCAATGAG GCTGGGTTGT ACTTCGTATA     240

TTCCAAAGTA TACTTCCGGG GTCAGTCTTG CAACAGCCAG CCCCTAAGCC ACAAGGTCTA     300

TATGAGGAAC TTTAAGTATC CTGGGGATCT GGTGCTAATG GAGGAGAAGA AGTTGAATTA     360

CTGCACTACT GGCCAGATAT GGGCCCACAG CAGCTACCTA GGGGCAGTAT TTAATCTTAC     420

CGTTGCTGAC CATTTATATG TCAACATATC TCAACTCTCT CTGATCAATT TTGAGGAATC     480

TAAGACCTTT TTTGGCTTAT ATAAGCTTTA AAGGAAAAAG CATTTTAGAA TGATCTATTA     540

TTCTTTATCA TGGATGCCAG GAATATTG                                       568
```

(2) INFORMATION FOR SEQ ID NO:50:

(i) SEQUENCE CHARACTERISTICS:
        (A) LENGTH: 191 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "PCR product probe 2 DNA"

(iii) HYPOTHETICAL: NO (xi) SEQUENCE DESCRIPTION: SEQ ID NO:50:

```
AGGAGGAAAC CCTTTCCTGG GGCTGGGTGC CATGCAGCAG CCCGTGAATT ACCCATGTCC      60

CCAGATCTAC TGGGTAGACA GCAGTGCCAC TTCTCCTTGG GCTCCTCCAG GGTCAGTTTT     120

TTCTTGTCCA TCCTCTGGGC CTAGAGGGCC AGGACAAAGG AGACCACCGC CTCCACCACC     180

ACCTCCATCA C                                                         191
```

(2) INFORMATION FOR SEQ ID NO:51:

(i) SEQUENCE CHARACTERISTICS:
        (A) LENGTH: 444 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "PCR product probe 3 DNA"

(ix) FEATURE:
        (A) NAME/KEY: -
        (B) LOCATION: 1..444
        (D) OTHER INFORMATION: /label= probe_3
           /note= "corresponds to residues 524-967 of SEQ. ID. NO.
           25"

(xi) SEQUENCE DESCRIPTION: SEQ ID NO:51:

```
CGCTCAAGGT CCATCCCTCT GGAATGGGAA GACACATATG GAACTGCTTT GATCTCTGGA      60

GTGAAGTATA AGAAAGGCGG CCTTGTGATC AATGAGGCTG GGTTGTACTT CGTATATTCC     120

AAAGTATACT TCCGGGGTCA GTCTTGCAAC AGCCAGCCCC TAAGCCACAA GGTCTATATG     180

AGGAACTTTA AGTATCCTGG GGATCTGGTG CTAATGGAGG AGAAGAAGTT GAATTACTGC     240

ACTACTGGCC AGATATGGGC CCACAGCAGC TACCTAGGGG CAGTATTTAA TCTTACCGTT     300

GCTGACCATT TATATGTCAA CATATCTCAA CTCTCTCTGA TCAATTTTGA GGAATCTAAG     360
```

```
ACCTTTTTTG GCTTATATAA GCTTTAAAGG AAAAAGCATT TTAGAATGAT CTATTATTCT    420

TTATCATGGA TGCCAGGAAT ATTG                                          444
```

(2) INFORMATION FOR SEQ ID NO:52:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 5 synthetic
            DNA"

(iii) HYPOTHETICAL: NO (iv) ANTI-SENSE: NO (xi) SEQUENCE DESCRIPTION: SEQ ID NO:52:

```
GCTCTAGACT ACAGGACTGA GAAGAAGT                                       28
```

(2) INFORMATION FOR SEQ ID NO:53:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 5
            synthetic DNA"

(iii) HYPOTHETICAL: NO (iv) ANTI-SENSE: YES (xi) SEQUENCE DESCRIPTION: SEQ ID NO:53:

```
GCTCTAGAAC ATTCTCGGTG CCTGTAAC                                       28
```

(2) INFORMATION FOR SEQ ID NO:54:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 6 synthetic
            DNA"

(iii) HYPOTHETICAL: NO (iv) ANTI-SENSE: YES (xi) SEQUENCE DESCRIPTION: SEQ ID NO:54:

```
GCTCTAGAGA GAAGGAAACC CTTTCCTG                                       28
```

(2) INFORMATION FOR SEQ ID NO:55:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 6
            synthetic DNA"

(iii) HYPOTHETICAL: NO (iv) ANTI-SENSE: YES (xi) SEQUENCE DESCRIPTION: SEQ ID NO:55:

GCTCTAGAAT ATTCCTGGTG CCCATGAT                                                    28

(2) INFORMATION FOR SEQ ID NO:56:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (v) FRAGMENT TYPE: internal (ix) FEATURE:
            (A) NAME/KEY: Peptide
            (B) LOCATION: 1..11
            (D) OTHER INFORMATION: /label= peptide
                /note= "peptide 1"

(xi) SEQUENCE DESCRIPTION: SEQ ID NO:56:

Leu Val Met Met Glu Gly Lys Met Met Ser Tyr
1               5                   10

(2) INFORMATION FOR SEQ ID NO:57:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (v) FRAGMENT TYPE: internal (ix) FEATURE:
            (A) NAME/KEY: Peptide
            (B) LOCATION: 1..20
            (D) OTHER INFORMATION: /label= peptide
                /note= "peptide 2"

(xi) SEQUENCE DESCRIPTION: SEQ ID NO:57:

Lys Ser Asn Ser Arg Ser Met Pro Leu Glu Trp Glu Asp Thr Tyr Gly
1               5                   10                  15

Ile Val Leu Leu
            20

(2) INFORMATION FOR SEQ ID NO:58:

(i) SEQUENCE CHARACTERISTICS:
            (A) LENGTH: 16 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (v) FRAGMENT TYPE: internal

```
    (ix) FEATURE:
         (A) NAME/KEY: Peptide
         (B) LOCATION: 1..16
         (D) OTHER INFORMATION: /label= peptide
              /note= "peptide 3"

(xi) SEQUENCE DESCRIPTION: SEQ ID NO:58:

Ser Lys Tyr Pro Gln Asp Leu Val Met Met Glu Gly Lys Met Met Ser
1               5                  10                  15

(2) INFORMATION FOR SEQ ID NO:59:

(i) SEQUENCE CHARACTERISTICS:
         (A) LENGTH: 13 amino acids
         (B) TYPE: amino acid
         (C) STRANDEDNESS: Not Relevant
         (D) TOPOLOGY: linear (ii) MOLECULE TYPE: peptide (iii) HYPOTHETICAL: NO (v) FRAGMENT TYPE: internal (ix) FEATURE:
         (A) NAME/KEY: Peptide
         (B) LOCATION: 1..13
         (D) OTHER INFORMATION: /label= peptide
              /note= "peptide 4"

(xi) SEQUENCE DESCRIPTION: SEQ ID NO:59:

Leu Ser Leu Val Asn Phe Glu Glu Ser Gln Thr Phe Phe
1               5                  10

(2) INFORMATION FOR SEQ ID NO:60:

(i) SEQUENCE CHARACTERISTICS:
         (A) LENGTH: 24 base pairs
         (B) TYPE: nucleic acid
         (C) STRANDEDNESS: single
         (D) TOPOLOGY: Not Relevant (ii) MOLECULE TYPE: other nucleic acid
         (A) DESCRIPTION: /desc = "sense primer 7 synthetic
              DNA"

(iii) HYPOTHETICAL: NO (iv) ANTI-SENSE: NO (xi) SEQUENCE DESCRIPTION: SEQ ID NO:60:

CACCTGCAGA AGGAGCTGGC AGAA                                          24

(2) INFORMATION FOR SEQ ID NO:61:

(i) SEQUENCE CHARACTERISTICS:
         (A) LENGTH: 33 base pairs
         (B) TYPE: nucleic acid
         (C) STRANDEDNESS: single
         (D) TOPOLOGY: Not Relevant (ii) MOLECULE TYPE: other nucleic acid
         (A) DESCRIPTION: /desc = "antisense primer 7
              synthetic DNA"

(iii) HYPOTHETICAL: NO (iv) ANTI-SENSE: YES (xi) SEQUENCE DESCRIPTION: SEQ ID NO:61:

AATAAGCTTG GTACCCTATT AGAGCTTATA TAA                                33
```

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 8 synthetic DNA"

(iii) HYPOTHETICAL: NO (iv) ANTI-SENSE: NO (xi) SEQUENCE DESCRIPTION: SEQ ID NO:62:

TGCGAATTCA CCATGCTGGG CATCTGG                    27

(2) INFORMATION FOR SEQ ID NO:63:

(i) SEQUENCE CHARACTERISTICS:
        (A) LENGTH: 36 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 8 synthetic DNA"

(iii) HYPOTHETICAL: NO (iv) ANTI-SENSE: YES (xi) SEQUENCE DESCRIPTION: SEQ ID NO:63:

AACCTGCAGG TGGAAGAGCT GAGCAACAGA CGTAAG          36

(2) INFORMATION FOR SEQ ID NO:64:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..15
        (D) OTHER INFORMATION: /label= peptide
            /note= "human Fas ligand"

(xi) SEQUENCE DESCRIPTION: SEQ ID NO:64:

Pro Ser Pro Pro Pro Glu Lys Lys Glu Leu Arg Lys Val Ala His
1           5               10            15

(2) INFORMATION FOR SEQ ID NO:65:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "PS type S20"

(iv) ANTI-SENSE: NO (xi) SEQUENCE DESCRIPTION: SEQ ID NO:65:

TAAAACCGTT TGCTGGGGCT GG                                                    22

(2) INFORMATION FOR SEQ ID NO:66:

(i) SEQUENCE CHARACTERISTICS:
                (A) LENGTH: 22 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "PS type A41"

(iv) ANTI-SENSE: YES (xi) SEQUENCE DESCRIPTION: SEQ ID NO:66:

CCAGCCCCAG CAAACGGTTT TA                                                    22

(2) INFORMATION FOR SEQ ID NO:67:

(i) SEQUENCE CHARACTERISTICS:
                (A) LENGTH: 20 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "PS type S50"

(iv) ANTI-SENSE: NO (xi) SEQUENCE DESCRIPTION: SEQ ID NO:67:

ACCAGCTGCC ATGCAGCAGC                                                       20

(2) INFORMATION FOR SEQ ID NO:68:

(i) SEQUENCE CHARACTERISTICS:
                (A) LENGTH: 20 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "PS type A69"

(iv) ANTI-SENSE: YES (xi) SEQUENCE DESCRIPTION: SEQ ID NO:68:

GCTGCTGCAT GGCAGCTGGT                                                       20

(2) INFORMATION FOR SEQ ID NO:69:

(i) SEQUENCE CHARACTERISTICS:
                (A) LENGTH: 22 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "PS type S163"

(iv) ANTI-SENSE: NO (xi) SEQUENCE DESCRIPTION: SEQ ID NO:69:

CTGTGCCCAG AAGGCCTGGT CA                                                    22

(2) INFORMATION FOR SEQ ID NO:70:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "PS type A184"

(iv) ANTI-SENSE: YES (xi) SEQUENCE DESCRIPTION: SEQ ID NO:70:

TGACCAGGCC TTCTGGGCAC AG                                            22

(2) INFORMATION FOR SEQ ID NO:71:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "PS type s338"

(iv) ANTI-SENSE: NO (xi) SEQUENCE DESCRIPTION: SEQ ID NO:71:

CTTGGTAGGA TTGGGCCT                                                 18

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "PS type A355"

(iv) ANTI-SENSE: YES (xi) SEQUENCE DESCRIPTION: SEQ ID NO:72:

AGGCCCAATC CTACCAAG                                                 18

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "PS type S484"

(iv) ANTI-SENSE: NO (xi) SEQUENCE DESCRIPTION: SEQ ID NO:73:

AGCTGAGGAA AGTGGCCCAT TT                                            22

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single (D) TOPOLOGY: Not Relevant (ii) MOLECULE TYPE: other nucleic acid
            (A) DESCRIPTION: /desc = "PS type A505"

(iv) ANTI-SENSE: YES (xi) SEQUENCE DESCRIPTION: SEQ ID NO:74:

AAATGGGCCA CTTTCCTCAG CT                                                    22

(2) INFORMATION FOR SEQ ID NO:75:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "PS type S714"

(iv) ANTI-SENSE: NO (xi) SEQUENCE DESCRIPTION: SEQ ID NO:75:

CCCCAGGATC TGGTGATGAT                                                       20

(2) INFORMATION FOR SEQ ID NO:76:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "PS type A733"

(iv) ANTI-SENSE: YES (xi) SEQUENCE DESCRIPTION: SEQ ID NO:76:

ATCATCACCA GATCCTGGGG                                                       20

(2) INFORMATION FOR SEQ ID NO:77:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "PS type S905"

(iv) ANTI-SENSE: NO (xi) SEQUENCE DESCRIPTION: SEQ ID NO:77:

AGAGAAGCAC TTTGGGATTC                                                       20

(2) INFORMATION FOR SEQ ID NO:78:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "PS type A924"

(iv) ANTI-SENSE: YES (xi) SEQUENCE DESCRIPTION: SEQ ID NO:78:

GAATCCCAAA GTGCTTCTCT                                                       20

(2) INFORMATION FOR SEQ ID NO:79:

(i) SEQUENCE CHARACTERISTICS:
        (A) LENGTH: 141 amino acids
        (B) TYPE: amino acid
        (C) STRANDEDNESS: Not Relevant
        (D) TOPOLOGY: Not Relevant (ii) MOLECULE TYPE: protein (v) FRAGMENT TYPE: internal (ix) FEATURE:
        (A) NAME/KEY: Protein
        (B) LOCATION: 1..141
        (D) OTHER INFORMATION: /note= "polypeptide ND38"

(xi) SEQUENCE DESCRIPTION: SEQ ID NO:79:

Lys Glu Leu Arg Lys Val Ala His Leu Thr Gly Lys Ser Asn Ser Arg
1               5                   10                  15

Ser Met Pro Leu Glu Trp Glu Asp Thr Tyr Gly Ile Val Leu Leu Ser
                20                  25                  30

Gly Val Lys Tyr Lys Lys Gly Gly Leu Val Ile Asn Glu Thr Gly Leu
            35                  40                  45

Tyr Phe Val Tyr Ser Lys Val Tyr Phe Arg Gly Gln Ser Cys Asn Asn
    50                  55                  60

Leu Pro Leu Ser His Lys Val Tyr Met Arg Asn Ser Lys Tyr Pro Gln
65                  70                  75                  80

Asp Leu Val Met Met Glu Gly Lys Met Met Ser Tyr Cys Thr Thr Gly
                85                  90                  95

Gln Met Trp Ala Arg Ser Ser Tyr Leu Gly Ala Val Phe Asn Leu Thr
                100                 105                 110

Ser Ala Asp His Leu Tyr Val Asn Val Ser Glu Leu Ser Leu Val Asn
            115                 120                 125

Phe Glu Glu Ser Gln Thr Phe Phe Gly Leu Tyr Lys Leu
        130                 135                 140

(2) INFORMATION FOR SEQ ID NO:80:

(i) SEQUENCE CHARACTERISTICS:
        (A) LENGTH: 139 amino acids
        (B) TYPE: amino acid
        (C) STRANDEDNESS: Not Relevant
        (D) TOPOLOGY: Not Relevant (ii) MOLECULE TYPE: protein (v) FRAGMENT TYPE: internal (ix) FEATURE:
        (A) NAME/KEY: Protein
        (B) LOCATION: 1..139
        (D) OTHER INFORMATION: /note= "polypeptide ND40"

(xi) SEQUENCE DESCRIPTION: SEQ ID NO:80:

Leu Arg Lys Val Ala His Leu Thr Gly Lys Ser Asn Ser Arg Ser Met
1               5                   10                  15

Pro Leu Glu Trp Glu Asp Thr Tyr Gly Ile Val Leu Leu Ser Gly Val
                20                  25                  30

Lys Tyr Lys Lys Gly Gly Leu Val Ile Asn Glu Thr Gly Leu Tyr Phe
            35                  40                  45

Val Tyr Ser Lys Val Tyr Phe Arg Gly Gln Ser Cys Asn Asn Leu Pro
    50                  55                  60

Leu Ser His Lys Val Tyr Met Arg Asn Ser Lys Tyr Pro Gln Asp Leu
65                  70                  75                  80

Val Met Met Glu Gly Lys Met Met Ser Tyr Cys Thr Thr Gly Gln Met
                85                  90                  95

Trp Ala Arg Ser Ser Tyr Leu Gly Ala Val Phe Asn Leu Thr Ser Ala
                100                 105                 110

Asp His Leu Tyr Val Asn Val Ser Glu Leu Ser Leu Val Asn Phe Glu
            115                 120                 125

Glu Ser Gln Thr Phe Phe Gly Leu Tyr Lys Leu
    130                 135

(2) INFORMATION FOR SEQ ID NO:81:

(i) SEQUENCE CHARACTERISTICS:
        (A) LENGTH: 138 amino acids
        (B) TYPE: amino acid
        (C) STRANDEDNESS: Not Relevant
        (D) TOPOLOGY: Not Relevant (ii) MOLECULE TYPE: protein (v) FRAGMENT TYPE: internal (ix) FEATURE:
        (A) NAME/KEY: Protein
        (B) LOCATION: 1..138
        (D) OTHER INFORMATION: /note= "polypeptide ND41"

(xi) SEQUENCE DESCRIPTION: SEQ ID NO:81:

Arg Lys Val Ala His Leu Thr Gly Lys Ser Asn Ser Arg Ser Met Pro
1               5                   10                  15

Leu Glu Trp Glu Asp Thr Tyr Gly Ile Val Leu Leu Ser Gly Val Lys
                20                  25                  30

Tyr Lys Lys Gly Gly Leu Val Ile Asn Glu Thr Gly Leu Tyr Phe Val
            35                  40                  45

Tyr Ser Lys Val Tyr Phe Arg Gly Gln Ser Cys Asn Asn Leu Pro Leu
    50                  55                  60

Ser His Lys Val Tyr Met Arg Asn Ser Lys Tyr Pro Gln Asp Leu Val
65                  70                  75                  80

Met Met Glu Gly Lys Met Met Ser Tyr Cys Thr Thr Gly Gln Met Trp
                85                  90                  95

Ala Arg Ser Ser Tyr Leu Gly Ala Val Phe Asn Leu Thr Ser Ala Asp
                100                 105                 110

His Leu Tyr Val Asn Val Ser Glu Leu Ser Leu Val Asn Phe Glu Glu
            115                 120                 125

Ser Gln Thr Phe Phe Gly Leu Tyr Lys Leu
    130                 135

(2) INFORMATION FOR SEQ ID NO:82:

(i) SEQUENCE CHARACTERISTICS:
        (A) LENGTH: 137 amino acids
        (B) TYPE: amino acid
        (C) STRANDEDNESS: Not Relevant
        (D) TOPOLOGY: Not Relevant (ii) MOLECULE TYPE: protein (v) FRAGMENT TYPE: internal

```
    (ix) FEATURE:
         (A) NAME/KEY: Protein
         (B) LOCATION: 1..137
         (D) OTHER INFORMATION: /note= "polypeptide ND42"

(xi) SEQUENCE DESCRIPTION: SEQ ID NO:82:

Lys Val Ala His Leu Thr Gly Lys Ser Asn Ser Arg Ser Met Pro Leu
1               5                  10                 15

Glu Trp Glu Asp Thr Tyr Gly Ile Val Leu Leu Ser Gly Val Lys Tyr
            20                  25                 30

Lys Lys Gly Gly Leu Val Ile Asn Glu Thr Gly Leu Tyr Phe Val Tyr
                35                  40                 45

Ser Lys Val Tyr Phe Arg Gly Gln Ser Cys Asn Asn Leu Pro Leu Ser
    50                  55                 60

His Lys Val Tyr Met Arg Asn Ser Lys Tyr Pro Gln Asp Leu Val Met
65                  70                 75                 80

Met Glu Gly Lys Met Met Ser Tyr Cys Thr Thr Gly Gln Met Trp Ala
                85                  90                 95

Arg Ser Ser Tyr Leu Gly Ala Val Phe Asn Leu Thr Ser Ala Asp His
                100                 105                110

Leu Tyr Val Asn Val Ser Glu Leu Ser Leu Val Asn Phe Glu Glu Ser
            115                 120                125

Gln Thr Phe Phe Gly Leu Tyr Lys Leu
            130                 135

(2) INFORMATION FOR SEQ ID NO:83:

(i) SEQUENCE CHARACTERISTICS:
        (A) LENGTH: 136 amino acids
        (B) TYPE: amino acid
        (C) STRANDEDNESS: Not Relevant
        (D) TOPOLOGY: Not Relevant (ii) MOLECULE TYPE: protein (ix) FEATURE:
         (A) NAME/KEY: Protein
         (B) LOCATION: 1..136
         (D) OTHER INFORMATION: /note= "polypeptide ND43"

(xi) SEQUENCE DESCRIPTION: SEQ ID NO:83:

Val Ala His Leu Thr Gly Lys Ser Asn Ser Arg Ser Met Pro Leu Glu
1               5                  10                 15

Trp Glu Asp Thr Tyr Gly Ile Val Leu Leu Ser Gly Val Lys Tyr Lys
            20                  25                 30

Lys Gly Gly Leu Val Ile Asn Glu Thr Gly Leu Tyr Phe Val Tyr Ser
            35                  40                 45

Lys Val Tyr Phe Arg Gly Gln Ser Cys Asn Asn Leu Pro Leu Ser His
    50                  55                 60

Lys Val Tyr Met Arg Asn Ser Lys Tyr Pro Gln Asp Leu Val Met Met
65                  70                 75                 80

Glu Gly Lys Met Met Ser Tyr Cys Thr Thr Gly Gln Met Trp Ala Arg
            85                  90                 95

Ser Ser Tyr Leu Gly Ala Val Phe Asn Leu Thr Ser Ala Asp His Leu
            100                 105                110

Tyr Val Asn Val Ser Glu Leu Ser Leu Val Asn Phe Glu Glu Ser Gln
        115                 120                125

Thr Phe Phe Gly Leu Tyr Lys Leu
        130                 135
```

(2) INFORMATION FOR SEQ ID NO:84:

(i) SEQUENCE CHARACTERISTICS:
        (A) LENGTH: 178 amino acids
        (B) TYPE: amino acid
        (C) STRANDEDNESS: Not Relevant
        (D) TOPOLOGY: Not Relevant (ii) MOLECULE TYPE: protein (v) FRAGMENT TYPE: internal (ix) FEATURE:
        (A) NAME/KEY: Protein
        (B) LOCATION: 1..178
        (D) OTHER INFORMATION: /note= "polypeptide CD179"

(xi) SEQUENCE DESCRIPTION: SEQ ID NO:84:

```
Gln Leu Phe His Leu Gln Lys Glu Leu Ala Glu Leu Arg Glu Ser Thr
  1               5                  10                  15

Ser Gln Met His Thr Ala Ser Ser Leu Glu Lys Gln Ile Gly His Pro
             20                  25                  30

Ser Pro Pro Glu Lys Lys Glu Leu Arg Lys Val Ala His Leu Thr
         35                  40                  45

Gly Lys Ser Asn Ser Arg Ser Met Pro Leu Glu Trp Glu Asp Thr Tyr
 50                  55                  60

Gly Ile Val Leu Leu Ser Gly Val Lys Tyr Lys Lys Gly Leu Val
 65                  70                  75                  80

Ile Asn Glu Thr Gly Leu Tyr Phe Val Tyr Ser Lys Val Tyr Phe Arg
                 85                  90                  95

Gly Gln Ser Cys Asn Asn Leu Pro Leu Ser His Lys Val Tyr Met Arg
                100                 105                 110

Asn Ser Lys Tyr Pro Gln Asp Leu Val Met Met Glu Gly Lys Met Met
                115                 120                 125

Ser Tyr Cys Thr Thr Gly Gln Met Trp Ala Arg Ser Ser Tyr Leu Gly
            130                 135                 140

Ala Val Phe Asn Leu Thr Ser Ala Asp His Leu Tyr Val Asn Val Ser
145                 150                 155                 160

Glu Leu Ser Leu Val Asn Phe Glu Glu Ser Gln Thr Phe Phe Gly Leu
                165                 170                 175

Tyr Lys
```

(2) INFORMATION FOR SEQ ID NO:85:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense oligonucleotide 9"

(iv) ANTI-SENSE: YES (xi) SEQUENCE DESCRIPTION: SEQ ID NO:85:

CTTCTGCAGG TGGAAGAGCT GAGCGACACT AGTCAGAACC AGAGG           45

(2) INFORMATION FOR SEQ ID NO:86:

(i) SEQUENCE CHARACTERISTICS:
        (A) LENGTH: 45 base pairs

```
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense oligonucleotide 9"

(iv) ANTI-SENSE: NO (xi) SEQUENCE DESCRIPTION: SEQ ID NO:86:

AATTCACCAT GCTGGGCATC TGGACCCTCC TACCTCTGGT TCTGA             45

(2) INFORMATION FOR SEQ ID NO:87:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense oligonucleotide
            10"

(iv) ANTI-SENSE: YES (xi) SEQUENCE DESCRIPTION: SEQ ID NO:87:

CTAGTCAGAA CCAGAGGTAG GAGGGTCCAG ATGCCCAGCA TGGTG             45

(2) INFORMATION FOR SEQ ID NO:88:

(i) SEQUENCE CHARACTERISTICS:
        (A) LENGTH: 30 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 11"

(iv) ANTI-SENSE: NO (xi) SEQUENCE DESCRIPTION: SEQ ID NO:88:

CTGACTAGTG TCGCTAAGGA GCTGAGGAAA                              30

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 11"

(iv) ANTI-SENSE: YES (xi) SEQUENCE DESCRIPTION: SEQ ID NO:89:

TAAGCCGAAA AACGTCTGAG                                         20

(2) INFORMATION FOR SEQ ID NO:90:

(i) SEQUENCE CHARACTERISTICS:
        (A) LENGTH: 30 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 12"
```

(iv) ANTI-SENSE: NO (xi) SEQUENCE DESCRIPTION: SEQ ID NO:90:

CTGACTAGTG TCGCTCTGAG GAAAGTGGCC                                          30

(2) INFORMATION FOR SEQ ID NO:91:

(i) SEQUENCE CHARACTERISTICS:
            (A) LENGTH: 30 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "sense primer 13"

(iv) ANTI-SENSE: NO (xi) SEQUENCE DESCRIPTION: SEQ ID NO:91:

CTGACTAGTG TCGCTAGGAA AGTGGCCCAT                                          30

(2) INFORMATION FOR SEQ ID NO:92:

(i) SEQUENCE CHARACTERISTICS:
            (A) LENGTH: 30 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "sense primer 14"

(iv) ANTI-SENSE: NO (xi) SEQUENCE DESCRIPTION: SEQ ID NO:92:

CTGACTAGTG TCGCTAAAGT GGCCCATTTA                                          30

(2) INFORMATION FOR SEQ ID NO:93:

(i) SEQUENCE CHARACTERISTICS:
            (A) LENGTH: 30 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "sense primer 15"

(iv) ANTI-SENSE: NO (xi) SEQUENCE DESCRIPTION: SEQ ID NO:93:

CTGACTAGTG TCGCTGTGGC CCATTTAACA                                          30

(2) INFORMATION FOR SEQ ID NO:94:

(i) SEQUENCE CHARACTERISTICS:
            (A) LENGTH: 27 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "antisense primer 16"

(iv) ANTI-SENSE: YES (xi) SEQUENCE DESCRIPTION: SEQ ID NO:94:

CTTGGTACCC TATTACTTAT ATAAGCC                                             27

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 16"

(iv) ANTI-SENSE: NO (xi) SEQUENCE DESCRIPTION: SEQ ID NO:95:

GAGCTACTGC ACTACTGGGC                                          20

(2) INFORMATION FOR SEQ ID NO:96:

(i) SEQUENCE CHARACTERISTICS:
        (A) LENGTH: 39 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 17"

(iv) ANTI-SENSE: YES (xi) SEQUENCE DESCRIPTION: SEQ ID NO:96:

CGCGGATCCG GTACCTTTTT TGGTAACCGG GGTAAACAG                     39

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 17"

(iv) ANTI-SENSE: NO (xi) SEQUENCE DESCRIPTION: SEQ ID NO:97:

CGCAAGTTCA CGTAAAAAGC                                          20

(2) INFORMATION FOR SEQ ID NO:98:

(i) SEQUENCE CHARACTERISTICS:
        (A) LENGTH: 46 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 18"

(iv) ANTI-SENSE: NO (xi) SEQUENCE DESCRIPTION: SEQ ID NO:98:

TTGAAGCTTA AAAAGGGTA TAAAATAAAA TGCAGCTCTT CCACCT              46

(2) INFORMATION FOR SEQ ID NO:99:

(i) SEQUENCE CHARACTERISTICS:
        (A) LENGTH: 29 base pairs
        (B) TYPE: nucleic acid
        (C) STRANDEDNESS: single (D) TOPOLOGY: Not Relevant (ii) MOLECULE TYPE: other nucleic acid
        (A) DESCRIPTION: /desc = "antisense primer 18"

(iv) ANTI-SENSE: YES (xi) SEQUENCE DESCRIPTION: SEQ ID NO:99:

AAGGTCGACT ATTAGAGCTT ATATAAGCC                                   29

(2) INFORMATION FOR SEQ ID NO:100:

(i) SEQUENCE CHARACTERISTICS:
        (A) LENGTH: 30 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 19"

(iv) ANTI-SENSE: NO (xi) SEQUENCE DESCRIPTION: SEQ ID NO:100:

GGGGGTTACC AAAGCCCAGC TCTTCCACCT                                  30

(2) INFORMATION FOR SEQ ID NO:101:

(i) SEQUENCE CHARACTERISTICS:
        (A) LENGTH: 25 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "sense primer 20"

(iv) ANTI-SENSE: NO (xi) SEQUENCE DESCRIPTION: SEQ ID NO:101:

CCCGGTTACC AAAGCCAAGG AGCTG                                       25

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "antisense primer 20"

(iv) ANTI-SENSE: YES (xi) SEQUENCE DESCRIPTION: SEQ ID NO:102:

TAAGCCGAAA AACGTCTGAG                                             20

(2) INFORMATION FOR SEQ ID NO:103:

(i) SEQUENCE CHARACTERISTICS:
        (A) LENGTH: 927 base pairs
        (B) TYPE: nucleic acid
        (C) STRANDEDNESS: Not Relevant
        (D) TOPOLOGY: Not Relevant (ii) MOLECULE TYPE: cDNA to rRNA (iii) HYPOTHETICAL: NO (vi) ORIGINAL SOURCE:

(A) ORGANISM: mouse
            (D) DEVELOPMENTAL STAGE: rearranged (ix) FEATURE:
            (A) NAME/KEY: mutation
            (B) LOCATION: replace(849, "")
            (D) OTHER INFORMATION: /note= "T residue 849 in SEQ. ID.
                36 is C in the present sequence"

(xi) SEQUENCE DESCRIPTION: SEQ ID NO:103:

```
GAGAAGGAAA CCCTTTCCTG GGGCTGGGTG CCATGCAGCA GCCCATGAAT TACCCATGTC        60

CCCAGATCTT CTGGGTAGAC AGCAGTGCCA CTTCATCTTG GGCTCCTCCA GGGTCAGTTT       120

TTCCCTGTCC ATCTTGTGGG CCTAGAGGGC CGGACCAAAG GAGACCGCCA CCTCCACCAC       180

CACCTGTGTC ACCACTACCA CCGCCATCAC AACCACTCCC ACTGCCGCCA CTGACCCCTC       240

TAAAGAAGAA GGACCACAAC ACAAATCTGT GGCTACCGGT GGTATTTTTC ATGGTTCTGG       300

TGGCTCTGGT TGGAATGGGA TTAGGAATGT ATCAGCTCTT CCACCTGCAG AAGGAACTGG       360

CAGAACTCCG TGAGTTCACC AACCAAAGCC TTAAAGTATC ATCTTTTGAA AAGCAAATAG       420

CCAACCCCAG TACACCCTCT GAAAAAAAAG AGCCGAGGAG TGTGGCCCAT TTAACAGGGA       480

ACCCCCACTC AAGGTCCATC CCTCTGGAAT GGGAAGACAC ATATGGAACC GCTCTGATCT       540

CTGGAGTGAA GTATAAGAAA GGTGGCCTTG TGATCAACGA AACTGGGTTG TACTTCGTGT       600

ATTCCAAAGT ATACTTCCGG GGTCAGTCTT GCAACAACCA GCCCCTAAAC CACAAGGTCT       660

ATATGAGGAA CTCTAAGTAT CCTGAGGATC TGGTGCTAAT GGAGGAGAAG AGGTTGAACT       720

ACTGCACTAC TGGACAGATA TGGGCCCACA GCAGCTACCT GGGGGCAGTA TTCAATCTTA       780

CCAGTGCTGA CCATTTATAT GTCAACATAT CTCAACTCTC TCTGATCAAT TTTGAGGAAT       840

CTAAGACCCT TTTCGGCTTG TATAAGCTTT AAAAGAAAAA GCATTTTAAA ATGATCTACT       900

ATTCTTTATC ATGGGCACCA GGAATAT                                          927
```

DNA ENCODING FAS LIGAND

FIELD OF THE INVENTION

This invention relates to a Fas ligand, a part of the Fas ligand and a novel DNA fragment which encodes the Fas ligand, which may be utilized in the field of medicines. This invention also relates to an antibody which can be used for detecting of the Fas ligand, which may be utilized in the field of diagnostic reagents. This invention also relates to a recombinant DNA molecule which contains the novel DNA fragment, a transformant, a process for purifying the novel protein and a process for producing of the novel protein. This invention also relates to an antisense oligonucleotide.

BACKGROUND OF THE INVENTION

Based on the morphology of dying cells, Cell death is generally divided into two categories, necrosis and apoptosis. In the necrotic cell death, degradation of cell membrane and release of cellular contents into extracellular matrix are observed. On the other hand, in the apoptotic cell death, fragmentation of chromosomal DNA and concentration of nuclei are observed while the degradation of the cell membrane and the release of the cellular contents as observed in the necrosis are not observed. Apoptosis has been conceived to be a form of programmed cell death. For example, phenomena of deletion of unnecessary cells and organs in the course of ontogenesis are considered to be caused by the apoptosis of cells. Another phenomenon that is considered to be the apoptosis is the cell death which occurs when virus-infected cells and tumor cells are attacked and removed by cytotoxic T cells (CTL), natural killer cells (NK cells), TNF-α, TNF-β and the like. As described above, apoptosis is one of the physiological phenomena which have recently attracted special attention, and studies are being conducted by many researchers with the aim of elucidating the function of the apoptosis as well as its physiological meaning and relation to diseases.

Fas antibody has been known as a substance which can induce the apoptosis of cells. Fas antibody is a monoclonal antibody obtained by immunizing a mouse with human fibloblast (Yonehara S. et al., *J. Exp. Med.*, vol. 169, pp. 1747–1756, 1989). Since Fas antibody has been obtained by the immunization of a mouse with cells, the type of molecules recognized by Fas antibody and the transfer mechanism of apoptosis signal to the cells were not revealed for a long time. Recently, however, Itoh N. et al. have succeeded in cloning the gene of the molecule (Fas antigen) which is specifically-recognized by the Fas antibody (*Cell*, vol. 66, pp. 233–243, 1991). It was then found that the Fas antigen is a cell membrane protein having a size of about 45 kD, and its amino acid sequence analysis has revealed that the Fas antigen belongs to the family of TNF receptors. In addition, a mouse Fas antigen gene was cloned (Watanabe-Fukunaga R. et al., *J. Immunol.*, vol. 148, pp. 1274–1279, 1992), and the mRNA for Fas antigen was confirmed to be expressed in thymus, liver, lung, heart and ovary of the mouse.

After the cloning of the Fas antigen gene, a number of studies have been conducted and reported on the relationship between the apoptosis mediated by Fas antigen and various diseases.

Kobayashi N. et al. have reported that expression of Fas antigen on T cell membrane is induced upon infection with AIDS virus, suggesting a possibility that the apoptosis of T cells found in AIDS is a Fas antigen-mediated phenomenon (*Nikkei Science*, vol. 6, pp. 34–41, 1993).

Ogasawara J. et al. have observed that a phenomenon similar to fulminant hepatitis occurs upon administration of Fas antibody to a mouse, and suggested a possibility of the occurrence of a Fas antigen-mediated apoptosis in the inflammatory lesion of the fulminant hepatitis or the like (*Nature*, vol. 364, pp. 806–809, 1993). Hiramatsu N. et al. have reported that, in a patient suffering chronic type C hepatitis, Fas antigen is frequently expressed in the inflammatory lesion of the liver where leukocyte infiltration is observed (Hepatology, vol. 19, pp. 1354–1359, 1994).

In addition, Watanabe-Fukunaga R. et al. have confirmed that a mutation in the Fas antigen gene is present in the lpr mouse, which is one of autoimmune disease model animals and that the cells expressing such mutation in the Fas antigen gene do not undergo the apoptosis (*Nature*, vol. 356, pp. 314–317, 1992). Watanabe-Fukunaga R. et al. have estimated that autoimmune disease-like symptoms are generated by the autoreactive T cells remaining in the body, that should have been removed from the body through the apoptosis.

As described above, a number of studies have been reported on the relation between the Fas antigen and diseases. An unsolved question is whether or not there is a molecule (Fas ligand) that binds to the Fas antigen on the cell surface to induce the cell apoptosis, namely, a molecule that acts in a manner similar to the above described Fas antibody.

Watanabe-Fukunaga R. et al. have presumed that, in a gld mouse which exhibits autoimmune disease-like symptoms, an abnormality should be present in a biological molecule which binds to Fas antigen, as in the case of the lpr mouse.

In addition, Rouvier E. et al. have reported that a certain type of T cells show a specific cytotoxic action on the cells expressing Fas antigen (*J. Exp. Med.*, vol. 177, pp. 195–200, 1993). More illustrating, they have shown that a $Ca^{2+}$-independent cytotoxic action by mouse peripheral blood lymphocytes (PBL) and PC60-d10S cells, the latter being a hybridoma of mouse CTL and rat T-lymphoma cells, is observed only for the Fas antigen-expressing cells. They have also suggested the possibility that such lymphocytes, especially T cells, could recognize the Fas antigen or certain Fas antigen-related molecules, and the possibility that these cells might express to Fas ligand.

Though the possibility of the presence of a Fas ligand has been suggested by the researchers as described above, its specific nature is not yet revealed.

It is important to isolate the Fas ligand in order to elucidate mechanism of the Fas antigen-mediated apoptosis and reveal relationship between the Fas antigen-mediated apoptosis and diseases more clearly. In consequence, confirmation of the presence of the Fas ligand and revelation of its true nature have been called for in various fields including the medicine.

A primary object of the present invention is to provide the field of medical care with a Fas ligand and its gene and a means for artificially regulating apoptosis generated in the body.

As described in the foregoing, the diseases considered to be related to the Fas antigen-mediated apoptosis include those which are caused by the Fas antigen-mediated apoptosis, and, those which are caused by the absence of the Fas antigen-mediated apoptosis. For example, it is estimated that death of hepatocytes and the subsequent reduction in the liver function in the case of hepatitis and decrease in the number of HIV-infected T cells and the subsequent reduction in the immunological function in the case of AIDS would be improved by inhibiting the apoptosis. In the case of certain autoimmune diseases, on the other hand, the symptoms are estimated to be improved by allowing the Fas antigen-mediated apoptosis to occur normally and by enhancing the removal of autoantigen reactive T cells. With regard to the treatment of AIDS in its early stage, induction of the apoptosis of the cells infected with HIV and their removal from the body would be effective. Morimoto H. et al. have reported that the Fas antigen-mediated apoptosis induced in cancer cells could synergistically enhance carcinostatic effects of adriamycin and cisplatin (Cancer Res., vol. 53, pp. 2591–2596, 1993). A substance capable of binding to Fas antigen to induce apoptosis should be useful in the treatment of cancers.

Such a treatment which is based on the principle of artificially regulating the Fas antigen-mediated apoptosis can be established only after the identification of the Fas ligand. In other words, artificial enhancement of the apoptosis in the living body would be enabled when the Fas ligand is specified.

In order to use the Fas ligand or a part of the ligand in medical treatments and researches, it would be necessary to produce the Fas ligand protein in a large scale and at a high purity. Cloning of the gene coding for such protein will enable the production of the protein by means of genetic engineering techniques, and the thus produced protein can be used for the main effective component in therapeutic drugs and in the production of antibodies. In addition, the gene itself could be used in gene therapy and development of antisense drugs, as well as for the preparation of model animals, such as transgenic mice, of apoptosis-related diseases.

SUMMARY OF THE INVENTION

The inventors of the present invention have conducted intensive studies with the aim of isolating -Fas ligand, taking note of the aforementioned PC60-d10S cells. PC60-d10S is a hybridoma of mouse CTL and rat T-lymphoma, which induces apoptosis only in Fas antigen-expressing cells when stimulated with PMA (phorbol myristate acetate) and ionomycin. As a result of intensive studies, the present inventors have succeeded in obtaining a cell population, PC60-d10S-2, which shows higher cytotoxicity without stimulation and is useful for the cloning of the Fas ligand gene. Thereafter, the rat Fas ligand gene was cloned making use of this cell population. Also, th e present inventors have conducted intensive studies with the aim of isolating a human Fas ligand suitable for use in pharmaceutical drugs and the like and succeeded in obtaining a gene which encodes human Fas ligand, as well as a gene which encodes mouse Fas ligand. It was confirmed thereafter that these genes have similar sequences having a common partial sequence. The inventors of the present invention have also identified the part of the sequence that should be necessary in exhibiting Fas ligand function. The present invention has been accomplished on the basis of these efforts.

According to first aspect of the present invention, there is provided a polypeptide which is a Fas ligand.

According to second aspect of the present invention, there is provided a fragment of the Fas ligand polypeptide according to the first aspect of the invention.

According to third aspect of the present invention, there is provided a DNA fragment containing a nucleotide sequence coding for the polypeptide according to the first or second aspect of the invention.

According to fourth aspect of the present invention, there is provided a recombinant DNA molecule including the DNA according to the third aspect of the invention.

According to fifth aspect of the present invention, there is provided a transformant which has been transformed with the DNA fragment according to the third aspect of the invention.

According to sixth aspect of the present invention, there is provided a transformant which has been transformed with the recombinant DNA molecule according to the fourth aspect of the invention.

According to seventh aspect of the present invention, there is provided a process for producing the polypeptide according to the first or second aspect of the invention wherein the transformant according to the fifth or sixth aspect of the invention is used.

According to eighth aspect of the present invention, there is provided a process for purifying the polypeptide of the first or second aspect of the invention.

According to ninth aspect of the present invention, there is provided an antibody capable of recognizing the polypeptide according to the first or second aspect of the invention.

According to tenth aspect of the present invention, there is provided an oligonucleotide or a derivative thereof which includes a nucleotide sequence which is complementary to a part of a Fas ligand gene or a part of mRNA for the Fas ligand.

According to eleventh aspect of the present invention, there is provided a process for screening a Fas ligand-related substance wherein the polypeptide according to the first or second aspect of the invention, or a transformant capable of expressing the polypeptide according to the first or second aspect of the invention is used.

Other objects and advantages of the present invention will become apparent as the description progresses.

BRIEF DESCRIPTION OF THE DRAWINGS

FIG. 2 shows the nucleotide sequence in clone pTN24-15 and the amino acid sequence deduced therefrom, (SEQ ID NO: 25).

FIG. 3 shows the nucleotide sequence in clone pTN24-15 and the amino acid sequence deduced therefrom (SEQ ID NO: 25).

FIG. 15 shows the nucleotide sequence of plasmid pBL-hFL4H and the amino acid sequence deduced therefrom (SEQ ID NO: 27).

FIG. 16 shows the nucleotide sequence of human Fas ligand chromosomal gene, (SEQ. ID. NO. 29).

FIG. 17 shows the nucleotide sequence of human Fas ligand chromosomal gene, (SEQ ID NO. 29).

FIG. 18 shows the nucleotide sequence of human Fas ligand chromosomal gene.

FIG. 19 shows the nucleotide sequence in clone pBX-hFL1 (coding portion=SEQ. ID. NO. 16).

FIG. 20 shows the nucleotide sequence in clone pBX-hFL1 (SEQ ID NO: 16).

FIG. 21 shows cytotoxic activity of COS cells transformed with pEX-hFL1 and COS cells transformed with pEF-MFLW4F when WR19L and WC8A are used as target cells.

FIG. 23 shows the nucleotide sequence in clone pBL-MFLW4 and the amino acid sequence deduced therefrom, (SEQ. ID. NO. 31).

FIG. 24 shows the nucleotide sequence in clone pBL-MFLW4 and the amino acid sequence deduced therefrom (SEQ ID NO: 31).

FIG. 25 shows cytotoxic activity of COS cells transformed with pEF-MFLW4F when WR19L and W4 are used as target cells.

DETAILED DESCRIPTION OF THE INVENTION

Figure 1A:
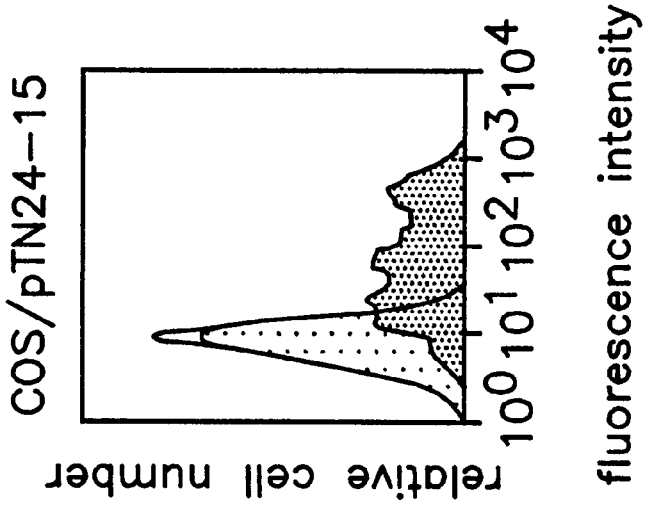
FIGS. 1; a, b and c show the results of flow cytometry of COS-7 cells transformed with d10S, d10S-2 or pTN24-15, respectively.

The present invention is hereinafter described in further detail.

First, the polypeptide according the first aspect of the present invention is described.

In the description of the present invention, the term, "polypeptide containing (or including) the amino acid sequence of formula X (or SEQ ID NO: X)" designates the polypeptide having the amino acid sequence defined in formula X (or SEQ ID NO: X) wherein one or more amino acid residues are optionally added on either one or both of its N terminus and C terminus.

The term, "polypeptide having the amino acid sequence of formula X (or SEQ ID NO: X)" designates the polypeptide having the amino acid sequence defined in formula X (or SEQ ID NO: X).

The term, "Fas ligand" designates a substance provided with an activity to induce apoptosis of a Fas antigen-expressing cell. Apoptosis of the Fas antigen-expressing cells is estimated to have been induced by the binding of the Fas ligand with the Fas antigen on the cell surface, which results in the transfer of the apoptosis signal to the cell via the Fas antigen.

The "Fas antigen" as used herein may be any Fas antigen of animal origin including human Fas antigen, rat Fas antigen and mouse Fas antigen. In this connection, amino acid sequence of human Fas antigen has been determined by Itoh, N. et al., *Cell*, vol. 66, pp. 233–243, 1991. Amino acid sequence of mouse Fas antigen has been determined by Watanabe-Fukunaga, R. et al., *J. Immunol.*, vol. 148, pp. 1274–1279, 1992. Amino acid sequence of rat Fas antigen has been determined by Kimura, K. et al., *Biochem. Biophys. Res. Commun.*, vol. 198, pp. 666–674, 1994.

The polypeptides according to the first aspect of the present invention may include any one of the sequences defined in formulae 1 to 12.

The amino acid sequences defined in SEQ ID NOS: 2, 4, 6 and 8 are the amino acid sequences of the Fas ligands of human cell origin. The amino acid sequences defined in SEQ ID NOS: 10, 12, 14 and 16 are the amino acid sequences of the Fas ligands of rat cell origin. The amino acid sequences defined in SEQ ID NOS: 18, 20, 22 and 24 are the amino acid sequences of the Fas ligands of mouse cell origin.

The amino acid sequences defined in SEQ ID NOS: 8, 16 and 24 includes all the intracellular, transmembrane, and extracellular domains, and it is estimated that such polypeptides should exist in organisms as cell surface polypeptides. Therefore, production of polypeptides with such amino acid sequences would require purification of the polypeptides from the cells or tissue expressing such polypeptides.

The extracellular domain of a cell surface polypeptide is often cleaved off the cell membrane to be released into the supernatant of the cell culture producing such polypeptide or into body fluids such as urine and blood. In general, purification of a polypeptide is more efficient and productive when the polypeptide is purified from a supernatant or urine compared to the purification from cells or a tissue. The situation is the same for the Fas ligand, and purification of the extracellular domain of the Fas ligand is more productive than the purification of the entire Fas ligand.

In the present invention, there is also provided polypeptides corresponding to such extracellular domain of the Fas ligands. The cleavage site of the Fas ligand at which the extracellular domain is separated from the cell membrane is not limited to any particular site, and the cleavage site may vary according to the conditions of the cell culture or proteases present inside or outside the cell. Preferably, the extracellular domains of the Fas ligands are polypeptides having the amino acid sequences defined in SEQ ID NOS: 6, 14 and 22, which correspond to the extracellular domains of the human, rat, and mouse Fas ligands, respectively. The amino acid sequence of SEQ ID NO: 6 corresponds to the sequence of from 103rd amino acid residue to 281st amino acid residue from the N terminus in the amino acid sequence of SEQ ID NO: 8. The amino acid sequence of SEQ ID NO: 14 corresponds to the sequence of from 100th amino acid residue to 278th amino acid residue from the N terminus in the amino acid sequence of SEQ ID NO: 16. The amino acid sequence of SEQ ID NO: 22 corresponds to the sequence of from 101st amino acid residue to 279th amino acid residue from the N terminus in the amino acid sequence of formula SEQ ID NO: 24.

As is known in the art, in producing polypeptides by recombinant DNA technology, amount of the polypeptide expressed, and hence, production efficiency would be higher when the polypeptide produced has a lower molecular weight. In addition, a polypeptide solely comprising the part required for its action would have an antigenicity lower than the polypeptides including additional sequences. Furthermore, if the polypeptide of interest has a low molecular weight, it would be possible to fuse the polypeptide with another polypeptide having another activity to provide the polypeptide with another activity, or to bind the polypeptide with an antibody to specify the target cell to which the polypeptide exerts its activity. In the present invention, there is provided polypeptides having the amino acid sequence defined by SEQ ID NOS: 2, 10 and 18 which have lower molecular weight, therefore, higher productivity and lower antigenicity are expected. There is also provided in the present invention polypeptides having the amino acid sequences defined by SEQ ID NOS: 4, 12 and 20.

SEQ ID NOS: 2, 4, 10, 12, 18 and 20 respectively represent parts of the amino acid sequences of the extracellular domain of the human, rat and mouse Fas ligands.

More illustratively, the amino acid sequences of SEQ ID NOS: 2, 10 and 18 respectively represent the amino acid sequences of SEQ ID NOS: 6, 14 and 22 wherein 42 amino acid residues on their N terminus are missing; and the amino acid sequences of SEQ ID NOS: 4, 12 and 20 respectively represent the amino acid sequences of SEQ ID NOS: 6, 14 and 22 wherein 41 amino acid residues on their N terminus are missing. As demonstrated in the Examples, the polypeptides (of SEQ ID NOS: 2 and 4) having the amino acid sequences of SEQ ID NO: 6 wherein 42 or 41 amino acid residues on the N terminus are missing still have the apoptosis-inducing activity. The polypeptides having the amino acid sequences of SEQ ID NO: 6 wherein 40,38 or 34 amino acid residues on the N terminus are missing also have the apoptosis-inducing activity.

It was then indicated that the amino acid sequence in the downstream from the 43rd amino acid residue should be critical for the apoptosis-inducing activity, and a polypeptide including such critical sequence as defined by SEQ ID NOS: 2, 10 or 18 as a part of its sequence would have the apoptosis-inducing activity. Accordingly, the polypeptides of the present invention may be characterized by the inclusion of the amino acid sequence defined by SEQ ID NOS: 2, 10 or 18.

Of the polypeptides according to the first aspect of the present invention, the polvpeptides having the amino acid sequence of SEQ ID NO: 6 corresponding to the extracellular domain of the Fas ligand of human origin wherein amino acid residues of a number selected from 1 to 42 on the N terminus are missing are favor able in view of their lower antigenicity for human in comparison with Fas ligands of animal origin and higher productivity due to the lower molecular weight. Such polypeptides can also be collected from the culture supernatant when they are expressed with a suitable signal peptide by a transformant. In particular, the polypeptides having the amino acid sequence of SEQ ID NO: 6 wherein 40 or 34 amino acid residues on the N terminus are missing is favorable in view of its high activity.

In general, depending on the difference in species and individuals, mutation of amino acid sequence sometimes occurs in protein without spoiling its basic function. The term "mutation of amino acid sequence" as used herein means deletion of one or more amino acid residues from an amino acid sequence or their substitution by other amino acid residues and insertion or addition of one or more amino acid residues into or to optional sites of the amino acid sequence. Such a mutation can be introduced artificially by means of genetic engineering techniques.

In consequence, polypeptides having other amino acid sequences, for example, having derivatives of any one of the aforementioned amino acid sequences represented by the SEQ ID NOS: 1–24 in which mutation of amino acid sequence occurred at one or more optional positions, are also included in the polypeptide of the present invention, provided that these polypeptide are possessed of similar properties of the polypeptide of the present invention.

In general, DNA molecules which encode polypeptide having the same function show mutual homology and hybridize each other in many cases. Diversity of amino acid sequences also occurs in many cases within such a range that DNA molecules encoding them can be hybridized each other. For example, as will be described later in EXAMPLES, DNA fragments which encode amino acid sequences of the aforementioned SEQ ID NOS: 6 and 22 can hybridize with a DNA fragment which encodes amino acid sequences of the aforementioned SEQ ID NO: 14. In addition, the Fas ligand which contains the amino acid sequence of the SEQ ID NO: 6 can bind not only to human Fas antigen but also to mouse Fas antigen. Also, the Fas ligand which contains the amino acid sequence of the SEQ ID NO: 14 can bind not only to rat Fas antigen but also to mouse Fas antigen. The Fas ligand which contains the amino acid sequence of the SEQ ID NO: 22 can bind not only to mouse Fas antigen but also to human Fas antigen. Thus, it is considered that polypeptides having amino acid sequences encoded by mutually hybridizable DNA fragments have substantially the same function. In consequence, the novel polypeptide of the present invention characterized in that it contains an amino acid sequence encoded by a nucleotide sequence that hybridizes with a nucleotide sequence complementary to any one of the nucleotide sequences coding for the aforementioned amino acid sequences of SEQ ID NOS: 1–24, preferably, SEQ ID NOS: 2, 10, or 18.

In addition to the above mentioned features, the novel polypeptide of the present invention is preferably characterized in that it binds to at least one selected from the group consisting of human Fas antigens, rat Fas antigens and mouse Fas antigens, and more preferably, it shows an activity to induce apoptosis in Fas antigen-expressing cells.

Next, the polypeptide according to the second aspect of the present invention is described.

The polypeptide according to the second aspect of the present invention may comprise a fragment of a Fas ligand, or a fusion product of a plurality of the same or different fragments of the Fas ligand. Such polypeptide may preferably have a part of the amino acid sequence defined by any one of SEQ ID NOS: 8, 16 and 24, and such polypeptide may be fused in an arbitrary order to constitute fusion polypeptides.

The polypeptide having a part of the amino acid sequence defined by SEQ ID NOS: 8, 16 or 24 may have any desired length. The polypeptide, however, may preferably have a length of 5 or more amino acid residues, and more preferably, a length of 10 or more amino acid residues to enable the inclusion the characteristic part of the amino acid sequence defined by SEQ ID NOS: 8, 16 or 24.

The polypeptide according to the second aspect of the present invention may be either capable or incapable of binding with the Fas antigen. Of the polypeptides according to the second aspect of the present invention, those capable of binding with the Fas antigen, but incapable of inducing the apoptosis, may be used as a substance that competitively acts against the Fas ligand in an organism, and such polypeptides may be administered for the purpose artificially inhibiting the apoptosis. As demonstrated in the Example, the polypeptide according to the second aspect of the present invention may be used as an antigen in producing an antibody against the polypeptide of the first aspect of the invention, irrespective of the presence or the absence of the binding ability with the Fas antigen or the apoptosis-inducing activity.

As described above, the polypeptide according to the second aspect of the present invention may comprise a fusion of two or more polypeptides each having the amino acid sequence which is a part of the amino acid sequence defined by SEQ ID NOS: 8, 16 or 24, which has been fused in an arbitrary order. Exemplary such fusion polypeptides include, a fusion of two polypeptides each having the amino acid sequence which is a part of the amino acid sequence defined by SEQ ID NO: 8; and a fusion of a polypeptide having the amino acid sequence which is a part of the amino acid sequence defined by SEQ ID NO: 8 with a polypeptide having the amino acid sequence which is a part of the amino acid sequence defined by SEQ ID NOS: 16 or 24. A preferred example are the polypeptide comprising the amino acid sequence of from 50th amino acid residue to 179th amino acid residue from the N terminus in the amino acid sequence defined by SEQ ID NO: 6 fused to the C-terminus of the polypeptide comprising the amino acid sequence of from 1st amino acid residue to 49th amino acid residue from the N terminus in the amino acid sequence defined by SEQ ID NO: 14 or 22. Such fusion polypeptides are chimera polypeptides of the Fas ligand of human origin with the Fas ligand of rat and mouse origin, respectively. Such fusion polypeptides are expected to have the apoptosis-inducing activity on Fas antigen-expressing cells.

The fusion polypeptide as described above may be produced with recombinant DNA technology by ligating the DNAs respectively coding for the polypeptide components to produce a DNA coding for the chimera Fas ligand; introducing the thus produced DNA in a suitable expression vector to transform a suitable host cell; and collecting the chimera Fas ligand of interest from the transformant cells or the culture supernatant.

The novel polypeptide according to the first and the second aspect of the present invention may have or may not have sugar chain.

Each of the amino acid sequences represented by the aforementioned SEQ ID NOS: 8 and 16 contains 4 sites to which a sugar chain can be added (N-glycosylation sites). That is, amino acid residues of the positions 76 to 78, 184 to 186, 250 to 252 and 260 to 262 in the SEQ ID NO: 8 and those of the positions 116 to 118, 130 to 132, 247 to 249 and 257 to 259 in the SEQ ID NO: 16 correspond to the N-glycosylation sites. Also, the amino acid sequence of the aforementioned formula 12 has 5 N-glycosylation sites (amino acid residues of the positions 117 to 119, 131 to 133, 182 to 184, 248 to 250 and 258 to 260).

In consequence, addition of sugar chains to such polypeptides may occur when they are produced by animal cells or by means of genetic engineering techniques using eucaryotic cells such as of yeast and animals as the host. On the other hand, the novel polypeptide does not have a sugar chain when produced by means of genetic engineering techniques using procaryotic cells such as of *Escherichia coli* as the host.

Irrespective of the presence or the absence of additional sugar chains, the polypeptides according to the first and the second aspect of the present invention are useful, and may be used as the antigen in producing the antibody according to the ninth aspect of the present invention, or in screening the substances that would bind to such polypeptides.

The novel polypeptide of the first and the second aspects of the present invention may be produced by any method. For example, it may be chemically synthesized using a peptide synthesizer (e.g., Peptide Synthesizer 430A, Perkin-Elmer Japan) or purified from tissues, cells or body fluids of human and any other organism. Examples of the body fluids of human and animals include blood, urine and the like. Useful cells may be selected optionally from those which are capable of producing the novel polypeptide of the present invention. For example, cells capable of expressing the novel polypeptide of the present invention in a high quantity may be selected from splenocytes, thymocytes, lymphocytes and established cell lines thereof, through their analysis by northern blotting, western blotting and the like.

If necessary, production of the polypeptide may be induced by stimulating the cells with one or more appropriate stimulating agent selected from PMA (phorbol myristate acetate), ionomycin, PHA (phytohemagglutinin), ConA (concanavalin A), IL-2 (interleukin-2) and the like. Thereafter, the protein of interest is purified from the cells or a culture supernatant of the cells. Its purification may be carried out through an appropriate combination of usually used polypeptide purification steps such as concentration, various types of chromatography, salting out and the like, making use of the affinity of the polypeptide for Fas antigen or its cytotoxicity on Fas antigen-expressing cells as a marker. A preferred example of the purification method will be described later in relation to the eighth aspect of the present invention.

Preferably, however, the novel polypeptide may be produced by means of genetic engineering techniques in the form of a recombinant polypeptide in view of its purity. In order to obtain the novel polypeptide by means of genetic engineering techniques, appropriate host cells are transformed with the novel DNA of the third aspect of the present invention or the recombinant DNA molecule of the fourth aspect of the present invention, both of which will be described later, and the thus obtained transformant is cultured to recover the culture mixture with the transformant from which the polypeptide of interest is subsequently purified. The novel polypeptide may also be produced by another genetic engineering means making use of the novel DNA or the recombinant DNA molecule by employing a cell-free synthesis method (Sambrook J. et al., *Molecular Cloning A Laboratory Manual* 2nd. ed., Cold Spring Harbour Laboratory, New York, 1989).

A preferred example of the process for the production of the novel polypeptide of the present invention by means of genetic engineering techniques will be described later in relation to the seventh aspect of the present invention.

Recent advance in protein engineering techniques has made possible to bind polypeptide to high molecular compounds such as polyethylene glycol, styrene-maleic acid copolymer, dextran, pyran copolymer, polylysine and the like, as well as to natural high molecular compounds such as polysaccharides, polypeptides and the like, physiologically active substances such as hormones and inorganic compounds such as magnetite and the like (see for example, *Proc. Natl. Acad. Sci. USA*, vol. 84, pp. 1487–1491, 1981, and *Biochemistry*, vol. 28, pp. 6619–6624, 1989).

An example of the binding method of polypeptide to polyethylene glycol is described briefly in the following. Firstly, a polypeptide of interest is dissolved in a buffer solution having a basic pH value within such a range that activity of the polypeptide is not spoiled. The thus prepared solution is mixed with an activated polyethylene glycol such as methoxypolyethylene glycol succinimidyl succinate to react with each other at room temperature for a certain period of time. Thereafter, a fraction having the activity of the polypeptide is collected by gel filtration or the like means.

The novel polypeptide of 1st and second aspect of the present invention can also be modified in such a manner through a combination of known techniques. In consequence, the novel polypeptide of the first and second aspects of the present invention also include those which received such modifications.

It is generally known that polypeptides often take the form of multimer by covalent bonding or non-covalent bonding in an organism or in a culture medium. Such multimer is formed by the binding of the polypeptides of the same type or different types. For example, TNF has been known to form a trimer, and actibin has been known to form a dimer.

The polypeptide according to the first and the second aspect of the present invention may be present either in the form of a monomer or a multimer. For example, the polypeptide of the present invention having the amino acid sequence defined by any one of SEQ ID NOS: 1–24 may take the form of a trimer by binding with each other.

The polypeptide according to the first and the second aspect of the invention may be used for regulating the apoptosis induced in a living body.

For example, the polypeptide of the present invention which typically has an amino acid sequence defined by any one of SEQ ID NOS: 1–24, and which is capable of binding with the Fas antigen to induce the apoptosis may be used for treating a cancer that have acquired carcinostatic resistance. Alternatively, the polypeptide of the present invention may be used for treating an early stage AIDS by inducing apoptosis of the HIV infected cells. Such treatments should constitute a new series treatments in the field of medicine.

Of the polypeptides according to the second aspect of the present invention, those which are capable of binding with the Fas antigen, but incapable of inducing the apoptosis, may be used for preventing the apoptosis of cells such as hepatocytes to thereby prevent a rapid decrease in the number of cells that constitute the organs critical for the patients such as liver, and hence, to prevent a rapid dysfunction of such organs, for example, in the case of hepatitis.

The polypeptides of the present invention may produced into medicaments in the form of, for example, an injection, a tablet, a capsule, a suppository, a spray, an ointment, a cataplam, or eye drops, in accordance with any of the conventional methods used for producing polypeptide-containing medicaments. For example, a medicament containing the polypeptide of the present invention as its effective ingredient in the form of an injection may be prepared by filling an ampul with a solution of the polypeptide that has been prepared under aseptic conditions, and lyophilizing the solution. The injection may additionally contain pharmaceutically acceptable additives such as a stabilizer. The thus prepared injection can be dissolved in distilled water of injection purpose before the intravenous or topical administration. Of the polypeptides according to the present invention, those which are most suitable for use as an effective ingredient in a medicament are the polypeptides having a low antigenicity for human such as the polypeptides containing the amino acid sequence defined by any one of SEQ ID NOS: 2, 4, 6 and 8 or a fragment thereof, and in particular, those defined by SEQ ID NOS: 2 and 8, or a fragment thereof.

The novel polypeptide of the present invention can be used by setting its administration method and dose depending on the age and sex of each patient and the kind and degree of each disease. In other words, it may be used in a dose which is effective in controlling apoptosis and hence in improving morbid states, by selecting a proper route of administration from oral administration and parenteral administration such as inhalation, percutaneous absorption, ophthalmic administration, vaginal administration, intraarticular injection, rectal administration, intravenous injection, topical application, intramuscular injection, subcutaneous injection, intraperitoneal administration and the like.

Also, the polypeptides according to the first or the second aspect of the invention may be used for preparing an antibody by immunizing an animal such as rabbit with the polypeptide of the present invention. Preparation of the antibody will be set forth in the description of the ninth aspect of the present invention. The resulting antibody may be used for staining tissues or cells, or for preparing an affinity column adapted for use in purifying the polypeptide of the present invention.

Next, the DNA according to the third aspect of the present invention is described.

In the description of the present invention, the term, "a DNA containing (or including) the nucleotide sequence defined by formula Y (or SEQ ID NO: Y)" designates a DNA having the nucleotide sequence defined by formula Y (or SEQ ID NO: Y) optionally having at least one nucleotide added on one or both of its 3' and 5' ends. The nucleotide added is not limited to any particular type so long as such addition of the nucleotide does not result in a frame shift.

Exemplary sequences added include a linker sequence, termination codon sequence, a nucleolide sequences coding for signal peptide or other polypeptide, a sequence added in the production of a DNA probe for the purpose of increasing the detection sensitivity. The term, "DNA having the nucleotide sequence defined by formula Y (or SEQ ID NO: Y)" designates the DNA substantially represented by the nucleotide sequence defined by formula Y (or SEQ ID NO: Y).

The novel DNA of the third aspect of the present invention includes whole or a part of DNA which codes Fas ligand.

The novel DNA of the third aspect of the present invention is characterized in that it contains a nucleotide sequence which encodes the novel polypeptide of the first or the second aspect of the present invention.

That is, the novel DNA of the present invention preferably contains a nucleotide sequence which encodes at least a part of any one of the amino acid sequences of the aforementioned (SEQ ID NOS: 1–24).

Since it is known that 1 to 6 amino acid-encoding DNA triplets are present for each amino acid, the nucleotide sequence which encodes any one of the amino acid sequences of the aforementioned SEQ ID NOS: 1–24 is not limited to one kind. In consequence, all DNA fragments comprising any kind of sequence are included in the novel DNA fragment of the present invention, provided that they contain a nucleotide sequence which encodes at least a part of any one of the amino acid sequences of the aforementioned SEQ ID NOS: 1–24.

More preferably, the novel DNA fragment of the present invention is a fragment which contains at least a part of a nucleotide sequence represented by any one of the (SEQ ID NOS: 1, 3, 5, 7, 9, 11, 13, 15, 17, 19, 21 and 23).

The nucleotide sequences represented by the SEQ ID NOS: 7, 15, and 23 encode the amino acid sequences represented by the SEQ ID NOS: 8, 16, and 24, respectively. The nucleotide sequences represented by the SEQ ID NOS: 5, 13 and 21 encode the amino acid sequences represented by the SEQ ID NOS: 6, 14, and 22, respectively which are the extracellular regions of human, rat and mouse Fas ligand represented by the amino acid sequences of the SEQ ID NOS: 8, 16 and 24, respectively. The nucleotide sequences represented by the SEQ ID NOS: 1, 3, 9, 11, 17 and 19 encode the amino acid sequences represented by the SEQ ID NOS: 2, 4, 10, 12, 18 and and 20 which are shorter amino acid sequences than that of the polypeptides of the extracellular regions of human, rat and mouse Fas ligand.

The novel DNA fragment of the present invention may be either cDNA or chromosomal DNA, provided that it includes nucleotide sequences which encodes the novel polypeptide of the first and the second aspects of the present invention. As an example of such a type of chromosomal DNA, a nucleotide sequence of chromosomal DNA which contains a part of the aforementioned nucleotide sequence of SEQ ID NOS: 1 or 7 is shown in FIGS. 16 to 18. It is desirable however that the novel DNA fragment of the present invention is cDNA, because it can be handled easily in carrying out genetic engineering techniques, such as the easiness to introduce it into a vector.

The DNA of the present invention is useful to produce the novel polypeptide of the first or the second aspect of the present invention by the recombinant DNA technique. The DNA of the present invention can be inserted into the vector containing an appropriate nucleotide sequence for expressing the polypeptides of the present invention such as promoter sequence, then, the thus obtained vector may be used to transformation of an appropriate host cell to produce the polypeptide of the first or the second aspect of the present invention. The polypeptide can be recovered from the transformant or the culture supernatant thereof.

As will be described in Examples, Fas ligand, namely, the polypeptides having the activity inducing apoptosis can be obtained from the culture supernatant of the transformant transformed with a recombinant DNA molecule which contain the DNA having the sequence represented by the SEQ ID NOS: 7, 15 and 23.

The DNA having the nucleotide sequences represented by the SEQ ID NOS: 1, 3, 5, 9, 11, 13, 17, 19 and 21 are useful to obtain low molecular Fas ligands. The DNAs code the amino acid sequences represented by the SEQ ID NOS: 2, 4, 6, 10, 12, 14, 18, 20 and 22 which are the amino acid sequences of a part or whole the extracellular region of Fas ligand. When the DNA is bound to the downstream of a nucleotide sequence encoding an appropriate signal peptide to be expressed by a transformant the polypeptide of the present invention coded by the DNA can be obtained from the culture supernatant of the transformant.

As already described, it is more effective to recovering the polypeptides from the culture supernatant than from the lysate of cells. The DNA having the nucleotide sequences represented by the SEQ ID NOS: 1, 3, 5, 9, 11, 17, 19 and 21 are also useful, because it is low molecule and can be handled easily in carrying out by genetic engineering.

As mentioned above, the polypeptides derived from different animal species or different individuals of the same species may have different amino acid sequences, and hence, the DNAs coding for such polypeptides may have different nucleotide sequences. In spite of such variation in the sequence, the nucleotide sequences of the DNAs coding for proteins having an identical function are generally homologous with each other in spite of their different origin. In view of such situation, a DNA having the nucleotide sequence at least partly homologous to the nucleotide sequence defined in any one of SEQ ID NOS: 1, 3, 5, 7, 9, 11, 13, 15, 17, 19, 21 and 23, namely, a DNA hybridizable with at least a part of the nucleotide sequence complimentary to the nucleotide sequence defined in any one of SEQ ID NOS: 1, 3, 5, 7, 9, 11, 13, 15, 17, 19, 21 and 23 should code for a polypeptide having a function identical with the function of the polypeptide coded by the nucleotide sequence defined in any one of SEQ ID NOS: 1, 3, 5, 7, 9, 11, 13, 15, 17, 19, 21 and 23. The term "hybridizable" used herein means that the sequence was hybridizable when the hybridization was carried out in accordance with a known method (see, for example, Sambrook, J. et al., *Molecular Cloning, a Laboratory Manual* 2nd ed., 1989, Cold Spring Harbor Laboratory, New York) by using at least a part of the sequence complimentary to the nucleotide sequence defined in any one of SEQ ID NOS: 1, 3, 5, 7, 9, 11, 13, 15, 17, 19, 21 and 23 for the probe. In the Examples, hybridization is carried out by using a part of the nucleotide sequence complimentary to the nucleotide sequence of SEQ ID NO: 13 for the probe.

As described above, the DNA hybridizable with the nucleotide sequence complimentary to the nucleotide sequence defined in any one of SEQ ID NOS: 1, 3, 5, 7, 9, 11, 13, 15, 17, 19, 21 and 23 is included in the DNA according to the third aspect of the present invention. In particular, a DNA which is hybridizable with the nucleotide sequence complimentary to the nucleotide sequence defined in any one of SEQ ID NOS: 1, 9 and 17, and which encodes the Fas ligand, is a preferred embodiment of the DNA according to the third aspect of the present invention.

The DNA according to the third aspect of the present invention may be a DNA fragment having a nucleotide sequence which is a part of the nucleotide sequence defined in any one of SEQ ID NOS: 29, 25 and 31. As demonstrated in the Examples, the nucleotide sequences of SEQ ID NOS: 29, 25 and 31 are containing the nucleotide sequences of the cDNAs obtained from the human, rat and mouse cDNA libraries in an effort to find the DNAs having the nucleotide sequences coding for the Fas ligand. The nucleotide sequence of SEQ ID NOS: 29, 25 and 31 include the nucleotide sequence of SEQ ID NOS: 7, 15 and 23, respectively, within their sequences.

The nucleotide sequence which is a part of the nucleotide sequence defined in any one of SEQ ID NOS: 29, 25 and 31 may comprise any desired part of the nucleotide sequence. Such fragment is not limited in its length, and may comprise, for example, a part of the nucleotide sequence of SEQ ID NOS: 7, 15 or 23, or a part of the non-coding region on 5' or 3' end of the nucleotide sequence.

The DNA as described above may be used for the prove in cloning the DNA coding for the apoptosis-inducing polypeptides, or as a primer in PCR.

The DNA as described above may also be used for a diagnostic DNA prove in detecting or quantitating the polypeptides according to the first or the second aspect of the present invention in the tissue of cells after labeling the DNA with an enzyme such as horse radish peroxidase (HRPO), a radioisotope, a fluorescent substance, or a chemiluminescent substance.

The DNA according to the third aspect of the present invention is not limited for its production process or source. In other words, the DNA according to the third aspect of the present invention may be a DNA chemically synthesized on the bases of any one of (SEQ ID NOS: 1, 3, 5, 7, 9, 11, 13, 15, 17, 19, 21 and 23) or SEQ ID NOS: 29, 25 and 31; or a DNA cloned from an appropriate DNA library.

The chemical synthesis of the DNA according to the present invention may be conducted by dividing the desired nucleotide sequence into regions each comprising about 20 nucleotides by referring to any one of SEQ ID NOS: 1, 3, 5, 7, 9, 11, 13, 15, 17, 19, 21 and 23 and SEQ ID NOS: 29, 25 and 31; synthesizing the fragments corresponding to such regions with a DNA chemical synthesizer (for example, 394, Perkin-Elmer Japan K.K.); annealing the thus synthesized fragments after optional phosphorylation of the 5' end of the fragments; and ligating the thus annealed fragments to produce the desired DNA.

Isolation of the novel DNA of the present invention from a DNA library may be effected for example by a method in which an appropriate genomic DNA library or cDNA library is screened by means of a hybridization or immunoscreening using antibody, the thus screened clones having the DNA fragment of interest is cultured and then the DNA fragment is cut out using restriction enzymes and the like.

Hybridization can be effected by labeling a DNA fragment containing entire portion or a part of the nucleotide sequence of any one of the aforementioned SEQ ID NOS: 1, 3, 5, 7, 9, 11, 13, 15, 17, 19, 21 and 23 and SEQ ID NOS: 29, 25, and 31 with $^{32}P$ or the like and then carrying out screening from any cDNA library using the labeled DNA fragment as a probe in accordance with known methods (for example, see Maniatis T. et al., *Molecular Cloning, a Laboratory Manual*, Cold Spring Harbor Laboratory, New York, 1982).

With regard to the antibody to be used in the immunoscreening, the antibody of the ninth aspect of the present invention which will be described later may be used.

The novel DNA of the present invention can also be obtained by PCR (polymerase chain reaction) using a genomic DNA library or a cDNA library as a template.

That is, the novel DNA of the present invention can be obtained by preparing sense and antisense primers based on any one of the nucleotide sequences of the aforementioned SEQ ID NOS: 1, 3, 5, 7, 9, 11, 13, 15, 17, 19, 21 and 23 or SEQ ID NOS: 29, 25, and 31, and carrying out PCR using any DNA library in accordance with any known method (e.g. see Michael A. I. et al., *PCR Protocols, a Guide to Methods and Applications*, Academic Press, 1990).

Any type of DNA library can be used in the aforementioned various methods, provided that it contains the DNA fragment of the present invention, such as a commercially available DNA library or a cDNA library prepared from appropriate cells which contain the DNA and in suitable to obtain a cDNA library in accordance with a known method (c.f. Sambrook J. et al., *Molecular Cloning, a Laboratory Manual*, 2nd. ed., Cold Spring Harbor Laboratory, New York, 1989).

When a DNA nucleotide sequence is provided, an RNA sequence and the complementary DNA and RNA sequence are determined automatically. In consequence, an RNA sequence which corresponds to the DNA fragment of the third aspect of the present invention and a DNA and RNA fragment having a sequence complementary to the DNA fragment of the third aspect of the present invention are also provided by the disclosure of the present invention.

The DNA of the third aspect of the present invention may be single-stranded or may form a double-stranded or triple-stranded chain through the binding of a DNA or RNA fragment.

The novel DNA may also be labeled with an enzyme such as horseradish peroxidase (HRPO), a radioactive isotope, a fluorescent material, a chemiluminescent material or the like.

The novel DNA of the present invention can be used for the large scale production of the novel polypeptide of the first and the second aspects of the present invention. An example of the process for the production of the novel polypeptide of the present invention making use of the novel DNA will be described later in relation to the seventh aspect of the present invention. The novel DNA can also be used for the inspection of the expression condition of the novel protein of the first or the second aspect of the present invention in tissues, by labeling the fragment with the enzyme or the like as described above. By confirming expression quantity of the novel protein of the first or the second aspect of the present invention in cells making use of the novel DNA, cells and culture condition of the cells suitable for use in the production of the novel protein of the first or the second aspect of the present invention can be determined.

Also, the novel DNA of the present invention can be used in the gene therapy of diseases in which the mechanism of apoptosis is deleted hereditarily, such as autoimmune diseases and the like, by introducing the DNA fragment into cells of the living body.

In addition, it is possible also to develop an antisense pharmaceutical preparation based on the nucleotide sequence contained in the novel DNA of the present invention for use in the regulation of the expression of Fas ligand in the living body. That is, it is possible to regulate expression of Fas ligand making use of an oligonucleotide or a derivative thereof which contains a sequence complementary to any one of the nucleotide sequences of the aforementioned SEQ ID NOS: 1, 3, 5, 7, 9, 11, 13, 15, 17, 19, 21 and 23 or SEQ ID NOS: 25, 29 and 31. Techniques for the production of antisense pharmaceutical preparations will be described later in detail in relation to the tenth aspect of the present invention.

Next, a recombinant DNA molecule as a fourth aspect of the present invention is described.

The recombinant DNA molecule of the fourth aspect of the present invention is a recombinant DNA molecule which is characterized in that it contains the aforementioned novel DNA of the third aspect of the present invention. The recombinant DNA molecule of the present invention may have any form such as circular, linear or the like structure. Also, the recombinant DNA molecule of the present invention may be used for any purpose. For example, it may be used when the novel polypeptide of the first and the second aspects of the present invention is produced or when the novel DNA of the third aspect of the present invention is amplified and produced in a large quantity.

If necessary, the recombinant DNA molecule of the fourth aspect of the present invention may contain other nucleotide sequence in addition to the novel DNA of the third aspect of the present invention. Examples of the "other nucleotide sequence" as used herein include an enhancer nucleotide sequence, a promoter nucleotide sequence, a ribosome binding sequence, a nucleotide sequence which is used for the purpose of amplifying copy numbers, a nucleotide sequence which encodes a signal peptide, a nucleotide sequence which encodes other polypeptide, adenylation site, a splicing sequence, a replication origin and a nucleotide sequence of a gene to be used as a selection marker. The necessity of these nucleotide sequences is determined depending on the use of the recombinant DNA molecule. Preferably, however, the recombinant DNA molecule of the present invention may contain at least a replication origin and a marker gene in addition to the novel DNA of the third aspect of the present invention. Examples of the marker gene include ampicillin resistant gene, kanamycin resistant gene, neomycin resistant gene, thymidine kinase gene and the like.

A preferred example of the recombinant DNA molecule is a molecule which can transform E. coli so that the novel protein of the first and the second aspects of the present invention can be expressed in the host cells. It is preferable therefore that the recombinant DNA molecule of the present invention contains at least an E. coli replication origin, a marker gene and a promoter sequence which functions in E. coli cells in addition to the novel DNA fragment of the third aspect of the present invention. Also, in addition to these sequences, it may preferably contain a sequence which encodes a signal peptide. Ideal examples of the promoter sequence which functions in E. coli cells include trp promoter and lac promoter, and ideal examples of the signal peptide which functions in E. coli cells include the E. coli alkaline phosphatase signal peptide.

Another preferred example of the recombinant DNA molecule is a molecule which can transform eucaryotic cells such as yeast cells, insect cells, animal cells and the like so that the novel polypeptide of the present invention can be expressed in the host cells. It is preferable therefore that the recombinant DNA molecule of the present invention contains at least a marker gene, adenylation site and a promoter sequence which functions in eucaryotic cells in addition to the novel DNA fragment of the third aspect of the present invention. Ideal examples of the promoter which functions in eucaryotic cells include alcohol oxidase (AOX) 1 promoter which functions in yeast, polyhedrin promoter which functions in insect cells and SV40 promoter, SRα promoter and human elongation factor 1α (EF-1α) promoter which function in animal cells. More preferably, the recombinant DNA molecule may further contain an E. coli replication origin.

The recombinant DNA molecule of the fourth aspect of the present invention can be obtained by introducing the novel DNA fragment of the third aspect of the present invention into an optional vector. In this step, the novel DNA may be introduced with optional sequence into a vector as occasion demand. Alternatively, the recombinant DNA molecule of the present invention can be obtained by carrying out ligation of the novel DNA fragment of the third aspect of the present invention with a DNA fragment which contains an optional nucleotide sequence. Introduction of a DNA fragment into a vector can be made in accordance with any known method (e.g., see Sambrook J. et al., *Molecular Cloning, a Laboratory Manual*, 2nd. ed., Cold Spring Harbor Laboratory, New York, 1989). That is, a DNA fragment and a vector are respectively digested with appropriate restriction enzymes and the resulting fragments are subjected to ligation using DNA ligase. The vector may be any of plasmid vectors, phage vectors, virus vectors and the like. For example, it may be selected optionally from pUC118, pBR322, pSV2-dhfr, pBluescript II, PHIL-S1, λZap II, λgt10, pAc700, YRP17, PEF-BOS, pEFN-II and the like.

Next, a transformant as a fifth aspect of the present invention is described.

The transformant of the fifth aspect of the present invention is characterized in that it is transformed with the novel DNA fragment of the third aspect of the present invention. In other words, the transformant of the fifth aspect of the present invention is characterized in that it is transformed by introducing the novel DNA fragment of the third aspect of the present invention directly into appropriate cells or microorganism used as the host.

Introduction of the novel DNA fragment of the third aspect of the present invention into host cells can be effected by any of the known methods such as electroporation, protoplast method, alkali metal method, calcium phosphate precipitation, DEAE dextran method, microinjection, and a method in which virus particles are used [see Jikken Igaku (Experimental Medicine) supplement, Idenshi Kogaku (Gene engineering) *Hand Book*, Mar. 20, 1991, Yohdo-sha).

The transformant of the present invention can be used for the purpose of producing the novel DNA fragment of the third aspect of the present invention in a large quantity. In addition, when the novel DNA of the third aspect of the present invention is integrated into downstream of an appropriate promoter in the host cells, the resulting transformant produces the novel polypeptide of the first and the second aspects of the present invention. In consequence, such a transformant can be used for the purpose of producing the novel polypeptide of present invention.

Next, another transformant as a sixth aspect of the present invention is described.

The transformant of the sixth aspect of the present invention is characterized in that it is transformed by introducing the recombinant DNA molecule of the fourth aspect of the present invention into cells or microorganism used as the host. In this case, it is necessary to select a recombinant DNA molecule which suits the host. In other words, said recombinant DNA molecule should be obtained by introducing the novel DNA fragment of the third aspect of the present invention into a vector which suits the host. Also, said recombinant DNA molecule should have a promoter, a nucleotide sequence encoding a signal peptide, a marker gene and the like which suit the host. Examples of preferred combination of vectors and hosts include pUC118 with *E. coli*, pEF-BOS with COS cells or CHO cells, Yac with yeast and AcNPV with Sf cells [see Jikken Igaku (Experimental Medicine) supplement, Idenshi Kogaku (Gene engineering) *Hand Book*, Mar. 20, 1991, Yohdo-sha).

Similar to the case of the preparation of the transformant of the fifth aspect of the present invention, introduction of the recombinant DNA molecule of the fourth aspect of the present invention into host cells can be effected by any of the known methods such as electroporation, protoplast method, alkali metal method, calcium phosphate precipitation, DEAE dextran method, microinjection, and a method in which virus particles are used [see Jikken Igaku (Experimental Medicine) supplement, Idenshi Kogaku (Gene engineering) *Hand Book*, Mar. 20, 1991, Yohdo-sha).

The host to be transformed may be either procaryotic or eucaryotic cells. Typical examples of procaryotic cells include those of *Escherichia coli* and *Bacillus subtilis*. Typical examples of eucaryotic cells include mammalian cells such as CHO cells, HeLa cells, COS cells, Namalwa cells and the like, insect cells such as Sf cells and the like and yeast cells.

The transformant of the sixth aspect of the present invention may be obtained by transforming any type of cells, but preferably *E. coli*, mammalian cells or yeast. As mammalian cells, a dhfr deletion mutant of CHO cells is preferred because of its ability to increase gene copy numbers. With regard to yeast cells, a strain belonging to the genus Pichia is preferred in view of the high expression and secretion quantity of exogenous polypeptide.

The transformant of the sixth aspect of the present invention can be used for the purpose of obtaining the novel DNA fragment of the third aspect of the present invention in a large quantity and producing the novel polypeptide of the first and the second aspects of the present invention.

Said transformant may be used for any purpose, but preferably for the production of the novel polypeptide of the present invention.

In other words, a preferred transformant of the present invention is a transformant which produce the novel polypeptide of the first or the second aspect of the present invention.

More preferably, the transformant of the present invention is a transformant which secretes the novel polypeptide into culture medium.

The transformant capable to express and secrete the polypeptide of the present invention can be obtained by transforming host cells with a recombinant DNA molecule which comprises the novel DNA of the third aspect of the present invention and a signal peptide-encoding sequence linked to the 5'-end of the DNA fragment.

Preferred example of the transformant of the present invention is an *E. coli* strain transformed with a recombinant DNA molecule which contains, in a DNA molecule capable of functioning as a vector, at least a replication origin, a promoter that functions in *E. coli* cells, a marker gene, a nucleotide sequence that encodes a signal peptide such as of *E. coli* alkaline phosphatase or the like and the novel DNA fragment of the third aspect of the present invention. Another preferred example of the transformant of the present invention is a mammalian cell strain transformed with a recombinant DNA molecule which contains, in a DNA molecule capable of functioning as a vector, at least a marker gene, adenylation site, a promoter that functions in mammalian cells and the novel DNA fragment of the third aspect of the present invention. Also preferred as the transformant of the present invention is a strain of yeast belonging to the genus Pichia transformed with a recombinant DNA molecule which contains, in a DNA molecule capable of functioning as a vector, at least an AOX1 promoter, a marker gene and the novel DNA fragment of the third aspect of the present invention.

Next, a production process as a seventh aspect of the present invention is described.

The production process of the seventh aspect of the present invention is a process for the production of the novel polypeptide of the first aspect of the present invention, which is characterized in that the transformant of the fifth or sixth aspect of the present invention is used. Method for the preparation of the transformant was already described.

According to the production process, the transformant of the fifth or sixth aspect of the present invention is firstly cultured. In this step, amplification and expression-induction of the gene of interest are carried out as occasion demands. Next, the resulting culture mixture is recovered to purify the novel polypeptide of the present invention by carrying out concentration, solubilization, dialysis, various types of chromatography and the like.

Host to be transformed for use in this production process are not particularly limited. However, a preferred transformant may be obtained by transforming host selected from mammalian cells such as CHO cells and the like, yeast and *E. coli*.

Culturing of the transformant can be carried out in the usual way with reference to various published papers and books (e.g., "Biseibutsu Jikken-ho" (Microbial Experiments), Japanese Biochemical Society, Tokyo Kagaku Dojin, 1992). Methods and necessity for the amplification and expression-induction of the gene vary depending on the kind of host and the promoter to be used. For example, the induction may be effected with 3b-indoleacrylic acid when the promoter is trp promoter, with dexamethasone in the case of MMTV promoter or with methanol in the case of AOX1 promoter.

On the other hand, when the host is dhfr$^-$ CHO cells and the vector to be used in the transformation containing dhfr$^+$, the gene of interest can be amplified by treating the transformant with methotrexate.

Examples of the culturing and expression induction are shown below when *E. coli*, CHO cells or a yeast strain belonging to the genus Pichia are used as the host of each transformant.

In the case of an *E. coli* strain transformed with a recombinant DNA molecule which contains trp promoter, cells are pre-cultured in L-broth, inoculated into M9-CA medium in a 1/50 volume and then cultured at 37° C. When the $OD_{550}$ value of the medium reaches 1 to 4 several hours after commencement of the culturing (namely logarithmic growth phase), 3b-indoleacrylic acid is added to a final concentration of 10 μg/ml to effect expression-induction. By continuing the culturing for about 1 to 2 days, a culture mixture containing the polypeptide of interest is obtained.

When a Pichia strain transformed with a recombinant DNA molecule which contains AOX1 promoter is used, the yeast cells are pre-cultured in BMGY medium for about 2 days and, after medium exchange, methanol is added to effect expression induction. By continuing the culturing at 30° C. for about 2 days, a culture mixture containing the polypeptide of interest is obtained.

In the case of a transformant of mammalian cells such as CHO cells or the like transformed with an expression plasmid which contains an elongation factor promoter, the transformant is cultured in D-MEM (Dulbecco's modified Eagle's Medium) containing 10% fetal bovine serum. The cells are inoculated in a density of about $5\times10^4$ cells/mi and cultured at 37° C. in an atmosphere of 5% $CO_2$/95% air. When the cells become confluent generally after 2 to 3 days of the culturing, the medium is exchanged with serum-free DMEM. By continuing the culturing for 2 to 3 days, a culture mixture containing the polypeptide of interest is obtained. When productivity of the polypeptide of interest is low, it is possible to increase the productivity in the aforementioned manner by using dhfr⁻ CHO cells and amplifying the gene with methotrexate.

According to the seventh aspect of the present invention, the term "culture mixture" means a culture supernatant or a cell. That is, when the transformant secretes the polypeptide of interest into the extracellular milieu, the novel polypeptide of interest of the first and second aspects of the present invention is recovered and purified from the culture supernatant.

On the other hand, when the novel polypeptide is accumulated in the host cells, the cells are disrupted by lysozyme treatment, surfactant treatment, freezing-thawing, pressurization or the like means and subjected to centrifugation to recover the supernatant fluid from which unnecessary cell debris and the like are subsequently removed by filtration or the like means, the supernatant fluid is used as the material for the purification of the novel polypeptide of the first aspect of the present invention. When the transformant to be used is *E. coli* and the produced novel polypeptide is accumulated in the periplasmic space of the cells, the polypeptide of interest can be purified with reference to, for example, the procedure of Willsky et al. (*J. Bacteriol.*, vol. 127, pp. 595–609, 1976).

The novel polypeptide of the first and the second aspects of the present invention can be purified from the culture mixture by optionally selecting appropriate techniques commonly used for the purification of polypeptide, such as salting out, ultrafiltration, isoelectric precipitation, gel filtration, electrophoresis, ion exchange chromatography, various types of affinity chromatography such as hydrophobic chromatography, antibody chromatography and the like, chromatofocusing and reverse phase chromatography, as well as an HPLC system and the like as occasion demands. These purification steps may be employed in any appropriate order. A preferred example of the purification process will be described later in relation to the eighth aspect of the present invention.

According to the production process of the present invention, the novel polypeptide of the present invention may be produced by the transformant in the form of a fusion polypeptide with other polypeptide. For example, a high productivity can be expected from a generally used process in which a DNA fragment coding for a polypeptide of interest is linked to a downstream site of another DNA fragment which encodes *E. coil* β-galactosidase and the polypeptide of interest is expressed as a fusion polypeptide with β-galactosidase.

When the novel polypeptide of the present invention is expressed in the form of a fusion polypeptide with other polypeptide, it is necessary to insert an additional step between certain steps of the purification process, in order to cut out the novel polypeptide by treating the fusion polypeptide with a chemical substance such as cyanogen bromide or the like or an enzyme such as protease or the like.

In addition, when the transformant to be used is an *E. coli* strain and the novel polypeptide is produced in the form of inclusion body which is an insoluble protein, an appropriate step of the purification process may be followed by a procedure in which the inclusion body is subjected to solubilization, denaturation and refolding (Thomas E. and Creighton J., *J. Molecular Biology*, vol. 87, pp. 563–577, 1974).

Illustratively, the transformants are firstly disrupted and subjected to centrifugation to recover the resulting pellet. Next, to the pellet is added a solubilization buffer containing appropriate amounts of urea or guanidine hydrochloride, a surface active agent, reduced type glutathione and oxidized type glutathione (for example, a buffer containing 5 M guanidine hydrochloride, 0.005% Tween 80, 50 mM tris hydrochloride (pH 8.0), 5 mM EDTA, 2 mM reduced type glutathione and 0.02 M oxidized type glutathione), followed by the addition of 2-mercaptoethanol to effect denaturation. Thereafter, refolding is effected by dialyzing the resulting solution against the above solubilization buffer from which guanidine hydrochloride is eliminated. When expressed as a fusion polypeptide, the unnecessary polypeptide portion is cut and removed after these treatment using a chemical substance such as cyanogen bromide or the like or an enzyme such as protease or the like, and the thus freed novel polypeptide of interest is subsequently subjected to an appropriate chromatography.

Next, a eighth aspect of the present invention is described.

The eighth aspect of the present invention is a process for the purification of the novel polypeptide of the first and the second aspects of the present invention from a sample which contains the novel polypeptide of the first aspect of the present invention, which is characterized in that at least one step selected from the following purification steps is carried out:

(1) an affinity chromatography making use of a Fas antigen, and (2) an affinity chromatography making use of an antibody which recognizes the novel polypeptide of the first or the second aspect of the present invention.

The purification process of the present invention may be effected by either one of the above steps (1) and (2) or by both of them. Alternatively, it may be effected by a combination of other purification method with at least one of the above steps (1) and (2). Preferably, however, either one of the above steps (1) and (2) or both of the steps may be carried out in an optional order before or after a generally used method for the purification of protein.

For example, the novel polypeptide of the first or the second aspect of the present invention can be obtained with a high purity by employing a chromatography in which a lectin-adsorbed carrier is used, in addition to either one of the above steps (1) or (2).

The term "a sample which contains the novel polypeptide of the first aspect of the present invention" means any sample provided that it contains said novel polypeptide. For example, it may be a culture supernatant of cells, a cell lysate or a body fluid such as urine, blood or the like.

In carrying out the affinity chromatography of the above step (1), it is necessary to adsorb the Fas antigen to an appropriate carrier. The Fas antigen to be used may be of any animal origin provided that it binds to the polypeptide of interest. However, it is preferable to use human Fas antigen when the polypeptide of interest to be purified contains at least a part of the amino acid sequence of the aforementioned SEQ ID NOS: 2, 4, 6 and 8, or rat Fas antigen or mouse Fas antigen when the polypeptide of interest contains at least a part of the amino acid sequence of the aforementioned SEQ ID NOS: 10, 12, 14 and 16, or mouse Fas antigen when the polypeptide of interest contains at least a part of the amino acid sequence of the aforementioned SEQ ID NOS: 18, 20, 22 and 24.

The carrier to which the Fas antigen is adsorbed is not particularly limited. When the Fas antigen is bound to a carrier, the Fas antigen is bound to the carrier directly or via a spacer. Alternatively, the Fas antigen may be bound to a carrier indirectly, by preparing the Fas antigen as a fusion polypeptide with other polypeptide and binding a portion of the fusion polypeptide other than the Fas antigen moiety to a bondable carrier. For example, a Fas antigen-adsorbed carrier to be used in said affinity chromatography can be obtained easily, by preparing the Fas antigen as a fusion polypeptide with the constant domain of immunoglobulin and adsorbing the fusion polypeptide to a protein A-adsorbed carrier packed in a column making use of the property of immunoglobulin to bind to protein A.

In order to carry out the affinity chromatography of the above step (2), a novel antibody of the ninth aspect of the present invention, which will be described later, may be used. That is, said novel antibody is allowed to bind to a proper carrier such as agarose or the like directly or via a spacer, and the resulting carrier is packed in a column for use in the affinity chromatography.

In this instance, preferred examples of the aforementioned lectin-adsorbed carrier include ConA-adsorbed carriers. Since products in which ConA is adsorbed to an agarose carrier and the like are commercially available, it may be convenient to use one of these products by optionally selecting therefrom.

The affinity chromatography of the above step (1) or (2) or the affinity chromatography in which a lectin-adsorbed carrier is used may be carried out by optionally selecting an eluting solution from solutions to be used in the polypeptide purification and confirming the amount of the polypeptide of interest in the eluted fractions. The presence of the novel polypeptide of the first or the second aspect of the present invention can be confirmed by measuring cytotoxic activity on Fas antigen-expressing cells or by means of EIA making use of an antibody which recognizes the novel polypeptide of the first or the second aspect of the present invention. The antibody which recognizes the novel polypeptide of the first or the second aspect of the present invention is described in the following ninth aspect of the present invention.

Next, a novel antibody as an ninth aspect of the present invention is described.

The novel antibody of the ninth aspect of the present invention is characterized in that it binds to the novel polypeptide of the first or the second aspect of the present invention.

The novel antibody of the ninth aspect of the present invention may be either a monoclonal antibody or a polyclonal antibody, provided that it binds to the novel polypeptide of the first or the second aspect of the present invention.

Antibody, namely immunoglobulin, has a structure which comprises H and L chains and is divided into 5 classes (IgG, IgA, IgM, IgD and IgE) depending on their physicochemical and immunological properties. Of these classes, IgG and IgA are further divided into subclasses depending on the types of H chains. The novel antibody of the present invention may belong to any of these classes and subclasses. In addition, immunoglobulin is split into F(ab')$_2$ and Fc' fragments when hydrolyzed with pepsin, or into Fab and Fc fragments when hydrolyzed with papain. The novel antibody of the present invention may be either a complete antibody molecule or a partial fragment thereof, provided that it binds to the novel polypeptide of the first aspect of the present invention. Also, the antibody of the present invention may be in the form of a chimera antibody.

The novel antibody of the present invention, either as a polyclonal antibody or a monoclonal antibody, can be obtained with reference to published methods [see for example, Men-eki Jikken Sosa-ho (Procedures for Immunological Experiments), The Japanese Society for Immunology]. The following briefly describes the method.

In order to obtain the novel antibody, the novel polypeptide of the first aspect of the present invention is inoculated as an immunizing antigen into an animal, if necessary, with an appropriate adjuvant such as Freund's complete adjuvant (FCA) or Freund's incomplete adjuvant (FIA) or the like, followed, if necessary, by the booster at 2 to 4 week intervals. After completion of the booster, blood is collected to obtain antiserum. The novel polypeptide of the present invention to be used as the antigen may be obtained by any method, provided that it has such a purity that it can be used for the production of the antibody.

When the novel polypeptide used as immunizing antigen is low molecular one, such as a polypeptide composed of about 10 to 20 amino acid residues, the thus polypeptide can be used after binding it to a carrier such as keyhole limpet hemocyanin (KLH) or the like. The animal to be immunized with the novel polypeptide is not particularly limited, but it may preferably be selected from animal species capable of producing the antibody of interest, such as rat, mouse, rabbit, sheep, horse, domestic fowl, goat, pig, cattle and the like which are generally used in immunological experiments.

The polyclonal antibody can be obtained by purifying the thus obtained antiserum through optional combination of known purification methods such as salting out, ion exchange chromatography, affinity chromatography and the like.

The monoclonal antibody can be obtained in the following manner. That is, antibody producing cells such as splenocytes, lymphocytes or the like are collected from the immunized animal and fused with myeloma cells or the like to make them into hybridoma cells by a known method in which polyethylene glycol, Sendai virus, electric pulse or the like is used. Thereafter, a clone capable of producing an antibody which binds to the novel protein of the present invention is selected and cultured, and the monoclonal antibody of interest is purified from the resulting culture supernatant. The purification may be effected through optional combination of known purification methods such as salting out, ion exchange chromatography, affinity chromatography and the like.

The novel antibody can also be obtained by means of genetic engineering techniques. That is, mRNA is isolated from splenocytes or lymphocytes of an animal which is immunized with the novel polypeptide of the first or the second aspect of the present invention or from a hybridoma capable of producing a monoclonal antibody which is specific for the novel polypeptide of the first aspect of the present invention, and a cDNA library is prepared using the thus isolated mRNA. Thereafter, a clone capable of producing an antibody which reacts with the antigen is screened from the cDNA library and cultured to obtain a culture supernatant from which the antibody of interest is purified through combination of known purification methods.

The novel antibody of the present invention may have an activity to modify the function of the Fas ligand on cells. Among antibodies which have the activity to modify the function of the Fas ligand on cells, most preferred is an antibody which has an activity to inhibit Fas ligand-induced apoptosis. Such an antibody may inhibit the Fas ligand-induced apoptosis completely or partially.

In order to obtain an antibody which has the activity to inhibit the Fas ligand-induced apoptosis, sera obtained during the aforementioned polyclonal or monoclonal antibody production process or culture supernatants of the aforementioned hybridoma cells are screened by subjecting them to an assay system such as an in vitro assay system in which Fas ligand or Fas ligand-expressing cells and Fas antigen-expressing cells are used. Thereafter, the antibody of interest is purified from a serum sample or a culture supernatant thus obtained as the result of the screening, through combination of known purification methods. A preferred example of the screening method in which Fas ligand or Fas ligand-expressing cells and Fas antigen-expressing cells are used will be described later in relation to the eleventh aspect of the present invention.

The antibody capable of inhibiting the Fas ligand-induced apoptosis completely or partially can be used in the regulation of apoptosis in the living body. For example, said antibody can be used as a pharmaceutical preparation for the treatment of diseases in which apoptosis of tissues and cells takes part, such as degradation of joint tissues in rheumatism, self tissue degradation in systemic lupus erythematosus (SLE), diabetes mellitus, influenza, AIDS, hepatitis and the like.

Next, a tenth aspect of the present invention is described.

The tenth aspect of the present invention is an oligonucleotide or a derivative thereof which contains a nucleotide sequence complementary to a part of the gene of a Fas ligand or a part of mRNA for a Fas ligand. Said oligonucleotide or a derivative thereof may contain, as its nucleotide sequence, either only said complementary nucleotide sequence or other bases and nucleotide sequences such as ribozyme sequence and the like in addition to the complementary nucleotide sequence.

The term "gene of a Fas ligand" as used herein means a gene which contains Fas ligand-encoding DNA, including not only a Fas ligand-encoding region but also its regulatory region. The regulatory region means both of which are located upstream and downstream of the Fas ligand-encoding region. The term "mRNA for the Fas ligand" means a mRNA which contains a Fas ligand-encoding nucleotide sequence. Said mRNA also includes a mRNA molecule which contains not only the Fas ligand-encoding nucleotide sequence but also non-coding regions located upstream and downstream of the nucleotide sequence.

As shown in FIGS. 16 to 18, the Fas ligand-encoding chromosomal DNA is composed of introns and exons. When a DNA fragment containing introns and exons is transcribed into mRNA, the introns and exons are firstly transcribed as such to form pre-mRNA. Thereafter, portions corresponding to the introns are eliminated by splicing to form mature mRNA in which only the exons are transcribed. The term "mRNA for the Fas ligand" as used herein means both pre-mRNA and mature mRNA.

The term "a part of the gene of a Fas ligand or a part of mRNA for the Fas ligand" as used herein means any part contained in the Fas ligand gene or mRNA for the Fas ligand, independent of their coding and non-coding regions and intron and exon sites.

According to the tenth aspect of the present invention, the "Fas ligand" may be of any animal origin, but it may preferably be obtained from human, rat or mouse. Human Fas ligand is particularly preferable when its application to diagnostic drugs and pharmaceutical preparations is taken into consideration.

A nucleotide sequence in and around the coding region of the human Fas ligand is shown in FIGS. 16 to 18. Nucleotide sequences contained mature mRNAs for human Fas ligand, rat Fas ligand and mouse Fas ligand are obtained by changing T to U in the DNA sequences of the SEQ ID NOS: 29, 25 and 31, which respectively encode these ligands.

The term "complementary nucleotide sequence" as used herein means a nucleotide sequence which forms complementary base pairs base-specific for the nucleotide sequence of DNA or mRNA. It is known in general that the complementary base pairs are formed between C (cytosine) and G (guanine), T (thymine) and A (adenine) and U (uracil) and A (adenine). In consequence, a nucleotide sequence complementary to the human Fas ligand gene and nucleotide sequences complementary to the mature mRNAs for human Fas ligand, rat Fas ligand and mouse Fas ligand are respectively obtained by changing A to T, C to G, G to C and T to C, or A to U, C to G, G to C and T to A, of the nucleotide sequences shown in FIGS. 16 to 18 and or the SEQ ID NOS: 35, 25 and 31. A DNA and RNA sequence complementary to the nucleotide sequence encoding the human Fas ligand of SEQ ID NO: 35 are shown by SEQ ID NOS: 33 and 34 respectively. In this instance, the "complementary nucleotide sequence" includes not only those composed of C, G, A, T and U but also those which contain derivatives of these bases.

The oligonucleotide of the present invention includes every oligonucleotide composed of a plurality of nucleotides, each of which comprising bases, phosphoric acid and sugars. Typical examples are DNA and RNA.

The oligonucleotide derivative of the present invention includes every derivative whose stereochemical structure and function are analogous to the oligonucleotide. Examples of such derivatives include a derivative resulting from the binding of an exogenous substance to the 3'- or 5'-end of the oligonucleotide, a derivative resulting from the substitution or modification of at least one of the bases, sugar moieties and phosphate moieties of the oligonucleotide, a derivative resulting from the inclusion of a base, a sugar or a phosphoric acid moiety which does not exist in nature and a derivative which contains a backbone other than phosphodiester.

Preferably, the oligonucleotide or a derivative thereof of the tenth aspect of the present invention has a nucleotide sequence which is complementary to a part of the Fas ligand gene or a part of mRNA for the Fas ligand and hybridizes with such gene and mRNA.

The oligonucleotide or a derivative thereof which hybridizes with the Fas ligand gene or mRNA for the Fas ligand can be used as a diagnostic oligonucleotide probe for the examination of the presence and expressing condition of the Fas ligand gene in tissues and cells.

More preferably, the oligonucleotide or a derivative thereof of the present invention hybridizes with the Fas ligand gene or mRNA for the Fas ligand and has an activity to control expression of the Fas ligand.

A method for controlling expression of a protein making use of an oligonucleotide which contains a nucleotide sequence complementary to a DNA or mRNA that encodes the protein is a technique called antisense method which is now studied by many researchers. It is considered that an oligonucleotide having a complementary sequence controls expression of protein by exerting an influence upon the normal flow of the transfer of genetic information through its binding to a DNA or mRNA which bears the genetic information, wherein the binding occurs at any one of the steps for the (1) transcription from the gene to pre-mRNA, (2) processing of the pre-mRNA into mature mRNA, (3) passing of the mature mRNA through nuclear membrane and (4) translation into protein.

As described in the foregoing, the cause of the cell death in the case of AIDS and hepatitis is considered to be Fas antigen-mediated apoptosis. In consequence, a oligonucleotide or a derivative thereof capable of inhibiting expression of the Fas ligand can be used for the treatment of diseases in which Fas ligand-mediated apoptosis takes part, such as AIDS and hepatitis, as well as degradation of joint tissues in rheumatism, self tissue degradation in systemic lupus erythematosus (SLE), diabetes mellitus, influenza and the like.

On the other hand, another oligonucleotide or a derivative thereof capable of enhancing expression of the Fas ligand can be used for the removal of cells which are unnecessary for the living body, for example for the treatment of AIDS at an early stage of the infection and for the inhibition of abnormal growth of synovial membrane cells in rheumatism or growth of autoantigen-reactive T cells in autoimmune diseases. Thus, both of the Fas ligand expression inhibiting and enhancing oligonucleotides are useful in the field of medical care. Most preferably, however, the oligonucleotide or a derivative thereof of the present invention may have a function to inhibit expression of the Fas ligand.

The oligonucleotide or a derivative thereof of the present invention may hybridize with any part of the Fas ligand gene or mRNA. In general, it is considered that easy hybridization can be made when aimed at the loop moiety of stem loop-forming mRNA [Y. Shoji, Rinsho Men-eki (Clinical Immunology), vol. 25, pp. 1200–1206, 1993], namely in case of an oligonucleotide or a derivative thereof having a sequence complementary to the sequence of these region.

Also, oligonucleotides which bind to translation initiation codon area, ribosome binding site, capping site and splice site, namely oligonucleotides having sequences complementary to the sequences of these sites, are generally considered to have high expression inhibition effect [Gan to Kagaku Ryoho (Cancer and Chemotherapy), vol. 20, no. 13, pp. 1899–1907](1993). In consequence, a high expression inhibition effect can be expected from the oligonucleotide or a derivative thereof of the present invention when it can bind to the translation initiation codon area of the Fas ligand gene or mRNA, ribosome binding site, capping site or splice site, namely when it contains a sequence complementary to each of these sites.

When its application to diagnostic and pharmaceutical use is taken into consideration, the oligonucleotide and a derivative thereof of the present invention may preferably have a function to hybridize with the Fas ligand gene or mRNA in a specific manner.

In general, a nucleotide sequence containing 15 or more bases is considered to be a sequence having specificity (K. Yokoyama, *Protein, Nucleic acid and Enzyme*, vol. 38, pp. 754–765, 1994). In consequence, specific binding to the Fas ligand gene or mRNA for Fas ligand can be expected from said oligonucleotide or a derivative thereof when it contains a nucleotide sequence which is complementary to the Fas ligand gene or mRNA for Fas ligand and composed of 15 or more bases.

On the other hand, its length if too long is not suitable for the incorporation of the oligonucleotide into cells. In consequence, when the oligonucleotide or a derivative thereof of the present invention is used for the control of the expression of Fas ligand by incorporating it into cells, it is preferable that said oligonucleotide or a derivative thereof contains a sequence which is complementary to the Fas ligand gene or mRNA for the Fas ligand and comprises 15 to 30 bases, preferably 15 to 25 bases, more preferably 18 to 22 bases.

With the advance in the antisense techniques, various oligonucleotide derivatives have been found with the aim of improving effects of oligonucleotides as pharmaceutical preparations, such as those having improved affinity for DNA or mRNA of interest, as well as those having improved tissue selectivity, cell permeability, nuclease resistance and intracellular stability.

As described in the foregoing, the "oligonucleotide derivative" of the present invention includes all kinds of derivatives including those which contains a base, a sugar, a phosphoric acid moiety and a backbone structure which do not exist in nature.

Examples of generally known derivatives include those in which entire portion or a part of the backbone structure has phosphodiester bonding, phosphorothioate bonding, phosphotriester bonding, methylphosphonate bonding, phosphoramidate bonding, phosphorodithioate bonding or morpholino group [Y. Shoji, Gan to Kagaku Ryoho (Cancer and Chemotherapy), vol. 20, No.13, pp. 1899–1907, 1993]. Also included are polyamide-nucleic acid (PAN) (P.E. Nielsen et al., Science, vol. 254, pp. 1497–1500, 1991) and certain derivatives in which the 2'-position of the sugar is substituted with other atom or substituent (α-ribose and the like) (Michael J. Gait, pp. 290–299; in *Antisense Research and Applications*, CRC Press Inc. Florida, 1993).

Also known as oligonucleotide derivatives are those in which the sugar moiety is substituted with other substance, certain bases are substituted with inosine (called universal base because of its ability to bind to A, T, C and G) and cholesterol, acridine, poly-L-lysine, psoralen, long alkyl chain or the like is linked to the 5'- or 3'-end or inside of an oligonucleotide (Makoto Matsukura, pp. 506–519, Paul S. Miller et al., pp. 190–202; in *Antisense Research and Applications*, CRC Press Inc, Florida, 1993).

The oligonucleotide derivative of the present invention include all derivatives including these derivatives exemplified above. However, said oligonucleotide derivative may preferably be a derivative in which at least one of its nuclease resistance, tissue selectivity, cell permeability and affinity is improved.

Particularly preferably, said oligonucleotide derivative is a derivative which has phosphorothioate bonding as its backbone structure.

The following describes a process for the production of the oligonucleotide and its derivatives of the present invention.

Oligonucleotides and their derivatives can be produced by known methods (see for instance, *Antisense Research and Applications*, ed. by Stanley T. Crooke and Bernald Lebleu, CRC Press Inc, Florida, 1993).

In the case of natural DNA or RNA, the oligonucleotide of the present invention can be obtained by chemically synthesizer or carrying out PCR using the Fas ligand gene as a template. Also, certain oligonucleotide derivatives such as of methylphosphonate type, phosphorothioate type and the like can be synthesized making use of a chemical synthesizer (for example, Model 394 Perkin-Elmer Japan). In that case, an oligonucleotide of interest or its derivative can be obtained also by carrying out operation of the chemical synthesizer in accordance with the manual attached thereto and purifying the thus synthesized product by an HPLC aided with a reverse chromatography or the like.

Next, use of the oligonucleotide and a derivative thereof of the present invention is described.

When the oligonucleotide and a derivative thereof of the present invention are used as diagnostic probes, they are labeled with a radioisotope, an enzyme, a fluorescent material, a luminescent material or the like in accordance with a usually used method. Next, DNA or mRNA is prepared from cells of a patient to be examined for the expression of Fas ligand, the thus prepared DNA or mRNA as a sample to be tested is allowed to react with the labeled probe prepared above and then the reaction mixture is washed to remove unreacted labeled probe. When the Fas ligand gene or RNA is present in the sample to be tested, said oligonucleotide or a derivative thereof binds to the gene or RNA. The presence of the thus bound product can be detected by using the labeled enzyme, fluorescent material, luminescent material or radioisotope as a marker.

Since relationship between expression of Fas ligand and autoimmune diseases and related information have been reported in recent years, diagnostic probes prepared by the use of the oligonucleotide of the present invention can be used for the diagnosis of autoimmune diseases such as rheumatism, SLE and the like. In addition, since the Fas ligand is also considered to be related to the cytotoxicity caused by T cells at the time of inflammation, such probes can also be used in diagnosis for the determination of the degree of inflammation and the therapeutic method.

When the oligonucleotide and a derivative thereof of the present invention is used for pharmaceutical purposes, it is desirable to use them with a purity which is suitable for use in pharmaceutical preparations and by pharmacologically acceptable use method.

The oligonucleotide or a derivative thereof of the tenth aspect of the present invention may be used by dissolving or suspending it directly in an appropriate solvent, or by enclosing it in liposomes or integrating it in an appropriate vector. As occasion demands, the oligonucleotide or a derivative thereof of the present invention may be used in appropriate dosage forms such as injections, tablets, capsules, eye drops, creams, suppositories, sprays, cataplasmas and the like, by mixing it with pharmacologically acceptable additive agents such as solvents, bases, stabilizing agents, antiseptics, solubilizing agents, fillers, buffers and the like.

The oligonucleotide or a derivative thereof of the present invention can be used by setting its administration method and dose depending on the age and sex of each patient and the kind and degree of each disease. In other words, it may be used in a dose which is effective in controlling apoptosis and hence in improving morbid states, by selecting a proper route of administration from oral administration and parenteral administration such as inhalation, percutaneous absorption, ophthalmic administration, vaginal administration, intraarticular injection, rectal administration, intravenous injection, topical application, intramuscular injection, subcutaneous injection, intraperitoneal administration and the like.

Finally, a screening method as a eleventh aspect of the present invention is described.

The screening method of the eleventh aspect of the present invention is characterized by the use of a novel polypeptide of the first and the second aspects of the present invention or a transformant transformed in such a manner that it expresses the polypeptides.

According to the screening method of the eleventh aspect of the present invention, substances which bind to the Fas ligand and other substances which exert influences upon expression of the Fas ligand can be screened. All substances including compounds, peptides, proteins, antibodies, nucleic acids and the like are included in the substances to be screened.

In addition, diagnosis of Fas ligand-related diseases can be made making use of the screening method of the present invention.

For example, the presence of abnormality in the function or expression of Fas antigen in a patient of an autoimmune disease can be diagnosed by isolating blood cells or tissue cells from the patient, allowing the isolated cells to react with the Fas ligand or the transformant which expresses the Fas ligand and then observing degree of apoptosis generated in the cells isolated from the patient. With reference to the result of the diagnosis, means for the treatment of the disease can be selected corresponding to its cause.

In addition to the Fas ligand or Fas ligand-expressing transformant, it is preferable to use Fas antigen-expressing cells in the screening method of the present invention. By the use of such a method, not only substances which bind to the Fas ligand or enhance or inhibit expression of the Fas ligand but also other substances which exert influences upon the function of the Fas ligand on cells, substances which enhance or inhibit expression of the Fas antigen and the like, can be screened. Though typical example of the function of the Fas ligand on cells is the induction of apoptosis, said screening method can be used suitably for the screening of not only substances which enhance or inhibit apoptosis but also other substances which enhance or inhibit certain changes generated in Fas antigen-expressing cells in the presence of the Fas ligand.

The screening method of the present invention may include any steps. However, preferably, the screening method of the present invention includes a step selected from the following steps (1) to (3);

(1) (a) one selected from the group consisting of a Fas ligand, a Fas ligand-expressing transformant and culture supernatant of the transformant is cultured together with cells which express Fas antigen, (b) a substance to be tested or a sample containing the substance to be tested is added to the above system (a), and (c) at least 1 item selected from viability, morphological changes and biochemical changes in the Fas antigen-expressing cells is measured, (2) (a) a substance to be tested or a sample containing the substance to be tested is incubated together with one selected from the group consisting of a Fas ligand, a transformant which expresses the Fas ligand and culture supernatant of the transformants, (b) cells which express Fas antigen are added to the above system (a), and cultured, and (c) at least 1 item selected from viability, morphological changes and biochemical changes in the Fas antigen-expressing cells is measured, and (3) (a) a substance to be tested or a sample containing the substance to be tested is incubated together with cells which express Fas antigen, (b) a Fas ligand, a transformant which expresses the Fas ligand or culture supernatant thereof is added to the above system (a) and cultured, and (c) at least 1 item selected from viability, morphological changes and biochemical changes in the Fas antigen-expressing cells is measured.

Method for the measurement of the viability, morphological changes or biochemical changes in the Fas antigen-expressing cells is not particularly limited, provided that it can detect such changes. The presence and degree of apoptosis in Fas antigen-expressing cells can be measured based on the amount of released $^{51}$Cr incorporated in advance in the Fas antigen-expressing cells. The number of survived cells, namely, number of not-apoptotic cells of the Fas antigen-expressing cells may be measured by trypan blue staining or an assay in which formation of formazan is used as a marker (MTT assay, Almarl Blue assay or the like).

The screening method of the present invention, is preferably characterized by the use of the polypeptide represented by any one of the SEQ ID NOS: 1–24, or the transformant expressing thereof.

It is generally conceived that a membrane protein present at the cell surface binds to other molecules by its extracellular domain. Accordingly, in the screening method according to the eleventh aspect of the invention, it would be preferable to use the polypeptides having the amino acid sequence of SEQ ID NOS: 2, 4, 6, 10, 12, 14, 18, 20 and 22, and the transformants capable of expressing such polypeptides. And in particular, the polypeptides having the amino acid sequence of SEQ ID NOS: 2, 4, and 6, and the transformants capable of expressing thereof are preferable. The polypeptide used in the screening may be produced by the process described for the seventh aspect of the present invention, and the transformant capable of expressing the polypeptide may be produced by the process described for the fifth or sixth aspect of the present invention.

According to the screening method of the eleventh aspect of the present invention, substances which bind to the Fas ligand and other substances which exert influences upon expression of the Fas ligand can be screened.

The term "substance" as used herein is not limited to any particles substance, and may be designate a compound, a peptide, a protein, an antibody, a nucleic acid, or the like. The screening as described above may be also be utilized in the diagnosis of the Fas ligand-associated diseases.

For example, the presence/absence of abnormality in the function of the Fas antigen of a patient suffering from an autoimmune disease can be diagnosed by isolating blood cells or cells of tissue origin from the patient, and reacting the thus isolated cells with the Fas ligand or the transformant capable of expressing the Fas ligand to observe the degree of apoptosis induced in the cells isolated from the patient. A suitable treatment may then be selected by taking the results of such diagnosis into consideration.

Any type of cells may be used as the Fas antigen-expressing cells, such as cells in which expression of the Fas antigen is induced by a virus or a drug like the case of AIDS virus-infected cells, or an established cells, a hybridoma or a transformant which expresses the Fas antigen. It is preferable to use human Fas antigen-expressing cells, especially cells of a human Fas antigen-expressing transformant such as WC8 cells (Itoh N. et al., *J. Immunol.*, vol. 151, pp. 621–627, 1993).

EXAMPLES

The following examples are provided to further illustrate the present invention. It is to be understood, however, that the examples are for purpose of illustration only and are not intended as a definition of the limits of the present invention.

The abbreviations used in the following descriptions are based on those which are commonly used in the related technical field.

Basic procedures described in the following examples were carried out in the light of "Molecular Cloning, A Laboratory Manual", 2nd ed.(Sambrook J. et al., Cold Spring Harbor Laboratory, New York 1989), "*Introduction of Recombinant Genes into Cells and Expression of the Genes*" (Imamoto F. et al., *Protein, Nucleic Acid and Enzyme*, supplement 28 (14), 1983; written in Japanese) and "*General Cell Technological Techniques*" (Okada Y., *Experimental Medicine*, supplement 7 (13), 1989; written in Japanese).

Inventive Example 1 Preparation of Chimera Protein (1) Preparation of Expression Plasmid pFas-FcII A plasmid, pFas-FcII, for use in the expression of a chimera protein (to be referred to as "mFas-Fc" hereinafter) of the extracellular domain of mouse Fas (mFas) antigen and the Fc region of human IgG1 (hIgG1) was prepared in the following manner to be used in Inventive Example 2.

Firstly, oligonucleotide primers containing a sense sequence in intron 4 (GATTTTCAACCACTCAGTCG) SEQ ID NO: 37 and an antisense sequence in intron 5 (ATGCGGCCGCTGGATCCTTTGTATGAAATTGAGT AAT) SEQ ID NO: 38 of the mouse Fas antigen chromosomal gene were synthesized chemically. The latter oligonucleotide primer contained a BamHI site. Using these oligonucleotide primers, PCR was carried out making use of a plasmid containing mouse Fas antigen chromosomal gene (pMF3ES; annual meeting of the Society of Molecular Biology, 1992) as a template. As the result, a DNA fragment of 383 bp having flanking regions at the 5'- and 3'-ends of the exon 5 was amplified.

The thus amplified product was digested with PstI and BamHI to obtain a DNA fragment of 128 bp containing the 3'-end of the exon 5 and a part of the intron 5. With the thus obtained DNA fragment, a PstI-BamHI DNA fragment moiety of a plasmid pMF1 (Watanabe-Fukunaga R. et al., *J. Immunol.*, vol. 148, pp. 1274–1279, 1992) was replaced to prepare a plasmid PMFX.

Separately from this, a plasmid pMH4 which contains an exon for the human IgG1 heavy chain constant region (Nishimura Y. et al., *Cancer Res.*, vol. 47, pp. 999–1005, 1987) was digested with HaeII, and the resulting DNA fragment of 1.7 kbp was subcloned into the XbaI site of pBluescript KS(+).

This was digested with HincII and ApaI to obtain a DNA fragment of 1.4 kbp containing exons coding for hinge, CH2 and CH3 domains. This fragment was inserted into the XbaI site of the aforementioned plasmid PMFX to prepare a plasmid pFas-Fc. The plasmid pFas-Fc was digested with KpnI, blunt-ended and then digested with NotI. Thereafter, the thus obtained DNA fragment of 2.3 kbp was ligated to a mammalian expression vector pEF-BOS (Mizushima S. and Nagata S., *Nucleic Acids Res.*, vol. 18, p. 5322, 1990) to obtain the expression plasmid pFas-FcII of interest.

(2) Preparation of Expression Plasmid phTNFRβ-Fc A plasmid phTNFRβ-Fc for use in the expression of a chimera protein (to be referred to as "hTNFRβ-Fc" hereinafter) of TNF receptor β and Fc region of human IgG1 was constructed in the following manner to be used in Inventive Example 2.

Firstly, a plasmid p55TNFr-HG1 (Leostscher H. et al., *J. Biol. Chem.*, vol. 266, pp. 18324–18329, 1991) was digested with KpnI and HindIII to prepare a DNA fragment of 650 bp. The plasmid p55TNFr-HG1 is a plasmid containing a cDNA sequence which encodes the extracellular domain of human TNF receptor (p55) contiguous to an artificial splice donor sequence.

Separately from this, the plasmid pFas-FcII was digested with HincII and HindIII. Thereafter, a DNA fragment of about 700 bp containing a sequence coding for the extracellular domain of mouse Fas antigen was exchanged with the aforementioned 650 bp KpnI-HindIII fragment to obtain the plasmid phTNFRβ-Fc of interest.

(3) Preparation of Expression Plasmid pBF-Fc1

A plasmid pBF-Fc1 for use in the expression of a chimera protein (to be referred to as "hFas-Fc" hereinafter) of the human Fas antigen extracellular domain and Fc region of human IgG1 was constructed in the following manner to be used in Inventive Example 10.

Firstly, a plasmid pBLF58-1 containing a human Fas antigen-encoding DNA fragment (Itoh N. et al., *Cell*, vol. 66, pp. 233–243, 1991) was digested with XhoI and BamHI to obtain a fragment of 700 bp. Next, the plasmid pFas-Fc used in the construction of the chimera protein mFas-Fc expression vector was digested with XhoI and BamHI, and the 700 bp fragment obtained above was inserted into the digested product to obtain an expression plasmid pBHF-C1.

Separately from this, a fragment in which an intron 5 sequence of the mouse Fas antigen chromosomal gene and a BamHI site is added to a sequence coding for the extracellular domain of human Fas antigen was prepared by carrying out PCR using a sense primer 1 (ATGCCCAAGTGACTGACATCAACT) SEQ ID NO: 39 and an antisense primer 1 (GCGCGGATCCAGGAAGTGGGAAAGGATTACCTT CCTCTTTGCACTTGGTG) SEQ ID NO: 40 making use of pBLF58-1 as a template.

The thus obtained PCR product was digested with MscI and BamHI, and the resulting DNA fragment of 360 bp was inserted into pBHF-C1 which has been digested in advance with MscI and BamHI. Next, the thus obtained plasmid was digested with KpnI, blunt-ended and then digested with NotI to obtain a DNA fragment coding for the extracellular domain of human Fas antigen and Fc region of human IgG1. Thereafter, the thus obtained fragment was inserted into PEF-BOS which has been digested with BstXI, blunt-ended and then digested with NotI, thereby obtaining the human Fas-Fc expression vector pBF-Fc1.

(4) Production and Purification of Chimera Protein

COS-7 cells and BTS-1 cells (Sedivy J. M., *Biol. Technology*, vol. 6, pp. 1192–1196, 1993) were respectively transfected with plasmids pFas-FcII and phTNFRβ-Fc. COS-7 cells were also transformed with plasmid pBF-Fc1.

Transfection of COS-7 cells was carried out in accordance with the DEAE-dextran method reported by Fukunaga R. et al. (*Cell*, vol. 61, pp. 341–350, 1990). After completion of the transformation, transformed COS-7 cells were incubated for 24 hours in a medium containing 10% of FCS (fetal calf serum) and then for 48 hours and 72 hours in a serum-free medium. Thereafter, the resulting culture supernatants were collected, centrifuged, filtered through a 0.45 μm filter to remove cell debris and then subjected to a column chromatography using protein A-Sepharose 4B (Pharmacia) to purify chimera proteins mFas-Fc, hTNFRβ-Fc and hFas-Fc, respectively.

On the other hand, transfection of BTS-1 cells was carried out by means of electroporation (Potter H. et al., *Proc. Natl. Acad. Sci. USA*, vol. 81, pp. 7161–7165, 1984). That is, after digesting plasmid pFas-FcII with ApaLI, and plasmid phTNFRβ-Fc with SacI, $1 \times 10^7$ of the cells were transformed with 50 μg of each of the resulting plasmid DNA fragments together with 5 μg of XhoI-digested pSTneoB. After 10 days of selection using D-MEM containing 10% FCS and 300 μg/ml of G-418, G-418 resistant clones were isolated and cultured at 39.5° C.

In order to identify a clone which produces the chimera protein of interest, some of the isolated clones were cultured at 33° C. for 3 days, and the chimera protein secreted into the medium was inspected by enzyme-linked immunosorbent assay (ELISA). In the ELISA, anti-human IgG-Fc antibody (Cappel, 55071) was used as the capture antibody and horseradish peroxidase-labeled anti-human IgG-Fc antibody (Jackson Immunoresearch Lab, 109-035098) was used as the detection antibody.

Each of two transformants capable of producing mFas-Fc and hTNFRβ-Fc respectively in high efficiency was cultured at 39.5° C. and then inoculated into a 15 cm plate to 50% confluent. After 1 week of culturing at 33° C., mFas-Fc and hTNFRβ-Fc were purified respectively from the resulting culture supernatants by protein A-Sepharose 4B column (Pharmacia) chromatography.

When the thus purified mFas-Fc was analyzed by SDS-PAGE, a band was observed at a position corresponding to a molecular weight of 55 kD under a reducing condition, and under a non reducing condition a band was observed at a position corresponding to a molecular weight of 110 kD. These results indicate that the thus obtained chimera protein mFas-Fc exists as a homodimer formed by S—S bonding.

Inventive Example 2

Analysis by Flow Cytometry and Selection of d10S-2 Cell Line (1) Biotinylation and FITC Labeling of Chimera Protein Biotinylation of mFas-Fc and hTNFRβ-Fc was carried out using sulfosuccinimidyl 6-(biotinamide) hexanoate (NHS-LC-biotin, Pierce Chemical, 21335) in accordance with the manufacturer's instructions.

Separately from this, 1 mg of hTNFRβ-Fc and 20 μg of fluorescein isothiocyanate (FITC) were mixed in 1 ml of 50 mM sodium carbonate buffer (pH 9.5) and allowed to react with each other at room temperature for 4 hours. Thereafter, unbound FITC was removed by a column chromatography making use of Sephadex G-25M to obtain FITC-labeled hTNFRβ-Fc.

(2) Flow Cytometry

PC60-d10S cells (to be referred to as "d10S" hereinafter; Rouvier E. et al., *J. Exp. Med.*, vol. 177, pp. 195–200, 1993) were washed with a staining solution (phosphate-buffered saline (to be referred to as "PBS" hereinafter) containing 2% FCS and 0.02% $NaN_3$). About $1 \times 10^6$ of the cells were suspended in 50 μl of the staining solution supplemented with 5 μg/ml of rat anti-mouse FcγRII blocking antibody (Pharmingen). This suspension was dispensed into wells of a 96 well plate and incubated for 10 minutes on an ice bath. A 20 μg/ml solution of the biotinylated mFas-Fc was dispensed into wells of the resulting plate in 50 μl portions, and the incubation was continued for additional 30 minutes on an ice bath. After washing the plate with the staining solution, phycoerythrin-labeled streptoavidin (25 times dilution, Becton Dickinson) was added to each well, the contents in each well was adjusted to 100 μl with the staining solution and then the reaction was carried out for 30 minutes on an ice bath.

After washing the cells with the staining solution, cytometric analysis was carried out using FACScan (Becton Dickinson). As the result, a slight shift in the fluorescence intensity was observed which confirmed that said cells were stained with the biotinylated mFas-Fc (see FIG. 1a). Control was expressed as an open area, and staining before 4 hours of treatment with PMA and ionomycin as a stippled area and staining after 4 hours of treatment with PMA and ionomycin as a closed area.

Contrary to this, staining was not observed when the d10S cells treated in the same manner with the bi-otinylated hTNFRβ-Fc were analyzed by the flow cytometry. On the basis of these results, it was confirmed that the mFas-Fc prepared in Inventive Example 1 binds to the Fas ligand on the d10S cells in specific fashion.

(3) Screening of d10S-2 Cell Strain

A total of $1-3\times10^7$ of the d10S cells which showed a high fluorescence activity in the above step (2) were allowed to react with the biotinylated mFas-Fc and FITC-labeled hTNFRβ-Fc in the same manner as described above, stained with phycoerythrin-labeled streptoavidin and then subjected to cell sorting using FACScan (Becton Dickinson). Cells which emitted the phycoerythrin fluorescence at high levels (upper 0.3 to 0.5% of the cells) were collected and cultured using D-MEM (Dulbecco's modified Eagle's Medium) containing 10% FCS and 50 nM 2-mercaptoethanol.

Figure 1B:
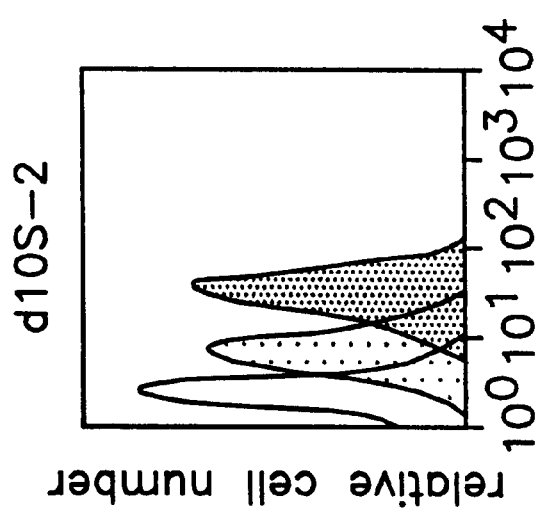

The cells thus sorted out were subjected to the above sorting procedure repeatedly, and the finally selected cell group was named d10S-2. The d10S-2 cell strain is a group of highly concentrated cells capable of showing a high Fas ligand expression quantity both in the presence and absence of stimulating agents (see FIG. 1b).

Inventive Example 3

Construction of cDNA Library

The d10S-2 cells obtained in Inventive Example 2 were cultured in D-MEM containing 10% FCS until the cell density reached $2\times10^5$ cells/ml and then stimulated with 20 ng/ml of PMA and 1 μg/ml of ionomycin at 37° C. for 3 hours. After isolating total RNA by the guanidine isothiocyanate/acid phenol method (Chomczynski P. and Sacchi N., *Anal. Biochem.*, vol. 162, pp. 156–159, 1987), poly (A) RNA was selectively isolated by repeating an oligo(dT)-cellulose column chromatography twice. Using a random hexamer or an oligo(dT) primer, double-stranded cDNA was synthesized in accordance with the procedure of Itoh N. et al. (*Cell*, vol.66, pp. 233–243, 1991). After adding a BstXI adapter to the thus obtained double-stranded cDNA, molecular weight fractionation was carried out by 1% agarose gel electrophoresis. Molecules of cDNA having a size of 1.5 kbp or more were recovered and ligated to a pCEV4 vector (Itoh N. et al., *Cell*, vol. 66, pp. 233–243, 1991) which has been digested with BstXI in advance. Using the ligation product, *E. coli* DH10B cells (Gibco BRL) were transformed by means of electroporation (Dower W. et al., *Nucleic Acids Res.*, vol. 16, pp. 6127–6145, 1988). About $1.0\times10^6$ independent clones obtained from the oligo(dT)-primed cDNA library were mixed with about $1.3\times10^6$ clones obtained from the random hexamer-primed cDNA library to prepare plasmid DNA for use in the transformation of COS-7 cells.

Inventive Example 4

Concentration of cDNA Clone by Panning

Transformation of COS-7 cells with the plasmid DNA obtained in Inventive Example 3 was carried out by electroporation. That is, $5\times10^6$ of the COS-7 cells were washed with K-PBS⁻ (a buffer solution containing 30.8 mM NaCl, 120.7 mM KCl, 8.1 mM $Na_2HPO_4$ and 1.46 mM $KH_2PO_4$) and suspended in 0.4 ml of K-PBS supplemented with 5 mM $MgCl_2$ (K-PBS⁺).

Next, 40 μg of the plasmid DNA was dissolved in 0.4 ml of K-PBS⁺ and added to the above cell suspension, and the mixture was incubated for 10 minutes on an ice bath. Electroporation was effected by applying 230 V of voltage to the cells with a capacitance of 960 μF. After 10 to 15 minutes of incubation on an ice bath, the cell suspension was diluted with 5 ml of cold serum-free D-MEM and incubated for 30 minutes at room temperature. Thereafter, the thus treated cells were inoculated into two plates having a diameter of 10 cm and cultured at 37° C. for 60 hours in D-MEM containing 10% FCS.

In the above procedure, a total of $1.2\times10^8$ COS-7 cells were transformed and cultured in the 10 cm plates. A 5 ml portion of $PBS/EDTA/NaN_3$ (PBS supplemented with 0.5 mM EDTA and 0.02% $NaN_3$) was added to each of the resulting plates and incubated at 37° C. for 30 minutes. The thus treated cells were detached from the plate and suspended again in $PBS/EDTA/NaN_3$ containing 3 mg/ml of BSA and 2.5 μg/ml of anti-mouse FcγII receptor antibody, with a cell density of $5-7\times10^6$ cells/ml. After 10 minutes of incubation on an ice bath, mFas-Fc was added to a final concentration of 4 μg/ml and the resulting cell suspension was incubated again for 60 minutes on an ice bath. The thus treated cells were washed with ice-cold PBS and suspended to a cell density of $5-7\times10^6$ cells/ml in PBS supplemented with 50 mM HEPES buffer (pH 8.3) and 0.2 mM bis (sulfosuccinimidoyl) suberate ($BS^3$, Pierce Chemical). After 30 minutes of incubation on an ice bath, 1 M Tris-HCl buffer (pH 8.0) was added to a final concentration of 50 mM, and the resulting cell suspension was incubated for 10 minutes on an ice bath. The thus treated cells were washed with PBS and suspended in 30 ml of $PBS/EDTA/NaN_3$ which has been supplemented with 3 mg/ml of BSA, and the suspension was filtered through a nylon mesh of 100 μm in pore size to remove aggregated materials.

The cell suspension was dispensed into 30 panning plates (10 cm in diameter) to which anti-human IgG-Fc antibody (Cappel, 55071) has been immobilized in advance. After 2 hours of incubation at room temperature, non-adherent cells were removed by gentle washing with PBS, and extrachromosomal DNA was extracted from the adherent cells in accordance with the procedure of Itoh N. et al. (*Cell*, vol. 66, pp. 233–243, 1991). Using the thus obtained DNA by the first panning, transformation of *E. coli* cells was carried out by means of electroporation to obtain $4.1\times10^6$ colonies. Using plasmid DNA prepared from these colonies, $9.6\times10^7$ COS-7 cells (60 plates) were transformed.

Second panning was carried out by dispensing the thus transformed cells into 30 panning plates, and plasmid DNA was prepared from the adherent cells in the same manner as the first panning. Using the thus recovered plasmid DNA, transformation of *E. coli* cells were carried out to obtain $8.0\times10^6$ clones. Using plasmid DNA prepared from these colonies, $4.0\times10^7$ COS-7 cells (10 plates) were transformed.

Third panning was carried out by dispensing the thus transformed cells into 30 panning plates. Plasmid DNA was prepared from the adherent cells in the same manner as the first and second pannings and used for the transformation of *E. coli* cells to obtain $3.8\times10^6$ clones. Using plasmid DNA prepared from these colonies, $1.0\times10^7$ COS-7 cells (25 plates) were transformed and dispensed into 10 panning plates to carry out fourth panning.

Figure 1C:
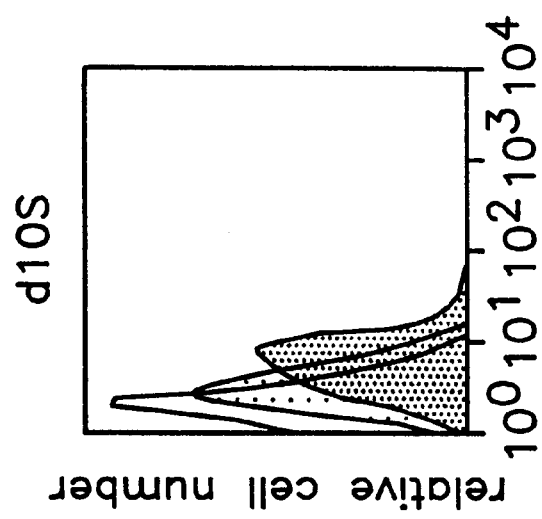

After completion of the fourth panning, extrachromosomal DNA was prepared from COS-7 cells and used for the transformation of *E. coli* cells. When plasmid DNA was prepared from each cell clone and analyzed, 16 of 48 clones contained plasmid DNA molecules each having an insert of 1.0 kbp or more. Each of these plasmid DNA molecules was introduced into COS-7 cells which were subsequently subjected to staining with the biotinated mFas-Fc and then to flow cytometry in accordance with the method of Inventive Example 2. As the results, 5 clones were found to be stained. FIG. 1c shows a result of the flow cytometry of COS-7 cells (COS/pTN24-15) transfected with one of these 5 clones, pTN24-15, which contains an insert of 1.6 kbp. The COS-7 cells transfected with pTN24-15 were not stained with the biotinylated hTNFRβ-Fc. Also, COS-7 cells transfected with pCEV4 having no foreign gene were not stained with the biotinylated mFas-Fc.

Inventive Example 5

Determination and Analysis of DNA Sequence

When the 5 clones obtained in Inventive Example 4 were analyzed by restriction enzyme mapping, it was found that they were overlapped with one another. In consequence, pTN24-15 as one of these 5 clones was further analyzed in detail. Determination of DNA sequence was carried out making use of a DNA sequencer (Model 370A, Perkin-Elmer Japan) and Taq Dye Deoxy Cycle Sequencing Kit (Perkin-Elmer Japan).

Nucleotide sequence of the clone pTN24-15 and an amino acid sequence deduced from the nucleotide sequence are shown in FIGS. 2 and 3 and SEQ ID NO: 25. This cDNA is composed of 1,623 bases and contains one open reading frame.

Though the sequence "CCA./GCCATGG" (SEQ ID NO: 41) proposed by Kozak M. (*J. Cell Biol.*, vol. 115, pp. 887–903, 1991) was not found in this sequence, its translation initiation site was considered to be ATG of the positions 74 to 76. The open reading frame is terminated with the termination codon TAA of the positions 908 to 910. It was found also that this cDNA encodes 278 amino acid residues. The molecular weight deduced from the amino acid sequence is 31,138, with an isoelectric point of 9.53.

Among 278 amino acid residues encoded by the cDNA, a sequence of 77 amino acid residues of the N-terminal side was found to be extremely rich in proline. Though a typical signal sequence was not found in the area of the N-terminal side, a hydropathy analysis confirmed the presence of 22 hydrophobic amino acid residues contiguous to the proline-rich region, which seemed to have a function as a transmembrane anchor. Because of the absence of signal sequence and the presence of inner hydrophobic domain, it was suggested that the Fas ligand is a type II transmembrane protein.

It was confirmed that an assumed region as the extracellular domain is present in the C-terminal side, which is composed of 179 amino acid residues and contains four N-glycosylation sites (Asn-X-Ser/Thr). These glycosylation sites are shown by * in FIGS. 2 and 3.

The d10S-2 cell strain used in the construction of cDNA library is a hybridoma of rat and mouse cells. In order to determine origin of the Fas ligand cDNA, primers were designed from the 3'-end noncoding region of the Fas ligand cDNA and synthesized to carry out PCR in which chromosomal DNA preparations obtained from rat and mouse splenocytes are used as templates respectively. That is, in the sequence of SEQ ID NO: 25, nucleotide positions 1006 to 1025 and 1305 to 1324 were used as sense primers 2 and 3 (SEQ ID NOS: 42 and 43), and positions 1327 to 1346 and 1543 to 1562 as antisense primers 2 and 3 (SEQ ID NOS: 43 and 44). As the results, bands of 341 bp and 258 bp in size were obtained only with the rat chromosomal DNA. These results suggest that the cDNA obtained from the clone pTN24-15 is originated from the rat gene in the d10S-2 hybridoma cells.

In this connection, *E. coli* cells were transformed with the aforementioned pTN24-15 in accordance with the method of Hanahan D. et al. ("Techniques for Transformation of *E. coli*", in *DNA Cloning*, vol. 1, ed. by Glover D. M., pp. 109–136, IRL Press, 1985). A resulting transformant, named DH10B(pTN24-15), has been deposited in National Institute of Bioscience and Human Technology, Agency of Industrial Science and Technology 1-3, Higoshi 1-chrome, 7sukuba-shi, faraki-ken 305 Japan , and has been assigned the designation as FERM P-13953, which was subsequently transferred to the International Depository Authority on Oct. 27, 1994, as FERM BP-4848.

Inventive Example 6

Northern Hybridization

Using a mRNA isolation kit (Pharmacia), poly (A) RNA was prepared from d10S, d10S-2, rat tissues (the brain, lungs, heart, liver, small intestines, kidney, ovaries, testes skeletal muscle) and rat cells (splenocytes and thymocytes). The RNA was denatured by heating at 65° C. for 5 minutes in 50% formamide, subjected to electrophoresis using 1.5% agarose gel containing 6.6% formaldehyde and then transferred on a nitrocellulose or nylon membrane (Schleicher and Schuell).

As a probe, a double-stranded DNA fragment of 925 bp containing a DNA sequence SEQ ID NO: 42 comprising the positions 43 to 967 of the pTN24-15 obtained in Inventive Example 4 was prepared by PCR and $^{32}$P-labeled making use of a random primer labeling kit (Boehringer-Mannheim). A 1.8 kbp BamHI fragment of human EF1α cDNA (Uetsuki T. et al., *J. Biol. Chem.*, vol. 264, pp. 5791–5798, 1989) was labeled with $^{32}$P and used as a control probe. The hybridization was carried out under high stringency condition in accordance with the method of Sambrook J. et al. (*Molecular Cloning, A Laboratory Manual*, 2nd ed., Cold Spring Harbor Laboratory, New York, 1989).

Figure 4:
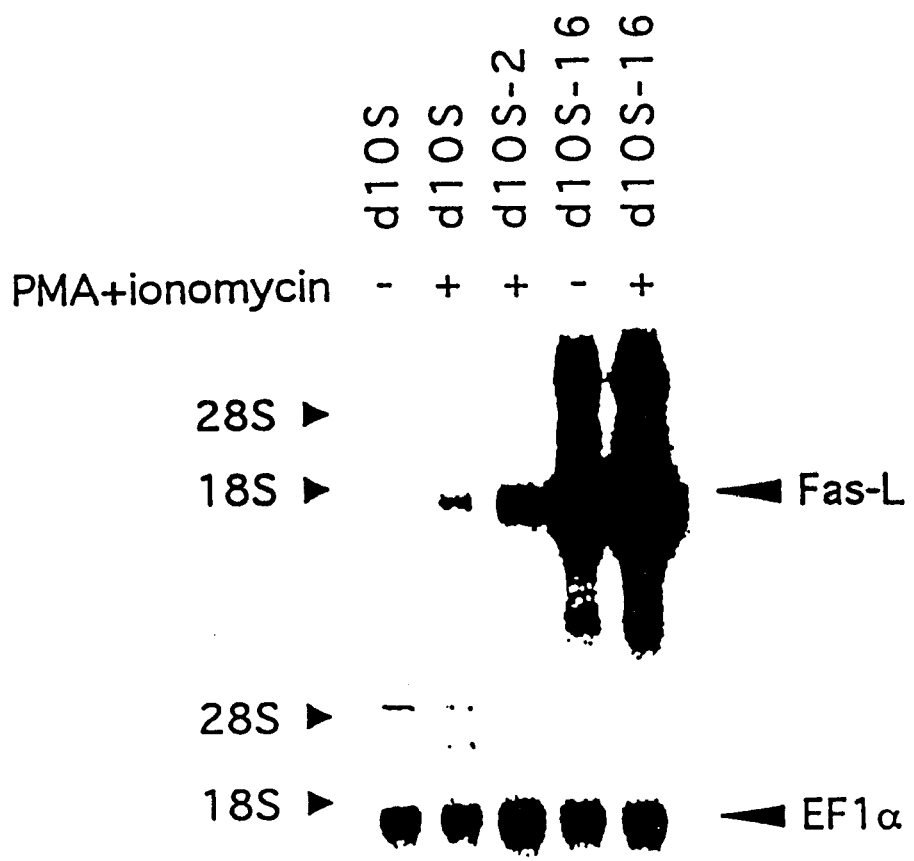
FIG. 4 shows the results of northern hybridization of d10S, d10S-2 and d10S-16.

FIG. 4 shows results of the northern hybridization in which d10S, d10S-2 and d10S-16 cells were respectively stimulated or not stimulated with PMA and ionomycin. As is evident from FIG. 4, the poly (A) RNA obtained from d10S cells showed a weak hybridization band of about 2.0 kbp. Strength of the signal of this band increases when d10S cells are stimulated with PMA and ionomycin. The poly (A) RNA obtained from d10S-2 cells showed a signal which was about 4 times stronger than that from d10S cells stimulated with PMA and ionomycin, indicating that the expression quantity of Fas ligand mRNA in d10S-2 cells is about 4 times higher than that in d10S cells.

In the case of the d10S-16 cells which has been obtained after 16 repetitions of the procedure of Inventive Example 2, the expression quantity of mRNA was about 100 times higher than the case of d10S cells. Since the cytotoxic activity of d10S-16 cells was 100 times higher than that of d10S cells, it was found that increase in the expression quantity of the Fas ligand mRNA has positive correlations with the cytotoxic activity and the staining strength by mFas-Fc.

Figure 5:
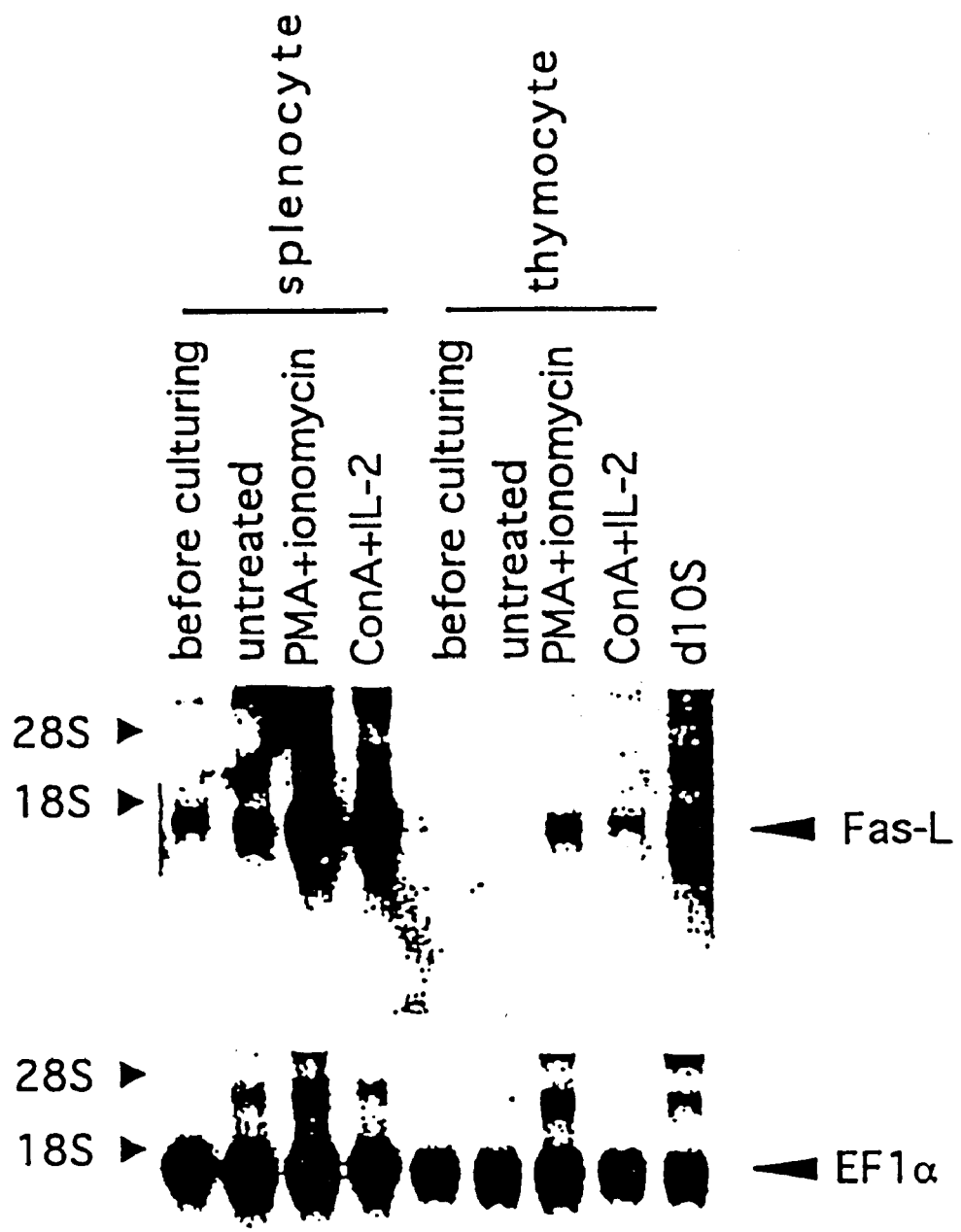
FIG. 5 shows the results of northern hybridization of rat splenocytes and thymocytes.

FIG. 5 shows results of the northern hybridization of splenocytes and thymocytes prepared from the spleen and the thymus of rat, comparing just after their preparation (before culturing), after their culturing at 37° C. for 8 hours without stimulating agent (untreated) and after their culturing at 37° C. for 8 hours in the presence of each stimulating agent. In the rat splenocytes, weak expression of the Fas ligand mRNA was observed. When the rat splenocytes were stimulated for 8 hours with PMA and ionomycin or ConA and IL-2, amount of the Fas ligand mRNA increased markedly. In the case of rat thymocytes, expression of the Fas ligand mRNA was hardly found before their culturing and after their untreated culturing. However, when the rat thymocytes were stimulated with PMA and ionomycin or ConA and IL-2, expression level of the Fas ligand mRNA increased to the same level of the case of splenocytes (FIG. 5).

Figure 6:
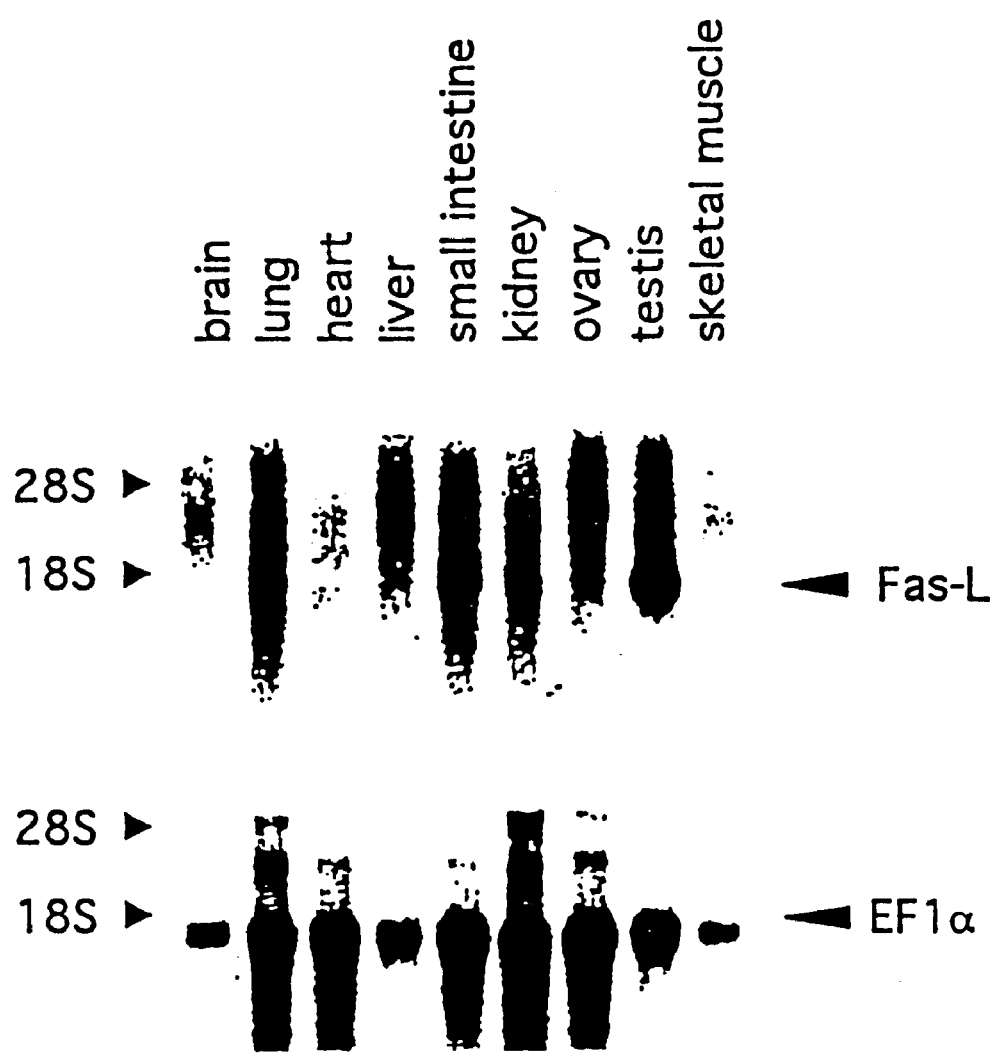
FIG. 6 shows the results of northern hybridization of rat tissues.

When expression level of the Fas ligand mRNA in each rat tissue was examined, a band of about 2.0 kbp having a strong signal was found in testis (FIG. 6). Bands having normal or weak signals were found in the small intestine, kidney and lung, but expression of the Fas ligand mRNA was not found in other tissues.

In this instance, all mRNA molecules were evidently intact, because a band of 1.8 kbp was found in all cells and tissues re-hybridized with the human EF1α cDNA probe (the lower column in each of FIGS. 4, 5 and 6).

Inventive Example 7

Biochemical Analysis of Fas Ligand

The Fas ligand expressed in d10S-12 cells and the Fas ligand expressed in COS-7 cells which have been transfected with pTN24-15 were checked for their biochemical properties.

The d10S-16 cells are a cell population which has been obtained after 12 repetitions of the procedure of Inventive Example 2. Firstly, the cell surface protein of the d10S-12 cells or the COS-7 cells transfected with pTN24-15 was biotinated by the method of Meier et al. (*Anal. Biochem.*, vol. 204, pp. 220–226, 1992) in which D-biotinyl-ε-aminocaproic acid N-hydroxysuccinimide ester (biotin-CNHS-ester, Boehringer Mannheim) is used. In this case, COS-7 cells transfected with the pCEV4 vector which does not contain extrinsic gene were used as a control of the COS-7 cells transfected with pTN24-15. Cells ($7.5 \times 10^6$) were added to 1 ml of a lysis buffer (1% NP-40, 50 mM Tris-HCl (pH 8.0), 150 mM NaCl, 1 mM (p-aminophenyl) methylsulfonyl fluoride hydrochloride (APMSF), 1 μg/ml pepstatin and 1 mM leupeptin) and incubated for 30 minutes on an ice bath to effect cell lysis.

After 15 minutes of centrifugation at 14,000 rpm, the resulting supernatant fluid was incubated with 10 μg/ml of hTNFRβ-Fc for 60 minutes on an ice bath and then with a 5% volume of protein A-Sepharose 4B for 60 minutes at 4° C. After removing protein A-Sepharose 4B, 10 μg/ml of mFas-Fc was added to the resulting supernatant fluid and incubated for 60 minutes on an ice bath. To the resulting mixture was added 1% volume of protein A-Sepharose 4B, followed by overnight incubation at 4° C. After centrifugation, the precipitate was washed with the lysis buffer, suspended in 20 μl of Laemmli's sample buffer (62.5 mM Tris-HCl buffer (pH 6.3) containing 2% SDS, 10% glycerol and 0.002% Bromophenol Blue) supplemented with 5% 2-mercaptoethanol and then heated at 95° C. for 2 minutes. Thereafter, the thus prepared sample was subjected to a gradient gel electrophoresis using a 10 to 20% gradient polyacrylamide gel containing 0.1% SDS, and the protein molecules were transferred on a PVDF membrane and detected with an ECL system (Amersham).

Figure 7:
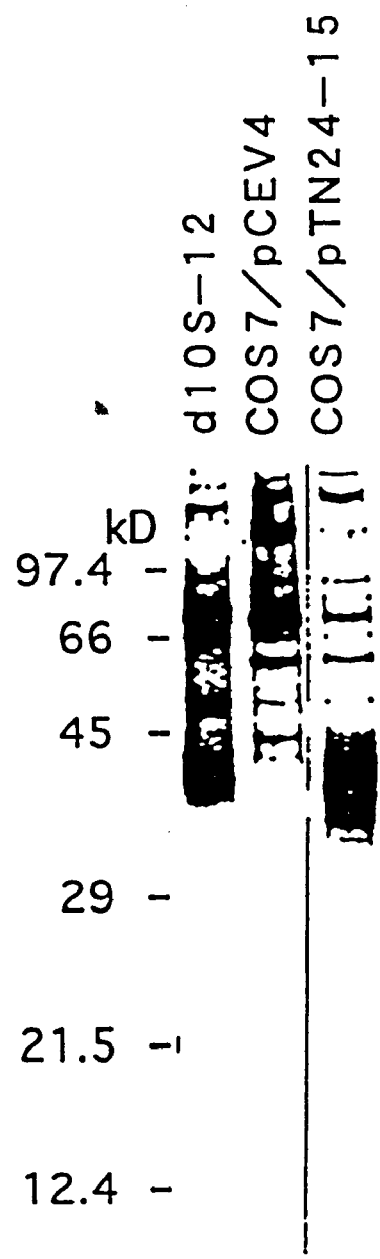
FIG. 7 shows the results of immunoprecipitation of COS-7 cells transformed with d10S-12 or pTN24-15.

As shown in FIG. 7, mFas-Fc immunoprecipitated with a protein having a molecular weight of about 40,000 contained in the d10S-12 cell lysate and with a protein having a molecular weight of about 37,000 to 45,000 contained in the lysate of COS-7 cells transfected with pTN24-15 (COS7/pTN24-15). Products of immunoprecipitation were not found in the case of COS-7 cells transfected with the pCEV4 vector which does not contain foreign gene (COS7/pCEV4).

Molecular weight of each of the proteins immunoprecipitated in the COS-7 cells transfected with pTN24-15 and in the d10S-12 cells was larger than the molecular weight deduced from the aforementioned amino acid sequence. The difference in the molecular weight between these two cell populations and the difference between the molecular weight of immunoprecipitated proteins and the molecular weight deduced from the amino acid sequence were considered to be due to different glycosylation occurred in some of the four N-glycosylation sites.

Inventive Examole 8

Measurement of Cytotoxicity of Fas Ligand

Cytotoxic activities of d10S cells and COS-7 cells transfected with pTN24-15 were measured using W4 cells as the target cells (Ogasawara J., et al., Nature, vol. 364, pp. 806–809, 1993). The W4 cells are cells which acquired mouse Fas antigen-expressing ability by transformation of mouse WR19L cells that can hardly express mouse Fas antigen and are sensitive to the cytotoxicity of TNF.

ExaminatIon of cytotoxic activity was carried out in accordance with the method of Rouvier E. et al. (*J. Exp. Med.*, vol. 177, pp. 195–200, 1993).

Firstly, d10S cells ($2.5–5 \times 10^5$ cells/ml) were suspended in 10% FCS-containing D-MEM supplemented with 10 ng/ml of PMA (Sigma Chemical) and 500 ng/ml of a calcium ionophore, ionomycin (Calbiochem). After 3 hours of incubation at 37° C., the cells were washed with D-MEM to be used as effector cells. Also, COS-7 cells were transfected with pTN24-15 by DEAE-dextran method to be used as effector cells. On the other hand, $1 \times 10^6$ of WR19L cells or W4 cells were suspended in 100 μl of RPMI 1640 containing 10% FCS and incubated at 37° C. for 2 hours together with 20 μCi of [$^{51}$Cr] sodium chromate (Amersham). The resulting cells were washed with the culture solution (RPMI 1640) and used as the target cells.

$1 \times 10^4$ of $^{51}$Cr-labeled target cells were mixed with effector cells at the various ratios in each well of a round-bottomed microtiter plate. Total volume of the cell suspension in each well was adjusted to 200 μl. The thus prepared plate was centrifuged at 700 rpm for 2 minutes and then incubated at 37° C. for 4 hours. After 5 minutes of centrifugation at 1,200 rpm, a 100 μl portion of supernatant fluid was collected from each well and its radioactivity was measured using a γ counter to calculate specific cytolysis ratio.

Spontaneous release of $^{51}$Cr was determined by incubating the target cells solely in the medium, and maximum release was determined by adding Triton X-100 to the target cells to a final concentration of 0.1%. The specific cytolysis ratio was calculated based on the following formula.

$$\text{Specific cytolysis ratio} = \frac{A - B}{C - B}$$

A, experimental release of $^{51}$Cr
B, spontaneous release of $^{51}$Cr
C, maximum release of $^{51}$Cr.

Figure 8:
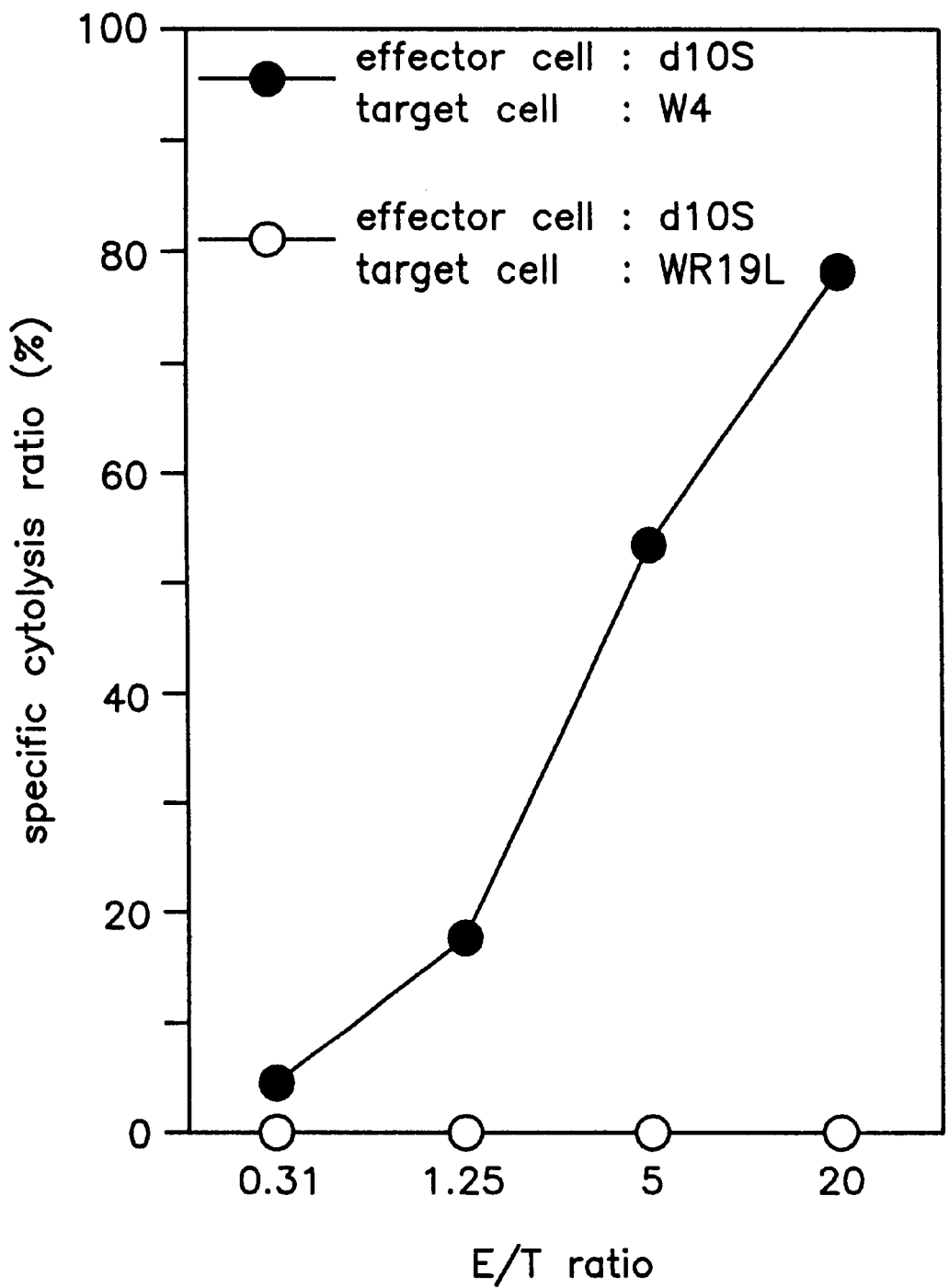
FIG. 8 shows cytotoxic activity of d10S cells when W4 and W19L are used as target cells.
Figure 9:
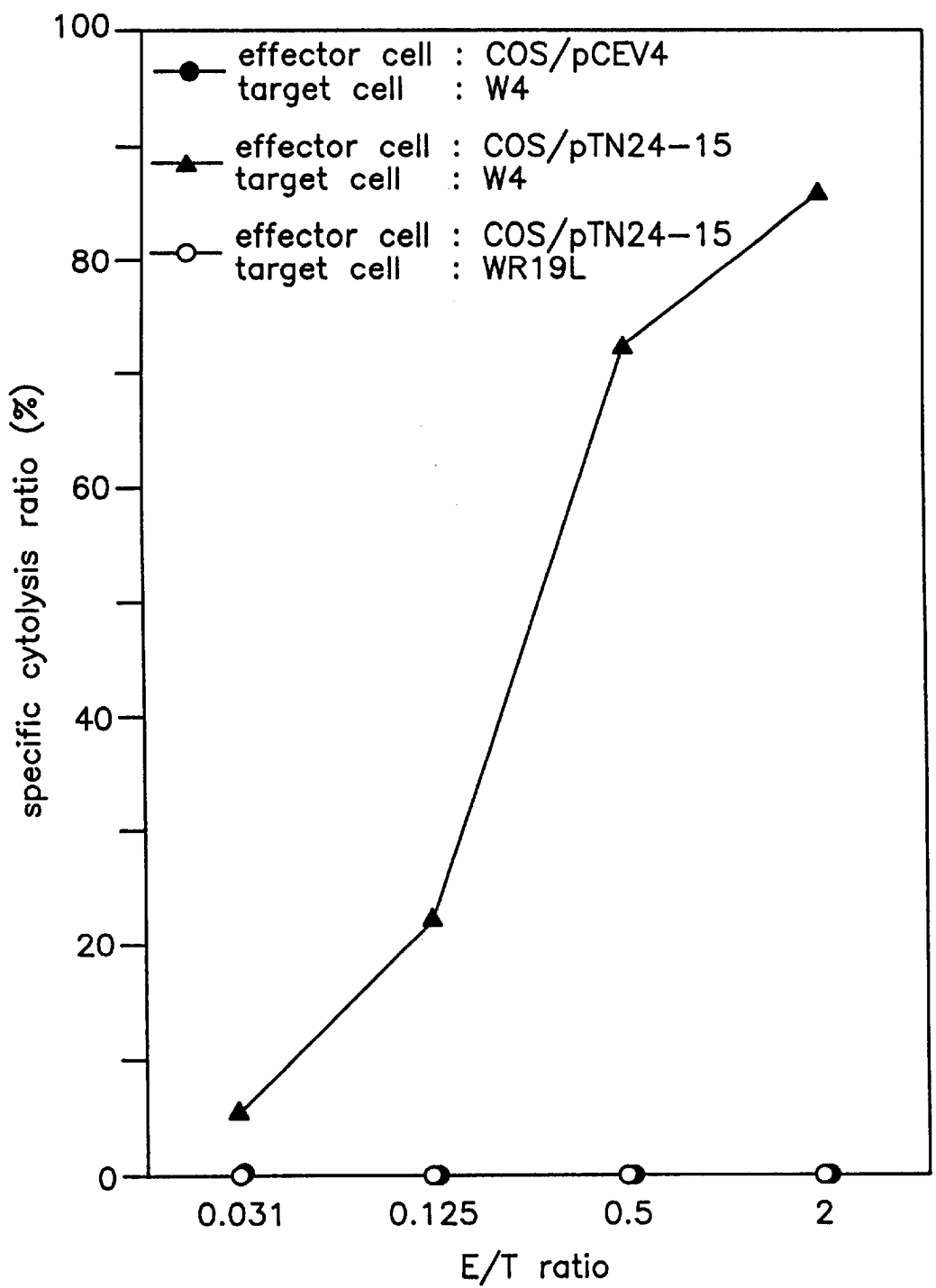
FIG. 9 shows cytotoxic activities of COS-7 cells transformed with pTN24-15 and COS-7 cells transformed with pCEV4 when W4 and W19L are used as target cells.

As shown in FIG. 9, the COS-7 cells transfected with pTN24-15 (COS/pTN24-15) lysed W4 cells, but lysis of W4 cells was not observed by another COS-7 cells transformed with the pCEV4 vector having no foreign gene (COS/pCEV4). When cytotoxic activities of the COS-7 cells transfected with pTN24-15 (COS/pTN24-15) and d10S cells are compared by their ratio to W4 cells (effector cells/target cells), the former showed at least 10 times higher activity than the latter. In addition, both of the d10S cells and the COS-7 cells transfected with pTN24-15 (COS/pTN24-15) showed no cytotoxicity upon WR19L cells (FIGS. 8 and 9).

(2) Cytotoxicity by Adding of Culture Supernatant

Figure 10:
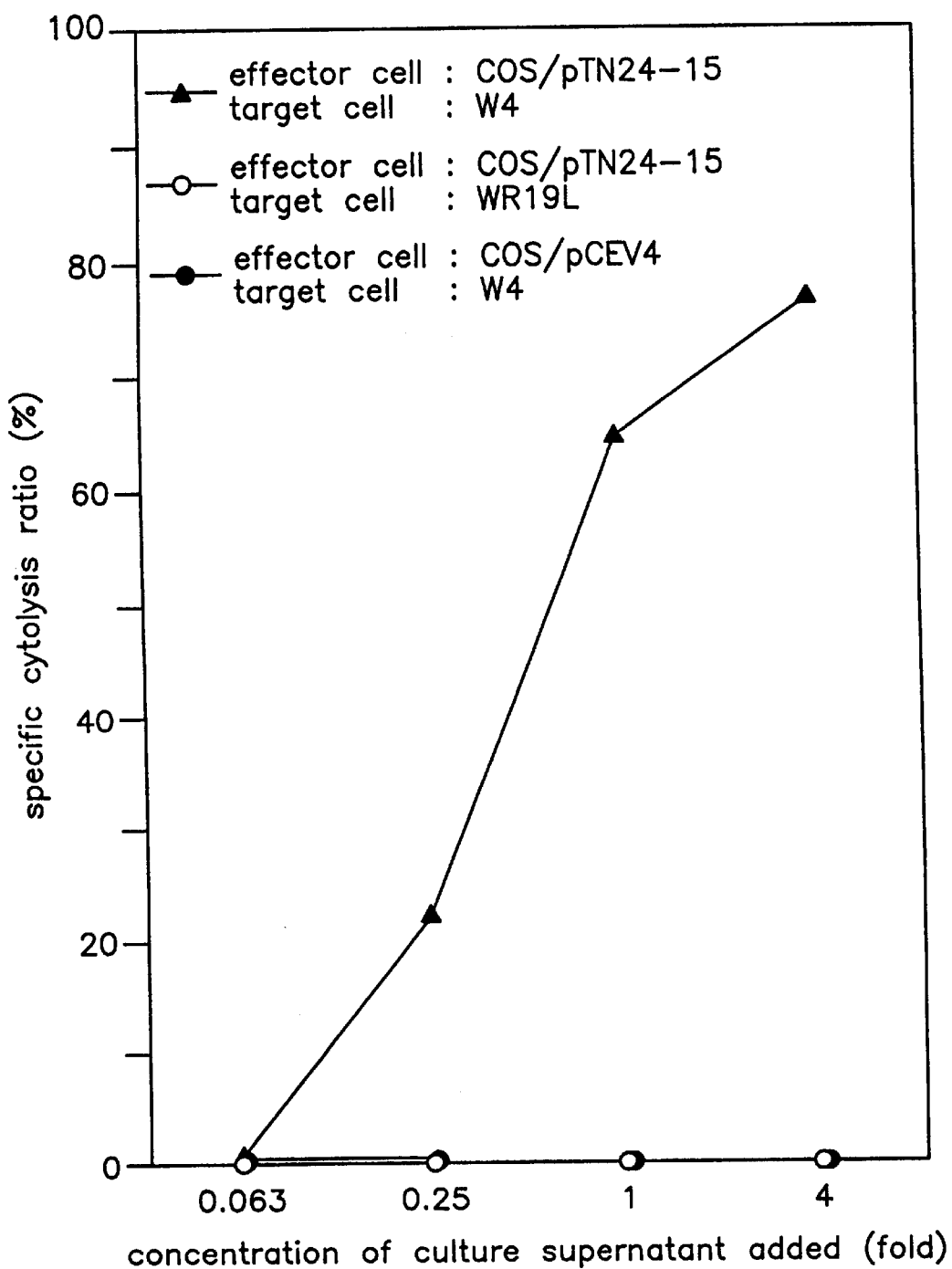
FIG. 10 shows cytotoxic activities of COS-7 cells transformed with pTN24-15 and COS-7 cells transformed with pCEV4 when W4 and W19L are used as target cells.

FIG. 10 shows the examined cytotoxic activity by adding a culture filtrate of various concentrations of the COS/pTN24-15 (the COS-7 cells transfected with pTN24-15) or COS/pCEV4 against the respective effector cells (W4, WR19L).

When cytotoxic activity of a culture supernatant of the COS-7 cells transfected with pTN24-15 (COS/pTN24-15) was examined, significant activity was observed on the W4 cells but not on the WR19L cells (FIG. 10). This result shows that the recombinant Fas ligand was expressed by the COS-7 cells and cleaved to be a soluble form.

(3) Inhibition of the Cytotoxic Activity by mFas-Fc and hTNFRβ-Fc.

Figure 11:
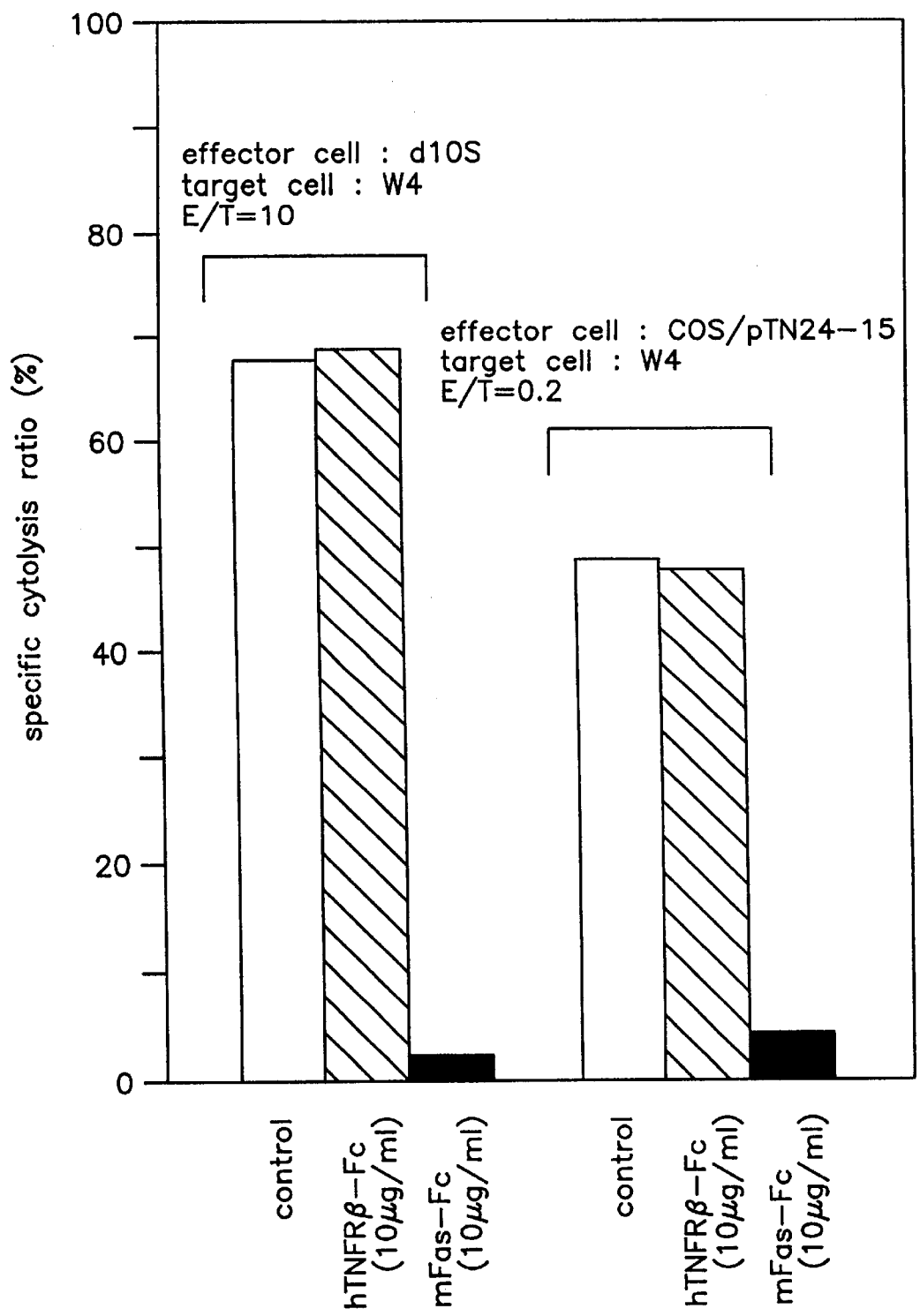
FIG. 11 shows the inhibition effect of mFas-Fc on cytotoxic activity of COS-7 cells transformed with d10S cells or pTN24-15 against W4 cells.

In addition, when mFas-Fc and hTNFRβ-Fc were added to the assay system, and the cytotoxicity was examined. The results are shown in FIG. 11. As FIG. 11 shows, the cytotoxicity of the Fas ligand-expressing COS-7 cells (COS/pTN24-15) was inhibited by 10 μg/ml of mFas-Fc but not by the same amount of hTNFRβ-Fc similar to the case of the d10S cells.

Inventive Example 9

Fragmentation of Chromosomal DNA

Using a 24 well plate, $8 \times 10^4$ of COS-7 cells in each were transfected with 10 μg of pTN24-15. After 72 hours of the transformation, $2 \times 10^5$ of WR19L cells or W4 cells were added to each well and incubated at 37° C. for 1 to 3 hours in RPMI 1640 containing 10% FCS. Non-adherent cells which did not adsorbed to the wall of each well were collected to prepare chromosomal DNA in accordance with the method of Laird P. W. et al. (*Nucleic Acids Res.*, vol. 19, p. 4293, 1991), and the thus prepared DNA was subjected to an agarose gel electrophoresis in the presence of 0.5 μg/ml of ethidium bromide.

Figure 12:
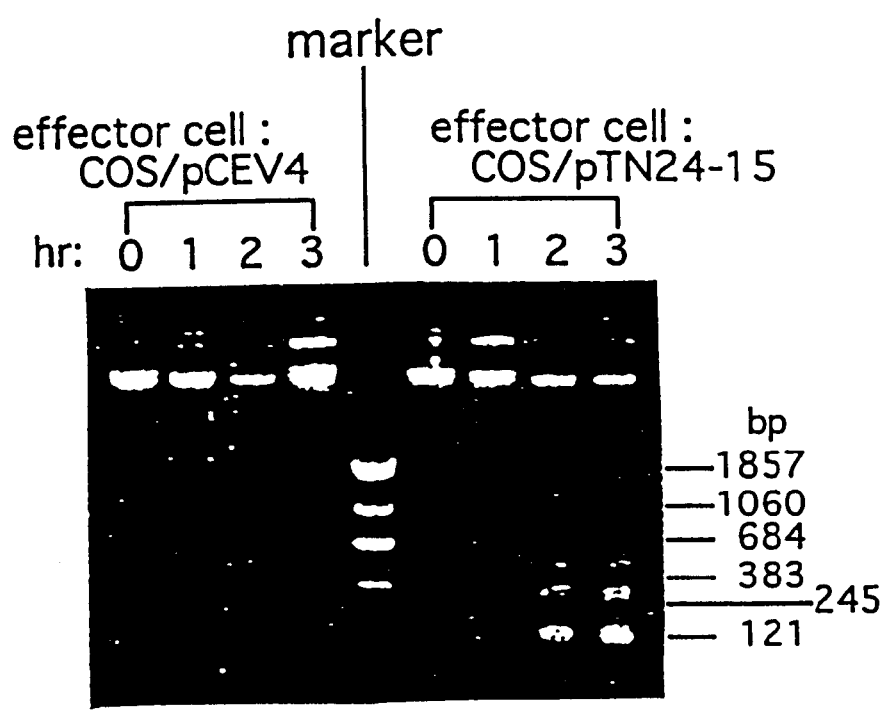
FIG. 12 shows gel electrophoresis showing changes in the chromosomal DNA in target cells when COS-7 cells transformed with pTN24-15 are used as effector cells and W4 and W19L cells are used as the target cells.

The results are shown in FIG. 12. As is evident from the drawing, the chromosomal DNA in the W4 cells co-cultured with COS-7 cells which have been transfected with pTN24-15 (COS/pTN24-15) became fragments in a step-ladder fashion which is an important feature of apoptosis.

The DNA ladder was observed after 1.0 hour of the incubation, and most portion of the DNA became fragments after 2 hours of the incubation.

Such a fragmentation of DNA was not observed in W4 cells co-cultured with COS-7 cells which have been transfected with pCEV4 that contains no foreign gene. In addition, such a fragmentation of DNA was not found in WR19L cells but only in W4 cells co-cultured with transformed COS-7 cells.

Inventive Example 10

Purification of Fas Ligand by Affinity Chromatography (1) Biotinylation of Cell Surface Protein In order to use as a tracer protein in the following experiments, biotinylation of cell surface protein was carried out in accordance with the method of Meier et al. (*Anal. Biochem.*, vol. 204, p. 220, 1992). That is, the d10S-12 cells prepared in the following step (3) were suspended in 10 mM sodium borate-buffered physiological saline containing 50 μg/ml of NHS-LC-biotin to a cell density of $1 \times 10^7$ cells/ml and incubated at room temperature for 15 minutes. After adding ammonium chloride to a final concentration of 10 mM to terminate the reaction, the thus treated cells were washed three times with 50 mM Tris-HCl buffer containing 150 mm of NaCl (pH 8.0, to be referred to as "TBS" hereinafter), thereby effecting biotinylation of cell surface protein.

(2) Preparation of mFas-Fc Affinity Column

A 4 mg portion of the purified chimera protein, mFas-Fc, prepared in Inventive Example 1 was dissolved in 4 ml of PBS (pH 7.4) and mixed with 2 ml of protein A-Sepharose 4B, and the mixture was incubated at 4° C. for 1 hour to effect their binding. In order to remove free protein molecules, the resin was washed three times with TBS and then once with 200 mM sodium borate solution (pH 9.0). Thereafter, the thus treated resin was incubated at room temperature for 45 minutes in 200 mM sodium borate solution (pH 9.0) containing dimethylpimelimidate (DMP) to effect covalent binding of mFas-Fc to the resin.

(3) Purification of Fas Ligand

The d10S subline, d10S-12, obtained by 12 times of repetition of the procedure of Inventive Example 2 was cultured at 37° C. using 10 roller bottles containing 10% FCS-containing D-MEM further supplemented with 50 nM of 2-mercaptoethanol and 20 mM HEPES (pH 7.4). When the cell density reached $2 \times 10^5$ cells/ml, 10 ng/ml of PMA and 500 ng/ml of ionomycin were added and the culturing was continued for additional 4 hours.

After completion of the culturing, the cell suspension was subjected to 20 minutes of centrifugation at 250×g to recover the resulting pellet which was subsequently washed three times with PBS and then once with TBS. The thus washed pellet was stored at −80° C. for use in the following membrane fraction preparation. A portion of the pellet was also used for the biotinylation of cell surface protein carried out in the above step (1).

The frozen cell pellet was added to 4 volumes of 0.3 M sucrose solution containing 1 mM p-aminophenyl methane-sulfonyl fluoride hydrochloride (APMSF), 1 μg/ml of pepstatin, 1 μg/ml of leupeptin and 0.02% NaN₃ and, using Ultra-Turrax T25 (Janke & Kunkel, Staufen), homogenizd at blue position for 2 minutes on an ice bath.

Nuclei and un-homogenizd cells were removed by 20 minutes of centrifugation at 1,000×g and at 4° C. The resulting supernatant fluid was then subjected to 90 minutes of centrifugation at 100,000×g and at 4° C. to obtain a membrane fraction. The thus obtained membrane fraction was dissolved in 40 ml of a lysis buffer (TBS containing 1% NP-40, 1 mM APMSF, 1 μg/ml of pepstatin and 1 μg/ml of leupeptin), and the solution was shaken overnight at 4° C. to effect solubilization. The thus solubilized membrane fraction was centrifuged at 100,000×g for 60 minutes at 4° C., and the resulting supernatant fluid was stored at −80° C. The aforementioned cells whose cell surface protein was biotinylated were also treated in the same manner and stored at −80° C.

A 100 ml portion of the membrane fraction solubilized to be used as a tracer of Fas ligand was mixed with 10 ml of the solubilized membrane fraction of the biotinylated cells. The resulting mixture was applied to an mFas-Fc column (1.4 ml) which has been equilibrated in advance with TBS containing 1% NP-40.

The column was washed with 50 ml of TBS containing 1% NP-40 and 50 ml of TBS containing 0.1% NP-40 and then elution of Fas ligand was carried out with 50 mM Tris-HCl buffer (pH 8.0) containing 1 M NaCl and 0.1% NP-40.

The eluates were collected in 1 ml fractions, and a 10 μl portion of each fraction was subjected to SDS-PAGE and then transferred on a PVDF membrane. The biotinylated protein was stained by allowing it to react with HRPO-labeled streptoavidin and detected by ECL system (Amersham) in accordance with the manufacturer's instructions.

Fractions containing 40 kD biotinylated Fas ligand were pooled and incubated overnight at 4° C. together with 10 μl of ConA-agarose beads (EY Laboratories). After 4 times of washing with TBS containing 0.1% NP-40, Fas ligand was eluted with 200 μl of PBS containing 0.1% NP-40 and 2 M α-methylmannoside to obtain purified Fas ligand.

(4) SDS-polyacrylamide Gel Electrophoresis

Figure 13:
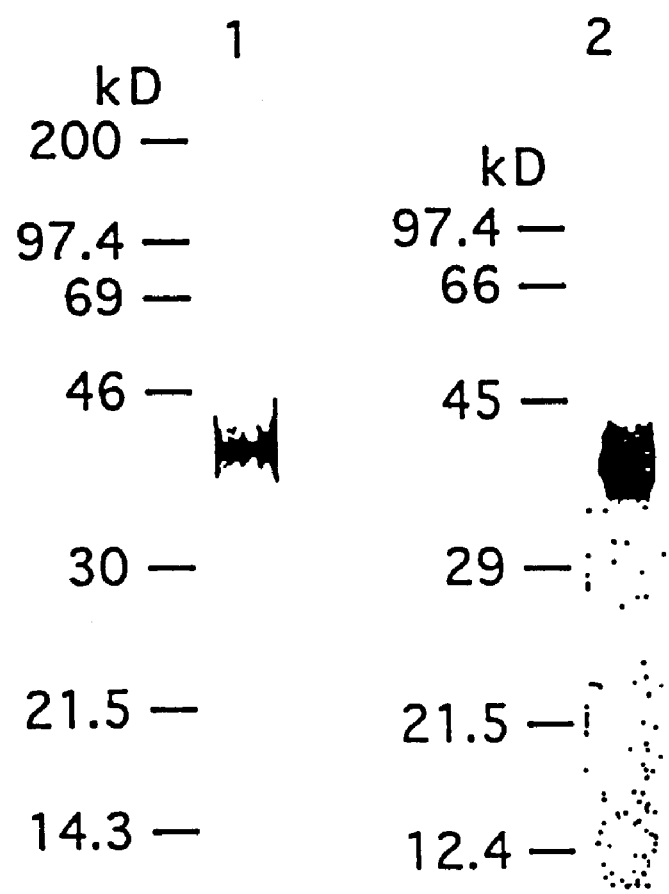
FIG. 13 shows the results of SDS-polyacrylamide electrophoresis of purified Fas ligand.

The purified Fas ligand obtained in the above step (3) was subjected to electrophoresis using a 10 to 20% gradient polyacrylamide gel containing 0.1% SDS, stained using a silver staining kit (Wako Pure Chemical Industries), transferred on a PVDF membrane and then detected by the aforementioned ECL system. As shown in FIG. 13, the purified Fas ligand was detected as a single band of about 40 kD in molecular weight by both silver staining and ECL system under non-reducing conditions.

The results are shown in FIG. 13. In the drawing, the lane 1 shows results of the silver staining and the lane 2 shows the detection results by the ECL system.

(5) Cytotoxic Activity

Figure 14:
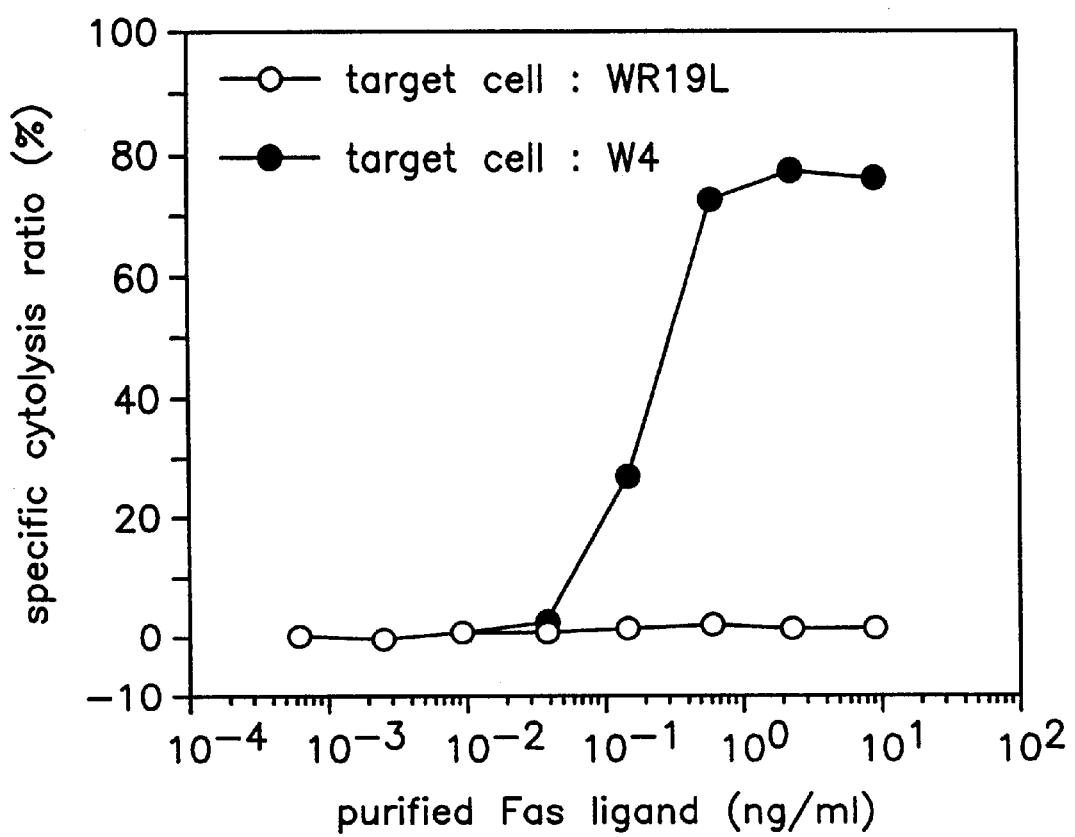
FIG. 14 shows cytotoxic activity of purified Fas ligand when W4 and W19L cells are used as target cells.

Cytotoxic activity of the purified Fas ligand was measured in accordance with the procedure of Inventive Example 8. In this case, however, the purified Fas ligand obtained in the above step (3) was used instead of the d10S effector cells and the COS cells transfected with pTN24-15, and the cytotoxic activity was measured using the specific cytolysis ratio on the W4 and WR19L target cells as an index. As shown in FIG. 14, cytotoxic activity was not found against WR19L cells which do not express Fas antigen, but a concentration-dependent cytotoxic activity was found against the Fas antigen-expressing W4 cells.

Inventive Example 11

Screening Using a Part of Rat Fas Ligand DNA (1) Screening of Human Chromosomal DNA Library Indicator cells (*E. coli* strain VCS257) were infected with a human (placental) chromosomal DNA phage library (EMBL3 SP6/T7, Clontech), mixed with soft agar and overlaid on agar plates. The overlaid plates were incubated overnight at 37° C. to effect formation of phage plaques. After cooling at 4° C. for about 4 hours, the phage particles were transferred on nitrocellulose filters.

Separately from this, PCR was carried out using the plasmid pTN24-15 obtained in Inventive Example 4 as a template, a sequence (AGAACTCCGTGAGTTCACCA) as a sense primer 4 (SEQ ID NO: 47 and a sequence (CAATATTCCTGGCATCCATG) as an antisense primer 4 (SEQ ID NO: 48), thereby effecting amplification of a cDNA fragment which encodes the extracellular domain of rat Fas ligand cDNA (nucleotide positions 400 to 967 of SEQ ID NO: 25). A probe 1 (SEQ ID NO: 49) was prepared by labeling the amplified product with $^{32}$P using a random primer labeling kit (Boehringer-Mannheim) in accordance with the procedure of Inventive Example 6. In the same manner, a 5'-end sequence of SEQ ID NO: 25, namely nucleotide positions 43 to 233, was amplified by PCR and labeled with $^{32}$P to prepare a probe 2 (SEQ ID NO: 50).

The nitrocellulose filters obtained above and the thus prepared each probe was subjected to hybridization by slightly modifying the method of Shaw et al. (Nucleic Acids Res., vol. 11, pp. 555–573, 1983). That is, the filters were washed overnight at 65° C. in 3×SSC containing 0.1% SDS and then subjected to 5 hours of prehybridization at 42° C. in 5×SSC containing 50% formamide, 5× Denhardt solution, 0.1% SDS and 250 μg/ml of denatured salmon sperm DNA. Next, the aforementioned each probe (1.1×10$^6$ cpm/ml) was added to 5×SSCP containing 50% formamide, 1× Denhardt solution, 0.1% SDS, 100 μg/ml of denatured salmon sperm DNA and 10% (w/v) dextran sulfate, and the above filters were subjected to 18 hours of hybridization at 28° C. The filters were washed twice with 2×SSCP containing 0.1% SDS at room temperature and then three times with 0.3× SSCP containing 0.1% SDS at 37° C. When the thus treated filters were checked by autoradiography, a plurality of positive clones were detected.

(2) Analysis of Positive Clones—1

Phage DNA fragments were prepared from 2 clones, λhFL4 and λhFL7, selected from the positive clones obtained by the hybridization with the probe 1, in accordance with a known method (for example, see Sambrook J. et al., *Molecular Cloning: a Laboratory Manual*, 2nd. ed., Cold Spring Harbor Laboratory, New York, 1989). The clones λhFL4 and λhFL7 respectively contained human chromosomal DNA fragments of 18 kbp and 17 kbp, and results of their restriction enzyme mapping revealed that they have a mutually overlapped area.

A DNA fragment (SEQ ID NO: 51) corresponding to the nucleotide positions of 524 to 967 of SEQ ID NO: 25 was prepared from the plasmid pTN24-15 obtained in Inventive Example 4 and labeled with $^{32}$P in accordance with the procedure of Inventive Example 6 to be used as a probe. The clones λhFL4 and λhFL7 were digested with several restriction enzymes and subjected to Southern hybridization using the just obtained probe 3. As the result, a 2.8 kbp HindIII fragment in the clones λhFL4 and λhFL7 hybridized with the probe 3.

DNA was prepared from the clone λhFL4 and digested with HindIII. The thus obtained 2.8 kbp fragment was inserted into HindIII-digested pBluescript KS(+), and the resulting plasmid was named pBL-hFL4H. When DNA sequence of the plasmid pBL-hFL4H was analyzed using a DNA sequencer (Model 370A, Perkin-Elmer Japan), it was confirmed that this plasmid contains a DNA sequence which encodes C-terminal side 130 amino acid residues of the extracellular domain of the human Fas ligand. The results are shown in FIG. 15 and SEQ ID NO: 27. In FIG. 15, a region until the 12th position counting from the 5'-end is an intron, the exon moiety starts from the 13th position G, and the sequence TAA from the 405th to 407th positions is a termination codon.

This nucleotide sequence was compared with the nucleotide sequence of pTN24-15 analyzed in Inventive Example 5, and amino acid residues and bases of rat Fas ligand which were different from those of the human Fas ligand were underlined in FIG. 15. The confirmed moiety of sequence showed high homology with the nucleotide sequence of 514th to 910th positions of SEQ ID NO: 25; 86.7% homology in the nucleotide sequence and 81.5% homology in the amino acid sequence.

A transformant, *E. coli* DH10B(pBL-hFL4H), obtained by transforming an *E. coli* strain with the plasmid pBL-hFL4H has been deposited in National Institute of Bioscience and Human Technology, Agency of Industrial Science and Technology 1-3, Higoshi 1- chrome, Tsukuba-shi Ibaraki-ken 305, Japan, and has been assigned the designation as FERM P-14014, which was subsequently transferred to the International Depository Authority on Oct. 27, 1994, as FERM BP-4849.

(3) Analysis of Positive Clones—2

Phage DNA was prepared in the same manner from a clone, λhFL5, selected from the positive clones obtained by the hybridization with the probe 2. it was confirmed that this clone contains a chromosomal DNA fragment of 18 kbp. DNA was prepared from the clone λhFL5 and digested with BamHI. The thus obtained fragment of 4.4 kbp was introduced into BamHI-digested pBluescript KS(+), and the resulting plasmid was named pBL-hFL5B1. When DNA sequence in the plasmid pBL-hFL5B1 was analyzed using a DNA sequencer, it was confirmed that this plasmid contains a DNA sequence which encodes 130 amino acid residues including the cytoplasmic domain of the human Fas ligand. By comparing the thus obtained nucleotide sequence with the nucleotide sequence of pTN24-15, the promoter, intron and exon regions were determined.

The results obtained in the above steps (2) and (3) are shown in FIGS. 16 to 18. In these drawings, a portion indicated by - - - is an unidentified nucleotide sequence. The chromosomal gene for the human Fas ligand comprises 4 exons. All the splicing donor and acceptor sites were confirmed to the GT - - - AG rule (Padgett et al., Annu. Rev. Biochem. vol. 55, pp. 1119–1150, 1986). Further flanking sequences are in good agreement with favored nucleotide frequencies noticed in other split genes.

Inventive Example 12

Cloning and Expression of Human Fas Ligand-encoding cDNA (1) Cloning of Human Fas Ligand cDNA by PCR Firstly, lymphocytes collected from human peripheral blood were suspended to a cell density of $2\times10^6$ cells/ml in RPMI 1640 medium (NISSUI PHARMACEUTICAL) containing 10% FCS, 50 μM β-mercaptoethanol and 20 ng/ml of IL-2 and cultured overnight at 37° C. Next, ConA was added to a final concentration of 5 μg/ml, and the culturing was continued for 4 days at 37° C. Dead cells were removed by a density gradient centrifugation using HistoPak 1083 (Sigma Chemical), and poly (A) RNA was prepared using a mRNA preparing kit (Pharmacia). Synthesis of single-stranded cDNA and PCR were carried out in the following manner in accordance with the method of Kawasaki E. S. et al. (*Amplification of RNA in PCR Protocols, A Guide to Methods and Amplifications*, ed. by M. A. Innis et al., Academic Press, San Diego, pp. 21–27, 1990).

Firstly, a sense primer 5 (GCTCTAGACTACAGGACTGAGAAGAAGT) (SEQ ID NO: 52) and an antisense primer 5 (GCTCTAGAACATTCTCGGTGCCTGTAAC) (SEQ ID NO: 53) were prepared. This sense primer contains an upstream region of the ATG initiation codon and a XbaI site (GCTCTAGA) at 5'-end. On the other hand, the antisense primer contains a downstream region of the TAA termination codon and a XbaI site (GCTCTAGA) at 5'-end.

To 1 μg of the poly (A) RNA were added 50 ng of random hexamers and 200 units of MMLV RNase H⁻ reverse transcriptase (Gibco BRL) and reverse transcriptation reaction was carried out. A 2.0 μl portion of the resulting reaction solution was diluted with 100 μl of a PCR buffer containing 100 pmol of the sense primer and the same amount of the antisense primer, 4×dNTP and Taq DNA Polymerase. PCR was carried out using DNA Thermal Cycler (Perkin-Elmer) by 20 cycles of the reaction, each cycle comprising incubation at 94° C. for 1 minute, 55° C. for 2 minutes and 72° C. for 3 minutes.

The thus obtained PCR product was digested with a restriction enzyme XbaI and then isolated using a 1% agarose gel (Low Gel Temperature, BioRad). A DNA fragment of about 970 bp was recovered from the gel and inserted into the XbaI site of pBluescript II, and the resulting plasmid was named pBX-hFL1. DNA sequence in the plasmid pBX-hFL1 was determined using a DNA sequencer. It was confirmed that the nucleotide sequence of the 970 bp DNA fragment contained in this plasmid coincides with the chromosomal gene sequence obtained in Inventive Example 11. The results are shown in SEQ ID NO: 35 and FIGS. 19 and 20. It was found that, though the human Fas ligand does not have a signal sequence at the N-terminal side similar to the case of the rat Fas ligand, it is a type II membrane protein because it contains 22 hydrophobic amino acid residues in a central region of its protein molecule. The cytoplasmic domain comprises 80 amino acid residues starting from Met, and 32 of the 80 residues are proline. The C-terminal extracellular domain comprises 179 amino acid residues and contains 3 N-glycosylation sites (Asn-x-Ser/Thr).

A transformant, *E. coli* DH10B(pBX-hFL1), obtained by transforming an *E. coli* strain DH10B with the plasmid pBX-hFL1 in accordance with the Hanahan's method (op.cit.) has been deposited in National Institute of Bioscience and Human Technology, Agency of Industrial Science and Technology 1-3, Higoshi 1-chrome, Tsukuba-shi, Ibaraki-ken 305, Japan, and has been assigned the designation as FERM P-14225, which was subsequently transferred to the International Depository Authority on Oct. 27, 1994, as FERM BP-4850.

(2) Introduction into COS Cells

The 970 bp XbaI DNA fragment obtained in the above step (1) was inserted into the XbaI site of an animal cell expression vector PEF-BOS (Mizushima & Nagata, *Nucleic Acids Res.*, vol. 18, p.5322, 1990), and the resulting plasmid was named pEX-hFL1. Thereafter, COS-7 cells were inoculated into D-MEM medium containing 10% FCS in cell density of $2\times10^6$ cells per one Petri dish of 10 cm in diameter, and 5 μg of the plasmid pEX-hFL1 was introduced into the cells to obtain a transformant named COS/pEX-hFL1.

(3) Cytotoxic Activity of Transformant

Cytotoxic activity of recombinant cells was measured in the same manner as described in Inventive Example 8, using the COS-7 cells transformed in the above step (2) as the effector cells and $10^6$ cells of WR19L or WC8A as the target cells. The WC8A is a transformant which acquired human Fas antigen-expressing ability through the transformation of mouse WR19L cells (Itoh N. et al., *J. Immunol.*, vol. 151, pp. 621–627, 1993).

That is, $10^6$ cells of WR19L or WC8A were labeled with $^{51}$Cr by culturing the cells at 37° C. for 2 hours in RPMI 1640 medium containing 20 μCi of [$^{51}$Cr] sodium chromate (Amersham)

Figure 22:
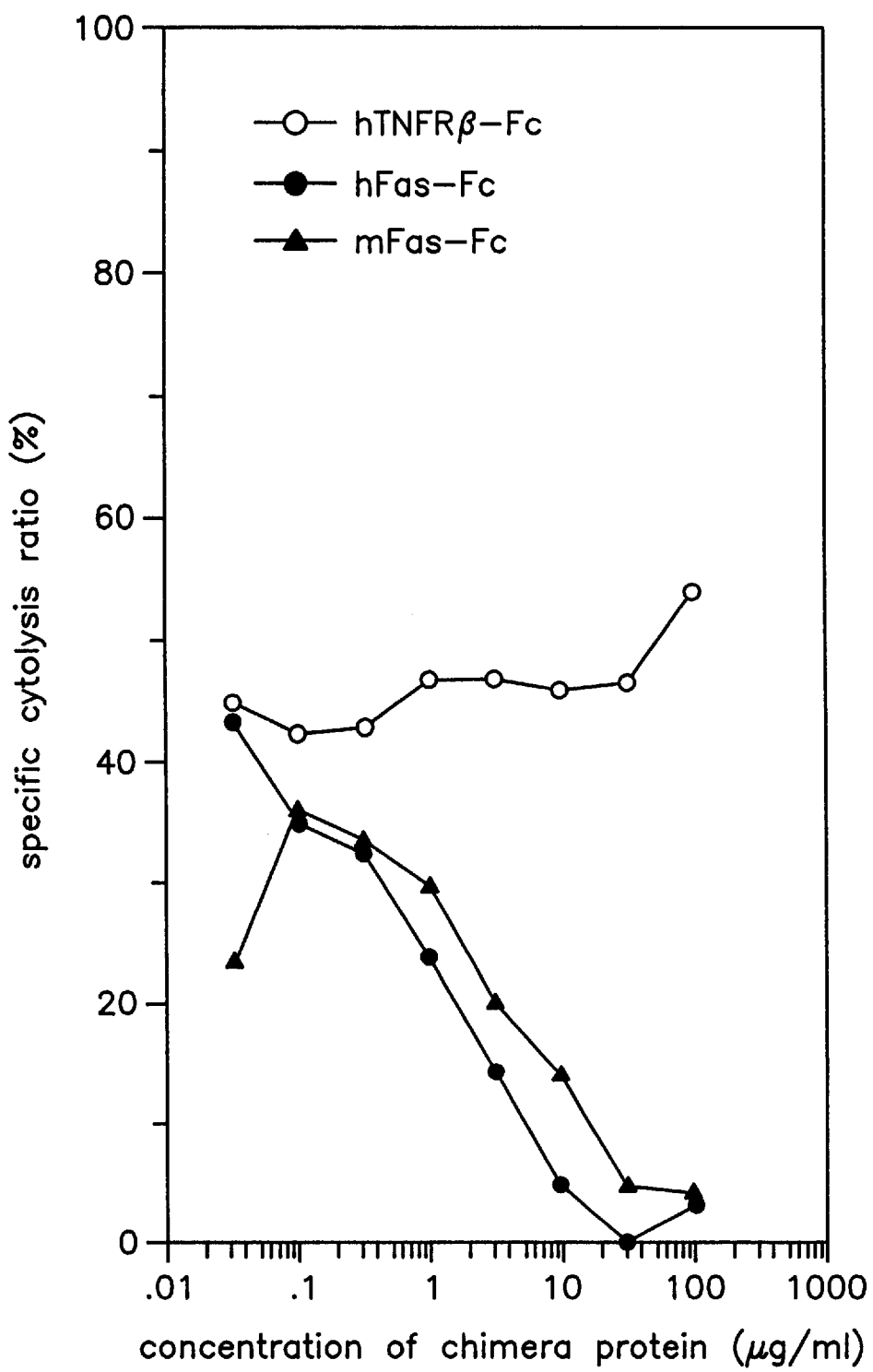
FIG. 22 shows inhibition effect of hFas-Fc and mFas-Fc on cytotoxicity of COS cells transformed with pBL-hFL1 against WC8A cells.

The thus $^{51}$Cr-labeled cells ($1\times10^4$) were mixed with COS/pEX-hFL1 cells at various mixing ratios and cultured at 37° C. for 4 hours, subsequently measuring cytotoxic activity using released $^{51}$Cr as an index. As shown in FIG. 21, the COS/pEX-hFL1 showed a cytotoxic activity against the WC8A cells in a concentration-dependent fashion. It did not induce apoptosis against WR19L. In addition, as shown in FIG. 22, the cytotoxicity of COS/pEX-hFL1 was inhibited by the addition of the chimera protein containing the extracellular domain of human Fas antigen (hFas-Fc) or the chimera protein containing the extracellular domain of mouse Fas antigen (mFas-Fc) prepared in Inventive Example 1, but was not inhibited by the addition of a soluble type human TNF receptor (hTNFRβ-Fc).

On the basis of the above results, it was confirmed that the protein encoded by the 970 bp cDNA isolated in the above step (1) is a Fas ligand which induces apoptosis by binding to the Fas antigen.

Inventive Example 13

Isolation of Mouse Fas Ligand Chromosomal Gene

Indicator *E. coli* cells were infected with a mouse chromosomal DNA library (Stratagene) which has been prepared by introducing 129/Sv mouse chromosomal DNA into lambda FIX II vector. The thus infected cells were mixed with soft agar and overlaid on agar plates to obtain $1.3 \times 10^6$ phage plaques. After cooling at 4° C. for about 4 hours, the phage particles were transferred on nitrocellulose filters.

Separately from this, PCR was carried out using the plasmid pTN24-15 obtained in Inventive Example 4 as a template, a sequence (AGAACTCCGTGAGTTCACCA) as a sense primer 4 (SEQ ID NO: 47) and a sequence (CAATATTCCTGGCATCCATG) as an antisense primer 4 (SEQ ID NO: 48), thereby effecting amplification of a cDNA fragment which encodes the extracellular domain (nucleotide positions 400 to 967 of SEQ ID NO: 25). A probe 3 was prepared by labeling the amplified product with $^{32}$P using a random primer labeling kit (Boehringer-Mannheim) in accordance with the procedure of Inventive Example 6. In the same manner, a 5'-end side sequence of SEQ ID NO: 25, namely nucleotide positions 43 to 233, was amplified by PCR and labeled with $^{32}$P to prepare a probe 4.

The nitrocellulose filters obtained above and each of the thus prepared probes 3 and 4 were subjected to hybridization. The hybridization was carried out under mild conditions similar to the case of Inventive Example 16. That is, after 18 hours of hybridization at 33° C., the filters were washed twice with 2×SSCP containing 0.1% SDS at room temperature and then with 0.3×SSCP containing 0.1% SDS at 37° C. By subjecting the thus treated filters to autoradiography, 2 positive clones were obtained (λMFL5 and λMFL18). Each plaque of the positive clones was isolated and subcloned into pBluescript IIKS(+) (Stratagene) to prepare a restriction enzyme map of the inserted mouse chromosomal DNA fragment and determine its nucleotide sequence using a DNA sequencer.

Preparation of the restriction enzyme map of each of these 2 clones and analysis of the clones by Southern hybridization revealed that the clones λMFL5 and λMFL18 respectively have 5' and 3' regions of the Fas ligand chromosomal DNA. In addition, when nucleotide sequences including the promoter and the region corresponding to the rat Fas ligand cDNA were determined, the thus determined nucleotide sequence showed high homology with that of the rat Fas ligand cDNA, thus confirming that the cloned λDNA contains the mouse Fas ligand gene.

Nucleotide sequence of the promoter, exon and 3' flanking regions of the mouse Fas ligand gene is shown in FIGS. 23 and 24. The mouse Fas ligand gene contains an open reading frame of 837 bp starting from the ATG initiation codon 107 bp downstream from the TATA box, which encodes 279 amino acid residues (molecular weight of the amino acid moiety, 31,440). Similar to the case of the rat Fas ligand, the mouse Fas ligand does not have a signal sequence in its N-terminal side, but contains 22 hydrophobic amino acid residues in the central region of the protein molecule. Thus, it was revealed that the mouse Fas ligand is a type II membrane protein. Its cytoplasmic domain consists of 78 amino acid residues of which 25 are proline residues. Its C-terminal extracellular domain consists of 179 amino acid residues contains 5 N-glycosylation sites (Asn-X-Ser/Thr).

Also, it was confirmed that the mouse Fas ligand cDNA has high homology with the rat Fas ligand cDNA; 90.6% in nucleotide sequence of coding region, 91.4% in amino acid sequence and 84.5% in nucleotide sequence of 3' noncoding region.

Inventive Example 14

Cloning of Mouse Fas Ligand-encoding cDNA by PCR and Expression Thereof (1) Preparation of Plasmid pBL-MFLW4

Splenocytes of a wild type (C3H+/+) mouse were suspended to a cell density of $2 \times 10^6$ cells/ml in RPMI 1640 medium (NISSUI PHARMACEUTICAL) containing 10% FCS, 50 μM β-mercaptoethanol, 1.5 μg/ml of ConA and 20 ng/ml of IL-2 and cultured for 2 days at 37° C. After 4 hours of treatment with 10 ng/ml of PMA and 500 ng/ml of ionomycin, dead cells were removed by a density gradient centrifugation using HistoPak 1083 (Sigma Chemical), and poly (A) RNA was prepared using a mRNA preparing kit (Pharmacia). Synthesis of single-stranded cDNA and PCR were carried out in the following manner in accordance with the method of Kawasaki E. S. et al. (*Amplification of RNA in PCR Protocols, A Guide to Methods and Amplifications*, ed. by M. A. Innis et al., Academic Press, San Diego, pp. 21–27, 1990).

Firstly, a sense primer 6 (GCTCTAGAGAGAAGGAAACCCTTTCCTG) (SEQ ID NO: 54) and an antisense primer 6 (GCTCTAGAATATTCCTGGTGCCCATGAT) (SEQ ID NO: 55) were prepared. This sense primer contains an upstream region of the ATG initiation codon and a XbaI site (GCTCTAGA) at 5'-end. On the other hand, the antisense primer contains a downstream region of the TAA termination codon and a XbaI site (GCTCTAGA) at 5'-end.

To 1 μg of the poly (A) RNA were added 50 ng of random hexamers and 200 units of MMLV RNase H⁻ reverse transcriptase (Gibco BRL) and reverse transcriptation reaction was carried out. A 1.0 μl portion of the resulting reaction solution was diluted with 100 μl of a PCR buffer containing 100 pmol of the sense primer and the same amount of the antisense primer, 4×dNTP and Taq DNA Polymerase. PCR was carried out using DNA Thermal Cycler (Perkin-Elmer). The thus obtained PCR product was digested with a restriction enzyme XbaI and then isolated using a 1% agarose gel (Low Gel Temperature, BioRad). A DNA fragment of about 940 bp was recovered from the gel and inserted into the XbaI site of pBluescript IIKS(+), and the resulting plasmid was named pBL-MFLW4. DNA sequence in the plasmid pBL-MFLW4 was determined using a DNA sequencer. It was confirmed that the plasmid pBL-MFLW4 contains the nucleotide sequence of SEQ ID NO: 32, and said nucleotide sequence coincides with the sequence of the chromosomal gene obtained in Inventive Example 13.

A transformant, *E. coli* DH10B(pBL-MFLW4), obtained by transforming *E. coli* DH10B with the plasmid pBL-MFLW4 in accordance with the Hanahan's method (op.cit.) has been deposited in National Institute of Bioscience and Human Technology, Agency of Industrial Science and Technology, 1-3, Higoshi 1-chrome, Tsukuba-shi, Ibaraki-ken 305, Japan, and has been assigned the designation as FERM P-14226, which was subsequently transferred to the International Depository Authority on Oct. 27, 1994, as FERM BP-4851.

(2) Introduction into COS Cell

The 940 bp XbaI fragment obtained in the above step (1) was inserted into the XbaI site of an animal cell expression vector PEF-BOS (Mizushima & Nagata, 1990), and the resulting plasmid was named pEF-MFLW4. Thereafter, COS-7 cells were inoculated into D-MEM medium containing 10% FCS in an inoculum size of $2\times10^6$ cells per one Petri dish of 10 cm in diameter, and 5 µg of the plasmid pEF-MFLW4 was introduced into the cells by means of the DEAE-dextran method (Fukunaga, 1990).

(3) Cytotoxic Activity of Transformant

Cytotoxic activity of recombinant cells was measured in the same manner as described in Inventive Example 8, using the transformed COS cells (COS/pEF-MFLW4F) obtained in the above step (2) as the effector cells and $10^6$ cells-of WR19L or W4 as the target cells. The W4 is a transformant which acquired mouse Fas antigen-expressing ability through the transformation of mouse WR19L cells. That is, $10^6$ cells of WR19L or W4 were labeled with $^{51}$Cr by culturing the cells at 37° C. for 2 hours in RPMI 1640 medium containing 20 µCi of [$^{51}$Cr] sodium chromate (Amersham).

The thus $^{51}$Cr-labeled cells ($1\times10^4$) were mixed with COS/pEF-MFLW4F cells at various mixing ratios and cultured at 37° C. for 4 hours, subsequently measuring cytotoxic activity using released $^{51}$Cr as an index. The results are shown in FIG. 25. As shown in FIG. 25, the COS/pEF-MFLW4F cells showed a cytotoxic activity against the W4 cells in a concentration-dependent fashion, but did not induce apoptosis against WR19L cells. The results are shown in FIG. 25. As shown in FIG. 21, the COS/pEF-MFLW4F cells also showed a cytotoxic activity against the WC8A cells in a concentration-dependent fashion. In addition, the cytotoxicity of COS/pEF-MFLW4F cells was inhibited by the addition of 20 µg/ml of the chimera protein containing the extracellular domain of mouse Fas antigen (mFas-Fc) prepared in Inventive Example 1, but was not inhibited by the addition of the soluble type human TNF receptor (hTNFRβ-Fc).

On the basis of the above results, it was confirmed that the protein encoded by the 940 bp cDNA isolated in the above step (1) is a Fas ligand which induces apoptosis by binding to the Fas antigen.

Inventive Example 15

Production of Monoclonal Antibody (1) Synthesis of Peptide and Preparation of Immunizing Antigen Four peptides were synthesized based on the amino acid sequence determined in Inventive Example 12. Peptide (1) (LVMMEGKMMSY) (SEQ ID NO: 56) was synthesized using a Fmoc method-aided peptide synthesis kit (Kokusan Kagaku) in accordance with the manufacturer's instructions, released from the used resin by deprotection and then treated with ether to obtain 275.7 mg of crude peptide. Next, a 10 mg portion of the crude peptide was dissolved in 5% aqueous ammonia and subjected to desalting using Sephadex G10.

The thus obtained solution was subjected to purification using a reverse phase HPLC column (CAPCELLPAK C18, 120 Å, 5 µm, 4.6 mm×250 mm, Shiseido), and the resulting eluats were freeze-dried to obtain purified peptide.

Peptide (2) (KSNSRSMPLEWEDTYGIVLL) (SEQ ID NO: 57), peptide (3) (SKYPQDLVMMEGKMMS) (SEQ ID NO: 58) and peptide (4) (LSLVNFEESQTFF) (SEQ ID NO: 59) were obtained by requesting their synthesis to Fujiya Bioscience Laboratory.

The thus obtained peptides were linked to keyhole limpet hemocyanin (KLH: Pierce Chemical) and cationic BSA (Pierce Chemical) in the following manner to be used as immunizing antigens.

Each of the KLH and cationic BSA was dissolved in distilled water to prepare a 10 mg/ml solution. Each of the peptides was dissolved in distilled water or 5% aqueous ammonia to prepare a 1 mg/ml solution. The KLH was mixed with each peptide at a mixing ratio of 1:100, and the cationic BSA at a ratio of 1:10, and the resulting mixtures were adjusted to pH 5 with hydrochloric acid. Next, a water soluble carbodiimide (1-ethyl-3-(3-dimethylaminopropyl)-carbodiimide hydrochloride, Dojin Laboratories) was added to the mixture in an amount of 1 mg/mg KLH or cationic BSA and stirred at room temperature for 4 hours. The reaction mixture was purified by Sephadex G25 (Pharmacia), and the first eluate was used as the administration antigen.

(2) Immunization and Production of Antiserum

A 100 µg portion of the immunizing antigen prepared in the above step (1) was mixed with the same amount of Freund's complete adjuvant and administered to Balb/c or ddy mice intraperitoneally (5 to 6 weeks of age, female). After 1 week of the first administration, the same amount of the antigen was mixed with Freund's incomplete adjuvant and administered intraperitoneally. The booster was further repeated twice at one-week intervals. One week thereafter, 20 µg of the immunizing antigen was diluted with physiological saline and administered by intravenous injection. Cell fusion was carried out 2 days after the final administration. After 2 times of the administration, antiserum was obtained by collecting blood from the ophthalmic vein and separating serum.

(3) Measurement of the Reactivity of Antiserum with Peptide

A 2.5% glutaraldehyde solution was dispensed into wells of Amino Plate (Sumitomo Bakelite) in 70 µl portions and allowed to stand still for 1 hour at room temperature, subsequently discarding the liquid contents. A 50 µl portion of each peptide solution diluted to 5 µg/ml with 0.076 M PBS (pH 6.4) was added to each well of the thus treated plate and incubated at 37° C. for 1 hour. The plate was cooled with ice water and then washed 5 times with ion-exchanged water. Thereafter, 0.2% gelatin solution in PBS was dispensed into wells of the resulting plate in 100 µl portions and allowed to stand still for 30 minutes to effect blocking.

Next, each antiserum was diluted 500 times with PBS and dispensed in 50 µl portions into the wells. After 1 hour of reaction at 37° C., the plate was washed twice with physiological saline containing 0.005% Tween 20 (to be referred to as "washing solution" hereinafter). A peroxidase-labeled anti-mouse immunoglobulins antibody (DAKO) was diluted 2,000 times with PBS containing 0.25% gelatin and added to the washed plate. After 1 hour of reaction at 37° C., the plate was washed 5 times with the washing solution. Thereafter, McIlvaine buffer solution (pH 5.0) containing 3 mg/ml of o-phenylene diamine and 0.027% hydrogen peroxide was dispensed into wells of the thus treated plate in 50 µl portions, and the reaction was carried out for 10 minutes at room temperature.

The reaction was terminated by adding 50 µl of 2 N sulfuric acid to each well and then absorbance at 492 nm was measured. As the result, all of the tested antisera showed reactivity with the immunizing peptide.

(4) Production of Monoclonal Antibody

The immunized mouse obtained in the above step (2) was sacrificed to excise the spleen which was subsequently sliced, passed through a stainless steel mesh and then suspended in RPMI 1640 medium to obtain a splenocyte suspension. The thus obtained splenocytes were mixed with mouse myeloma cells (P3X63Ag8U1) at a mixing ratio of 10:1, and the mixture was subjected to 8 minutes of centrifugation at 1,400 rpm. To the resulting precipitate was quickly added 0.5 ml of RPMI 1640 containing 42.5% polyethylene glycol 1540 and 15% dimethyl sulfoxide. After 1 minute of vigorous shaking, 10 ml of RPMI 1640 was gradually added to the cells, and the resulting mixture was subjected to 5 minutes of centrifugation at 800 rpm.

The thus obtained precipitate was suspended in HAT medium (RPMI 1640 medium supplemented with $1\times10^{-4}$ M hypoxanthine, $4\times10^{-7}$ M aminopterin, $1.6\times10^{-5}$ M thymidine and 10% FCS) to a final cell density of $2\times10^5$ cells/ml, and the suspension was dispensed into wells of a 96 well microplate in 0.2 ml portions. Half of the medium was exchanged with fresh medium every 2 to 3 days, and the medium was then exchanged entirely with HT medium (RPMI 1640 medium supplemented with $1\times10^{-4}$ M hypoxanthine, $1.6\times10^{-5}$ M thymidine and 10% FCS).

When growth of hybridoma cells was observed, screening was carried out by means of ELISA. That is, a 96 well plate to which the peptide prepared in Inventive Example 15 (1) has been immobilized was washed twice with the aforementioned washing solution, and a 100 μl portion of each culture supernatant which has been diluted 10 times with PBS containing 0.25% gelatin was added to each well of the thus washed plate and allowed to undergo 2 hours of reaction at room temperature. After completion of the reaction, the plate was washed 5 times with the washing solution, and 50 μl of a peroxidase-labeled rabbit anti-mouse Igs antibody (DAKO) which has been diluted 2,000 times with PBS containing 0.25% gelatin was added as the second antibody to each well of the thus washed plate.

After 2 hours of reaction at room temperature, the plate was washed 5 times with the washing solution, and 0.1 M McIlvaine buffer solution (pH 5.0) containing 3 mg/ml of o-phenylene diamine and 0.027% hydrogen peroxide was dispensed into wells of the thus treated plate in 100 μl portions. After 10 minutes of enzyme reaction at room temperature, the reaction was terminated by adding 100 μl of 2 N sulfuric acid to each well and then absorbance at 492 nm was measured. Hybridomas in wells which showed positive by ELISA were diluted with RPMI 1640 containing 10% FCS at such a ratio that each well of 96 well microplate contained 2, 1 or 0.5 cell.

Thymocytes of Wistar rat were inoculated into each well of the plate as feeder cells to carry out cloning.

Wells, each containing a single cell colony, were selected by observing them under a microscope, and culture supernatants in the selected wells were screened by the ELISA procedure of the above step (3) to obtain a hybridoma capable of producing the monoclonal antibody of interest.

(5) Confirmation of Reactivity by Western Blotting

Reactivity of the antiserum obtained in the above step (2) (immunized with the antigen prepared using the peptide (2), lot. 19-3) and the monoclonal antibody obtained in the above step (4) (immunized with the antigen prepared using the peptide (2), F864-5-1) with human Fas ligand was confirmed by western blotting. As samples, COS cells transfected with a vector containing the sequence of the human Fas ligand expressed in COS cells in Inventive Example 12 or of the mouse Fas ligand expressed in Inventive Example 14 or containing no Fas ligand sequence were used.

Firstly, about $1\times10^4$ of each of the transformed COS cells were mixed with 9 μl of 50 mM Tris-HCl buffer (pH 7.5) containing 150 mM NaCl, 1% NP-40, 0.1% sodium deoxycolate, 0.1% SDS and 0.2 U/ml of aprotinin and then with the same volume of 0.25 M Tris-HCl buffer (pH 6.8) containing 2% SDS, 30% glycerol, 10% 2-mercaptoethanol and 0.01% BPB (Bromophenol Blue).

After 1 hour of treatment at 37° C., SDS-polyacrylamide gel electrophoresis (4 to 20% gradient gel) was carried out, and the contents in the gel were subsequently transferred on a PVDF membrane (Millipore Corp.) under reaction conditions of 200 mA for 90 minutes at 4° C. The resulting membrane was subjected to 2 hours of blocking at 37° C. using Block Ace (Snow Brand Milk Products).

Next, the membrane was washed twice with the washing solution (4 minutes of stirring at 37° C.) and then allowed to react for 1.5 hours at 37° C. with the antiserum 19-3 or culture supernatant of hybridoma F864-5-1 which has been diluted 500 times with Block Ace that has been diluted 5 times with PBS. After completion of the reaction, the membrane was washed twice with the washing solution and then soaked in a solution of peroxidase-labeled rabbit anti-mouse immunoglobulins antibody (Cat. No. P260, DAKO) which has been diluted 1,000 times with 5 times-diluted Brock Ace with PBS. After 1.5 hours of reaction at 37° C., the membrane was washed 3 times with the washing solution and then twice with distilled water. Thereafter, water on the surface of the membrane was removed to carry out color development with TMB reagent (Cat. No. TM9125, SCYTK).

Figure 27:
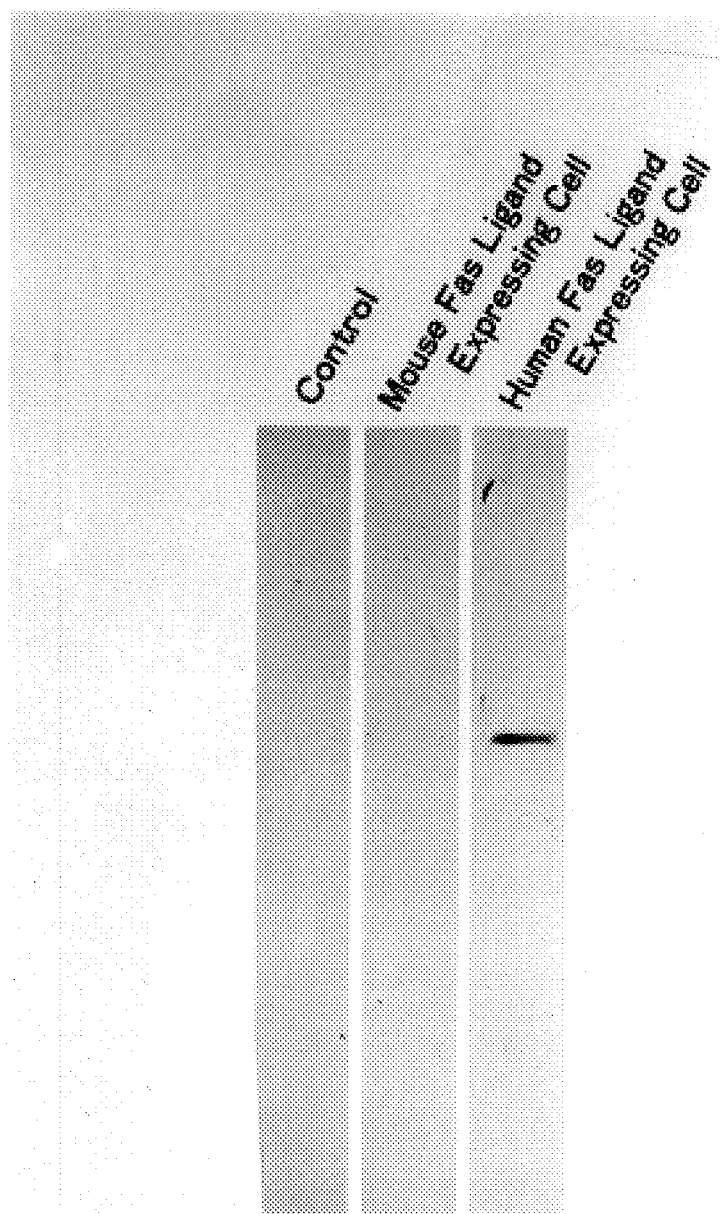
FIG. 27 is a photograph showing the results of the western blotting in which antiserum 19-3 and human Fas ligand-expressing cells are used.
Figure 28:
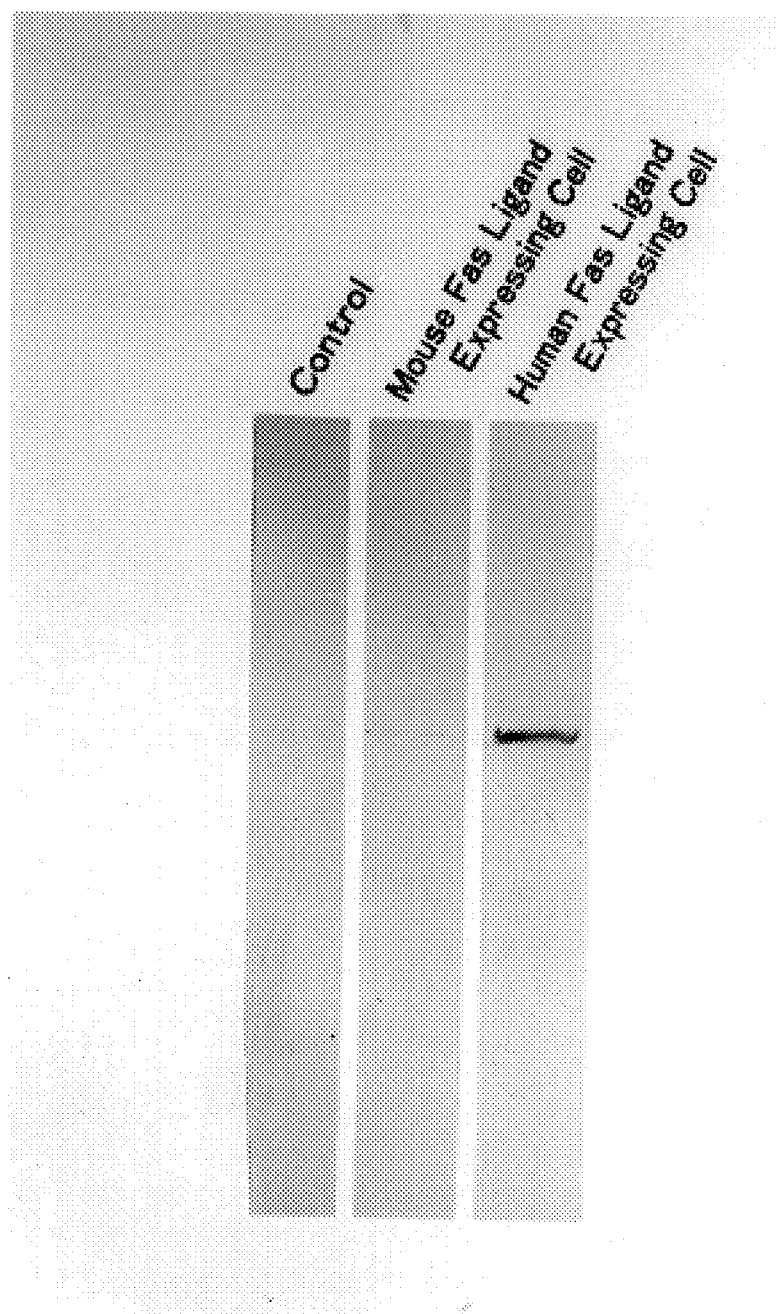
FIG. 28 is a photograph showing the results of the western blotting in which a monoclonal antibody F864-5-1 and human Fas ligand-expressing cells are used.

Results of the western blotting using the antiserum 19-3 and the monoclonal antibody F864-5-1 are respectively shown in FIGS. 27 and 28. As is evident from these drawings, a band capable of reacting with the extract of the human Fas ligand-expressing COS cells was observed, while such a band was not found in the case of mouse Fas ligand and control.

(6) Confirmation of the Reactivity of the Monoclonal Antibody with Peptide (2) by Blocking Reaction-1

Reactivity of the monoclonal antibody obtained in the above step (4) (immunized with the antigen prepared using the peptide (2), F883-1-1) with the immunizing peptide (2) was confirmed by blocking reaction.

A 2.5% glutaraldehyde solution was dispensed into wells of Amino Plate (Sumitomo Bakelite) in 70 μl portions and allowed to stand still for 1 hour at room temperature, subsequently discarding the liquid contents. A 50 μl portion of a solution of the peptide (2) diluted to 5 μg/ml with 0.076 M PBS (pH 6.4) was added to each well of the thus treated plate and incubated at 37° C. for 1 hour. The plate was cooled with ice water and then washed 5 times with ion-exchanged water. Thereafter, PBS containing 0.2% gelatin and 0.1 M glycine was dispensed into each well of the resulting plate in 100 μl portion and allowed to stand still for 30 minutes to effect blocking.

Separately from this, each of the aforementioned peptides (2), (3) and (4) was diluted with PBS to a concentration of 10 μg/ml to be used as a blocking antigen solution. Also, a solution containing no blocking antigen was prepared to be used as a negative control. After adding 25 μl of each of these solutions to each well of the above plate, the antibody F883-1-1 which has been diluted to 0.4 μg/ml with 0.2% gelatin-containing PBS was dispensed in 25 μl portions into the wells. After 1 hour of reaction at 37° C., the plate was washed twice with the washing solution.

Next, a peroxidase-labeled anti-mouse immunoglobulins antibody (DAKO) was diluted 2,000 times with PBS containing 0.2% gelatin and dispensed into wells of the washed plate in 50 μl portions. After 1 hour of reaction at 37° C., the plate was washed 5 times with the washing solution. Thereafter, McIlvaine buffer solution (pH 5.0) containing 3 mg/ml of o-phenylene diamine and 0.027% hydrogen peroxide was dispensed into wells of the thus treated plate in 50 μl portions, and the reaction was carried out for 10 minutes at room temperature. The reaction was terminated by adding 50 μl of 2 N sulfuric acid to each well and then absorbance at 492 nm was measured. The results are shown in FIG. 29.

Figure 29:
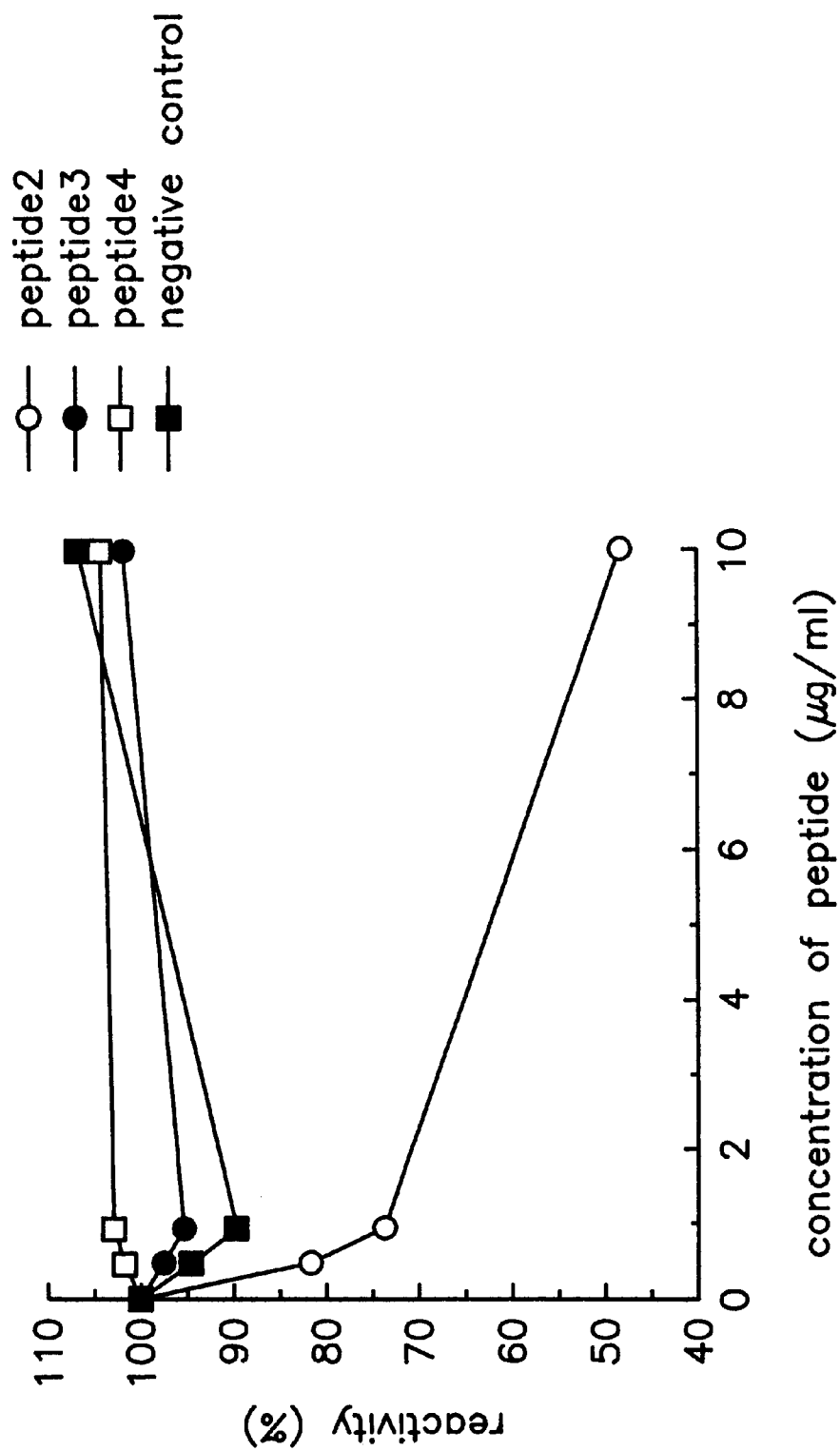
FIG. 29 shows reactivity of monoclonal antibody F883-1-1 with a peptide.

In FIG. 29, absorbance of a well to which the blocking antigen was not added (negative control) was taken as 100, and relative absorbance in each of other wells was shown.

As is evident from FIG. 29, it was confirmed that the reactivity of the F883-1-1 antibody with the antigen peptide is inhibited only when the peptide (2) is used as a blocking peptide.

(7) Confirmation of the Reactivity of the Monoclonal Antibody with the Peptide (3) by Blocking Reaction-2

Reactivity of the IgM monoclonal antibody produced in the above (4) (antibody F897-1-2 produced by hybridoma F897-1-2, which has been produced from the spleen cell of the mouse immunized with the antigen produced using the peptide (2) and the myeloma cell) with the immunizing antigen peptide (3) (peptide (3)) was confirmed by means of blocking reaction.

First, peptide (3) was labeled with peroxidase in accordance with Nakane et al., Immunofluorescence and Related Staining Techniques, W. Knapp, K. Holubar and G. Wick eds., 1978) as described below.

6 mg of peroxidase (RZ3.11, Toyobo Co., Ltd.) was dissolved in 1.5 ml of distilled water. To the solution was added 0.3 ml of 0.1M sodium m-periodate in distilled water, and the solution was allowed to stand at room temperature for 15 minutes. To the solution was then added 0.3 ml of 1.5% ethylene glycol in distilled water, and the solution was allowed to stand for 20 minutes. The resulting solution was dialyzed against 0.001M acetate buffer, pH 4.4 at 4° C. overnight.

To 159 μl of the resulting activated peroxidase solution (corresponding to 500 μg of peroxidase) was added 9 μl of 1M carbonate buffer solution, pH 9.5, and then, 428 μl of the solution of peptide (3) which had been prepared by dissolving the peptide (3) in distilled water to a concentration of 1 mg/ml (the amount of the peptide (3) being 20 times the molar amount the peroxidase), and the solution was allowed to react at 25° C. for 2 hours. To the solution was added 15 μl of sodium borohydride solution prepared by dissolving the sodium borohydride in 0.01M carbonate buffer solution, pH 9.5 to 4 mg/ml, and the solution was allowed to stand at 4° C. for 2 hours. To the solution was further added 25 μl of 0.2M glycine in distilled water, and the solution was allowed to stand at room temperature for 1 hour. The solution was then dialyzed against 0.076M PBS, pH 6.4 at 4° C. overnight, and to the resulting solution of peroxidase labeled peptide (3) was added an equal amount of glycerol. The mixture was stored at −20° C.

Next, 20 μg/ml anti-mouse immunoglobulins antibody (Z259, DAKO) in 0.076M PBS was dispensed into wells of an immunoplate (Maxi Sorp™, NUNC) in 50 μl portions, and the plate was incubated at 45° C. for 30 minutes. The plate was then cooled with ice water, and washed 5 times with ion exchanged water. To the wells were then dispensed PBS containing 0.2% gelatin in 100 μl portions, and the plate was kept at 4° C. overnight for blocking. After the blocking, the salted out antibody (F897-1-2) diluted to 100 times with PBS was dispensed in 50 μl portions, and the plate was incubated at 37° C. for 1 hour. The plate was then washed twice with 0.9% NaCl washing solution containing 0.005% Tween 20, and once with ion exchanged water.

In the meanwhile, peptide (3) was diluted with PBS to a concentration of 3 μg/ml and 10 μg/ml, respectively, and the resulting solutions were used for the blocking antigen solutions. A solution containing no blocking antigen was also prepared, and the solution was used for the negative control. To the wells of the plate were dispensed the thus prepared solutions in 25 μl portions, and then, the peroxidase-labeled peptide (3) diluted 200 times with PBS in 25 μl portions. The plate was incubated at 37° C. for 1 hour to promote the reaction. After the completion of the reaction, the plate was washed 5 times with the washing solution, and twice with the ion exchanged water. To the wells were dispensed 50 μl portions of McIlvaine buffer, pH 5.0 containing 3 mg/ml of o-phenylene diamine and 0.027% hydrogen peroxide, and the reaction was promoted at room temperature for 5 minutes. 50 μl portions of 2N sulfuric acid were dispensed into the wells to cease the reaction, and absorbance at 492 nm was measured.

Reactivity in percentage was calculated in terms of the relative absorbance of each well by taking the absorbance of the well free from the blocking antigen (the negative control) as 100. The results are shown in FIG. 31.

Figure 31:
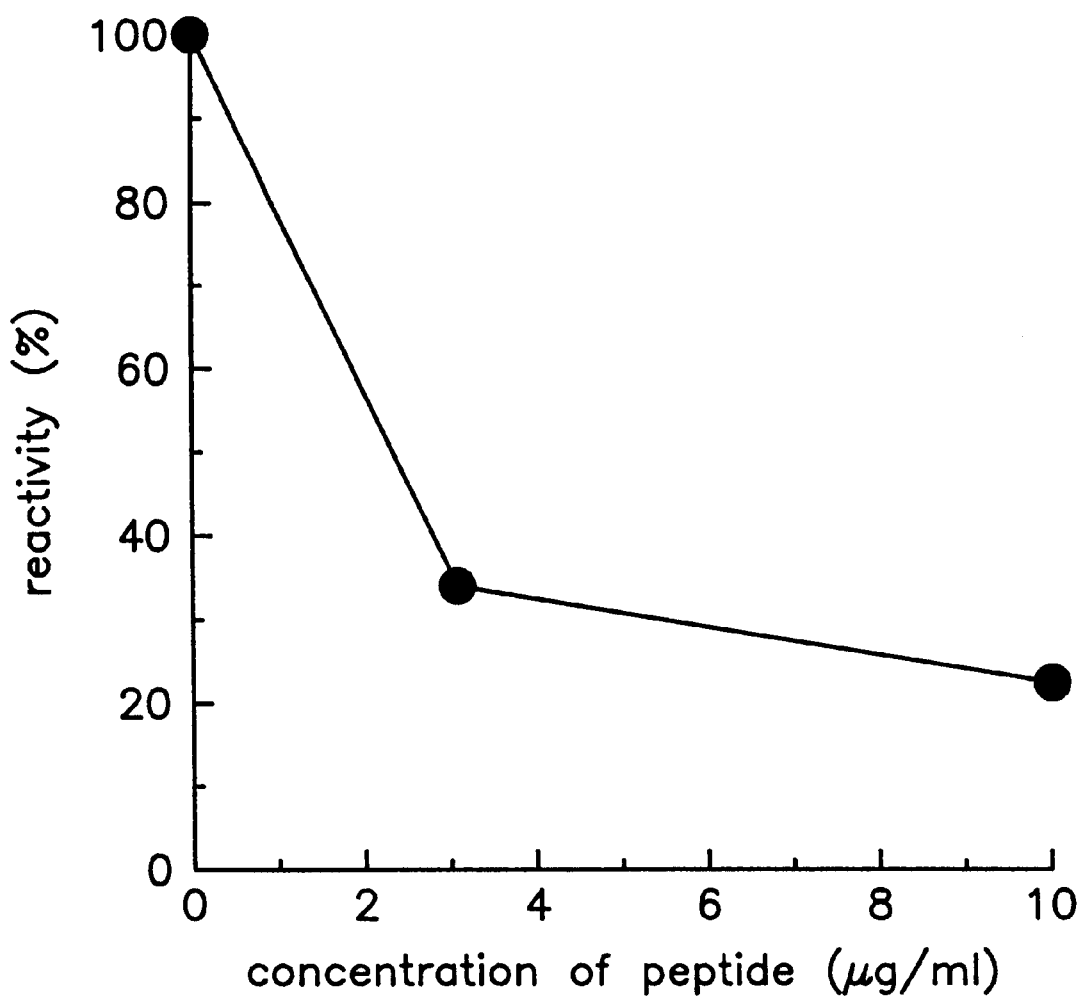
FIG. 31 shows reactivity of monoclonal antibody F897-1-2 with peptide (3).

As clearly shown in FIG. 31, it was confirmed that the reactivity of the antibody F897-1-2 with the antigen peptide is inhibited by the peptide (3).

Inventive Example 16

Evaluation of Apoptosis Inhibition Activity-1

Apoptosis inhibition activity of antibody F883-1-1 produced in Inventive Example 15 was confirmed in the following manner using a Fas ligand-expressing transformant and a Fas antigen-expressing transformant.

First, cell line FDC-P1 derived from a normal mouse myeloid cell was transformed with plasmid pEX-hFL1 (see Inventive Example 12), which includes cDNA coding for the human Fas ligand. FLh1 cells, which are one of the resulting clones, were incubated at 37° C. for 4 days in the presence of 5% $CO_2$ in RPMI 1640 medium (Gibco BRL) supplemented with 50 U/ml of mouse IL-3 (INTERGEN) and 10% FCS. After the incubation, FLh1 cells were suspended in 10% FCS-containing RPMI 1640 medium to a cell concentration of $5 \times 10^5$ cells/ml, and the cell suspension was dispensed into wells of a 96 well flat bottom plate in 50 μl portions.

In the meanwhile, antibody F883-1-1 produced in Inventive Example 15 was diluted with PBS− to various concentrations. The thus diluted antibody solutions were dispensed into the above-described wells in 10 μl portions, and the plate was incubated at 37° C. for 30 minutes in the presence of 5% $CO_2$.

Next, transformant cells WC8 capable of expressing the human Fas antigen (Itoh N. et al., J. Immunol., vol. 151, pp621–627, 1993) were suspended in 10% FCS-containing RPMI 1640 medium to a cell concentration of $6.3 \times 10^5$ cells/ml, and the suspension was dispensed into the wells in 40 μl portions. After 16 hours of incubation at 37° C. in the presence of 5% $CO_2$, 100 μl of trypan blue was added to each well to count the number of survived cells in each well.

Figure 30:
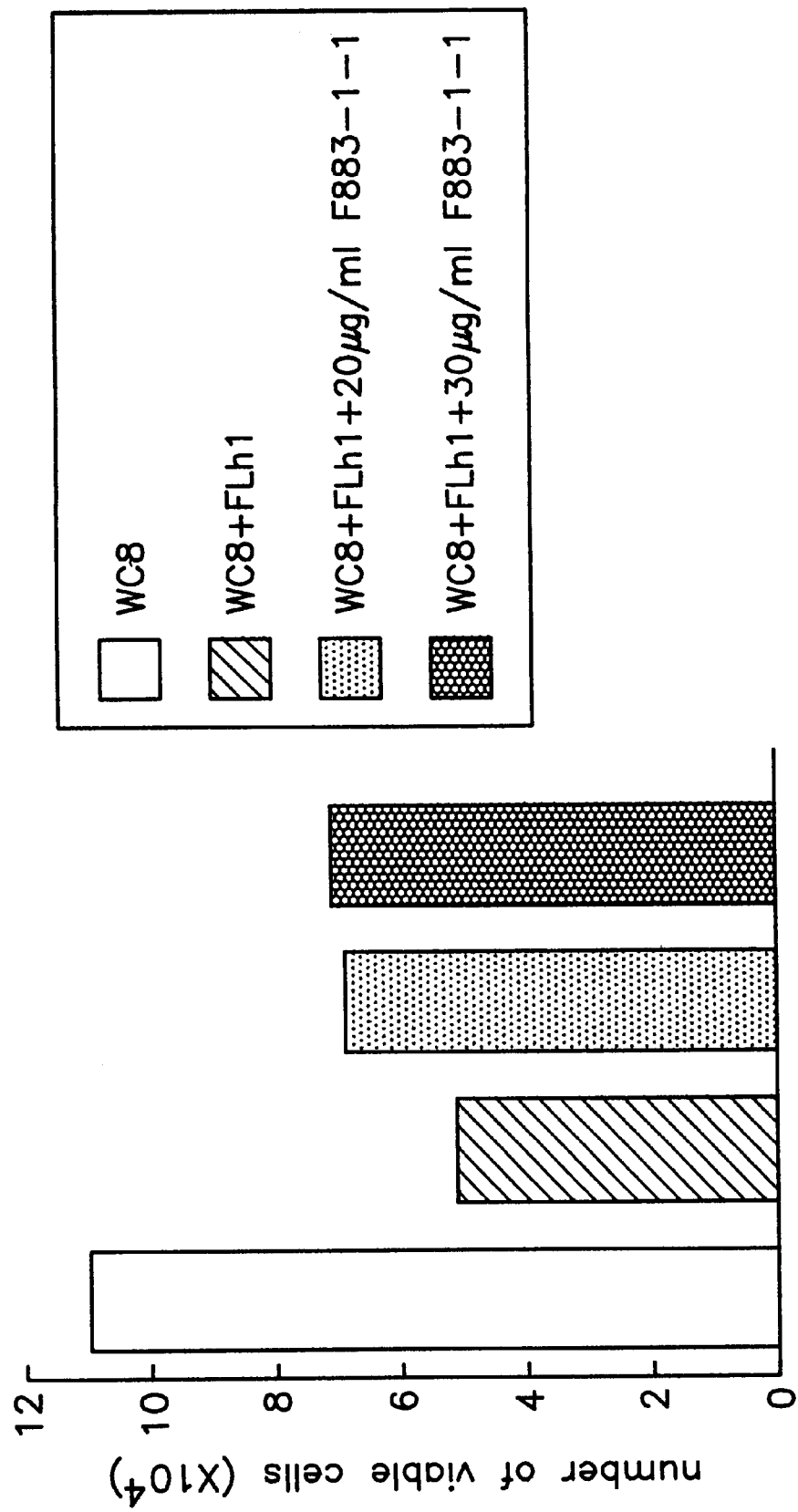
FIG. 30 shows apoptosis inhibiting activity of monoclonal antibody F883-1-1.

FIG. 30 shows apoptosis inhibition activity of antibody F883-1-1 produced in Inventive Example 15. As clearly shown in FIG. 30, apoptosis of WC8 cells induced by FLh1 is inhibited by antibody F883-1-1 in a dose-dependent manner. It should be noted that the inventors of the present application have deposited hybridoma F883-1-1, which produces monoclonal antibody F883-1-1, in National Institute of Bioscience and Human Technology, Agency of Industrial Science and Technology, 1-3, Nigoshi 1-chrome, Tsukuba-shi, Ibaraki-ken 305, Japan on Aug. 9, 1994 (Deposit No. FERM P-14464), which was subsequently transferred to the International Depository Authority on Oct. 27, 1994, as FERM BP-4852.

Inventive Example 17

Evaluation of Apoptosis Inhibition Activity-2

Apoptosis inhibition activity of antibody F897-1-2 produced in Inventive Example 15 was confirmed as described below in accordance with the procedure of Inventive Examples 8 and 12 using the supernatant of transformant COS-1/pEX-hFL1 produced in accordance with the procedure of Inventive Example 18(3) and the human Fas antigen-expressing transformant cells WC8.

First, $10^6$ cells of WC8 were incubated in PRMI 1640 medium supplemented with 20 µCi [$^{51}$Cr]sodium chromate (NEN) and 10% heat-inactivated FCS at 37° C. for 2 hours to label the cells with the $^{51}$Cr.

Next, to each well of a 96 well U-bottom plate (CORNING) were dispensed 6 µl of the supernatant of COS-1/pEX-hFL1 to a final concentration of 3%, and 74 µl of 10% FCS-containing RPMI 1640 medium. To each well was then dispensed 20 µl of the dilution of antibody F-897-1-2 produced in Inventive Example 15, which has been adjusted with 0.1% BSA-containing PBS- to 300 µg/ml, to a final concentration of 30 µg/ml. The plate was incubated at 37° C. for 30 minutes. The $^{51}$Cr-labeled WC8 cells were then dispensed at 1×$10^4$ cells/100 µl/well, and the plate was incubated at 37° C. for another 4 hours. After the incubation, cytotoxic activity was evaluated by using the release of $^{51}$Cr for the index.

Figure 32:
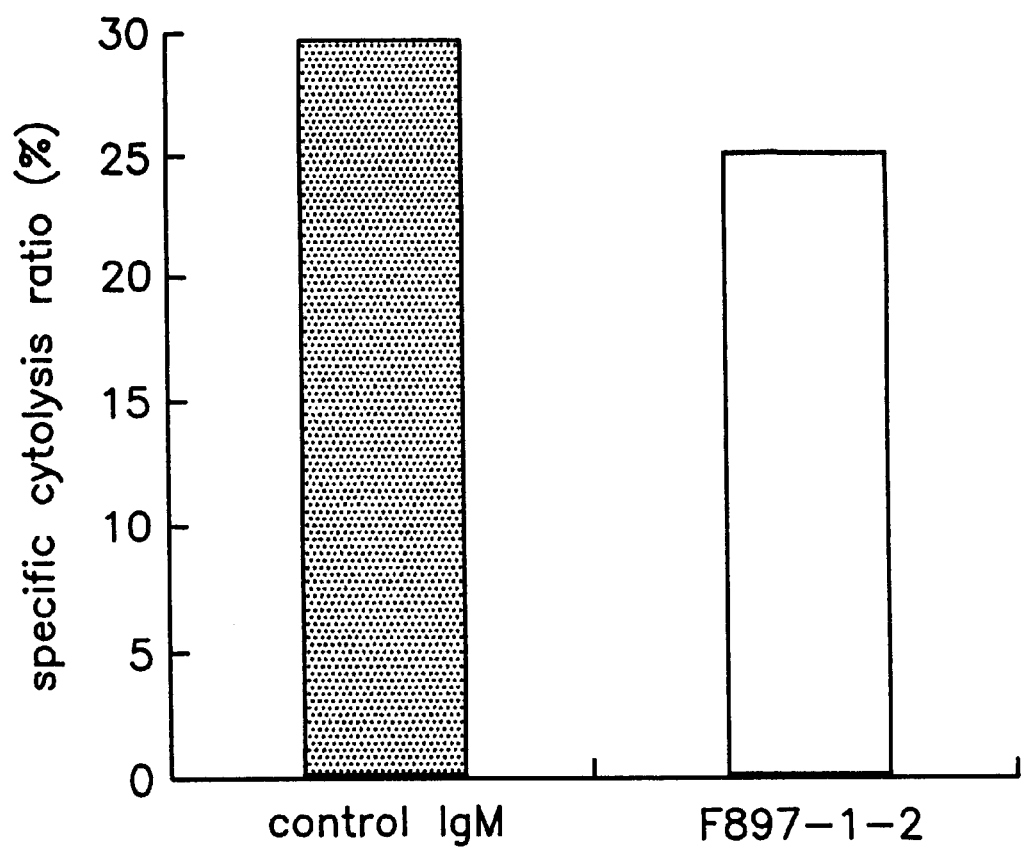
FIG. 32 shows apoptosis inhibiting activity of monoclonal antibody F897-1-2.

The results are shown in FIG. 32. As clearly shown in FIG. 32, apoptosis of WC8 cells induced by the Fas ligand present in the supernatant of transformant COS-1/pEX-hFL1 was inhibited by antibody F897-1-2 in a dose-dependent manner.

It should be noted that the inventors of the present application have deposited hybridoma F897-1-2, which produces monoclonal antibody F897-1-2, in National Institute of Bioscience and Human Technology, Agency of Industrial Science and Technology, 1-3, Higoshi 1-chrome, Tsukuba-shi, Ibaraki-ken 305, Japan, on Sep. 1, 1994 (Deposit No. FERM P-14497), which was subsequently transferred to the International Depository Authority on Oct. 27, 1994, as FERM BP-4853.

Inventive Example 18

Expression of the Extracellular Domain of the Human Fas Ligand (1) Preparation of Plasmid pM1067

A sense primer 7 (CACCTGCAGAAGGAGCTGGCAGAA) (SEQ ID NO: 60) and an antisense primer 7 (AATAAGCTTGGTACCCTATTAGAGCTTATATAA) (SEQ ID NO: 61) were synthesized in a chemical synthesizer. The sense primer contains the nucleotide sequence coding for the amino acid sequence located at the N terminus of the extracellular domain of the human Fas ligand, of which amino acid sequence is shown in SEQ ID NO: 6 and PstI site (CTGCAG). The antisense primer contains SEQ containing the termination codon (TAA), HindIII site (AAGCTT), and KpnI site (GGTACC).

A 100 µl solution containing 100 pmol each of the sense primer and the antisense primer; 50 ng of plasmid pBX-hFL1 produced in Inventive Example 12(1); 20 nmol each of dATP, dCTP, dGTP, and dTTP; and 2.5 units of pfu polymerase and 10 µl of pfu buffer attached therewith (Stratagene) was prepared. PCR was carried out using DNA Thermal Cycler (PCR System 9600, Perkin-Elmer) by repeating 30 cycles each comprising 94° C. for 30 seconds, 55° C. for 30 seconds and 72° C. for 1 minutes. The resulting PCR product was double digested with PstI and HindIII, and the DNA fragment was inserted between the PstI site and the HindIII site of pUC118. The resulting plasmid was designated plasmid pM1067.

(2) Preparation of Plasmid pM1070

A sense primer 8 (TGCGAATTClACCATGCTGGGCATCTGG) (SEQ ID NO: 62) and an antisense primer 8 (AACCTGCAGGTGGAAGAGCTGAGCAACAGACGT AAG) (SEQ ID NO: 63) were synthesized in a chemical synthesizer. The sense primer contains the sequence located at the 5' terminus of a sequence coding for the signal peptide of the human Fas antigen; and EcoRI site (GAATTC). The antisense primer contains the sequence located at the 3' terminus of a sequence coding for the signal peptide of the human Fas antigen; the nucleotide sequence coding for the N terminus of the extracellular domain of the human Fas ligand, and PstI site.

A 100 µl solution containing 100 pmol each of the sense primer and the antisense primer; 50 ng of plasmid pBLF58-1 used in Inventive Example 1(3); 20 nmol each of dATP, dCTP, dGTP, and dTTP; and 2.5 units of pfu polymerase and 10 µl of pfu buffer attached therewith (Stratagene) was prepared, and PCR was carried out by repeating the procedure of the above (1).

The resulting PCR product was double digested with EcoRI and PstI, and the resulting DNA fragment was inserted between the EcoRI site and the PstI site of plasmid pM1067 produced in the above (1) to obtain plasmid pM 1250. The thus produced plasmid was double digested with EcoRI and KpnI, and the digestion product was electrophoresed on agarose gel. A DNA fragment of about 600 bp was recovered, and the DNA was purified with QIAEX™ kit QIAGEN. The thus purified DNA fragment of about 600 bp was inserted between the EcoRI site and the KpnI site of plasmid pM1103 that had been produced by inserting DHFR gene into plasmid pEF-BOS used in Inventive Example 14(2). The resulting plasmid was designated plasmid pM1070.

(3) Introduction into COS Cells pM1070 produced in the above (1) and pEX-hFL1 produced in Inventive Example 12(1) were respectively introduced in COS-1 cells to produce transformants COS-1/pM1070 and COS-1/pEX-hFL1 by the procedure as described below.

To 40 µl of 10 mM Tris-HCl buffer solution (pH 7.4)/1 mM ethylenediaminetetraacetic acid (hereinafter referred to as Tris/EDTA) was added 8.1 µg of pM1070 or pEX-hFL1. To the resulting solutions were then added 11.3 ml of D-MEM (Nissui Pharmaceutical) containing 0.2 mg/ml DEAE-dextran and 50 mM Tris-HCl, pH 7.4 to prepare DNA-DEAE-dextran mixed solutions.

The resulting DNA-DEAE-dextran mixed solutions were respectively added dropwise to a monolayer culture of COS-1 cells in 150 $cm^2$ Roux flasks that had grown to their semi-confluent stage, and the cultures were incubated at 37° C. in the presence of 5% $CO_2$ to produce the transformants COS-1/pM1070 and COS-1/pEX-hFL1. After 4 hours of incubation, the DNA-DEAE-dextran mixed solutions were removed, and D-MEM containing 10% FCS (IRVINE Scientific K.K.) was added to the flasks. The incubation was continued for another 48 to 96 hours, and culture supernatants were collected from the COS-1/pM1070 and COS-1/pEX-hFL1 for use in the (4) and (5) as described below.

(4) Cytotoxic Activity of the Transformant

The cytotoxic activity of the culture supernatants of COS-1/pM1070 and COS-1/pEX-hFL1 produced in the above (3) was evaluated as in the case of Inventive Examples 8 and 12 by using WC8A cells and W4 cells for the target cells, respectively. The evaluation was carried out as described below.

In RPMI1640 medium containing 20 μCi of [$^{51}$Cr] sodium chromate (NEN) were incubated $10^6$ cells of WC8 or W4 cells at 37° C. for 2 hours to label the cells with the $^{51}$Cr.

The cell culture supernatants produced in the above (3) were added to the reaction solution containing $1\times10^4$ $^{51}$Cr-labeled cells to a final concentration of 3% and 10%, respectively. The cultures were incubated at 37° C. for 4 hours, and cytotoxic activity was evaluated by using the release of the $^{51}$Cr for the index.

Figure 33:
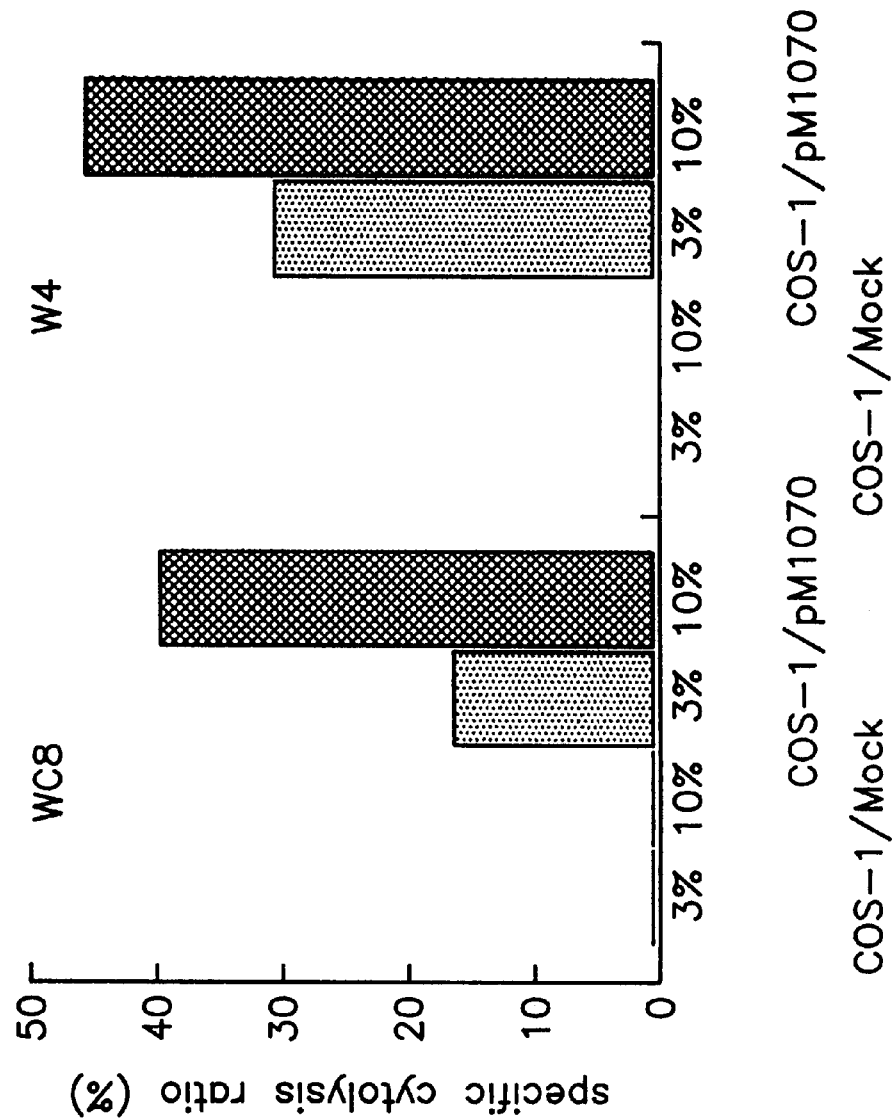
FIG. 33 shows cytotoxic activity of the culture supernatant of transformant COS-1/pM1070 when WC8 and W4 are used as target cells.
Figure 34:
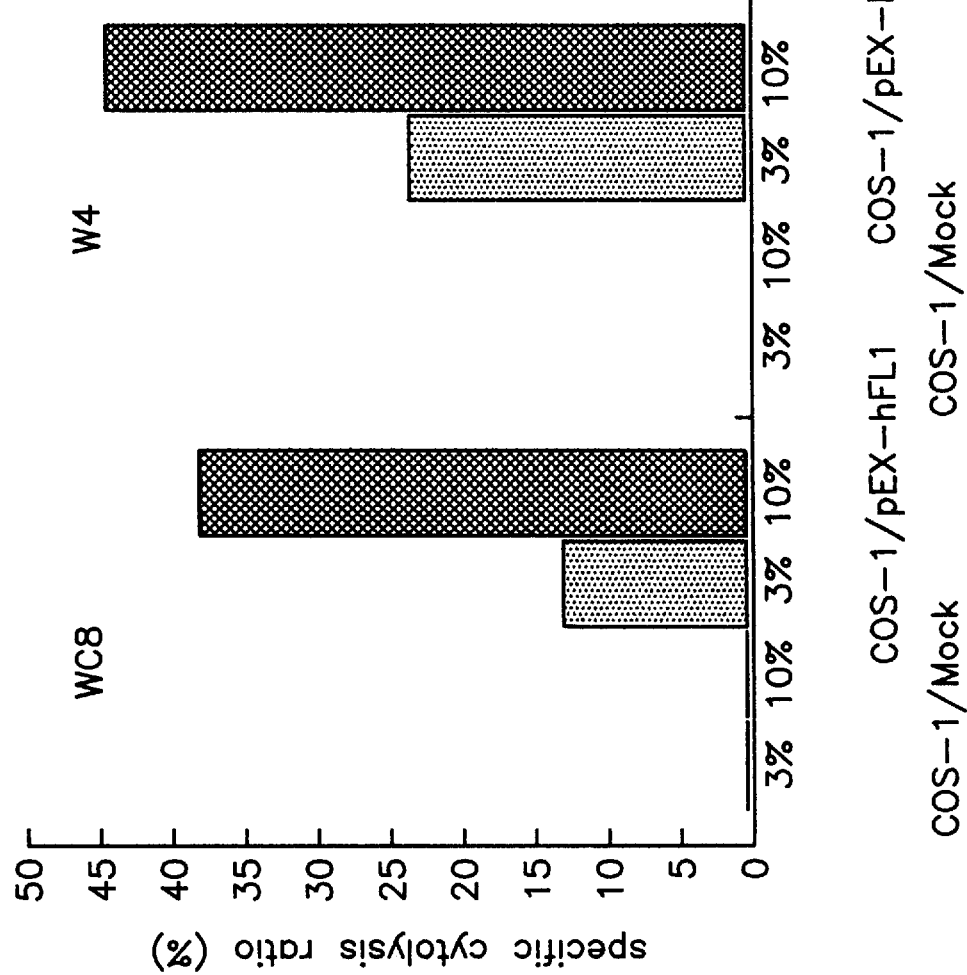
FIG. 34 shows cytotoxic activity of a culture supernatant of transformant COS-1/pEX-hFL1 when WC8 and W4 are used as target cells.

The results are shown in FIGS. 33 and 34. As apparent in FIGS. 33 and 34, the culture supernatants of COS-1/pM1070 and COS-1/pEX-hFL1 exhibited concentration dependent cytotoxic activity on WC8A cells and W4 cells, respectively. In FIGS. 33 and 34, "Mock" designates the control.

Presence in such culture supernatants of the Fas ligand having the activity of binding with the human Fas antigen to induce apoptosis was thus confirmed.

(5) Western Blotting Using the Culture Supernatants of Transformants COS-1/pM1070 and COS-1/pEX-hFL1

A rabbit antiserum capable of recognizing a part of the amino acid sequence of the human Fas ligand (PSPPPEKKELRKVAH, SEQ ID NO: 64) was prepared in accordance with a known procedure, and western blotting was carried out by using the thus prepared rabbit antiserum as described below.

10 μl of the culture supernatants of transformants COS-1/pM1070 and COS-1/pEX-hFL1 produced in the above (3) were respectively mixed with 5 μl of distilled water. To such mixtures were respectively added a 5 μl of distilled water containing 4% SDS, 80% glycerol, and 0.04% BPB, or a 5 μl of distilled water containing 4% SDS, 80% glycerol, 8% DTT, and 0.04% BPB. The resulting mixtures were incubated at 37° C. for 1 hour, and then, subjected to SDS-polyacrylamide gel electrophoresis on 5 to 20% gradient gel. After completing the electrophoresis, the gel was transferred to PVDF membrane (Atto K.K.) at room temperature, at 200 mA for 60 minutes, and the membrane was blocked by the solution of skim milk (Snow Brand Milk Products, Co., Ltd.) at 4° C. overnight. The thus blocked membrane was washed once with PBS (by incubating at room temperature for 15 minutes), and twice with 0.1% Tween 20/PBS (by incubating at room temperature for 5 minutes).

The rabbit antiserum as described above was diluted 1,000 times with 0.5% BSA/0.1% Tween 20/PBS, and the membrane was allowed to react with the thus diluted rabbit antiserum at 37° C. for 1 hour. After the completion of the reaction, the membrane was washed twice with 0.1% Tween 20/PBS. The membrane was then immersed in a solution of peroxidase-labeled anti-rabbit immunoglobulins antibody (Cat. No. P448, DAKO) which had been diluted 1,000 times with 0.5% BSA/0.1% Tween 20/PBS, and allowed to react at room temperature for 1 hour. The membrane was washed 5 times with 0.1% Tween 20/PBS, and water on the surface was removed. The membrane was then evaluated in ECL system (Amersham).

In the case of the supernatant of COS-1/pM1070, a band was observed at about 29 kD under reduced conditions, and at about 26 kD under non-reduced conditions.

In the case of the supernatant of COS-1/pEX-hFL1, a band was observed at about 26 kD under reduced conditions, and at about 24 kD under non-reduced conditions.

Figure 35:
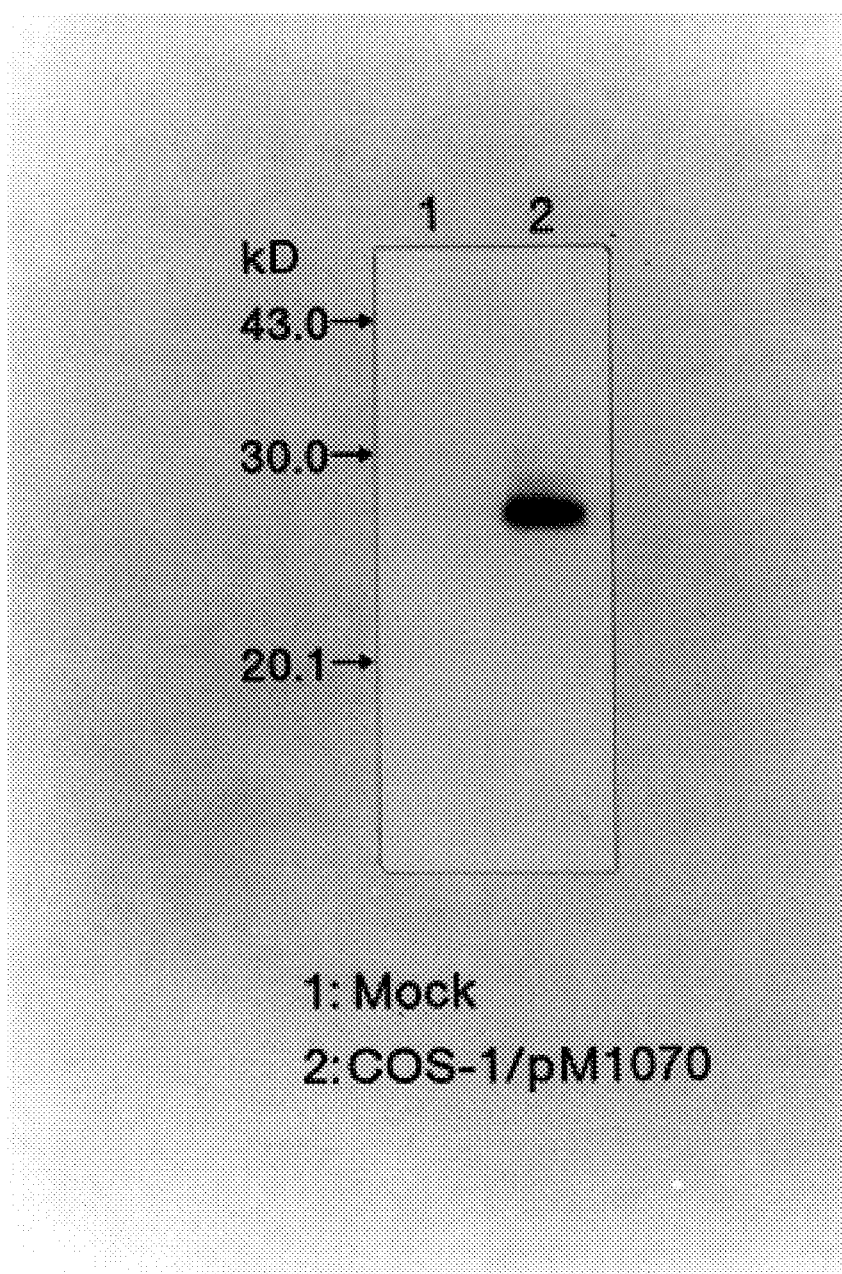
FIG. 35 is a photograph showing the results of the western blotting of a culture supernatant of the transformant COS-1/pM1070 carried out under non-reducing condition.
Figure 36:
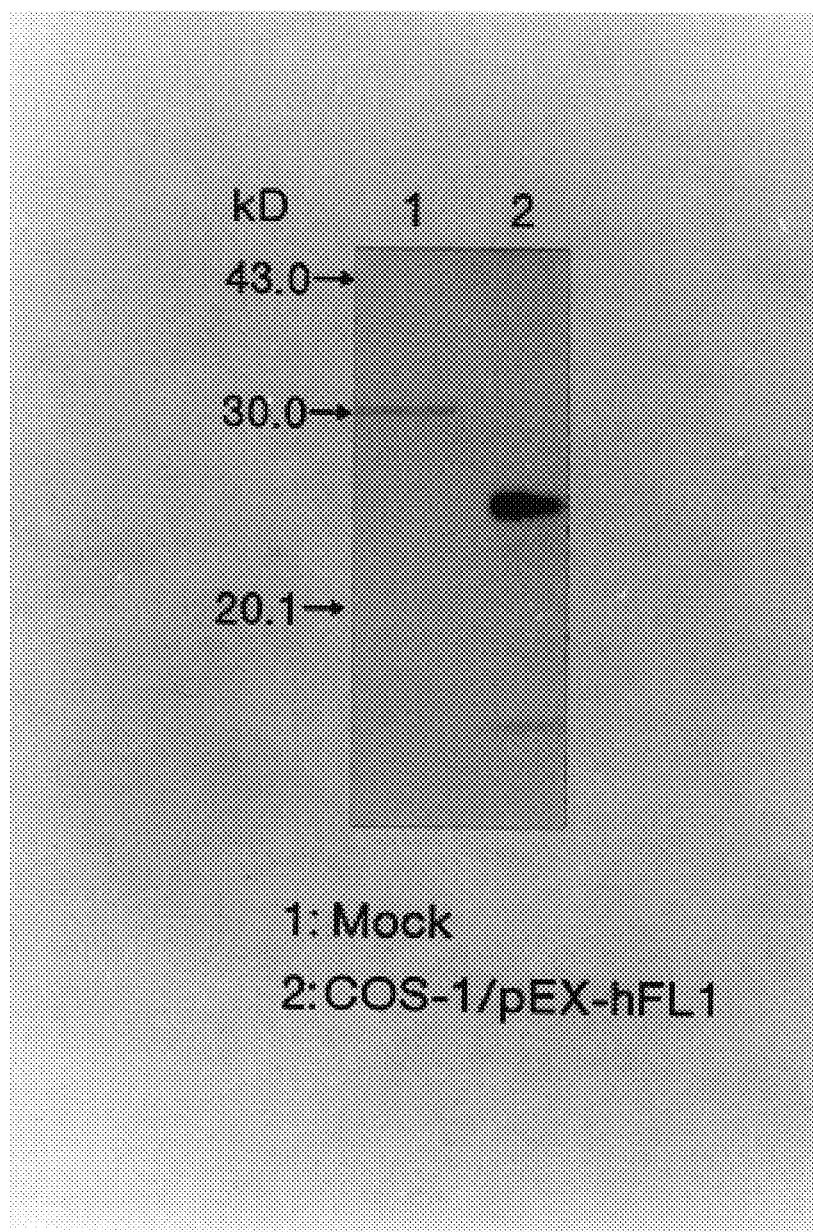
FIG. 36 is a photograph showing the results of the western blotting of a culture supernatant of the transformant COS-1/pEX-hFL1 carried out under non-reducing condition.

The results of the western blotting under non-reduced conditions are shown in FIGS. 35 and 36.

Inventive Example 19

Inhibition of the Expression of Fas Ligand by Antisense Oligonucleotide (1) Synthesis of Antisense Oligonucleotide A phosphorothioate sense oligonucleotide of 22 nucleotides containing the nucleotide sequence (TAAAACCGTTTGCTGGGGCTGG) (SEQ ID NO: 65) from 20th to 41st nucleotides in SEQ ID NO: 35 (hereinafter referred to as sense oligonucleotide S20), and a phosphorothioate antisense oligonucleotide having the complementary sequence (CCAGCCCCAGCAAACGGTTTTA) (SEQ ID NO: 66) to the sense oligonucleotide S20 (hereinafter referred to as antisense oligonucleotide A41) were synthesized in accordance with a known method. The resulting synthetic oligonucleotides were respectively dissolved in TE buffer to a concentration of 1 mM.

(2) Introduction of Antisense Oligonucleotide into the Cell

Transformant FLh1 cells expressing the human Fas ligand (see Inventive Example 16) were suspended in RPMI 1640 medium containing 10% heat-inactivated FCS, and the cell suspension was dispensed into wells of a 96 well plate (NUNC) at $2.0\times10^4$ cells/196 μl/well.

The 1 mM solution of antisense oligonucleotide A41 produced in the above (1) was dispensed in the wells in 4 μl portions to a final concentration of 20 μM, and the plate was incubated in the presence of 5% $CO_2$ for 3 days to introduce the oligonucleotide into the cells.

Into the wells containing the cell suspension were also dispensed 4 μl portions of the 1 mM solution of sense oligonucleotide S20 produced in the above (1) and the TE buffer, respectively, and the plate was incubated in the presence of 5% $CO_2$ for 3 days. Such wells were used for the control.

(3) Evaluation of Cytotoxic Activity

FLh1 cells that had been incubated for 3 days in the above (2) were used for the effector cells to evaluate the cytotoxic activity on human Fas antigen-expressing transformant WC8.

The cytotoxic activity was evaluated as described below in accordance with the method used in Inventive Examples 8 and 12.

In RPMI1640 medium containing 20 μCi of [$^{51}$Cr] sodium chromate (NEN), $10^6$ cells of WC5 were incubated at 37° C. for 2 hours to label the WC8 cells with the $^{51}$Cr. The effector cells as described above were mixed with $1\times10^4$ 51Cr-labeled cells at an E/T ratio of 3:1. The culture was incubated at 37° C. for 5 hours, and cytotoxic activity was evaluated by using the release of the $^{51}$Cr for the index.

Figure 37:
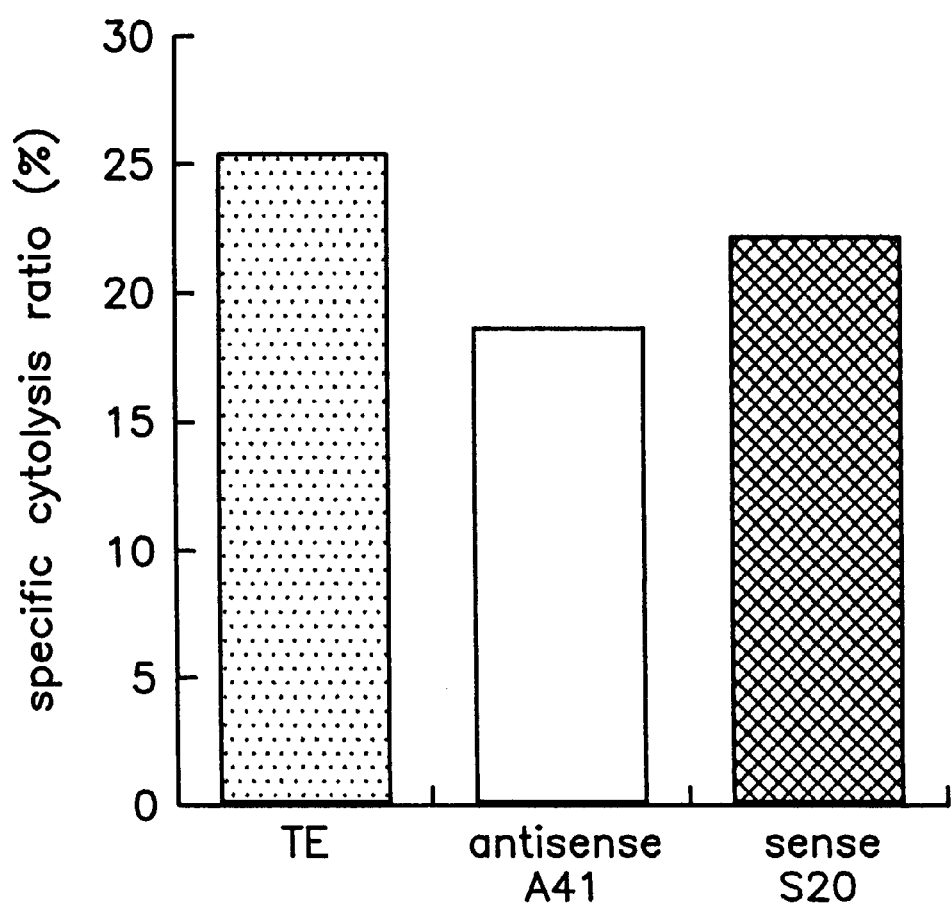
FIG. 37 shows apoptosis inhibiting activity of antisense oligomer A41.

The results are shown in FIG. 37. As shown in FIG. 37, the FLh1 cells carrying antisense oligonucleotide A41 introduced therein exhibited an apoptosis inhibition activity on WC8 cells.

Inventive Example 20

Inhibition of the Expression of Fas Ligand by Antisense Oligonucleotide-2

(1) Synthesis of Antisense Oligonucleotides

Phosphorothioate sense oligonucleotides S50, S163, S338, S484, S714, and S905 and phosphorothioate antisense oligonucleotides A69, A184, A355, A505, A733, and A924

(SEQ ID NOS: 67 to 78) were synthesized in accordance with a known method by referring to the DNA sequence coding for the human Fas ligand (SEQ ID NO: 35).

Of the thus synthesized oligonucleotides, sense oligonucleotide S50 and antisense oligonucleotide A69 are oligonucleotides of 20 nucleotides respectively containing the nucleotide sequence (ACCAGCTGCCATGCAGCAGC) from 50th to 69th nucleotides in SEQ ID NO: 35, and the complementary sequence (GCTGCTGCATGGCAGCTGGT) to such sequence.

Sense oligonucleotide S163 and antisense oligonucleotide A184 are oligonucleotides of 22 nucleotides respectively containing the nucleotide sequence (CTGTGCCCAGAAGGCCTGGTCA) from 163rd to 184th nucleotides in SEQ ID NO: 35, and the complementary sequence (TGACCAGGCCTTCTGGGCACAG) to such sequence.

Sense oligonucleotide S338 and antisense oligonucleotide A355 are oligonucleotides of 18 nucleotides respectively containing the nucleotide sequence (CTTGGTAGGATTGGGCCT) from 338th to 355th nucleotides in SEQ ID NO: 35, and the complementary sequence (AGGCCCAATCCTACCAAG) to such sequence.

Sense oligonucleotide S484 and antisense oligonucleotide A505 are oligonucleotides of 22 nucleotides respectively containing the nucleotide sequence (AGCTGAGGAAAGTGGCCCATTT) from 484th to 505th nucleotides in SEQ ID NO: 35, and the complementary sequence (AAATGGGCCACTTTCCTCAGCT) to such sequence.

Sense oligonucleotide S714 and antisense oligonucleotide A733 are oligonucleotides of 20 nucleotides respectively containing the nucleotide sequence (CCCCAGGATCTGGTGATGAT) from 714th to 733rd nucleotides in SEQ ID NO: 35, and the complementary sequence (ATCATCACCAGATCCTGGGG) to such sequence.

Sense oligonucleotide S905 and antisense oligonucleotide A924 are oligonucleotides of 20 nucleotides respectively having the nucleotide sequence (AGAGAAGCACTTTGGGATTC) from 905th to 924th nucleotides in SEQ ID NO: 35, and the complementary sequence complementary (GAATCCCAAAGTGCTTCTCT) to such sequence.

The resulting synthetic oligonucleotides were respectively dissolved in TE buffer to a concentration of 1 mM.
(2) Introduction of Antisense Oligonucleotides into the Cells First, mouse fibroblas-lie cell line L929 was transformed with plasmid pEX-hFL1 (see Inventive Example 12(2)), which carries the cDNA coding for the human Fas ligand. LFLh3 cells, which are one of the resulting clones, were suspended in D-MEM supplemented with 10% FCS, and the suspension was dispensed into wells of a 6 well plate (NUNC) at 3.0×10$^5$ cells/2.0 ml/well. The plate was incubated at 37° C. overnight in the presence of 5% CO$_2$.

On the next day, the oligonucleotides synthesized in the above (1) were respectively suspended in 1,000 µl of OPTI-MEM™I (Gibco BRL) supplemented with lipofectamine (Gibco BRL) to prepare oligonucleotide-lipofectamine mixed solutions. The medium was removed and the mixed solutions were respectively added to LFLh3 cells which were incubated at 37° C. overnight in the presence of 5% CO$_2$. After incubating at 37° C. for 4 hours in the presence of 5% CO$_2$, 1,000 µl of D-MEM supplemented with 20% heat-inactivated FCS and 1 µM oligonucleotide was added to the culture, and the culture was incubated for another 16 hours to introduce the oligonucleotides synthesized in the above (1) respectively into the LFLh3 cells.

(3) Evaluation of Cytotoxic Activity

LFLh3 cells into which the oligonucleotides had been respectively introduced in the above (2) were collected, and treated in trypsin solution for 3 minutes. The cells were then used for the effector cells to evaluate the cytotoxic activity.

The cytotoxic activity was evaluated as described below in accordance with the method used in Inventive Examples 8 and 12.

In RPMI1640 medium containing 20 µCi of [$^{51}$Cr] sodium chromate (NEN), 10$^6$ cells of WC8 were incubated at 37° C. for 2 hours to label the WC8 cells with the $^{51}$Cr. The effector cells as described above were mixed with 1×10$^4$ $_{51}$Cr-labeled cells at an E/T ratio of 1:1. The culture was incubated at 37° C. for 4 hours, and cytotoxic activity was evaluated by using the release of $^{51}$Cr for the index.

The LFLh3 cells carrying antiserise oligonucleotide A69, A184, A355, A505, A733, or A924 introduced therein exhibited an apoptosis-inhibition activity on WC8 cells. Inhibition of the specific cytolysis of the antisense oligonucleotides was calculated by the following formula:

Inhibition (%) of the={1−(D/E)}×100 specific cytolysis

D: Specific cytolysis rate of LFLh3 cells carrying the antisense oligonucleotide,
E: Specific cytolysis rate of LFLh3 cells carrying the sense oligonucleotide.

Figure 38:
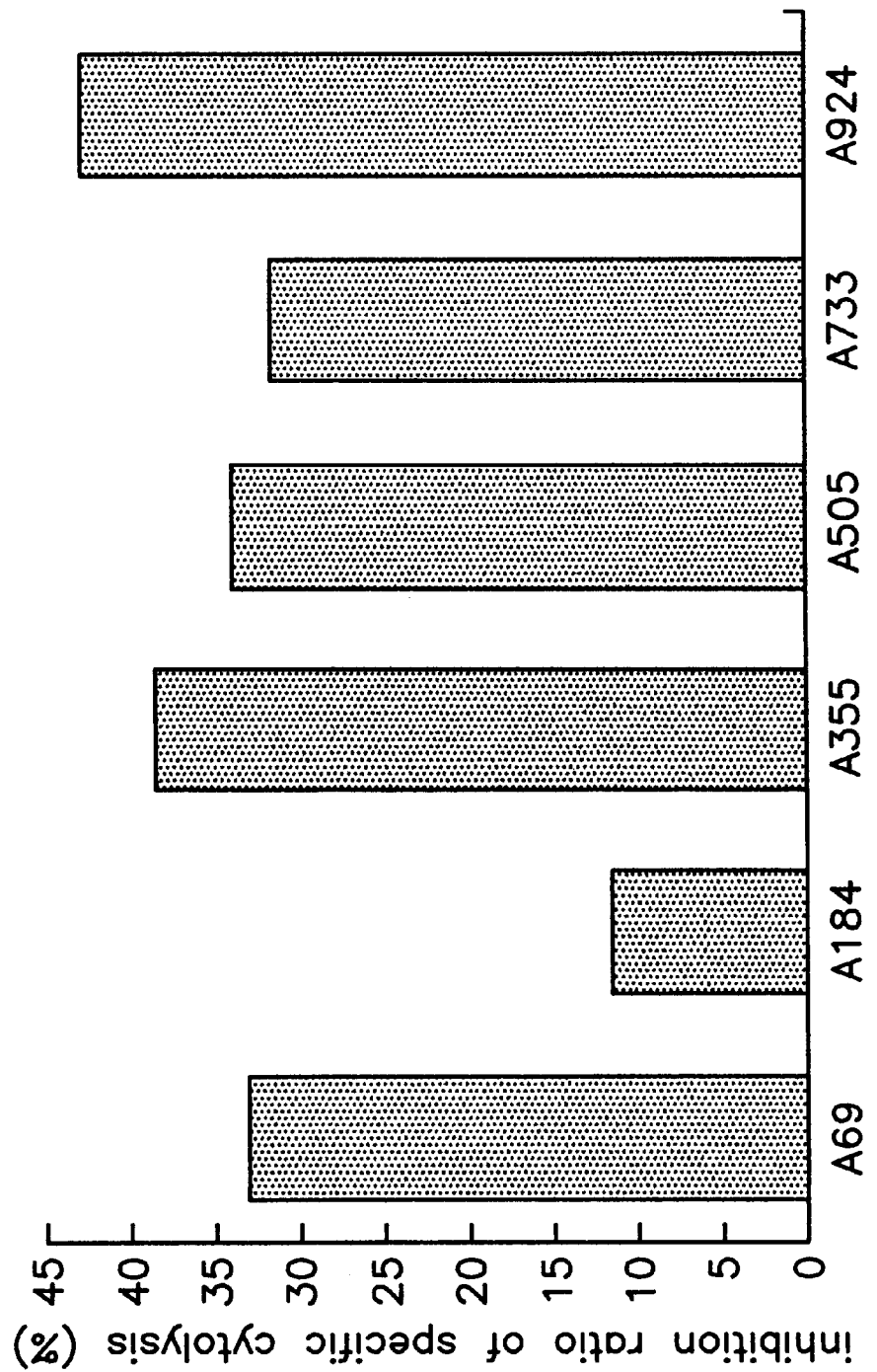
FIG. 38 shows apoptosis inhibiting activity of antisense oligonucleotides A69, A184, A355, A505, A733 and A924.

The results are shown in FIG. 38.

Inventive Example 21

Expression of Deletion Mutants of the Extracellular Domain of the Human Fas Ligand in an Animal Cell Host Polypeptides ND38 (SEQ ID NO: 79), ND40 (SEQ ID NO: 80), ND41 (SEQ ID NO: 81), ND42 (SEQ ID NO: 82), ND43 (SEQ ID NO: 83), and CD179 (SEQ ID NO: 84), which are deletion mutants of the extracellular domain of the human Fas ligand, were expressed as described below. It should be noted that ND38, ND40, ND41, ND42, ND43 are polypeptides having the amino acid sequences of SEQ ID NO: 6 from which 38, 40, 41, 42, and 43 amino acids on the N terminus are respectively deleted. In other words, ND38, ND40, ND41, ND42, and ND43 are polypeptides respectively having the amino acid sequences of amino acid NOS: 39 to 179, 41 to 179, 42 to 179, 43 to 179, and 44 to 179 in SEQ ID NO: 6. CD179 is a polypeptide having the amino acid sequence of SEQ ID NO: 6 from which 1 amino acid on the C terminus is deleted. In other words, CD179 is a polypeptide having the amino acid sequence of amino acid NOS: 1 to 178 in SEQ ID NO: 6.

(1) Preparation of Plasmid pM1081

Plasmid pM1081 is a plasmid carrying a nucleotide sequence coding for the signal peptide of the human Fas antigen and the extracellular domain of the human Fas ligand, wherein SpeI and PshAI recognition sequences have been introduced in the nucleotide sequence coding for the signal peptide of the human Fas antigen, and a PstI recognition sequence has been introduced in the nucleotide sequence coding for the human Fas ligand by means of silent mutation. The plasmid pM1081 was prepared as described below.

First, an antisense primer 9 (CTTCTGCAGGTGGAAGAGCTGAGCGACACTAGT CAGAACCAGAGG) (SEQ ID NO: 85) was synthesized. This antisense primer includes a nucleotide sequence coding for the N terminus of the human Fas ligand and the C terminus of the signal peptide of the human Fas signal; PstI site (CTGCAG); SpeI site (ACTAGT); and PshAI site (GACTAGTATC).

A 100 μl solution containing 100 pmol of the resulting antisense primer; 100 pmol of the sense primer 8 (TGCGAATTCACCATGCTGGGCATCTGG (SEQ ID NO: 62), containing EcoRI site (GAATTC) and a sequence coding for the N terminus of the signal peptide of the human Fas antigen) used in Inventive Example 18(2); 50 ng of plasmid pBLF58-1 used in Inventive Example 1(3); and 2.5 units of pfu DNA polymerase and 10 μl of pfu buffer attached therewith was prepared. PCR was carried out by repeating the procedure of Inventive Example 18(1), and the PCR product was double digested with EcoRI and PstI, and the digestion product was electrophoresed on agarose gel. A DNA fragment of about 70 bp was recovered, and the DNA was purified with QIAEX™ kit. The thus purified DNA fragment of about 70 bp was inserted between the EcoRI site and the PstI site of plasmid pM1067 prepared in Inventive Example 18(1).

The resulting plasmid was examined for its nucleotide sequence, and it was then detected that 16 nucleotides were missing between the EcoRI site and the SpeI site. In order to construct the sequence between the EcoRI site and the SpeI site, a sense oligonucleotide 9 (AATTCACCATGCTGGGCATCTGGACCCTCCTACC TCTGGTTCTGA) SEQ ID NO: 86 and an antisense oligonucleotide 10 (CTAGTCAGAACCAGAGGTAGGAGGGTCCAGATG CCCAGCATGGTG) SEQ ID NO: 87 were synthesized, and a 20 μl TE solution containing 1 nmol of the thus synthesized sense oligonucleotide and 1 nmol of the antisense oligonucleotide was prepared. The solution was heated to 95° C. for 5 minutes and gradually cooled to 16° C. to anneal the oligonucleotides to thereby obtain a double stranded DNA fragment having the EcoRI cleavage site and the SpeI cleavage site on opposite ends. The thus obtained DNA fragment was inserted between the EcoRI site and the SpeI site of the plasmid wherein 16 nucleot-ides were missing as described above to produce the plasmid pM1081.

(2) Preparation of Plasmid pM1253 Carrying a Nucleotide Sequence Coding for Polypeptide ND38

First, a sense primer 11 (CTGACTAGTGTCGCTAAGGAGCTGAGGAAA) SEQ ID NO: 88 was synthesized. This sense primer 11 contains a nucleotide sequence coding for the signal peptide of the human Fas antigen; a nucleotide sequence coding for the amino acid sequence from lysine (39th amino acid) to lysine (43rd amino acid) in SEQ ID NO: 3; and SpeI site (ACTAGT). An antisense primer 11 (TAAGCCGAAAAACGTCTGAG) SEQ ID NO: 89 was also chemically synthesized on the basis of the nucleotide sequence in the downstream 3' side of the ApaI site (GGGCCC) in SEQ ID NO: 5.

A 100 μl solution containing 100 pmol each of the resulting sense primer and the antisense primer; 50 ng of plasmid pEX-hFL1 prepared in Inventive Example 12(1); and 2.5 U of pfu DNA polymerase and 10 μl of pfu buffer attached therewith was prepared. PCR was carried out by repeating the procedure of Inventive Example 18(1), and the PCR product was double digested with SpeI and ApaI, and the digestion product was electrophoresed on agarose gel. A DNA fragment of about 400 bp was recovered, and the DNA was ourified with QIAEX™ kit. The thus purified DNA fragment of about 400 bp was inserted between the SpeI site and the ApaI site of plasmid pM1081 produced in the above (1) to produce plasmid pM1253.

(3) Preparation of Plasmid pM1254 Carrying a Nucleotide Sequence Coding for Polypeptide ND40

First, a sense primer 12 (CTGACTAGTGTCGCTCTGAGGAAAGTGGCC) SEQ ID NO: 90 was synthesized. This sense primer contains a nucleotide sequence coding for the signal peptide of the human Fas antigen; a nucleotide sequence coding for the amino acid sequence from leucine (41st amino acid) to alanine (45th amino acid) in SEQ ID NO: 6; and SpeI site (ACTAGT).

Using the thus synthesized sense primer and antisense primer 11, PCR was carried out by repeating the procedure of the above (2), and the PCR product was inserted into plasmid pM1081 to produce plasmid pM1254.

(4) Preparation of Plasmid pM1255 Carrying a Nucleotide Sequence Coding for Polypeptide ND41

First, a sense primer 13 (CTGACTAGTGTCGCTAGGAAAGTGGCCCAT) SEQ ID NO: 91 was synthesized. This sense primer contains a nucleotide sequence coding for the signal peptide of the human Fas antigen; a nucleotide sequence coding for the amino acid sequence from arginine (42nd amino acid) to histidine (46th amino acid) in SEQ ID NO: 6; and SpeI site (ACTAGT).

Using the thus synthesized sense primer and antisense primer 11, PCR was carried out by repeating the procedure of the above (2), and the PCR product was inserted into plasmid pM1081 to produce plasmid pM1255.

(5) Preparation of Plasmid pM1256 Carrying a Nucleotide Sequence Coding for Polypeptide ND42

First, a sense primer 14 (CTGACTAGTGTCGCTAAAGTGGCCCATTTA) SEQ ID NO: 92 was synthesized. This sense primer contains a nucleotide sequence coding for the signal peptide of the human Fas antigen; a nucleotide sequence coding for the amino acid sequence from lysine (43rd amino acid) to leucine (47th amino acid) in SEQ ID NO: 6; and SpeI site (ACTAGT).

Using the thus synthesized sense primer and antisense primer 11, PCR was carried out by repeating the procedure of the above (2), and the PCR product was inserted into plasmid pM1081 to produce plasmid pM1256.

(6) Preparation of Plasmid pM1257 Carrying a Nucleotide Sequence Coding for Polypeptide ND43

First, a sense primer 15 (CTGACTAGTGTCGCTGTGGCCCATTTAACA) SEQ ID NO: 93 was synthesized. This sense primer contains a nucleotide sequence coding for the signal peptide of the human Fas antigen; a nucleotide sequence coding for the amino acid sequence from valine (44th amino acid) to threonine (48th amino acid) in SEQ ID NO: 6; and SpeI site (ACTAGT).

Using the thus synthesized sense primer and antisense primer 11, PCR was carried out by repeating the procedure of the above (2), and the PCR product was inserted into plasmid pM1081 to produce plasmid pM1257.

(7) Preparation of Plasmid pM1259 Carrying a Nucleotide Sequence Coding for Polypeptide CD179

An antisense primer 16 (CTTGGTACCCTATTACTTATATAAGCC) SEQ ID NO: 94 and a sense primer 16 (GAGCTACTGCACTACTGGGC) SEQ ID NO: 95 were synthesized. The antisense primer includes a nucleotide sequence coding for the amino acid sequence from glycine (175th amino acid) to lysine (178th amino acid) in SEQ ID NO: 6; termination codons (TAA, TAG); and KpnI site (GGTACC) . The sense primer is the sequence located in the upstream 5' side of the ApaI site (GGGCCC) in SEQ ID NO: 3, which is the DNA sequence of the extracellular domain of the human Fas ligand.

A 100 μl solution containing 100 pmol of the resulting antisense primer and the sense primer; 50 ng of plasmid pEX-hFL1 prepared in Inventive Example 12(1); and 2.5 U of pfu DNA polymerase and 10 μl of pfu buffer attached therewith was prepared. PCR was carried out by repeating the procedure of Inventive Example 18(1), and the PCR product was double digested with ApaI and KpnI, and the digestion product was electrophoresed on agarose gel. A DNA fragment of about 170 bp was recovered, and the DNA was purified with QIAEX™ kit. The thus purified DNA fragment of about 170 bp was inserted between the ApaI site and the KpnI site of plasmid pM1250 produced in Inventive Example 18(2). The resulting plasmid was designated pM1259.

(8) Preparation of pM1083, pM1084, pM1085, pM1086, pM1087 and pM1089 for Expression in a Mammalian Cell Plasmids pM1253, pM1254, pM1255, pM1256, pM1257 and pM1259 produced in the above (2) to (7) were respectively double digested with EcoRI and KpnI, and the digestion products were electrophoresed on agarose gel. A DNA fragment of about 450 bp was recovered in the case of pM1253, pM1254, pM1255, pM1256, and pM1257, and a DNA fragment of about 600 bp was recovered in the case of pM1259. The thus recovered DNAs were purified with QIAEX™ kit. The thus purified DNA fragments of about 450 bp and about 600 bp were respectively inserted between the EcoRI site and the KpnI site of plasmid pM1103 used in Inventive Example 18(2) for expression in an animal cell host. The resulting plasmids were designated pM1083 (ND38), pM1084 (ND40), pM1085 (ND41), pM1086 (ND42), pM1087 (ND43), and pM1089 (CD179), respectively.

(9) Introduction into COS Cells pM1070 prepared in Inventive Example 18(2) and pM1083, pM1084, pM1085, pM1086, pM1087, and pM1089 prepared in the above (8) were respectively introduced into COS-1 cells as in the case of Inventive Example 18(3) to produce transformants COS-1/pM1070, COS-1/pM1083, COS-1/pM1084, COS-1/pM1085, COS-1/pM1086, COS-1/pM1087, and COS-1/pM1089 by the procedure as described below.

In 2.5 μl of 10 mM Tris-HCl (pH 7.4)/1 mM EDTA were added 0.5 μg of pM1070, pM1083, pM1084, pM1085, pM1086, pM1087, and pM1089, respectively. To the resulting solutions were added 0.7 ml of D-MEM, (Nissui Pharmaceutical) containing 0.2 mg/ml DEAE-dextran and 50 mM Tris-HCl, pH 8 to prepare DNA-DEAE-dextran mixed solutions. The resulting DNA-DEAE-dextran mixed solutions were respectively added dropwise to a monolayer culture of COS-1 cells in a 6 well plate (9.4 cm²/well, NUNC) that had grown to their semi-confluent stage, and the plate was incubated at 37° C. in the presence of 5% $CO_2$ to produce the transformants COS-1/pM1070, COS-1/pM1083, COS-1/pM1084, COS-1/pM1085, COS-1/pM1086, COS-1/pM1087, and COS-1/pM1089. After 4 hours of incubation, the DNA-DEAE-dextran mixed solutions were respectively removed, and D-MEM containing 10% FCS (Urban Scientific) was added to the wells. The incubation was continued for another 96 hours, and culture supernatants were respectively collected from the COS-1/pM1070, COS-1/pM1083, COS-1/pM1084, COS-1/pM1085, COS-1/pM1086, COS-1/pM1087, and COS-1/pM1089. The thus collected culture supernatants were used for the following evaluation of their cytotoxic activity.

(10) Cytotoxic Activity of Culture Supernatants of the Transformants

The cytotoxic activity of the culture supernatants of the transformed COS cells produced in the above (9) was evaluated as in the case of Inventive Examples 8 and 12 by using WC8 cells for the target cells. The evaluation was carried out as described below.

In RPMI1640 medium containing 20 μCi of [$^{51}Cr$] sodium chromate (NEN) $10^6$ cells of WC8 were incubated at 37° C. for 2 hours to label the WC8 cells with the $^{51}Cr$.

The cell culture supernatants produced in the above (9) were respectively added to the reaction solution containing $1\times10^{4}$ $^{51}Cr$-labeled cells to a final concentration of 1%, 3%, 10% and 30%, respectively. The cultures were incubated at 37° C. for 4 hours, and cytotoxic activity was evaluated by using the release of $^{51}Cr$ for the index.

Figure 39:
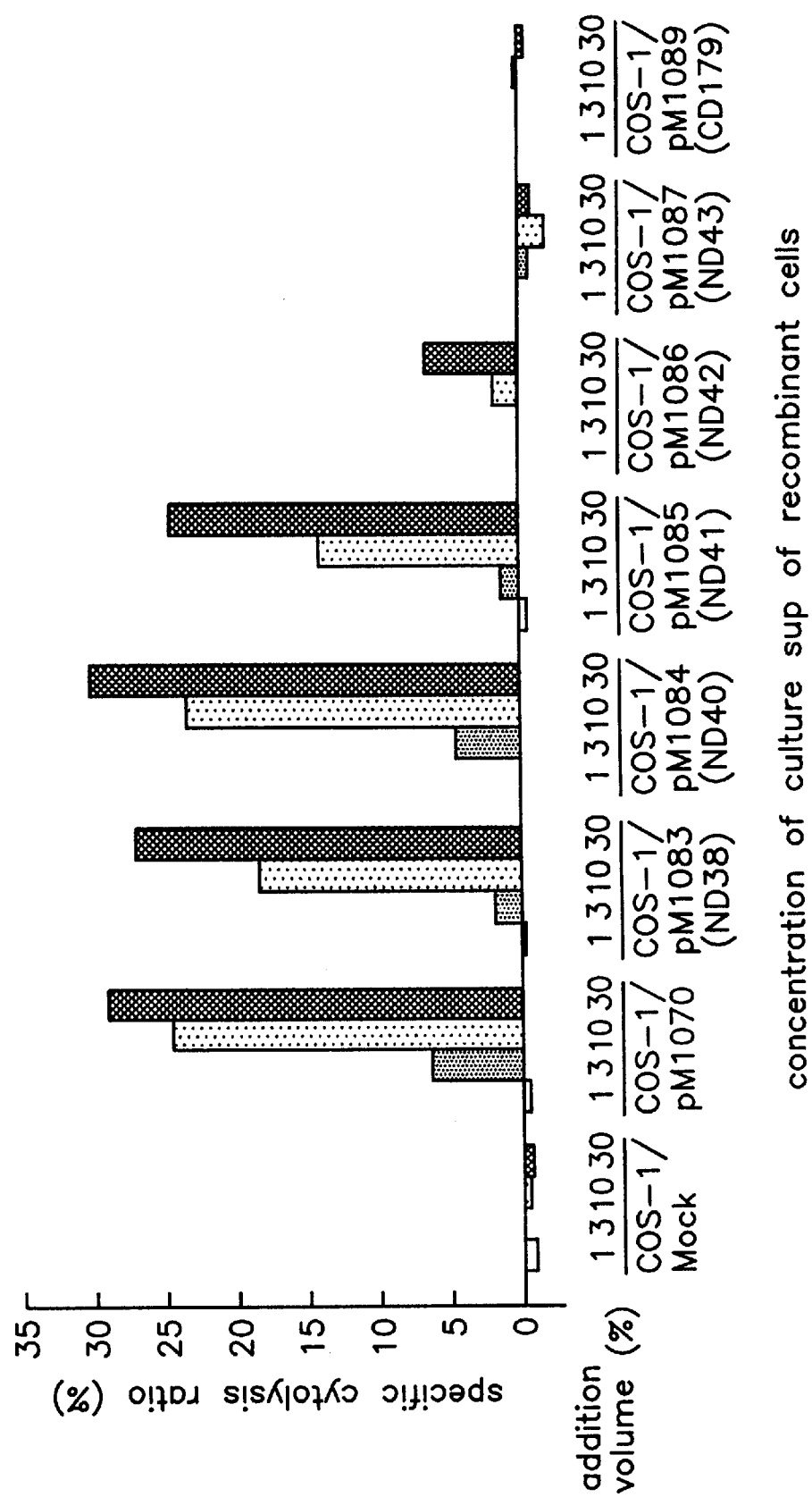
FIG. 39 shows cytotoxic activity of polypeptides ND38, ND40, ND41, ND42, ND43 and CD179 respectively in culture supernatant.

The results are shown in FIG. 39. As apparent in FIG. 39, the culture supernatants of COS-1/pM1083, COS-1/pM1084, COS-1/pM1085, and COS-1/pM1086 exhibited concentration dependent cytotoxic activity on WC8 cells as in the case of COS-1/pM1070. It was then estimated that the deletion mutants of the human Fas ligand present in such culture supernatants should have an activity of binding with the human Fas antigen to induce the apoptosis. On the other hand, culture supernatants of COS-1/pM1087 and COS-1/pM1089 exhibited a cytotoxic activity on WC8 cells significantly weaker than the supernatant of the COS-1/pM1070, and it was then estimated that the deletion mutants of the human Fas ligand present in such culture supernatants should have a slight or no apoptosis-inducing activity.

Such inactivation is believed to have been caused by the deletion of one or more amino acids on N or C terminus of the Fas ligand that resulted in the alteration of the steric conformation of the Fas ligand. It is then estimated that, when an amino acid sequence capable of restoring the original conformation of the Fas ligand is added on the N or C terminus of the polypeptide having deleted one or more amino acids from its N or C terminus to loose its original conformation, the polypeptide would recover its apoptosis-inducing activity even if the amino acid sequence added were different from the amino acid sequence that had been deleted. Similarly, it is estimated that the once lost apoptosis-inducing activity may be provided with the deletion mutant by introducing in the amino acid sequence of the deletion mutant another mutation that is capable of restoring its original conformation.

Inventive Example 22

Expression of Deletion Mutants of the Extracellular Domain of the Human Fas Ligand in *E. coli*

(1) Preparation of Plasmid pM468

Plasmid pM468 is a plasmid derived from plasmid pBR322. Plasmid pM468 has been constructed to include the DNA coding for the function enabling the replication in *E. coli*, ampicillin resistant gene, tryptophan promoter, the signal peptide of alkaline phosphatase (phoA), and human pancreatic trypsin inhibitor. In plasmid pM468, the kanamycin resistant gene of plasmid pM469 (Morishita, H. et al., Thrombosis Research vol. 73, pp 193–204, 1994) is replaced with the ampicillin resistant gene.

(2) Preparation of Plasmid pM1059

Plasmid pM468 prepared in the above (1) was double digested with HindIII and BamHI, and the digestion product was separated on 0.8% agarose gel (SeakemGTG, Takara Shuzo Co., Ltd.) to isolate the gel containing the DNA fragment of interest. A DNA fragment of about 3.3 kbp was purified with QIAEX™ kit.

An antisense primer 17 (CGCGGATCCGGTACCTTTTTTGGTAACCGGGGTA AACAG) (SEQ ID NO: 96) and a sense primer 17 (CGCAAGTTCACGTAAAAGC) (SEQ ID NO: 97) were chemically synthesized. The antisense primer includes BanHI site (GGATCC), KpnI site (GGTACC) and EstEII site (GGTTACC), and a sequence coding for the C terminus of the signal peptide of alkaline phosphatase. The sense primer is the sequence located on 5' upstream side of HindIII site in tryptophan promoter. PCR was carried out as described below by using the thus synthesized primers and the plasmid pM 468 as template.

To a 100 µl solution containing the above-described temperate DNA for PCR were added the above-described primers, and PCR was carried out by repeating 30 cycles each comprising 94° C. for 1 minute, 55° C. for 2 minutes, and 72° C. for 3 minutes using Gene Amp™ DNA Amplification Reagent Kit with AmpliTaq™ (Takara Shuzo Co., Ltd.).

The resulting PCR product was double digested with HindIII and BamHI, and the digestion product was electrophoresed on 4% agarose gel to separate a DNA fragment of about 120 bp. The thus separated DNA fragment was purified, and ligated with the above described DNA fragment of about 3.3 kbp from plasmid pM468 using T4DNA ligase (Takara Shuzo Co., Ltd.). E. coli JM109 was transformed with the resulting product to produce plasmid pM1059.

(3) Preparation of Plasmid pM1068 Expressing the Extracellular Domain of the Human Fas Ligand in the Cell of the Host E. coli A sense primer 18 (TTGAAGCTTAAAAAAGGGTATAAAATAAAATGCA GCTCTTCCACCT) SEQ ID NO: 98 and an antisense primer 18 (AAGGTCGACTATTAGAGCTTATATAAGCC) SEQ ID NO: 99 were synthesized in a chemical synthesizer. The sense primer carries a sequence coding for a part of E. coli tryptophan promoter/operator, initiation codon (ATG), a sequence coding for the N terminus of the extracellular domain of human Fas ligand of SEQ ID NO: 6, and HindIII site (AAGCTT). The antisense primer includes a sequence coding for the C terminus of the extracellular domain of human Fas ligand of sequence ID NO: 6, termination codons (TAA, TAG), and SalI site (GTCGAC).

A 100 µl solution containing 100 pmol each of the antisense primer and the sense primer; 50 ng of plasmid pBX-hFL1; 20 nmol each of dATP, dCTP, dGTP, and dTTP; and 2.5 units of pfu DNA polymerase and 10 µl of the pfu buffer attached therewith was prepared, and PCR was carried out by repeating the procedure of Inventive Example 18(1). The resulting PCR product was double digested with HindIII and SalI, and the digestion product was electrophoresed on agarose gel. A DNA fragment of about 600 bp was recovered and purified with QIAEX™ kit. The thus purified DNA fragment of about 600 bp was inserted between the HindIII site and the SalI site of plasmid pM468 prepared in the above (1) to produce plasmid pM1068.

(4) Preparation of Plasmid pM1069 Expressing the Extracellular Domain of the Human Fas Ligand by Secretion from the Host E. coli A sense primer 19 (GGGGGTTACCAAAGCCCAGCTCTTCCACCT) SEQ ID NO: 100 including a sequence coding for a part of the signal peptide of the alkaline phosphatase, a sequence coding for the N terminus of the extracellular domain of human Fas ligand of SEQ ID NO: 6, and BstEII site (GGTTACC) was synthesized.

A 100 µl solution containing 100 pmol of the thus synthesized sense primer; 100 pmol of the antisense primer 18 (AAGGTCGACTATTAGAGCTTATATAAGCC) (SEQ ID NO: 98) which was used in the above (3); 50 ng of plasmid pBX-hFL1; 20 nmol each of dATP, dCTP, dGTP, and dTTP; and 2.5 units of pfu DNA polymerase and 10 µl of pfu buffer attached therewith was prepared, and PCR was carried out by repeating the procedure of inventive Example 18(1). The resulting PCR product was double digested with BstEII and SalI, and the digestion product was electrophoresed on agarose gel. A DNA fragment of about 600 bp was recovered and purified with QIAEX™ kit. The thus purified DNA fragment of about 600 bp was inserted between the BstEII site and the SalI site of plasmid pM1059 prepared in the above (2) to produce plasmid pM1069.

(5) Preparation of Plasmid pM1073 Expressing the Deletion Mutant of the Extracellular Domain of the Human Fas Ligand (wherein 38 amino acids from the N terminus are deleted) by Secretion from the Host E. coli A sense primer 20 (CCCGGTTACCAAAGCCAAGGAGCTG) SEQ ID NO: 101 and an antisense primer 20 (TAAGCCGAAAAACGTCTGAG) SEQ ID NO: 102 were chemically synthesized. The sense primer 20 includes a sequence coding for a part of the signal peptide of the alkaline phosphatuase; a sequence coding for the N terminus of the extracellular domain of human Fas ligand of SEQ ID NO: 6 from which 38 amino acids from the N terminus are missing; and BstEII site (GGTTACC). The antisense primer 20 is the nucleotide sequence in the downstream 3' side of the ApaI site (GGGCCC) in SEQ ID NO: 5, which is the DNA sequence coding for the extracellular domain of the human Fas ligand.

A 100 µl solution containing 100 pmol each of the sense primer and the antisense primer; 50 ng of plasmid pBX-hFL1 prepared in Inventive Example 12(1); 20 nmol each of dATP, dCTP, dGTP, and dTTP; and 2.5 units of pfu DNA polymerase and 10 µl of pfu buffer attached therewith was prepared, and PCR was carried out by repeating the procedure of Inventive Example 18(1). The resulting PCR product was double digested with BstEII and ApaI, and the digestion product was electrophoresed on agarose gel. A DNA fragment of about 300 bp was recovered and purified with QIAEX™ kit. The thus purified DNA fragment of about 300 bp was inserted between the BstEII site and the ApaI site of plasmid pM1069 prepared in the above (4) to produce plasmid pM1073.

(6) Preparation of Transformant and Expression of Human Fas Ligand

E. coli JE5505 cell strain was transformed with pM1068, pM1069, and pM1073 prepared in the above (3), (4), and (5), respectively, in accordance with the method described in Hanahan, D., Techniques for Transformation of E. coli, In: DNA Cloning, vol. 1, Glover, D. M. ed., pp. 109–136, IRL Press, 1985, to produce recombinant E. coli JE5505 (pM1068), JE5505(pM1069), and JE5505(pM1073).

The resulting transformants were respectively incubated in 5 ml of L broth containing 50 µg/ml ampicillin overnight. 0.5 ml of the culture medium was inoculated in 25 ml of M9CA medium containing 50 µg/ml ampicillin, and the culture was incubated at 37° C. for 3 to 4 hours. When the culture medium exhibited an $OD_{550}$ of approximately 1, 3β-indol acrylic acid (Wako Pure Chemicals) was added to a final concentration of 10 µg/ml, and the culture was incubated for another about 24 hours. The resulting culture mixture was centrifuged to separately recover the supernatant and the cells.

(7) Western Blotting of the Transformant Supernatant and Cells

Western blotting was carried out by repeating the procedure of Inventive Example 18(5) using a rabbit antiserum capable of recognizing a part of the amino acid sequence of the human Fas ligand (PSPPPEKKELRKVAH), (SEQ ID NO: 64).

To the cells (cells corresponding to 1 ml of the culture medium) of transformants JE5505(pM1068), JE5505 (pM1069), and JE5505(pM1073) produced in the above (6) was added 1 ml of RIPA buffer (50 mM Tris-HCl, pH 7.5 containing 150 mM NaCl, 1% NP-40, 0.1% sodium deoxycholate, 0.1% SDS, and 0.2 U/ml Aprotinin), and the mixture was stirred for 30 minutes. The mixture was then centrifuged to recover the supernatant. 10 μl of the thus obtained supernatant from the cells and the supernatant of the culture of the transformant produced in the above (6) were respectively mixed with 5 μl of distilled water. To such mixtures were respectively added a 5 μl solution containing 4% SDS, 80% glycerol, and 0.04% BPB, and a 5 μl solution containing 4% SDS, 80% glycerol, 8% DTT, and 0.04% BPB. The resulting mixtures were respectively incubated at 37° C. for 1 hour, and then, subjected to SDS-polyacrylamide gel electrophoresis. After completing the electrophoresis, the gel was transferred to PVDF membrane (Atto K.K.) at room temperature, at 200 mA for 60 minutes, and the membrane was blocked by the solution of skim milk (Snow Brand Milk Products, Co., Ltd.) at 4° C. overnight. The thus blocked membrane was washed once with PBS, and twice with 0.1% Tween 20/PBS.

The rabbit antiserum as described above was diluted 1,000 times with 0.5% BSA/0.1% Tween 20/PBS, and the membrane was allowed to react with the thus diluted rabbit antiserum at 37° C. for 1 hour. After the completion of the reaction, the membrane was washed twice with 0.1% Tween 20/PBS. The membrane was then immersed in a solution of the peroxidase-labeled anti-rabbit immunoglobulins antibody (Cat. No. P448, DAKO) which had been diluted 500 times with 0.5% BSA/0.1% Tween 20/PBS, and allowed to react at room temperature for 1 hour. The membrane was washed 5 times with 0.1% Tween 20/PBS, and water on the surface was removed. The membrane was then evaluated in ECL system (Amersham).

Figure 40:
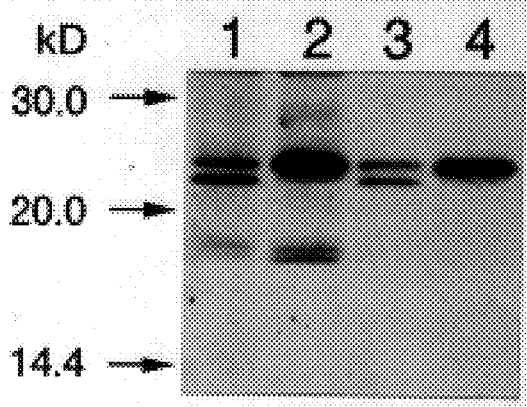
FIG. 40 is a photograph showing the results of the western blotting in which transformant JE5505 (pM1068) and culture supernatant thereof are used.

As shown in FIG. 40, in the case of the cells and the supernatant of JE5505(pM1068), 2 bands corresponding to the extracellular domain of the human Fas ligand were observed about 21 kD and about 23 kD under non-reduced conditions; and one band was found at about 23 kD under reduced conditions.

Figure 41:
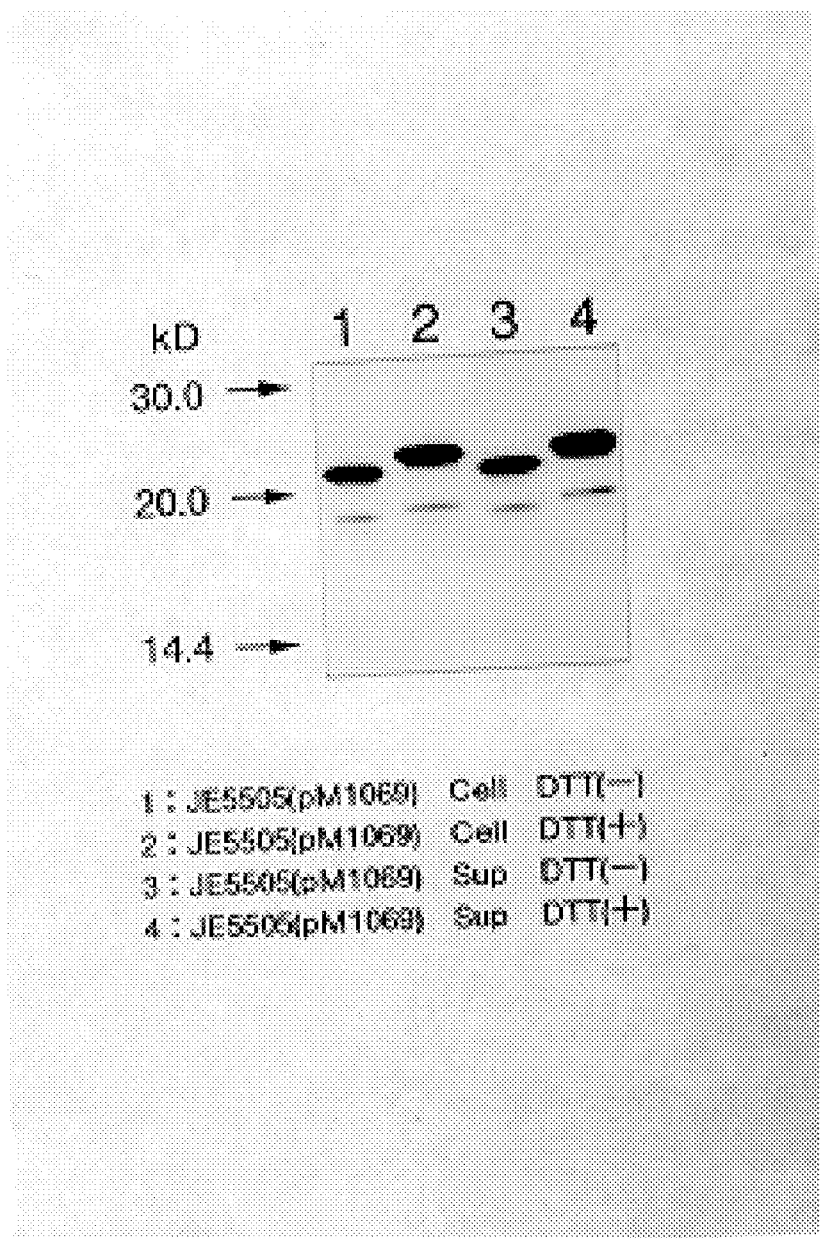
FIG. 41 is a photograph showing the results of the western blotting in which transformant JE5505 (pM1069) and culture supernatant thereof are used.

As shown in FIG. 41, in the case of the cells and the supernatant of JE5505(pM1069), a clear band corresponding to the extracellular domain of the human Fas ligand was observed at about 23 kD both under non-reduced conditions and under reduced conditions.

Reference Example 1

Cloning of cDNA for Fas Ligand Derived from gld (C3H gld/gld) Mouse

Splenocytes of gld (C3H gld/gld) mouse were cultured in accordance with the procedure described in Inventive Example 14, and synthesis of single-stranded cDNA and PCR were carried out in the same manner as described in Inventive Example 14. The thus obtained PCR product was digested with a restriction enzyme XbaI and isolated using 1%. agarose gel to recover a DNA fragment of about 940 bp. This was subcloned into the XbaI site of pBluescript IIKS(+) to determine its nucleotide sequence (SEQ ID NO: 100). When the thus determined nucleotide sequence was compared with the sequence confirmed in Inventive Example 14 (1), it was found that the sequence of the thus obtained PCR product has a mutation in which a T (Thymidine) close to the 3'-end of the sequence confirmed in Inventive Example 14 (1) (position 849 in SEQ ID NO: 36) is mutated into C (Cytosine) (SEQ ID NO: 103). By this mutation of a single base, a mutation occurred also in the amino acid sequence. That is, in the gld mouse, the 273rd amino acid residue in the extracellular domain of the mouse Fas ligand is mutated from phenylalanine to leucine.

Reference Example 2

Cytotoxic Activity of gld Mouse-derived Fas Ligand

Figure 26:
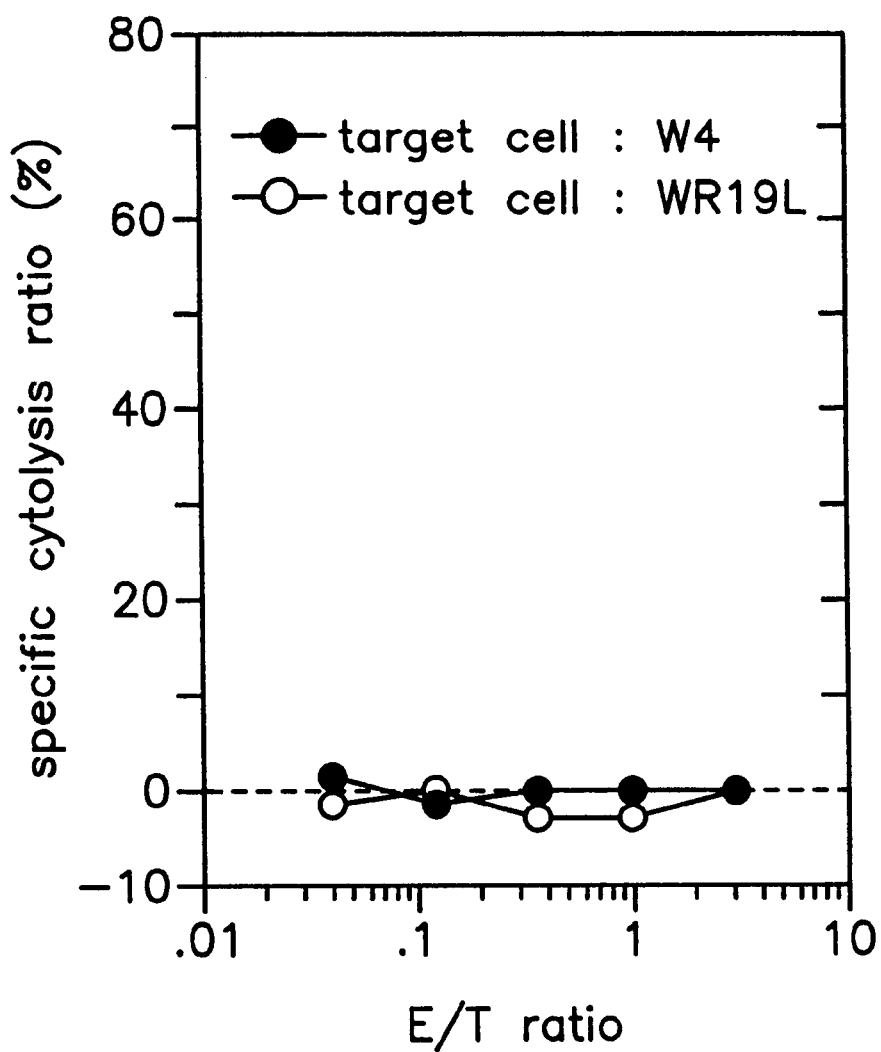
FIG. 26 shows cytotoxic activity of COS cells transformed with a plasmid containing Fas ligand cDNA isolated from gld mice when WR19L and W4 are used as target cells.

The XbaI fragment of about 940 bp obtained in Reference Example 1 was inserted into the XbaI site of an animal cell expression vector pEF-BOS. COS cells were transformed in the same manner as described in Inventive Example 14 (2). Using the transformed COS cells as effector cells, cytotoxic activity was measured in the same manner as described in Inventive Example 14 (3). As the result, the COS cells transformed with the Fas ligand cDNA obtained from gld mouse did not show the cytotoxic activity (FIG. 26). On the basis of the above results, it was confirmed that normal Fas ligand-induced apoptosis does not occur in the gld mouse which is a model animal of autoimmune diseases.

Based on the results of this time and those reported by Ogasawara J. et al., it was suggested that at least an abnormality in Fas antigen and an abnormality in Fas ligand could be included in the cause of autoimmune diseases. In each case, autoimmune diseases seem to occur because of the lack of ability to induce apoptosis in autoreactive T cells which therefore cannot be removed from the living body.

Thus, it is apparent that there has been provided, in accordance with the present invention, a novel protein which binds to Fas antigen. This novel protein can be developed as therapeutic drugs for the treatment of diseases in which Fas antigen-mediated apoptosis is concerned, such as autoimmune diseases and viral infection. Also, the novel protein can be used as an antigen for the preparation of antibodies and in an assay system in which said protein contained in samples is measured by a competitive reaction using antibodies.

Also, according to the present invention, there is provided a DNA fragment which encodes the novel protein that binds to Fas antigen. This DNA fragment can be used for the industrial production of the above novel protein in a large scale making use of genetic engineering techniques. It can be used also for the preparation of DNA probes. Also, the novel DNA fragment can be used in the gene therapy for the treatment of certain cases of autoimmune diseases in which the mechanism of apoptosis is deleted hereditarily.

In addition, disclosure of the DNA sequence leads to the provision of an oligonucleotide or a derivative thereof which contains a nucleotide sequence complementary to a part of Fas ligand gene or of mRNA for Fas ligand. This oligonucleotide can be used not only for the regulation of the expression of Fas ligand but also as a diagnostic probe.

What is claimed is:

1. A recombinant DNA molecule comprising a nucleotide sequence which encodes a Fas ligand comprising the amino acid sequence of SEQ ID NO: 28.

2. The recombinant DNA molecule of claim 1, which is a plasmid.

3. The recombinant DNA molecule of claim 2, wherein said plasmid is that which has been designated as pBL-hFL4H.

4. A transformed cell which has been transformed with the plasmid of claim 3.

5. The transformed cell of claim 4, wherein said cell is that which has been designated as DH10B (pBL-hFL4H) and which has been assigned deposition number FERM BP-4849.

6. A transformed host cell comprising a DNA molecule, which DNA molecule comprises a nucleotide sequence which encodes a Fas ligand comprising the amino acid sequence of SEQ ID NO: 28.

7. The transformed host cell of claim 6, wherein said transformed host cell is a bacteria, yeast or mammalian cell.

8. An isolated DNA comprising a nucleotide sequence which encodes a Fas ligand comprising the amino acid sequence of SEQ ID NO:28.

9. The DNA of claim 8, which comprises the nucleotide sequence from nucleotide 15 to nucleotide 404 of SEQ ID NO:27.

10. An isolated DNA comprising a nucleotide sequence which encodes a Fas ligand comprising the amino acid sequence of SEQ ID NO:14.

11. The DNA of claim 10, which comprises the nucleotide sequence set forth in SEQ ID NO:13.

12. A recombinant DNA molecule comprising a nucleotide sequence which encodes a Fas ligand comprising the amino acid sequence of SEQ ID NO:14.

13. The recombinant DNA molecule of claim 12, which is a plasmid.

14. A transformed host cell comprising a DNA molecule which DNA molecule comprises a nucleotide sequence which encodes a Fas ligand comprising the amino acid sequence of SEQ ID NO:14.

15. The transformed host cell of claim 14, wherein said transformed host cell is a bacteria, yeast or mammalian cell.

16. A process for producing Fas ligand which comprises cultivating the transformed host cell of claim 6 or claim 14 under conditions which produce said Fas ligand.

17. The process of claim 16, which further comprises the step of recovering said Fas ligand.

18. The process of claim 17, which further comprises the step of purifying said Fas ligand.

19. An isolated DNA which hybridizes to a polynucleotide which has the sequence from nucleotide 15 to nucleotide 404 of SEQ ID NO:27 or which hybridizes to a polynucleotide which has the sequence complementary to the nucleotide sequence from nucleotide 15 to nucleotide 404 of SEQ ID NO:27 under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3×SSCP containing 0.1 % SDS at a temperature of 37° C.

20. An isolated DNA which hybridizes to a polynucleotide which has a sequence which encodes a polypeptide according to SEQ ID NO:16 or which hybridizes to a polynucleotide which has a sequence complementary to the nucleotide sequence encoding the polypeptide according to SEQ ID NO:16 under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3×SSCP containing 0.1% SDS at a temperature of 37° C.

21. An isolated DNA which hybridizes to a polynucleotide which has a sequence of SEQ ID NO:15 or which hybridizes to a polynucleotide which has a sequence complementary to the nucleotide sequence of SEQ ID NO:15 under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3×SSCP containing 0.1% SDS at a temperature of 37° C.

22. An isolated DNA which hybridizes to a polynucleotide which has a sequence which encodes a polypeptide according to SEQ ID NO:14 or which hybridizes to a polynucleotide which has a sequence complementary to the nucleotide sequence encoding the polypeptide according to SEQ ID NO:14 under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3×SSCP containing 0.1% SDS at a temperature of 37° C.

23. An isolated DNA which hybridizes to a polynucleotide which has a sequence of SEQ ID NO:13 or which hybridizes to a polynucleotide which has a sequence complementary to the nucleotide sequence of SEQ ID NO:13 under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3×SSCP containing 0.1% SDS at a temperature of 37° C.

24. An isolated DNA which hybridizes to a polynucleotide which has a sequence complementary to the nucleotide sequence of a sequence selected from the group consisting of SEQ ID NOS: 13, 15 and the nucleotide sequence from nucleotide 15 to nucleotide 404 of SEQ ID NO:27, said DNA encoding a mammalian Fas ligand, under conditions comprising hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3× SSCP containing 0.1% SDS at a temperature of 37° C.

25. An isolated DNA which hybridizes to a polynucleotide with the sequence complementary to the sequence of SEQ ID NO:13 or which hybridizes to a polynucleotide with the sequence of SEQ ID NO:13 under the conditions consisting of hybridizing a nitrocellulose filter in a solution of 5×SSCP, 50% formamide, 1× Denhardt solution, 0.1% SDS, 100 µg/ml denatured salmon sperm DNA and 10% (W/V) dextran sulfate at a temperature of 28° C. for 18 hours, followed by washing two times in 2×SSCP containing 0.1% SDS at room temperature and washing three times in 0.3× SSCP containing 0.1% SDS at a temperature of 37° C., and wherein said DNA comprises a nucleotide sequence which encodes the polypeptide according to SEQ ID NO:28.

\* \* \* \* \*